US012618053B2

(12) United States Patent
Kogut et al.

(10) Patent No.: US 12,618,053 B2
(45) Date of Patent: May 5, 2026

(54) METHODS AND COMPOSITIONS FOR CELL AND TISSUE REJUVENATION

(71) Applicant: The Regents of the University of Colorado, A Body Corporate, Denver, CO (US)

(72) Inventors: Igor Kogut, Greenwood Village, CO (US); Ganna Bilousova, Greenwood Village, CO (US); Nicole Frances Diette, Lakewood, CO (US); Patrick Sean McGrath, Thornton, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 1068 days.

(21) Appl. No.: 17/641,598

(22) PCT Filed: Sep. 14, 2020

(86) PCT No.: PCT/US2020/050665
§ 371 (c)(1),
(2) Date: Mar. 9, 2022

(87) PCT Pub. No.: WO2021/051054
PCT Pub. Date: Mar. 18, 2021

(65) Prior Publication Data
US 2022/0325258 A1     Oct. 13, 2022

Related U.S. Application Data

(60) Provisional application No. 62/899,861, filed on Sep. 13, 2019.

(51) Int. Cl.
*C12N 9/12* (2006.01)
*C12N 15/10* (2006.01)
*C12N 15/861* (2006.01)

(52) U.S. Cl.
CPC ......... *C12N 9/1241* (2013.01); *C12N 15/102* (2013.01); *C12N 15/861* (2013.01); *C12N 2710/10011* (2013.01)

(58) Field of Classification Search
CPC .. C12N 9/1241; C12N 15/102; C12N 9/1276; C12N 9/22; A61K 48/005; C07K 2319/71
See application file for complete search history.

(56) References Cited

U.S. PATENT DOCUMENTS

2014/0065112 A1     3/2014     Madonna et al.
2019/0330280 A1     10/2019    Endo et al.

FOREIGN PATENT DOCUMENTS

| JP | 2002509699 A | 4/2002 |
|---|---|---|
| WO | 2014197748 A2 | 12/2014 |
| WO | 2015100269 A2 | 7/2015 |
| WO | 2018110471 A1 | 6/2018 |

OTHER PUBLICATIONS

Wang et al. (An RNA-aptamer-based two-color CRISPR labeling system. Scientific Reports, 2016, 6:26857, p. 1-7) (Year: 2016).*
Suhani Vora (Highly efficient Cas9 mediated transcriptional programming and delivery via Adeno-associated virus. PhD Dissertation , Jun. 2017, p. 1-160). (Year: 2017).*
Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
Xiong, et al., "CRISPR/Cas9 for Human Genome Engineering and Disease Research", Annu. Rev. Genom. Hum. Genet., 2016, vol. 17, No. 13154, pp. 131-154.
Brane, A. et al., "Targeting Telomeres and Telomerase: Studies in Aging and Disease Utilizing CRISPR/Cas9 Technology", Cells, vol. 8, No. 2, Feb. 21, 2019, 13 pages.
Xi, L. et al., "A novel two-step genome editing strategy with CRISPR-Cas9 provides new insights into telomerase action and TERT gene expression", Genome Biology, vol. 16, No. 1, Nov. 10, 2015, pp. 1-17.
Chavez, A. et al., "Highly efficient Cas9-mediated transcriptional programming," Nature Methods, vol. 12, No. 4, Apr. 2015, pp. 326-328.

* cited by examiner

*Primary Examiner* — Iqbal H Chowdhury
(74) *Attorney, Agent, or Firm* — Snell & Wilmer, L.L.P.

(57)     ABSTRACT

The present disclosure provides compositions, methods and kits for the rejuvenation of target cells. In some aspects, the compositions, methods and kits comprise mRNAs the promote the expression of TERT and/or TERC.

19 Claims, 21 Drawing Sheets

Specification includes a Sequence Listing.

Schematic overview of the transfection regimen where all factors are delivered together in one transfection Adult Fibroblasts +
hTERT/dCas9-
VPR+gRNA Adult Fibroblasts

METHODS AND COMPOSITIONS FOR CELL AND TISSUE REJUVENATION

RELATED APPLICATIONS

This application is a U.S. National Phase application, filed under 35 U.S.C. § 371, of International Application No. PCT/US2020/050665, filed Sep. 14, 2020, which claims priority to, and the benefit of, U.S. Provisional Application No. 62/899,861, filed Sep. 13, 2019, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Feb. 18, 2022, is named "UNCO-028_N01_SeqList.txt" and is about 241 KB in size.

BACKGROUND OF THE INVENTION

The shortening of telomeres, repetitive DNA sequences at the ends of linear chromosomes, can lead to cellular senescence, apoptosis, or malignancy. In particular, the shortening of telomeres in cells cultured in vitro is an obstacle to the production of therapeutic cell populations, as shortened telomeres can limit further expansions of the therapeutic cell populations as well as degrade the cells' biological activity, leading to a decrease clinical efficacy. Increasing telomere length in cells can lead to cellular rejuvenation, but can also cause deleterious side-effects such as oncogenic cellular immortalization. Thus, there is a need in the art for compositions, kits and methods directed to effectively and safely increasing the length of telomeres in cells in a controllable way, thereby rejuvenating the cells.

SUMMARY OF THE INVENTION

The present disclosure provides a composition comprising: a) at least one first polynucleotide molecule comprising a nucleic acid sequence encoding at least a portion of telomerase reverse transcriptase (TERT); and b) at least one second polynucleotide molecule comprising a nucleic acid sequence encoding at least a portion of at least one DNA targeting polypeptide, wherein the DNA targeting polypeptide increases transcription of telomerase RNA component (TERC).

The present disclosure provides a composition comprising: a) at least one first polynucleotide molecule comprising a nucleic acid sequence encoding at least a portion of telomerase reverse transcriptase (TERT); and b) at least one DNA targeting polypeptide, wherein the DNA targeting polypeptide increases transcription of telomerase RNA component (TERC).

A first polynucleotide molecule can comprise an mRNA molecule encoding at least a portion of TERT. A first polynucleotide molecule can comprise a plasmid comprising a nucleic acid sequence encoding at least a portion of TERT operably linked to at least one promoter sufficient to drive expression of the at least one portion of TERT.

A second polynucleotide molecule can comprise an mRNA molecule encoding at least a portion of at least one DNA targeting polypeptide. A second polynucleotide molecule can comprise a plasmid comprising a nucleic acid sequence encoding at least a portion of at least one DNA targeting polypeptide operably linked to at least one promoter sufficient to drive expression of the at least one portion of the at least one DNA targeting polypeptide.

A DNA targeting polypeptide can comprise at least one Cas9 molecule, at least one Cas9 variant molecule, at least one Cas9 ortholog molecule or any combination thereof. A Cas9 molecule, a Cas9 variant molecule or a Cas9 ortholog molecule can be nuclease-deficient or nuclease-dead. A Cas9 variant molecule can comprise eSpCas9 (K855A), eSpCas9 (1.0), eSpCas9 (1.1), SpCas9-HF1 (VP12), HypaCas9, xCas9, SpyFi Cas9, iSpy Cas9, iSpyMac, Cas9 (VQR), Cas9 (EQR), Cas9 (VRER), Cas9 (D1135E), Cas9(QQR1), SaCas9 (KKH), Nme1Cas9, Nme2Cas9, Nme3Cas9 or any combination thereof. A Cas9 ortholog molecule can comprise *Streptococcus pyogenes* Cas9 (spCas9), *Francisella novicida* Cas9 (FnCas9), *Staphylococcus aureus* Cas9 (SaCas9), *Neisseria meningitidis* Cas9 (NmCas9; NmeCas9), *Streptococcus thermophilus* CRISPR1-Cas9 (St1Cas9), *Streptococcus thermophilus* CRISPR3-Cas9 (St3Cas9), *Campylobacter jejuni* Cas9 (CjCas9), *Acidaminococcus* sp. BV3L6 Cpf1 (AsCpf1), *Lachnospiraceae bacterium* ND2006 Cpf1 (LbCpf1), *Streptococcus canis* Cas9 (ScCas9), *Treponema denticola* Cas9 (TdCas9), *Streptococcus macacae* Cas9 (SmacCas9), Casφ (Cas12j), *Francisella tularensis* subsp. *novicida* Cas9, *Pasteurella multocida* Cas9, *Campylobacter lari* CF89-12 Cas9, *Mycoplasma gallisepticum* str. F Cas9, *Nitratifractor salsuginis* str DSM 16511 Cas9, *Parvibaculum lavamentivorans* Cas9, *Roseburia intestinalis* Cas9, *Neisseria cinerea* Cas9, *Gluconacetobacter diazotrophicus* Cas9, *Azospirillum* B510 Cas9, *Sphaerochaeta globus* str. Buddy Cas9, *Flavobacterium columnare* Cas9, *Fluviicola taffensis* Cas9, *Bacteroides coprophilus* Cas9, *Mycoplasma mobile* Cas9, *Lactobacillus farciminis* Cas9, *Streptococcus pasteurianus* Cas9, *Lactobacillus johnsonii* Cas9, *Staphylococcus pseudintermedius* Cas9, *Filifactor alocis* Cas9, *Legionella pneumophila* str. Paris Cas9, *Sutterella wadsworthensis* Cas9, *Corynebacter diphtheriae* Cas9 or any combination thereof.

A DNA targeting polypeptide can comprise at least one TALE molecule, at least one zinc-finger molecule, at least one meganuclease molecule or any combination thereof A DNA targeting polypeptide can comprise at least one transactivation molecule. A transactivation molecule can comprise at least one P65 molecule, at least one Rta molecule, at least one VP16 molecule, at least one VP64 molecule, at least one VP160 molecule, at least one VP64-P65-Rta (VPR) molecule, at least one SunTag peptide, at least one single guide RNA-MS2 (sgRNA-MS2) molecule or any combination thereof. In some aspects, a DNA targeting polypeptide can be a DNA targeting ribonucleoprotein (RNP) complex. A DNA targeting ribonucleoprotein complex can comprise both at least one protein component and at least one nucleic acid component. A DNA targeting polypeptide can comprise at least one guide RNA. A transactivation molecule can comprise at least one single guide RNA-MS2 (sgRNA-MS2) molecule. An sgRNA-MS2 molecule can comprise a nucleic acid sequence complementary to a nucleic acid sequence located upstream, within, or downstream of the endogenous TERC gene and at least about one, or at least about two, or at least about three, or at least about four, or at least about five, or at least about six, or at least about seven, or at least about eight, or at least about nine, or at least about ten MS2 RNA aptamers.

A DNA targeting polypeptide can comprise a dCas9 molecule and a VPR molecule.

A DNA targeting polypeptide can bind upstream of, 5' to, within, downstream of or 3' to the endogenous TERC gene.

An mRNA molecule can be a modified mRNA molecule. A modified mRNA molecule can comprise at least one modified ribonucleoside base. A modified ribonucleoside base can comprise a pseudouridine (Ψ) residue, a 5-methylcytidine (m$^5$C) residue or any combination thereof. A modified mRNA molecule can comprise at least one modified nucleoside. A modified nucleoside can comprise 5-methylcytidine (m$^5$C), 5-methyluridine (m$^5$U), N6-methyladenosine (m$^6$A), inosine 2'-0-methylated nucleosides or any combination thereof.

Any composition of the present disclosure can further comprise a plurality of guide RNA (gRNA) molecules, wherein at least one gRNA in the plurality is complementary to a nucleic acid sequence located upstream, within, or downstream of the endogenous TERC gene. A plurality of gRNA molecules can comprise at least about one, or at least about two, or at least about three, or at least about four, or at least about five, or at least about six, or at least about seven, or at least about eight, or at least about nine, or at least about ten distinct species of gRNA molecules, wherein each species has a different nucleic acid. Any composition of the present disclosure can further comprise at least one plasmid comprising at least one nucleic acid sequence encoding at least one species of gRNA operably linked to at least one promoter sufficient to drive expression of the at least one species gRNA. A plurality of gRNA molecules can comprise a plurality of single guide RNA (sgRNA) molecules, crRNA:tracrRNA molecules, truncated sgRNA molecules, high fidelity scaffold gRNA molecules or any combination thereof. A guide RNA molecule can be a modified guide RNA (mod gRNA) molecule. A guide RNA molecule can comprise any sequence recited in Table 1 or Table 2.

The present disclosure provides a composition comprising: a) at least one modified mRNA molecule comprising a nucleic acid sequence encoding at least a portion of human telomerase reverse transcriptase (hTERT); b) at least one modified mRNA molecule comprising a nucleic acid sequence encoding at least a portion of at least one DNA targeting polypeptide, wherein the at least one DNA targeting polypeptide comprises dCas9 and a VP64-P65-Rta (VPR) molecule; and c) a plurality of guide RNA (gRNA) molecules, wherein at least one gRNA in the plurality is complementary to a nucleic acid sequence located upstream of the endogenous hTERC gene.

Any composition of the present disclosure can comprise at least one mRNA and/or polynucleotide encoding at least one rejuvenating factor. A rejuvenating factor can comprise telomerase RNA component (TERC), telomerase associated reverse-transcriptase (TERT), protection of telomeres 1 (POT1), insulin-like growth factor 1 (IGF1), WD repeat containing antisense to TP53 (WRAP53), nuclear protein family A, member 3 (NOP3), heterogeneous nuclear ribonucleoprotein A1 (hnRNPA1), shelterin complex subunit and telomerase recruitment factor (ACD/TPP1), TRF-1 interacting ankyrin-related ADP-ribose polymerase (TNKS), telomeric repeat binding factor 1 (TRF-1), telomeric repeat binding factor 2 (TRF-2), TERF1 interacting nuclear factor 2 (TIN2), telomeric repeat binding factor 2 (Rap1), Dyskerin Pseudouridine Synthase 1 (DKC1), ribonucleoprotein NHP2 or any combination thereof.

TERT can be human TERT (hTERT). TERC can be human T ERC (hTERC).

The present disclosure provides a composition comprising at least one viral particle comprising any composition of the present disclosure. A viral particle can be an adeno-associated virus (AAV) particle, adenovirus particle, lentivirus particle, foamy-virus particle, herpes simplex virus (HSV) particle, retrovirus particle, alphavirus particle, flavivirus particle, rhabdovirus particle, measle virus particle, Newcastle disease virus particle, poxvirus particle, picornavirus particle, or any combination thereof. An AAV particle can be an AAV1, AAV2, AAV3, AAV4, AAV5, AAV6, AAV7, AAV8, AAV9, AAV10, AAV11, AAV12, AAV2/1, AAV2/2, AAV2/3, AAV2/4, AAV2/5, AAV2/6, AAV2/7, AAV2/8, AAV2/9, AAV-DJ or AAV-DJ8 particle. A retrovirus particle can be MMSV or MSCV particle. A lentivirus particle can be HIV-1 or HIV-2 particle. An alphavirus particle can be SFV, SIN, VEE, or M1 particle. A flavivirus particle can be Kunjin virus, West Nile virus, or Dengue virus particle.

The present disclosure provides a composition comprising at least one exosome, microvesicle or liposome, wherein the at least one exosome, microvesicle or liposome comprises any composition of the present disclosure. The present disclosure provides a composition comprising least one nanoparticle, wherein the at least one nanoparticle comprises any composition of the present disclosure. A nanoparticle can comprise a liposome, a micelle, a polymer-based nanoparticle, a lipid-polymer based nanoparticle, a metal based nanoparticle, a nanocrystal, a carbon nanotube based nanoparticle or a polymeric micelle.

The present disclosure provides a kit comprising any composition of the present disclosure.

The present disclosure provides a method of rejuvenating at least one cell, the method comprising contacting the at least one cell with any composition or kit of the present disclosure. The preceding method can further comprise expanding the at least one cell contacted with any composition or kit of the present disclosure to produce a plurality of rejuvenated cells.

The present disclosure provides a method of treating and/or preventing a disease in a subject comprising: a) contacting at least one cell with any composition or kit of the present disclosure; b) expanding the at least one cell contacted with any composition or kit of the present disclosure to produce a plurality of rejuvenated cells; and c) administering the plurality of rejuvenated cells to the subject.

The present disclosure provides a method of treating and/or preventing a disease in a subject comprising: a) contacting at least one cell with any composition or kit of the present disclosure; b) expanding the at least one cell contacted with any composition or kit of the present disclosure to produce a plurality of rejuvenated cells; c) culturing the plurality of rejuvenated cells under conditions sufficient to transform the plurality of rejuvenated cells into at least one tissue or organ; and d) administering the at least one tissue or organ to the subject.

The present disclosure provides a method of producing an in vitro tissue or organ comprising: a) contacting at least one cell with any composition or kit of the present disclosure; b) expanding the at least one cell contacted with any composition or kit of the present disclosure to produce a plurality of rejuvenated cells; c) culturing the plurality of rejuvenated cells under conditions sufficient to transform the plurality of rejuvenated cells into at least one tissue or organ.

The present disclosure provides a method of producing a plurality of rejuvenated edited cells comprising: a) contacting a plurality of cells with a gene editing system such that at least one gene in the genome of at least one cell in the plurality is edited, thereby producing at least one edited cell; b) isolating the at least one edited cell; c) contacting the isolated at least one edited cell with any composition or kit of the present disclosure; and d) expanding the at least one cell contacted with any composition or kit of the present disclosure to produce a plurality of rejuvenated edited cell.

The present disclosure provides a method of treating and/or preventing a disease in a subject comprising: a) contacting a plurality of cells with a gene editing system such that at least one gene in the genome of at least one cell in the plurality is edited, thereby producing at least one edited cell; b) isolating the at least one edited cell; c) contacting the isolated at least one edited cell with any composition or kit of the present disclosure; d) expanding the at least one cell contacted with any composition or kit of the present disclosure to produce a plurality of rejuvenated edited cells; and e) administering to the subject the plurality of rejuvenated edited cells.

The present disclosure provides a method of treating epidermolysis bullosa (EB) in a subject comprising: a) contacting a plurality of cells comprising keratinocytes, dermal fibroblasts, mesenchymal stem/stromal cells or any combination thereof with a gene editing system such that at least one gene in the genome of at least one cell in the plurality is edited, thereby producing at least one edited cell; b) isolating the at least one edited cell; c) contacting the isolated at least one edited cell with any composition or kit of the present disclosure; d) expanding the at least one cell contacted with any composition or kit of the present disclosure to produce a plurality of rejuvenated edited cells; and e) administering to the subject the plurality of rejuvenated edited cells.

Expanding the at least one cell can comprise culturing the at least one cell using adjusted Opti-MEM, non-adjusted Opti-MEM, human serum, fetal bovine serum (FBS) or any combination thereof.

Rejuvenating at least one cell comprises can increase the expression of TERC in the at least one cell, increasing the expression of TERT in the at least one cell, increasing the total number of population doublings exhibited by the at least one cell, increasing the length of telomeres in the at least one cell, increasing the mitochondrial DNA copy number in the at least one cell, increasing the amount of mitochondrial DNA in the at least one cell, increasing the number of mitochondria in the at least one cell, increasing the migration activity of the at least one cell, restoring the young-like state of thiol group oxidation levels in proteins in the at least one cell, reducing senescence-associated DNA methylation in the at least one cell or any combination thereof.

An at least one cell can be a fibroblast, a keratinocyte, a mesenchymal stem/stromal cell, a peripheral blood mononuclear cell, a chimeric antigen receptor T cell (CAR-T cell), an endothelial cell, a chondrocyte, a muscle stem cell, a neural stem cell, a hepatocyte, a limbal stem cell, a retinal pigmented epithelial cell, a hematopoietic stem cell, a macrophage, a cardiomyocyte, a pancreatic cell, a β-cell or any combination thereof.

A disease can comprise graft-vs-host diseases (GvHD), autoimmune diseases, epidermolysis bullosa (EB), recessive dystrophic form of EB (RDEB), junctional EB (JEB), EB simplex (EBS), congenital ichthyosis, congenital dyskeratosis, macular degeneration, Parkinson's disease, Alzheimer's disease, aging, Type I and II diabetes, burns, chronic skin wounds, diabetes-associated ulcers/wounds, heart disease, osteoporosis, cancer, connective tissue diseases such as Ehlers-Danlos Syndrome (EDS) or Marfan syndrome, liver diseases, lung diseases, and any combination thereof.

Contacting at least one cell can comprise transfection, transduction, electroporation, nucleofection, at least one cell-penetrating peptide or any combination thereof.

The present disclosure provides a method for rejuvenating at least one cell in a subject comprising administering to the subject at least one therapeutically effective amount of any composition or kit of the present disclosure.

The present disclosure provides a method for rejuvenating at least one subject comprising administering to the subject at least one therapeutically effective amount of any composition or kit of the present disclosure.

A subject can be a mammal. A subject can be a human, a primate, a mouse, a rat, a dog, a cat, a cow, a horse, a goat, a camel, a sheep, a pig or any other mammal. A subject can be a bird.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION OF THE INVENTION

Figure 1:
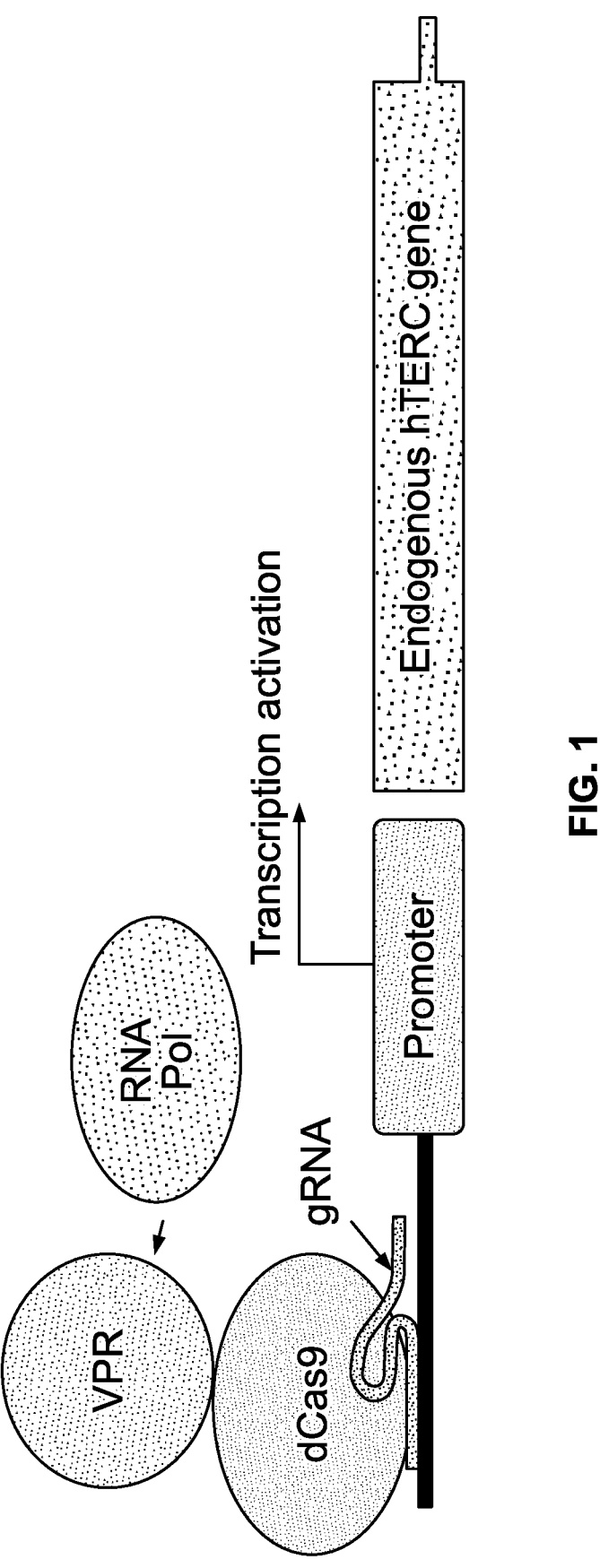
FIG. 1 is a schematic of a DNA-targeting molecule of the present disclosure binding upstream of an endogenous hTERC locus. In this non-limiting example, the DNA-targeting molecule comprises dCas9 and a transactivation molecule, wherein the transactivation molecule is a VP64-P65-Rta (VPR) molecule.
Figure 2:
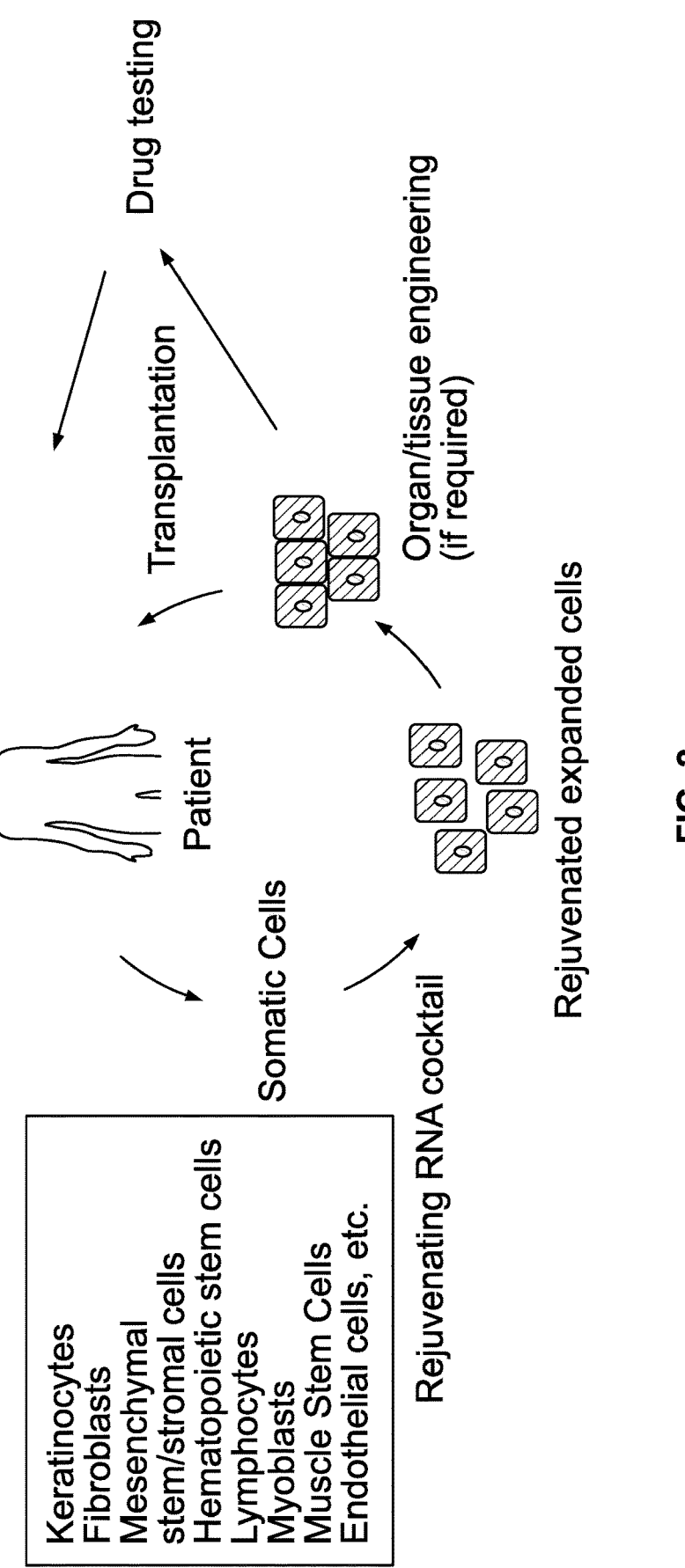
FIG. 2 is a schematic overview of a treatment method and/or a method of producing an in vitro tissue of the present disclosure
Figure 3:
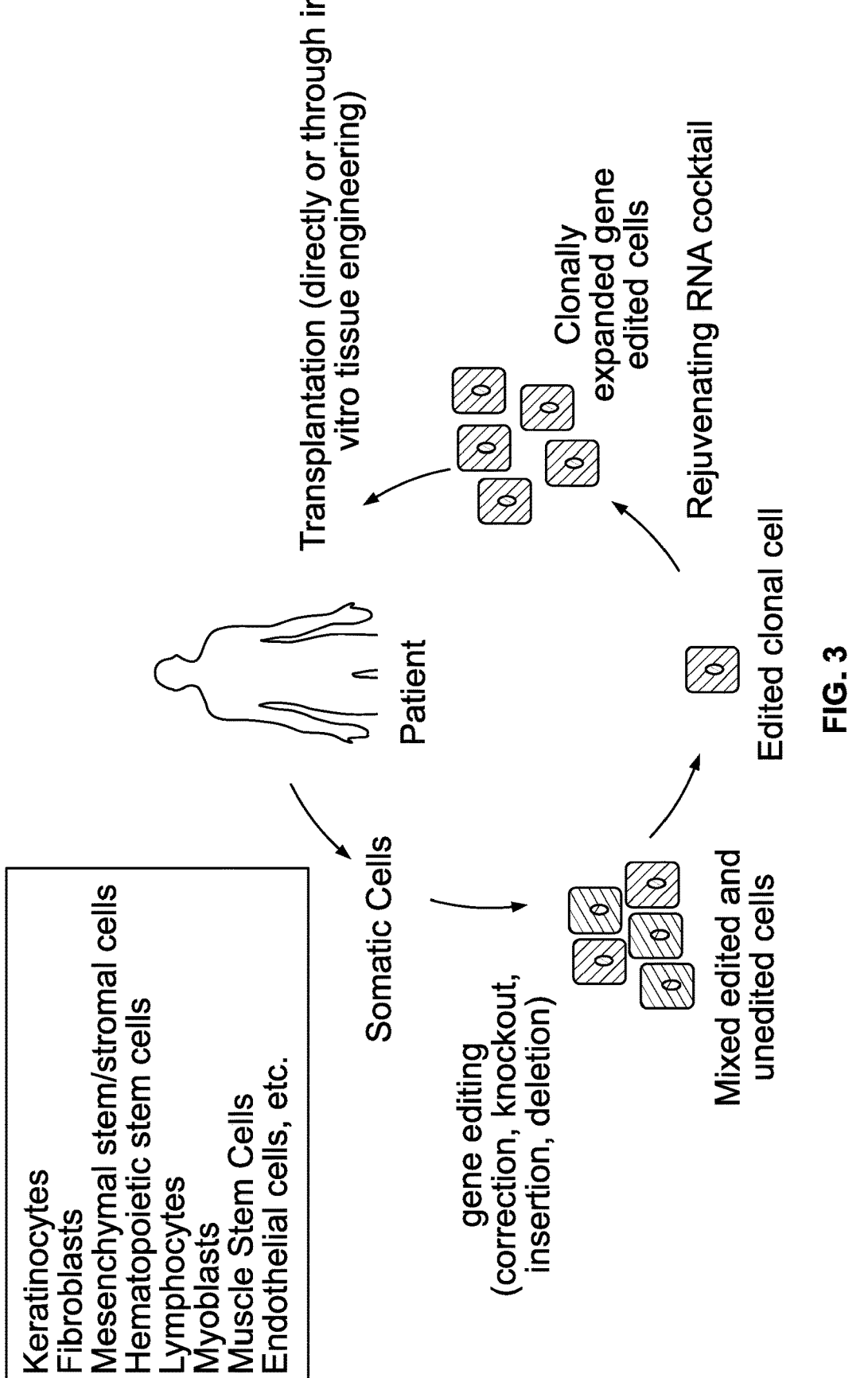
FIG. 3 is a schematic overview of a method of producing a plurality of rejuvenated edited cells of the present disclosure.

Telomeres comprise repetitive DNA sequences at the ends of linear chromosomes that, when sufficiently long, allow each chromosome end to form a loop that protects the ends from acting as double-stranded or single-stranded DNA breaks. Telomeres shorten over time, due in part to oxidative damage and incomplete DNA replication, eventually leading to critically short telomeres unable to form the protective loop, exposure of the chromosome ends, chromosome-chromosome fusions, DNA damage responses, and cellular senescence, apoptosis, or malignancy.

The enzyme complex telomerase extends telomeres and comprises two essential components: the telomerase reverse transcriptase (TERT), and an RNA component known as telomerase RNA component (TERC). Other components of the telomerase complex include the proteins TCAB1, Dyskerin, Gar1, Nhp2, Nop 10, and RHAU.

Due to the importance of telomere length maintenance in preventing cellular senescence and apoptosis and resulting cellular dysfunction, genetic mutations of TERT and TERC are linked to fatal inherited diseases of inadequate telomere maintenance, including forms of idiopathic pulmonary fibrosis, dyskeratosis congenita, and aplastic anemia. The effects of premature cellular senescence and apoptosis due to short telomeres in these diseases are devastating in themselves, and may be compounded by increased risk of cancer. Moreover, the shortening of telomeres in cells that are cultured in vitro results is also a major problem in the production of therapeutic cell populations, the creation of in vitro synthetic tissue and tumors and the in vitro creation of non-cancerous somatic cells lines for research and drug testing. Repeated passaging in vitro can lead to senescence and the lack of further expansion ability, and in the case of therapeutic cell populations, a decrease in clinically-relevant biological activity.

Thus, there is a clear need in the art for compositions, kits and methods directed to elongating telomeres in order to rejuvenate cells. Existing approaches directed to increasing the expression of TERT and/or TERC in target cells has relied on the use of integrating viruses to obtain the desired increase in TERT and/or TERC expression. However, these approaches suffer from safety concerns, as the integrating viruses can result in potentially dangerous, permanent genome modifications. Moreover, the sustained overexpression of TERT and/or TERC, and concomitant increases in telomere length, have been linked to cancer cell immortalization, making the integrating virus approach dangerous in a clinical context.

Without wishing to be bound by theory, the compositions, kits and methods of the present disclosure allow for the transient increase in TERT and/or TERC expression for a time period that is long enough to rejuvenate the target cells, but short enough to avoid deleterious and dangerous off-target effects. The use of non-integrating RNA molecules in the present disclosure allows for fine-tuning of the expression levels and stoichiometry of rejuvenating factors in a clinically safe manner.

The compositions, kits and methods of the present disclosure can be used for a variety of different research and clinical applications, including, but not limited to, the production of therapeutic cell populations (e.g. CAR-T cell populations, mesenchymal stem/stromal cell populations), the production of in vitro tissue and organs for subsequent transplantation, research or drug testing, the production of genome-edited cell populations for therapeutic and research applications, the rejuvenation of senescent, aged and disease associated cell lines, etc.

Various compositions, kits and methods of the present disclosure are described in full detail herein.

Rejuvenating Compositions

In some aspects, the present disclosure provides a composition comprising: a) at least one first polynucleotide molecule comprising a nucleic acid sequence encoding at least a portion of telomerase reverse transcriptase (TERT); and b) at least one second polynucleotide molecule comprising a nucleic acid sequence encoding at least a portion of at least one DNA targeting polypeptide, wherein the DNA targeting polypeptide increases transcription of telomerase RNA component (TERC).

In some aspects, the present disclosure provides a composition comprising: a) at least one first polynucleotide molecule comprising a nucleic acid sequence encoding at least a portion of telomerase reverse transcriptase (TERT); and b) at least one DNA targeting polypeptide, wherein the DNA targeting polypeptide increases transcription of telomerase RNA component (TERC).

In some aspects, the at least one first polynucleotide molecule comprising a nucleic acid sequence encoding at least a portion of telomerase reverse transcriptase (TERT) can be an mRNA molecule encoding at least a portion of TERT. In some aspects, the at least one first polynucleotide molecule can be a plasmid comprising a nucleic acid sequence encoding at least a portion of TERT operably linked to at least one promoter sufficient to drive expression of the at least one portion of TERT.

In some aspects, the at least one second polynucleotide molecule comprising a nucleic acid sequence encoding at least a portion of at least one DNA targeting polypeptide can be an mRNA molecule encoding at least a portion of at least one DNA targeting polypeptide. In some aspects, the at least one second polynucleotide molecule can be a plasmid comprising a nucleic acid sequence encoding at least a portion of at least one DNA targeting polypeptide operably linked to at least one promoter sufficient to drive expression of the at least one portion of the at least one DNA targeting polypeptide.

Thus, the present disclosure provides a composition comprising: a) at least one first mRNA molecule encoding at least a portion of telomerase reverse transcriptase (TERT); and b) at least one second mRNA molecule encoding at least a portion of at least one DNA targeting polypeptide, wherein the DNA targeting polypeptide increases transcription of telomerase RNA component (TERC).

The present disclosure also provides a composition comprising: a) at least one plasmid comprising a nucleic acid sequence encoding at least a portion of TERT operably linked to at least one promoter sufficient to drive expression of the at least one portion of TERT; and b) at least one second mRNA molecule encoding at least a portion of at least one DNA targeting polypeptide, wherein the DNA targeting polypeptide increases transcription of telomerase RNA component (TERC).

The present disclosure also provides a composition comprising: a) at least one first mRNA molecule encoding at least a portion of telomerase reverse transcriptase (TERT); and b) at least one plasmid comprising a nucleic acid sequence encoding at least a portion of at least one DNA targeting polypeptide operably linked to at least one promoter sufficient to drive expression of the at least one portion of the at least one DNA targeting polypeptide, wherein the DNA targeting polypeptide increases transcription of telomerase RNA component (TERC).

The present disclosure also provides a composition comprising: a) at least one plasmid comprising a nucleic acid sequence encoding at least a portion of TERT operably linked to at least one promoter sufficient to drive expression of the at least one portion of TERT; and b) at least one plasmid comprising a nucleic acid sequence encoding at least a portion of at least one DNA targeting polypeptide operably linked to at least one promoter sufficient to drive expression of the at least one portion of the at least one DNA targeting polypeptide, wherein the DNA targeting polypeptide increases transcription of telomerase RNA component (TERC).

In some aspects, a DNA targeting polypeptide can comprise at least one Cas9 molecule, at least one Cas9 variant molecule, at least one Cas9 ortholog molecule or any combination thereof.

In some aspects, a Cas9 molecule, a Cas9 variant molecule or a Cas9 ortholog molecule can be nuclease-deficient or nuclease-dead. As used herein, the term "dCas9" is used in its broadest sense to refer to a Cas9 molecule, ortholog and/or variant that is nuclease-deficient or nuclease dead. In a non-limiting example, a Cas9 molecule, a Cas9 variant molecule or a Cas9 ortholog molecule can comprise at least one mutation, deletion or insertion which renders the Cas9 molecule, the Cas9 variant molecule or the Cas9 ortholog molecule nuclease-deficient or nuclease-dead.

In some aspects, a Cas9 variant molecule can comprise eSpCas9 (K855A), eSpCas9 (1.0), eSpCas9 (1.1), SpCas9-HF1 (VP12), HypaCas9, xCas9, SpyFi Cas9, iSpy Cas9, iSpyMac, Cas9 (VQR), Cas9 (EQR), Cas9 (VRER), Cas9 (D1135E), Cas9(QQR1), SaCas9 (KKH), Nme1 Cas9, Nme2Cas9, Nme3Cas9 or any combination thereof.

In some aspects, a Cas9 ortholog molecule can comprise *Streptococcus pyogenes* Cas9 (spCas9), *Francisella novicida* Cas9 (FnCas9), *Staphylococcus aureus* Cas9 (SaCas9), *Neisseria meningitidis* Cas9 (NmCas9; NmeCas9), *Streptococcus thermophilus* CRISPR1-Cas9 (St1Cas9), *Streptococcus thermophilus* CRISPR3-Cas9 (St3Cas9), *Campylobacter jejuni* Cas9 (CjCas9), *Acidaminococcus* sp. BV3L6 Cpf1 (AsCpf1), *Lachnospiraceae bacterium* ND2006 Cpf1 (LbCpf1), *Streptococcus canis* Cas9 (ScCas9), *Treponema denticola* Cas9 (TdCas9), *Streptococcus macacae* Cas9 (SmacCas9), Casφ (Cas12j), *Francisella tularensis* subsp. *novicida* Cas9, *Pasteurella multocida* Cas9, *Campylobacter lari* CF89-12 Cas9, *Mycoplasma gallisepticum* str. F Cas9, *Nitratifractor salsuginis* str DSM 16511 Cas9, *Parvibaculum lavamentivorans* Cas9, *Roseburia intestinalis* Cas9, *Neisseria cinerea* Cas9, *Gluconacetobacter diazotrophicus* Cas9, *Azospirillum* B510 Cas9, *Sphaerochaeta globus* str. Buddy Cas9, *Flavobacterium columnare* Cas9, *Fluviicola taffensis* Cas9, *Bacteroides coprophilus* Cas9, *Mycoplasma mobile* Cas9, *Lactobacillus farciminis* Cas9, *Streptococcus pasteurianus* Cas9, *Lactobacillus johnsonii* Cas9, *Staphylococcus pseudintermedius* Cas9, *Filifactor alocis* Cas9, *Legionella pneumophila* str. Paris Cas9, *Sutterella wadsworthensis* Cas9, *Corynebacter diphtheriae* Cas9 or any combination thereof.

In some aspects, a Cas9 ortholog molecule can comprise a chimeric variant of *Streptococcus pyogenes* Cas9 (spCas9), *Francisella novicida* Cas9 (FnCas9), *Staphylococcus aureus* Cas9 (SaCas9), *Neisseria meningitidis* Cas9 (NmCas9; NmeCas9), *Streptococcus thermophilus* CRISPR1-Cas9 (St1Cas9), *Streptococcus thermophilus* CRISPR3-Cas9 (St3Cas9), *Campylobacter jejuni* Cas9

(CjCas9), *Acidaminococcus* sp. BV3L6 Cpf1 (AsCpf1), *Lachnospiraceae bacterium* ND2006 Cpf1 (LbCpf1), *Streptococcus canis* Cas9 (ScCas9), *Treponema denticola* Cas9 (TdCas9), *Streptococcus macacae* Cas9 (SmacCas9), Casϕ (Cas12j), *Francisella tularensis* subsp. *novicida* Cas9, *Pasteurella multocida* Cas9, *Campylobacter lari* CF89-12 Cas9, *Mycoplasma gallisepticum* str. F Cas9, *Nitratifractor salsuginis* str DSM 16511 Cas9, *Parvibaculum lavamentivorans* Cas9, *Roseburia intestinalis* Cas9, *Neisseria cinerea* Cas9, *Gluconacetobacter diazotrophicus* Cas9, *Azospirillum* B510 Cas9, *Sphaerochaeta globus* str. Buddy Cas9, *Flavobacterium columnare* Cas9, *Fluviicola taffensis* Cas9, *Bacteroides coprophilus* Cas9, *Mycoplasma mobile* Cas9, *Lactobacillus farciminis* Cas9, *Streptococcus pasteurianus* Cas9, *Lactobacillus johnsonii* Cas9, *Staphylococcus pseudintermedius* Cas9, *Filifactor alocis* Cas9, *Legionella pneumophila* str. Paris Cas9, *Sutterella wadsworthensis* Cas9, *Corynebacter diphtheriae* Cas9 or any combination thereof.

In some aspects, a DNA targeting polypeptide can comprise at least one TALE molecule, at least one zinc-finger molecule, at least one meganuclease molecule or any combination thereof.

In some aspects, a DNA targeting polypeptide can comprise at least one transactivation molecule. In some aspects, a transactivation molecule is a molecule that binds to transcription factors and/or transcriptional co-regulators that are capable of driving transcription of a target gene.

In some aspects, a transactivation molecule can comprise at least one P65 molecule, at least one Rta molecule, at least one VP16 molecule, at least one VP64 molecule, at least one VP160 molecule, at least one VP64-P65-Rta (VPR) molecule, at least one SunTag peptide, at least one single guide RNA-MS2 (sgRNA-MS2) molecule or any combination thereof.

In some aspects, a DNA targeting polypeptide can be a DNA targeting ribonucleoprotein (RNP) complex. A DNA targeting ribonucleoprotein complex can comprise both at least one protein component and at least one nucleic acid component. The at least one protein component can comprise any of the protein components described herein, including, but not limited to, a transactivation molecule, a Cas9 molecule, a Cas9 variant molecule or a Cas9 ortholog molecule, a TALE molecule, a zinc-finger molecule, a meganuclease molecule or any combination thereof. The at least one nucleic acid component can be a ribonucleic acid component. The at least one nucleic acid component can comprise any of the nucleic acid components described herein, including, but not limited to, a guide RNA molecule, a single guide RNA molecule, a single guide RNA-MS2 (sgRNA-MS2) molecule or any combination thereof.

In some aspects, a DNA targeting polypeptide can further comprise at least one cell-penetrating peptide. A cell-penetrating peptide can comprise at least a portion of an HIV-derived TAT protein, polyarginine, any other cell-penetrating peptide known in the art or any combination thereof.

In some aspects, a DNA targeting polypeptide can comprise at least one guide RNA. In some aspects, a transactivation molecule can comprise at least one single guide RNA-MS2 (sgRNA-MS2) molecule. In some aspects, a sgRNA-MS2 molecule can comprise a nucleic acid sequence complementary to a nucleic acid sequence located upstream, within, or downstream of the endogenous TERC gene and at least about one, or at least about two, or at least about three, or at least about four, or at least about five, or at least about six, or at least about seven, or at least about eight, or at least about nine, or at least about ten MS2 RNA aptamers.

In some aspects, a DNA targeting polypeptide can comprise a dCas9 molecule and a VPR molecule.

In some aspects, a DNA targeting polypeptide can bind upstream of, 5' to, within, downstream of or 3' to the endogenous TERC gene, e.g. the endogenous human TERC gene.

In some aspects, an at least one DNA targeting polypeptide can bind at least about 0.1 kilobases (kb), or at least about 0.5 kb, or at least about 1.0 kb, or at least about 1.5 kb, or at least about 2.0 kb, or at least about 2.5 kb, or at least about 3.0 kb, or at least about 3.5 kb, or at least about 4.0 kb, or at least about 4.5 kb, or at least about 5.0 kb, or at least about 5.5 kb, or at least about 6.0 kb, or at least about 6.5 kb, or at least about 7.0 kb, or at least about 7.5 kb, or at least about 8.5 kb, or at least about 9.0 kb, or at least about 9.5 kb, or at least about 10.0 kb, or at least about 15 kb, or at least about 20 kb, or at least about 30 kb, or at least about 40 kb, or at least about 50 kb, or at least about 60 kb, or at least about 15 kb, or at least about 70 kb, or at least about 80 kb, or at least about 90 kb, or at least about 100 kb, or at least about 250 kb, or at least about 500 kb, or at least about 750 kb, or at least about 1000 kb, or at least 5000 kb or at least about 10,000 kb upstream of the endogenous TERC gene, e.g. the endogenous human TERC gene.

In some aspects, an at least one DNA targeting polypeptide can bind at least about 0.1 kilobases (kb), or at least about 0.5 kb, or at least about 1.0 kb, or at least about 1.5 kb, or at least about 2.0 kb, or at least about 2.5 kb, or at least about 3.0 kb, or at least about 3.5 kb, or at least about 4.0 kb, or at least about 4.5 kb, or at least about 5.0 kb, or at least about 5.5 kb, or at least about 6.0 kb, or at least about 6.5 kb, or at least about 7.0 kb, or at least about 7.5 kb, or at least about 8.5 kb, or at least about 9.0 kb, or at least about 9.5 kb, or at least about 10.0 kb, or at least about 15 kb, or at least about 20 kb, or at least about 30 kb, or at least about 40 kb, or at least about 50 kb, or at least about 60 kb, or at least about 15 kb, or at least about 70 kb, or at least about 80 kb, or at least about 90 kb, or at least about 100 kb, or at least about 250 kb, or at least about 500 kb, or at least about 750 kb, or at least about 1000 kb, or at least 5000 kb or at least about 10,000 kb 3' to the endogenous TERC gene, e.g. the endogenous human TERC gene.

In some aspects, an at least one DNA targeting polypeptide can bind at least about 0.1 kilobases (kb), or at least about 0.5 kb, or at least about 1.0 kb, or at least about 1.5 kb, or at least about 2.0 kb, or at least about 2.5 kb, or at least about 3.0 kb, or at least about 3.5 kb, or at least about 4.0 kb, or at least about 4.5 kb, or at least about 5.0 kb, or at least about 5.5 kb, or at least about 6.0 kb, or at least about 6.5 kb, or at least about 7.0 kb, or at least about 7.5 kb, or at least about 8.5 kb, or at least about 9.0 kb, or at least about 9.5 kb, or at least about 10.0 kb, or at least about 15 kb, or at least about 20 kb, or at least about 30 kb, or at least about 40 kb, or at least about 50 kb, or at least about 60 kb, or at least about 15 kb, or at least about 70 kb, or at least about 80 kb, or at least about 90 kb, or at least about 100 kb, or at least about 250 kb, or at least about 500 kb, or at least about 750 kb, or at least about 1000 kb, or at least 5000 kb or at least about 10,000 kb downstream of the endogenous TERC gene, e.g. the endogenous human TERC gene.

In some aspects, an at least one DNA targeting polypeptide can bind at least about 0.1 kilobases (kb), or at least about 0.5 kb, or at least about 1.0 kb, or at least about 1.5 kb, or at least about 2.0 kb, or at least about 2.5 kb, or at least about 3.0 kb, or at least about 3.5 kb, or at least about 4.0 kb, or at least about 4.5 kb, or at least about 5.0 kb, or at least about 5.5 kb, or at least about 6.0 kb, or at least about 6.5 kb, or at least about 7.0 kb, or at least about 7.5 kb, or at least about 8.5 kb, or at least about 9.0 kb, or at least about 9.5 kb, or at least about 10.0 kb, or at least about 15 kb, or at least about 20 kb, or at least about 30 kb, or at least about 40 kb, or at least about 50 kb, or at least about 60 kb, or at least about 15 kb, or at least about 70 kb, or at least about 80 kb, or at least about 90 kb, or at least about 100 kb, or at least about 250 kb, or at least about 500 kb, or at least about 750 kb, or at least about 1000 kb, or at least 5000 kb or at least about 10,000 kb 5' to the endogenous TERC gene, e.g. the endogenous human TERC gene.

In some aspects, an mRNA molecule of any composition of the present disclosure can be a modified mRNA molecule.

In some aspects, a modified mRNA molecule can comprise at least one modified ribonucleoside base. A modified ribonucleoside base can comprise a pseudouridine ($\Psi$) residue, a 5-methylcytidine ($m^5C$) residue or any combination thereof.

In some aspects, a modified mRNA molecule can comprise at least one modified nucleoside. A modified nucleoside can comprise 5-methylcytidine ($m^5C$), 5-methyluridine ($m^5U$), N6-methyladenosine ($m^6A$), inosine and 2'-0-methylated nucleosides, in addition to N7-methylguanosine ($m^7G$), 2-thiouridine ($s^2U$), pseudouridine ($\psi$), 2'-0-methyl-U, $m^1A$ (1-methyladenosine); $m^2A$ (2-methyladenosine); Am (2'-0-methyladenosine); $ms^2m^6A$ (2-methylthio-$N^6$-methyladenosine); $i^6A$ ($N^6$-isopentenyladenosine); $ms^2i6A$ (2-methylthio-$N^6$isopentenyladenosine); $io^6A$ ($N^6$-(cis-hy-droxyisopentenyl)adenosine); $ms^2i^6A$ (2-methylthio-$N^6$-(cis-hydroxyisopentenyl)adenosine); $g^6A$ ($N^6$-glycinylcar-bamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$ ($N^6$-hydroxynorvalylcarbamoyladenosine); $ms^2hn^6A$ (2-methylthio-$N^6$-hydroxynorvalyl carbamoyladenosine); Ar(p) (2'-0-ribosyladenosine(phosphate)); I (inosine); $m^1I$ (1-methylinosine); $m^1Im$ (1,2'-0-dimethylinosine); $m^3C$ (3-methylcytidine); Cm (2'-0-methylcytidine); $s^2C$ (2-thio-cytidine); $ac^4C(N^4$-acetylcytidine); $f^5C$ (5-formylcytidine); $m^5$ Cm (5,2'-0-dimethylcytidine); $ac^4Cm$ ($N^4$-acetyl-2'-0-methylcytidine); $k^2C$ (lysidine); $m^1G$ (1-methylguanosine); $m^2G$ ($N^2$-methylguanosine); $m^7G$ (7-methylguanosine); Gm (2'-0-methylguanosine); $m^2_2G$ ($N^2,N^2$-dimethylguanosine); $m^2Gm$ ($N^2,2'$-0-dimethylguanosine); $m^2_2Gm$ ($N^2,N^2,2'$-0-trimethylguanosine); Gr(p) (2'-0-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methyl-wyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-0-dimethyluridine); $s^4U$ (4-thiouridine); $m^5s^2U$ (5-methyl-2-thiouridine); $s^2Um$ (2-thio-2'-0-methyluridine); $acp^3U$ (3-(3-amino-3-carboxypropyl)uridine); $ho^5U$ (5-hy-droxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-0-methyluridine); $mcm^5s^2U$ (5-methoxycarbonylmethyl-2-thiouridine); $nm^5s^2U$ (5-ami-nomethyl-2-thiouridine); $mnm^5U$ (5-methylaminomethylu-ridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbam-oylmethyl-2'-0-methyluridine); $cmnm^5U$ (5-carboxymethylaminomethyluridine); $cmnm^5Um$ (5-carboxymethylami-nomethyl-2'-0-methyluridine); $cmnm^5s^2U$ (5-carboxyme-thylaminomethyl-2-thiouridine); $m^6_2A$ ($N^6,N^6$-dimethylad-enosine); Im (2'-0-methylinosine); $m^4C(N^4$-methylcyti-dine); $m^4$ Cm ($N^4,2'$-0-dimethylcytidine); $hm^5C$ (5-hy-droxymethylcytidine); $m^3U$ (3-methyluridine); $cm^5U$ (5-carboxymethyluridine); $m^6Am$ ($N^6,2'$-0-dimethyladenos-ine); $m^6_2Am$ ($N^6,N^6,0$-2'-2 7 2 2 2 7 2 2trimethyladenosine); $m^{2,7}G$ ($N^2,7$-dimethylguanosine); $m^{2,2,7}G$ ($N^2$, $N^2,7$-trim-ethylguanosine); $m^3Um$ (3,2'-0-dimethyluridine); $m^5D$ (5-methyldihydrouridine); $f^5Cm$ (5-formyl-2'-0-methylcyti-dine); $m^1Gm$ (1,2'-0-dimethylguanosine); $m^1Am$ (1,2'-0-dimethyladenosine); $\tau m^5U$ (5-taurinomethyluridine); $\tau m^5s^2U$ (5-taurinomethyl-2-thiouridine)); imG-14 (4-dem-ethylwyosine); imG2 (isowyosine); $ac^6A$ ($N^6$-acetyladenos-ine), or any combination thereof.

In some aspects, an mRNA molecule can be chemically synthesized using methods standard in the art. In some aspects, an mRNA molecule can be chemically synthesized such that the mRNA molecule comprises at least one chemi-cal modification. In some aspects, an mRNA molecule can be produced by in vitro transcription methods standard in the art, including, but not limited to, in vitro transcription using a plasmid template, in vitro transcription using a PCR-based template. In some aspects, in vitro transcription methods can be performed such that the produced mRNA molecules comprise at least one chemical modification.

In some aspects, a purified DNA targeting polypeptide can be produced using methods standard in the art, including, but not limited to, recombinant protein expression and purification in a bacterial, fungal, insect and/or mammalian system, ion-exchange chromatography, affinity chromatog-raphy, immunoaffinity chromatography, size exclusion chro-matography, and/or other standard protein production/puri-fication methods known in the art.

In some aspects, a purified DNA-targeting ribonucleopro-tein (RNP) complex can be produced using methods stan-dard in the art, including, but not limited to recombinant protein expression and purification in a bacterial, fungal, insect and/or mammalian system, in vitro RNA transcrip-tion, ion-exchange chromatography, affinity chromatogra-phy, immunoaffinity chromatography, size exclusion chro-matography, other standard protein production/purification methods known in the art, and/or other standard nucleic acid production/purification methods known in the art. In some aspects, a preassembled RNP complex that comprises both at least one protein component and at least one nucleic acid can be assembled in vivo (i.e. in a bacterial, fungal, insect and/or mammalian recombinant expression system) and co-purified. In some aspects, a RNP complex can be assembled in vitro after the individual purification of the at least one protein component and the at least one nucleic acid component.

In some aspects, any of the compositions of the present disclosure can further comprise a plurality of guide RNA (gRNA) molecules, wherein at least one gRNA in the plurality is complementary to a nucleic acid sequence located upstream, within, or downstream of the endogenous TERC gene. In some aspects, a plurality of gRNA molecules can comprise at least about one, or at least about two, or at least about three, or at least about four, or at least about five, or at least about six, or at least about seven, or at least about eight, or at least about nine, or at least about ten, or at least about 11, or at least about 12, or at least about 13, or at least about 14, or at least about 15, at least about 16, or at least about 17, or about at least 18, or at least about 19, or at least about 20, or at least about 30, or at least about 40, or at least about 50, or at least about 60, or at least about 70, or at least about 80, or at least about 90, or at least about 100, or at least about 500 or at least about 1000 distinct species of gRNA molecules, wherein each species has a different nucleic acid sequence.

In some aspects, any of the compositions of the present disclosure can further comprise at least one plasmid comprising at least one nucleic acid sequence encoding at least one species of gRNA operably linked to at least one promoter sufficient to drive expression of the at least one species gRNA. In some aspects, any of the compositions of the present disclosure can further comprise at least one plasmid comprising at least one nucleic acid sequence encoding least about two, or at least about three, or at least about four, or at least about five, or at least about six, or at least about seven, or at least about eight, or at least about nine, or at least about ten, or at least about 11, or at least about 12, or at least about 13, or at least about 14, or at least about 15, at least about 16, or at least about 17, or about at least 18, or at least about 19, or at least about 20, or at least about 30, or at least about 40, or at least about 50, or at least about 60, or at least about 70, or at least about 80, or at least about 90, or at least about 100, or at least about 500 or at least about 1000 distinct species of gRNA molecules operably linked to at least one promoter sufficient to drive expression of the gRNA species, wherein each species has a different nucleic acid sequence.

In some aspects, a plurality of gRNA molecules can comprise a plurality of single guide RNA (sgRNA) molecules, crRNA:tracrRNA molecules, truncated sgRNA molecules, high fidelity scaffold gRNA molecules or any combination thereof.

In some aspects, a plurality of gRNA molecules can comprise a plurality of single guide RNA (sgRNA) molecules. In some aspects, a sgRNA molecule can comprise a nucleic acid sequence complementary to a nucleic acid sequence located upstream, within, or downstream of the endogenous TERC gene and at least one MS2 RNA aptamer. In some aspects, a sgRNA molecule can comprise at least about two, or at least about three, or at least about four, or at least about five, or at least about six, or at least about seven, or at least about eight, or at least about nine, or at least about ten MS2 RNA aptamers.

In some aspects, a guide RNA molecule of any composition of the present disclosure can be a modified guide RNA (mod gRNA) molecule.

In some aspects, a modified guide RNA can comprise at least one modified ribonucleoside base. A modified ribonucleoside base can comprise a pseudouridine ($\Psi$) residue, a 5-methylcytidine ($m^5C$) residue or any combination thereof.

In some aspects, a modified guide RNA can comprise at least one modified nucleoside. A modified nucleoside can comprise 5-methylcytidine ($m^5C$), 5-methyluridine ($m^5U$), N6-methyladenosine ($m^6A$), inosine and 2'-0-methylated nucleosides, in addition to N7-methylguanosine ($m^7G$), 2-thiouridine ($s^2U$), pseudouridine ($\psi$), 2'-0-methyl-U, $m^1A$ (1-methyladenosine); $m^2A$ (2-methyladenosine); Am (2'-0-methyladenosine); $ms^2m^6A$ (2-methylthio-$N^6$-methyladenosine); $i^6A$ ($N^6$-isopentenyladenosine); $ms^2i6A$ (2-methylthio-$N^6$isopentenyladenosine); $io^6A$ ($N^6$-(cis-hydroxyisopentenyl)adenosine); $ms^2i^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-0-ribosyladenosine(phosphate)); I (inosine); $m^1I$ (1-methylinosine); $m^1Im$ (1,2'-0-dimethylinosine); $m^3C$ (3-methylcytidine); Cm (2'-0-methylcytidine); $s^2C$ (2-thiocytidine); $ac^4C$($N^4$-acetylcytidine); $f^5C$ (5-formylcytidine); $m^5Cm$ (5,2'-0-dimethylcytidine); $ac^4Cm$ ($N^4$-acetyl-2'-0-methylcytidine); $k^2C$ (lysidine); $m^1G$ (1-methylguanosine); $m^2G$ ($N^2$-methylguanosine); $m^7G$ (7-methylguanosine); Gm (2'-0-methylguanosine); $m^2_2G$ ($N^2,N^2$-dimethylguanosine); $m^2Gm$ ($N^2$, 2'-0-dimethylguanosine); $m^2_2Gm$ ($N^2,N^2,2'$-0-trimethylguanosine); Gr(p) (2'-0-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-0-dimethyluridine); $s^4U$ (4-thiouridine); $m^5s^2U$ (5-methyl-2-thiouridine); $s^2Um$ (2-thio-2'-0-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-0-methyluridine); $mcm^5s^2U$ (5-methoxycarbonylmethyl-2-thiouridine); $nm^5_s{}^2U$ (5-aminomethyl-2-thiouridine); $mnm^5U$ (5-methylaminomethyluridine); $mnm^5_s{}^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-0-methyluridine); $cmnm^5U$ (5-carboxymethylaminomethyluridine); $cmnm^5Um$ (5-carboxymethylaminomethyl-2'-0-methyluridine); $cmnm^5_s{}^2U$ (5-carboxymethylaminomethyl-2-thiouridine); $m^6_2A$ ($N^6,N^6$-dimethyladenosine); Im (2'-0-methylinosine); $m^4C$($N^4$-methylcytidine); $m^4$ Cm ($N^4,2'$-0-dimethylcytidine); $hm^5C$ (5-hydroxymethylcytidine); $m^3U$ (3-methyluridine); $cm^5U$ (5-carboxymethyluridine); $m^6Am$ ($N^6,2'$-0-dimethyladenosine); $m^6_2Am$ ($N^6,N^6,0$-2'-2 7 2 2 2 7 2 2trimethyladenosine); $m^{2,7}G$ ($N^2,7$-dimethylguanosine); $m^{2,2,7}G$ ($N^2,N^2,7$-trimethylguanosine); $m^3Um$ (3,2'-0-dimethyluridine); $m^5D$ (5-methyldihydrouridine); $f^5Cm$ (5-formyl-2'-0-methylcytidine); $m^1Gm$ (1,2'-0-dimethylguanosine); $m^1Am$ (1,2'-0-dimethyladenosine); $\tau m^5U$ (5-taurinomethyluridine); $\tau m^5_s{}^2U$ (5-taurinomethyl-2-thiouridine)); imG-14 (4-demethylwyosine); imG2 (isowyosine); $ac^6A$ ($N^6$-acetyladenosine), or any combination thereof.

In some aspects, a guide RNA molecule can comprise any sequence recited in Table 1 or Table 2.

TABLE 1

| Guide RNA sequences | | |
|---|---|---|
| Seq Name | Sequence | Seq ID NO |
| 1015rev | UGUUCAUAAAUUUACUGACA | 1 |
| 1025forw | AAAAAAAUCGUUACAAUUUA | 2 |
| 1028forw | AAAAUCGUUACAAUUUAUGG | 3 |
| 1037rev | UCUUGAUGAGGUAAAAAGAG | 4 |
| 1038rev | GUCUUGAUGAGGUAAAAAGA | 5 |

TABLE 1-continued

Guide RNA sequences

| Seq Name | Sequence | Seq ID NO |
|---|---|---|
| 1039rev | UGUCUUGAUGAGGUAAAAAG | 6 |
| 103rev | AAUUUCUCUCCUUUGCAUAU | 7 |
| 1049rev | AGUAGUGCUGUGUCUUGAUG | 8 |
| 1059rev | AGGGGACCUACUUAGGUAAU | 9 |
| 1066rev | CAAUUCCAGGGGACCUACUU | 10 |
| 106forw | ACGGAGCGAGUCCCCGCGCG | 11 |
| 1073forw | UUUUAACCUAUUACCUAAGU | 12 |
| 1077rev | UAUCUGCUAGACAAUUCCAG | 13 |
| 1078rev | GUAUCUGCUAGACAAUUCCA | 14 |
| 1079rev | UGUAUCUGCUAGACAAUUCC | 15 |
| 1081forw | UAUUACCUAAGUAGGUCCCC | 16 |
| 1098rev | UCCCUUUUAUUAGGAAAGAA | 17 |
| 1107rev | GACUGAAUCUCCCUUUUAUU | 18 |
| 1116forw | CGCCUUUCUUUCCUAAUAAA | 19 |
| 1117forw | GCCUUUCUUUCCUAAUAAAA | 20 |
| 1129rev | CUACUACAUUAUUAAUCUUA | 21 |
| 1139rev | CCAGCAACAGUGGACUCUAG | 22 |
| 1149rev | GAGAACAUUACCAGCAACAG | 23 |
| 114forw | GCUAAAUAUCCAAUAUGCAA | 24 |
| 1159forw | CCUCUAGAGUCCACUGUUGC | 25 |
| 1168rev | GCCUCUCCUUGAGCAGAGGA | 26 |
| 116rev | GGUGCACGUCCCACAGCUCA | 27 |
| 1172rev | UCCAGCCUCUCCUUGAGCAG | 28 |
| 1178forw | CUGGUAAUGUUCUCUAAAUA | 29 |
| 117rev | GGGUGCACGUCCCACAGCUC | 30 |
| 1182forw | UUAAAGCCAUCCUCUGCUCA | 31 |
| 1187forw | GCCAUCCUCUGCUCAAGGAG | 32 |
| 1191forw | UCCUCUGCUCAAGGAGAGGC | 33 |
| 1193rev | UUCCACAAAACCAUGCUGAU | 34 |
| 1197forw | GCUCAAGGAGAGGCUGGAGA | 35 |
| 1203forw | AAAUAUUUUUCCUAUCAGCA | 36 |
| 1207forw | AGGCUGGAGAAGGCAUUCUA | 37 |
| 1211forw | UUCCUAUCAGCAUGGUUUUG | 38 |
| 1213forw | GAGAAGGCAUUCUAAGGAGA | 39 |
| 1214forw | AGAAGGCAUUCUAAGGAGAA | 40 |
| 1215forw | GAAGGCAUUCUAAGGAGAAG | 41 |
| 1216forw | AAGGCAUUCUAAGGAGAAGG | 42 |

TABLE 1-continued

Guide RNA sequences

| Seq Name | Sequence | Seq ID NO |
|---|---|---|
| 1220forw | CAUUCUAAGGAGAAGGGGGC | 43 |
| 1221forw | AUUCUAAGGAGAAGGGGGCA | 44 |
| 1221forw | CAUGGUUUUGUGGAAAAGUA | 45 |
| 1225forw | UAAGGAGAAGGGGGCAGGGU | 46 |
| 1232forw | AAGGGGGCAGGGUAGGAACU | 47 |
| 1234rev | CAAGACUCUAGACAAGUUCU | 48 |
| 1241rev | GAAUCUUGUCUCGGCUCAGU | 49 |
| 1242rev | AGAAUCUUGUCUCGGCUCAG | 50 |
| 1250rev | ACUACAGCAGAAUCUUGUCU | 51 |
| 1257forw | AGAACUUGUCUAGAGUCUUG | 52 |
| 126forw | CGGCGCGAUUCCCUGAGCUG | 53 |
| 127forw | GGCGCGAUUCCCUGAGCUGU | 54 |
| 1281rev | CUUUGUGAAAAUAGAUUCCC | 55 |
| 1281rev | AGAUCACCUUGAGUAAACUG | 56 |
| 1283forw | CUGCUGUAGUCAGUGCUGCC | 57 |
| 1284forw | UGCUGUAGUCAGUGCUGCCU | 58 |
| 1295forw | AGUAAGCCUCAGUUUACUCA | 59 |
| 1308rev | GUUUUGAUCAUCACAUUUUU | 60 |
| 1332forw | AAAAUGUGAUGAUCAAAACU | 61 |
| 1335forw | UUCUUCUCUUUCUUUUGAGA | 62 |
| 1341rev | CCAGCUCUGGGUGACAGAGU | 63 |
| 1342rev | UCCAGCUCUGGGUGACAGAG | 64 |
| 1353rev | GGACACUGCACUCCAGCUCU | 65 |
| 1354forw | GAAUUAGUGUUCUGUGUCUU | 66 |
| 1354rev | GGGACACUGCACUCCAGCUC | 67 |
| 1357rev | GAAUUCACAGGAAGAUUUUA | 68 |
| 1358rev | GGAAUUCACAGGAAGAUUUU | 69 |
| 1361forw | CCCACUCUGUCACCCAGAGC | 70 |
| 1369rev | ACCUUAAAAAUGGAAUUCAC | 71 |
| 1374rev | GGUUGCAGUGAGCCAAGAUG | 72 |
| 1375rev | AGGUUGCAGUGAGCCAAGAU | 73 |
| 1376rev | GAGGUUGCAGUGAGCCAAGA | 74 |
| 1379rev | CACCUCGACUACCUUAAAAA | 75 |
| 137rev | GCAUGUGUGAGCCGAGUCCU | 76 |
| 1382forw | GGAGUGCAGUGUCCCCAUCU | 77 |
| 1388forw | UCCUGUGAAUUCCAUUUUUA | 78 |
| 138rev | UGCAUGUGUGAGCCGAGUCC | 79 |
| 1395rev | GCUAGAAACCGAGGAGGCAG | 80 |

TABLE 1-continued

Guide RNA sequences

| Seq Name | Sequence | Seq ID NO |
|---|---|---|
| 1397forw | UUCCAUUUUUAAGGUAGUCG | 81 |
| 1401rev | AAAAUCGCUAGAAACCGAGG | 82 |
| 1404rev | UAUCCUCUGCAGACCAGACG | 83 |
| 1404rev | GAGAAAAUCGCUAGAAACCG | 84 |
| 1407forw | CACUGCAACCUCUGCCUCCU | 85 |
| 140forw | GAAAUUAAAGAUUUAAAAGC | 86 |
| 140forw | GAGCUGUGGGACGUGCACCC | 87 |
| 1411forw | UAGUCGAGGUGAACCGCGUC | 88 |
| 1421forw | GAACCGCGUCUGGUCUGCAG | 89 |
| 1431rev | UGUAAACCCAGCUACUUGGG | 90 |
| 1433forw | GUCUGCAGAGGAUAGAAAAA | 91 |
| 1434rev | GCCUGUAAACCCAGCUACUU | 92 |
| 1435rev | UGCCUGUAAACCCAGCUACU | 93 |
| 1436rev | AACUAACUUGAGGUAUCAGA | 94 |
| 1437rev | AAACUAACUUGAGGUAUCAG | 95 |
| 1444forw | CUCUCAGCCUCCCAAGUAGC | 96 |
| 1445forw | UCUCAGCCUCCCAAGUAGCU | 97 |
| 1446rev | UUAAAGGUGAAACUAACUUG | 98 |
| 1453forw | UCCCAAGUAGCUGGGUUUAC | 99 |
| 145rev | AUCAUAACAUAGUUUCCUUA | 100 |
| 1462rev | UUACUUCCGACCUUCUUUAA | 101 |
| 1462rev | AAAAAAUCAGCCGGGUAUGG | 102 |
| 1465rev | ACAAAAAAAUCAGCCGGGUA | 103 |
| 146forw | UGGGACGUGCACCCAGGACU | 104 |
| 1470rev | AAAAUACAAAAAAAUCAGCC | 105 |
| 1471rev | GAAAAUACAAAAAAAUCAGC | 106 |
| 1472forw | GUUAGUUUCACCUUUAAAGA | 107 |
| 1472forw | CAGGCACACACCACCAUACC | 108 |
| 1476forw | GUUUCACCUUUAAAGAAGGU | 109 |
| 1495rev | CCCUUCCGCACGUCCGGGAA | 110 |
| 1500rev | CGUUGCCCUUCCGCACGUCC | 111 |
| 1501rev | ACGUUGCCCUUCCGCACGUC | 112 |
| 1502forw | UAAAGACGCAAAGCCUUUCC | 113 |
| 1502forw | UUUUGUAUUUUCAGUAAAGU | 114 |
| 1503forw | UUUGUAUUUUCAGUAAAGUU | 115 |
| 1507forw | UAUUUUCAGUAAAGUUGGGC | 116 |
| 150forw | AUUUAAAAGCAGGAGCCAUA | 117 |

TABLE 1-continued

Guide RNA sequences

| Seq Name | Sequence | Seq ID NO |
|---|---|---|
| 1510forw | CAAAGCCUUUCCCGGACGUG | 118 |
| 1511forw | UUCAGUAAAGUUGGGCAGGC | 119 |
| 1514forw | GCCUUUCCCGGACGUGCGGA | 120 |
| 1514rev | CACCUGAGGUCAGGAGUUCG | 121 |
| 1515forw | CCUUUCCCGGACGUGCGGAA | 122 |
| 1523rev | CGGGCGGAUCACCUGAGGUC | 123 |
| 1524rev | UCCAUUUCCGGCCAUGAGGA | 124 |
| 1528rev | AAGUUCCAUUUCCGGCCAUG | 125 |
| 1528rev | AGAAGCGGGCGGAUCACCUG | 126 |
| 1532forw | GGCCUCGAACUCCUGACCUC | 127 |
| 1533forw | AAGGGCAACGUCCUUCCUCA | 128 |
| 1536rev | GGAAAUUAAAGUUCCAUUUC | 129 |
| 1537forw | GCAACGUCCUUCCUCAUGGC | 130 |
| 1539rev | CUUUGGGAGGCAGAAGCGGG | 131 |
| 1542rev | GCACUUUGGGAGGCAGAAGC | 132 |
| 1543forw | UCCUUCCUCAUGGCCGGAAA | 133 |
| 1543rev | AGCACUUUGGGAGGCAGAAG | 134 |
| 1552rev | UGUAAUCCCAGCACUUUGGG | 135 |
| 1555rev | GCCUGUAAUCCCAGCACUUU | 136 |
| 1556rev | CGCCUGUAAUCCCAGCACUU | 137 |
| 1557rev | GCGGGCUGGUUGGGGGGAAC | 138 |
| 1558rev | GGCGGGCUGGUUGGGGGGAA | 139 |
| 1563rev | UCUCGGGCGGGCUGGUUGGG | 140 |
| 1564rev | CUCUCGGGCGGGCUGGUUGG | 141 |
| 1565forw | GCUUCUGCCUCCCAAAGUGC | 142 |
| 1565rev | UCUCUCGGGCGGGCUGGUUG | 143 |
| 1566forw | CUUCUGCCUCCCAAAGUGCU | 144 |
| 1566rev | CUCUCUCGGGCGGGCUGGUU | 145 |
| 1567rev | ACUCUCUCGGGCGGGCUGGU | 146 |
| 1571rev | AGUCACUCUCUCGGGCGGGC | 147 |
| 1574forw | UCCCAAAGUGCUGGGAUUAC | 148 |
| 1575rev | UGAGAGUCACUCUCUCGGGC | 149 |
| 1576rev | GUGAGAGUCACUCUCUCGGG | 150 |
| 1579rev | CUCGUGAGAGUCACUCUCUC | 151 |
| 1580rev | UCUCGUGAGAGUCACUCUCU | 152 |
| 1583rev | GGAUCUUAGUCCCCGCACGG | 153 |
| 1586rev | AAGGGAUCUUAGUCCCCGCA | 154 |
| 1591forw | UACAGGCGUGAGCCACCGUG | 155 |

TABLE 1-continued

Guide RNA sequences

| Seq Name | Sequence | Seq ID NO |
|---|---|---|
| 1592forw | ACAGGCGUGAGCCACCGUGC | 156 |
| 1593forw | CAGGCGUGAGCCACCGUGCG | 157 |
| 1604rev | AUUGGCCAAGCUGACUCUCG | 158 |
| 1604rev | GAGUCCCCGCCCUUGCAAAA | 159 |
| 1605rev | GGAGUCCCCGCCCUUGCAAA | 160 |
| 1614forw | GGACUAAGAUCCCUUUUGCA | 161 |
| 1615forw | GACUAAGAUCCCUUUUGCAA | 162 |
| 1618forw | UAAGAUCCCUUUUGCAAGGG | 163 |
| 1619forw | GAGAGCCGCGAGAGUCAGCU | 164 |
| 1619forw | AAGAUCCCUUUUGCAAGGGC | 165 |
| 1620forw | AGAUCCCUUUUGCAAGGGCG | 166 |
| 1622rev | CGGCCGCCGACCGCACGGAU | 167 |
| 1626rev | AUGCACUUGUCUGUAGUUCA | 168 |
| 1627rev | GGGAGCGGCCGCCGACCGCA | 169 |
| 1632forw | GUCAGCUUGGCCAAUCCGUG | 170 |
| 1636forw | GCUUGGCCAAUCCGUGCGGU | 171 |
| 1639forw | UGGCCAAUCCGUGCGGUCGG | 172 |
| 1642rev | GAGUCGGCUUAUAAAGGGAG | 173 |
| 1647rev | CGGGCGAGUCGGCUUAUAAA | 174 |
| 1648rev | CCGGGCGAGUCGGCUUAUAA | 175 |
| 1658rev | CGGUGCGCUGCCGGGCGAGU | 176 |
| 1665rev | GAAGCAAAAGUACCACUAGA | 177 |
| 1666rev | CCGCAACCCGGUGCGCUGCC | 178 |
| 1667rev | UCCGCAACCCGGUGCGCUGC | 179 |
| 1668forw | CCUUUAUAAGCCGACUCGCC | 180 |
| 1673forw | UUUGUUCUUACUCCAUCUAG | 181 |
| 1678rev | CAGGCCCACCCUCCGCAACC | 182 |
| 1679forw | CGACUCGCCCGGCAGCGCAC | 183 |
| 1680forw | GACUCGCCCGGCAGCGCACC | 184 |
| 1686forw | CCCGGCAGCGCACCGGGUUG | 185 |
| 1689forw | GGCAGCGCACCGGGUUGCGG | 186 |
| 1689rev | CACCACAAAUGUUGUAAAUG | 187 |
| 1690forw | GCAGCGCACCGGGUUGCGGA | 188 |
| 1693forw | GCGCACCGGGUUGCGGAGGG | 189 |
| 1694forw | CGCACCGGGUUGCGGAGGGU | 190 |
| 1697rev | AAAUGGCCACCACCCCUCCC | 191 |
| 1699forw | CGGGUUGCGGAGGGUGGGCC | 192 |

TABLE 1-continued

Guide RNA sequences

| Seq Name | Sequence | Seq ID NO |
|---|---|---|
| 1700forw | GGGUUGCGGAGGGUGGGCCU | 193 |
| 1703forw | UUGCGGAGGGUGGGCCUGGG | 194 |
| 1704forw | UGCGGAGGGUGGGCCUGGGA | 195 |
| 1705forw | GCGGAGGGUGGGCCUGGGAG | 196 |
| 1707forw | CUCCACAUUUACAACAUUUG | 197 |
| 1708forw | GAGGGUGGGCCUGGGAGGGG | 198 |
| 170rev | UCGGCGUUCCCCCCACCAAC | 199 |
| 1710forw | CACAUUUACAACAUUUGUGG | 200 |
| 1711forw | GGUGGGCCUGGGAGGGGUGG | 201 |
| 1714rev | AGUUAGGGUUAGACAAAAAA | 202 |
| 1716forw | UACAACAUUUGUGGUGGUGC | 203 |
| 1717forw | ACAACAUUUGUGGUGGUGCA | 204 |
| 1720rev | CUGUGGCCAUUCUUGCUUCA | 205 |
| 1729rev | GCCUACGCCCUUCUCAGUUA | 206 |
| 1730rev | CGCCUACGCCCUUCUCAGUU | 207 |
| 1734forw | GCAGGGCCGUGAAGCAAGAA | 208 |
| 1737rev | AGAAAAACAUUCCCAGUCUG | 209 |
| 1741forw | UUGCUAACCCUAACUGAGA | 210 |
| 1742forw | UGUCUAACCCUAACUGAGAA | 211 |
| 1745forw | AAGCAAGAAUGGCCACAGAC | 212 |
| 1746forw | AGCAAGAAUGGCCACAGACU | 213 |
| 1748forw | ACCCUAACUGAGAAGGGCGU | 214 |
| 1753rev | GCGCGCGGGGAGCAAAAGCA | 215 |
| 175forw | CAUGCAGUUCGCUUUCCUGU | 216 |
| 1766rev | AGCGAGAAAAACAGCGCGCG | 217 |
| 1767rev | CAGCGAGAAAAACAGCGCGC | 218 |
| 1768rev | UCAGCGAGAAAAACAGCGCG | 219 |
| 178forw | GCAGUUCGCUUUCCUGUUGG | 220 |
| 1798forw | UUUUUCUCGCUGACUUUCAG | 221 |
| 1799forw | UUUUCUCGCUGACUUUCAGC | 222 |
| 179forw | CAGUUCGCUUUCCUGUUGGU | 223 |
| 1802forw | UCUCGCUGACUUUCAGCGGG | 224 |
| 180forw | AGUUCGCUUUCCUGUUGGUG | 225 |
| 1810rev | CGGUGGAAGGCGGCAGGCCG | 226 |
| 1813forw | UUCAGCGGGCGGAAAAGCCU | 227 |
| 1816rev | AAUGAACGGUGGAAGGCGGC | 228 |
| 181forw | UUAUGAUGAAUGUGAUAGUU | 229 |
| 181forw | GUUCGCUUUCCUGUUGGUGG | 230 |

23

TABLE 1-continued

Guide RNA sequences

| Seq Name | Sequence | Seq ID NO |
|---|---|---|
| 1820rev | CUAGAAUGAACGGUGGAAGG | 231 |
| 1823rev | GCUCUAGAAUGAACGGUGGA | 232 |
| 1827rev | GUUUGCUCUAGAAUGAACGG | 233 |
| 182forw | UUCGCUUUCCUGUUGGUGGG | 234 |
| 1830rev | UUUGUUUGCUCUAGAAUGAA | 235 |
| 1866forw | AAACAAAAAAUGUCAGCUGC | 236 |
| 1869rev | GGUCCCCGGGAGGGGCGAAC | 237 |
| 1870rev | AGGUCCCCGGGAGGGGCGAA | 238 |
| 1877rev | CCGCCGCAGGUCCCCGGGAG | 239 |
| 1878rev | CCCGCCGCAGGUCCCCGGGA | 240 |
| 1879rev | ACCCGCCGCAGGUCCCCGGG | 241 |
| 1882rev | GCGACCCGCCGCAGGUCCCC | 242 |
| 1883rev | GGCGACCCGCCGCAGGUCCC | 243 |
| 1884forw | GCUGGCCCGUUCGCCCCUCC | 244 |
| 1885forw | CUGGCCCGUUCGCCCCUCCC | 245 |
| 1886forw | UGGCCCGUUCGCCCCUCCCG | 246 |
| 1890rev | CUGGGCAGGCGACCCGCCGC | 247 |
| 1894forw | UCGCCCCUCCCGGGGACCUG | 248 |
| 1897forw | CCCCUCCCGGGGACCUGCGG | 249 |
| 1898forw | CCCUCCCGGGGACCUGCGGC | 250 |
| 189rev | GGGUGACGGAUGCGCACGAU | 251 |
| 1904rev | GCGGGGUUCGGGGGCUGGGC | 252 |
| 1908rev | CCAGGCGGGGUUCGGGGGCU | 253 |
| 1909rev | UCCAGGCGGGGUUCGGGGGC | 254 |
| 1913rev | GGCCUCCAGGCGGGGUUCGG | 255 |
| 1914rev | CGGCCUCCAGGCGGGGUUCG | 256 |
| 1915rev | GCGGCCUCCAGGCGGGGUUC | 257 |
| 1916rev | CGCGGCCUCCAGGCGGGGUU | 258 |
| 1921rev | CCGACCGCGGCCUCCAGGCG | 259 |
| 1922rev | GCCGACCGCGGCCUCCAGGC | 260 |
| 1923rev | GGCCGACCGCGGCCUCCAGG | 261 |
| 1926rev | CCGGGCCGACCGCGGCCUCC | 262 |
| 1928forw | CCCAGCCCCCGAACCCCGCC | 263 |
| 1931forw | AGCCCCCGAACCCCGCCUGG | 264 |
| 1934rev | GAGAAGCCCCGGGCCGACCG | 265 |
| 1937forw | CGAACCCGCCUGGAGGCCG | 266 |
| 1941forw | CCCCGCCUGGAGGCCGCGGU | 267 |

24

TABLE 1-continued

Guide RNA sequences

| Seq Name | Sequence | Seq ID NO |
|---|---|---|
| 1944rev | GGUGCCUCCGGAGAAGCCCC | 268 |
| 1945rev | GGGUGCCUCCGGAGAAGCCC | 269 |
| 1946forw | CCUGGAGGCCGCGGUCGGCC | 270 |
| 1947forw | CUGGAGGCCGCGGUCGGCCC | 271 |
| 1948forw | UGGAGGCCGCGGUCGGCCCG | 272 |
| 1956rev | GCGGUGGCAGUGGGUGCCUC | 273 |
| 1957forw | CGGUCGGCCCGGGGCUUCUC | 274 |
| 1960forw | UCGGCCCGGGGCUUCUCCGG | 275 |
| 1965rev | CAACUCUUCGCGGUGGCAGU | 276 |
| 1966rev | CCAACUCUUCGCGGUGGCAG | 277 |
| 1986forw | CCACUGCCACCGCGAAGAGU | 278 |
| 1987forw | CACUGCCACCGCGAAGAGUU | 279 |
| 199forw | UUUGGAGAAUAAAUUGAAUG | 280 |
| 1rev | CAGAGCCCAACUCUUCGCGG | 281 |
| 203forw | GAGAAUAAAUUGAAUGAGGA | 282 |
| 203rev | CCAUUGCCGGCGAGGGGUGA | 283 |
| 206rev | AACUGAUCACCAAAUCUCCA | 284 |
| 207rev | UAACUGAUCACCAAAUCUCC | 285 |
| 209forw | AAAUUGAAUGAGGAAGGCCC | 286 |
| 209rev | AAGCCCCCAUUGCCGGCGAG | 287 |
| 210rev | CAAGCCCCCAUUGCCGGCGA | 288 |
| 211rev | ACAAGCCCCCAUUGCCGGCG | 289 |
| 216rev | GGUUCACAAGCCCCCAUUGC | 290 |
| 217forw | UGAGGAAGGCCCUGGAGAUU | 291 |
| 217forw | GCGCAUCCGUCACCCCUCGC | 292 |
| 223forw | CCGUCACCCCUCGCCGGCAA | 293 |
| 224forw | CGUCACCCCUCGCCGGCAAU | 294 |
| 225forw | GUCACCCCUCGCCGGCAAUG | 295 |
| 226forw | UCACCCCUCGCCGGCAAUGG | 296 |
| 237rev | GCCCAGUCAGUCAGGUUUGG | 297 |
| 238rev | GGCCCAGUCAGUCAGGUUUG | 298 |
| 239rev | UGGCCCAGUCAGUCAGGUUU | 299 |
| 240rev | CUGGCCCAGUCAGUCAGGUU | 300 |
| 243rev | AAGACUUGGCACUUUAUAUG | 301 |
| 245rev | GCACACUGGCCCAGUCAGUC | 302 |
| 255forw | AACCCCCAAACCUGACUGAC | 303 |
| 256forw | ACCCCCAAACCUGACUGACU | 304 |
| 257rev | AUAAUCUUGAGUACAAGACU | 305 |

TABLE 1-continued

| Guide RNA sequences | | |
| --- | --- | --- |
| Seq Name | Sequence | Seq ID NO |
| 259rev | CCUGCCAAUUUGCAGCACAC | 306 |
| 275forw | UGGGCCAGUGUGCUGCAAAU | 307 |
| 279forw | CCAGUGUGCUGCAAAUUGGC | 308 |
| 287forw | UACUCAAGAUUAUAAGCAAU | 309 |
| 28rev | CCUCGCCCCCGAGAGACCCG | 310 |
| 290forw | CAAAUUGGCAGGAGACGUGA | 311 |
| 295rev | UUCAUUUUGGCCGACUUUGG | 312 |
| 298rev | CCAUUCAUUUUGGCCGACUU | 313 |
| 305forw | CGUGAAGGCACCUCCAAAGU | 314 |
| 308rev | GGCUCACUGCCCAUUCAUUU | 315 |
| 318forw | CCAAAGUCGGCCAAAAUGAA | 316 |
| 319forw | CAAAGUCGGCCAAAAUGAAU | 317 |
| 31forw | GAGUUGGGCUCUGUCAGCCG | 318 |
| 329rev | GGAACGGCUCCAGGCAACCC | 319 |
| 32forw | AGUUGGGCUCUGUCAGCCGC | 320 |
| 330forw | AAAAUGAAUGGGCAGUGAGC | 321 |
| 331forw | AAAUGAAUGGGCAGUGAGCC | 322 |
| 331rev | UUUCCCCUUCAUAUCUAAGU | 323 |
| 332forw | AAUGAAUGGGCAGUGAGCCG | 324 |
| 338rev | ACCCACGCAGGAACGGCUCC | 325 |
| 340forw | GGCAGUGAGCCGGGGUUGCC | 326 |
| 345rev | CGGGAGAACCCACGCAGGAA | 327 |
| 346forw | UAGUGCCUACUUAGAUAUGA | 328 |
| 347forw | AGUGCCUACUUAGAUAUGAA | 329 |
| 348forw | GUGCCUACUUAGAUAUGAAG | 330 |
| 350rev | GAAGACGGGAGAACCCACGC | 331 |
| 356forw | UUAGAUAUGAAGGGGAAAGA | 332 |
| 356forw | UGCCUGGAGCCGUUCCUGCG | 333 |
| 357forw | UAGAUAUGAAGGGGAAAGAA | 334 |
| 357forw | GCCUGGAGCCGUUCCUGCGU | 335 |
| 364rev | GGCAACAAAAAGCGGAAGAC | 336 |
| 365rev | AGGCAACAAAAAGCGGAAGA | 337 |
| 372forw | AAGAAGGGUUUGAGAUAAUG | 338 |
| 372rev | CCAUAAAAGGCAACAAAAAG | 339 |
| 373forw | AGAAGGGUUUGAGAUAAUGU | 340 |
| 385rev | AGUUGUAAUACAACCAUAAA | 341 |
| 388forw | AAUGUGGGAUGCUAAGAGAA | 342 |

TABLE 1-continued

| Guide RNA sequences | | |
| --- | --- | --- |
| Seq Name | Sequence | Seq ID NO |
| 391forw | GUGGGAUGCUAAGAGAAUGG | 343 |
| 392forw | CCGCUUUUUGUUGCCUUUUA | 344 |
| 40forw | UCUGUCAGCCGCGGGUCUCU | 345 |
| 413rev | CUCAACAAAAUCUGCAGAGC | 346 |
| 41forw | CUGUCAGCCGCGGGUCUCUC | 347 |
| 42forw | UGUCAGCCGCGGGUCUCUCG | 348 |
| 434forw | CUGCUCUGCAGAUUUUGUUG | 349 |
| 439forw | UUUAGCAUCUACUCUAUGUA | 350 |
| 43forw | GUCAGCCGCGGGUCUCUCGG | 351 |
| 448rev | GACUGGUCGAGAUCUACCUU | 352 |
| 449rev | GGACUGGUCGAGAUCUACCU | 353 |
| 452forw | UGAGGUUUUUGCUUCUCCCA | 354 |
| 465rev | CCACACCCCGUUGAGGGGAC | 355 |
| 470rev | UUCUCCCACACCCCGUUGAG | 356 |
| 471rev | GUUCUCCCACACCCCGUUGA | 357 |
| 472forw | AGUGCAAUAGUGCUAAAAAC | 358 |
| 472rev | UGUUCUCCCACACCCCGUUG | 359 |
| 478forw | AUCUCGACCAGUCCCCUCAA | 360 |
| 479forw | UCUCGACCAGUCCCCUCAAC | 361 |
| 480forw | CUCGACCAGUCCCCUCAACG | 362 |
| 485forw | CCAGUCCCCUCAACGGGGUG | 363 |
| 486forw | CAGUCCCCUCAACGGGGUGU | 364 |
| 488rev | CCAGGUUGUAAAGUUUUUUA | 365 |
| 48forw | CCGCGGGUCUCUCGGGGGCG | 366 |
| 49forw | CGCGGGUCUCUCGGGGGCGA | 367 |
| 4rev | UGACAGAGCCCAACUCUUCG | 368 |
| 506rev | UUUCUUUCAUAGCAUCUGCC | 369 |
| 508forw | CCGUAAAAAACUUUACAACC | 370 |
| 530forw | GCAGAUGCUAUGAAAGAAAA | 371 |
| 531forw | CAGAUGCUAUGAAAGAAAAA | 372 |
| 532forw | AGAUGCUAUGAAAGAAAAAG | 373 |
| 536forw | GCUAUGAAAGAAAAGGGGA | 374 |
| 537forw | CUAUGAAAGAAAAAGGGGAU | 375 |
| 549forw | AAGGGGAUGGGAGAGAGAGA | 376 |
| 54forw | GUCUCUCGGGGGCGAGGGCG | 377 |
| 552forw | GGGAUGGGAGAGAGAGAAGG | 378 |
| 553forw | GGAUGGGAGAGAGAGAAGGA | 379 |
| 561forw | UAGAAGAUCUAAAUGAACAU | 380 |

TABLE 1-continued

Guide RNA sequences

| Seq Name | Sequence | Seq ID NO |
|---|---|---|
| 563forw | GAGAGAAGGAGGGAGAGAGA | 381 |
| 568forw | AAGGAGGGAGAGAGAUGGAG | 382 |
| 569forw | AGGAGGGAGAGAGAUGGAGA | 383 |
| 574rev | CAUAAACCGAUGACCAUUAA | 384 |
| 57forw | AACAAGCGCUAUGACUAGCA | 385 |
| 581forw | UGGAAAUUGUGUUCCUUUAA | 386 |
| 588forw | UGUGUUCCUUUAAUGGUCAU | 387 |
| 597rev | AAAAAGAAACUUCUAACCUC | 388 |
| 598forw | UUUACUUUUCUUUCAGAUCG | 389 |
| 601forw | UGGUCAUCGGUUUAUGCCAG | 390 |
| 602rev | CUCCGUGGAGUUGUCGCUGU | 391 |
| 60forw | CGGGGGCGAGGGCGAGGUUC | 392 |
| 617rev | AUUCAGUUAGAUAAACUCCG | 393 |
| 620forw | GACCGACAGCGACAACUCCA | 394 |
| 632rev | ACUGCUCAAGGUCAUCGCCA | 395 |
| 635forw | UUUUUUGAAAAAUUAGACCU | 396 |
| 63rev | UCCUCUUCCUGCGGCCUGAA | 397 |
| 644rev | GGGUUUAUAUCCUACUGCUCA | 398 |
| 655forw | UGGCGAUGACCUUGAGCAGU | 399 |
| 663rev | CAGUUUUACAUAUAAAUGAC | 400 |
| 664rev | UUGGAACGCUAAGCUUGUGG | 401 |
| 665rev | AUUGGAACGCUAAGCUUGUG | 402 |
| 666rev | UAUUGGAACGCUAAGCUUGU | 403 |
| 667rev | UUAUUGGAACGCUAAGCUUG | 404 |
| 683rev | UAUGCCUAGUGUUCCGUUAU | 405 |
| 68forw | UGACUAGCAAGGUUAAGUGA | 406 |
| 690forw | CAAGCUUAGCGUUCCAAUAA | 407 |
| 694forw | UAUGUAAAACUGCACUAUAC | 408 |
| 697rev | CCGGCCGCGAAUUUUUAUAA | 409 |
| 699forw | CGUUCCAAUAACGGAACACU | 410 |
| 69forw | GGGCGAGGUUCAGGCCUUUC | 411 |
| 713forw | CUGGCCAUUAUAAAAAUUCG | 412 |
| 714forw | ACACUAGGCAUAAUGAAAGA | 413 |
| 716rev | CAGGUAUGAGCCACCGCACC | 414 |
| 717forw | CCAUUAUAAAAAUUCGCGGC | 415 |
| 718forw | CAUUAUAAAAAUUCGCGGCC | 416 |
| 71rev | ACUUUAAGCCUUUCAGUCCC | 417 |

TABLE 1-continued

Guide RNA sequences

| Seq Name | Sequence | Seq ID NO |
|---|---|---|
| 723forw | UAAAAAUUCGCGGCCGGGUG | 418 |
| 726forw | AAAUUCGCGGCCGGGUGCGG | 419 |
| 72rev | UCGCUCCGUUCCUCUUCCUG | 420 |
| 731rev | AGGGUUGGGGGUGGGGGGUG | 421 |
| 735rev | UCCCAAAGUGCUGGGAUUAC | 422 |
| 736rev | CUGGGAGGGUUGGGGGUGGG | 423 |
| 737rev | GCUGGGAGGGUUGGGGGUGG | 424 |
| 738rev | GGCUGGGAGGGUUGGGGGUG | 425 |
| 739rev | CGGCUGGGAGGGUUGGGGGU | 426 |
| 73forw | AGCAAGGUUAAGUGAAGGCC | 427 |
| 740rev | CCGGCUGGGAGGGUUGGGGG | 428 |
| 743rev | CUUCGGCCUCCCAAAGUGCU | 429 |
| 743rev | CUGCCGGCUGGGAGGGUUGG | 430 |
| 744rev | GCUUCGGCCUCCCAAAGUGC | 431 |
| 744rev | ACUGCCGGCUGGGAGGGUUG | 432 |
| 745rev | GACUGCCGGCUGGGAGGGUU | 433 |
| 746rev | AGACUGCCGGCUGGGAGGGU | 434 |
| 74forw | GCAAGGUUAAGUGAAGGCCA | 435 |
| 750rev | UGGGAGACUGCCGGCUGGGA | 436 |
| 751rev | GUGGGAGACUGCCGGCUGGG | 437 |
| 753forw | UACCUGUAAUCCCAGCACUU | 438 |
| 754forw | ACCUGUAAUCCCAGCACUUU | 439 |
| 754rev | CUUGUGGGAGACUGCCGGCU | 440 |
| 755rev | UCUUGUGGGAGACUGCCGGC | 441 |
| 757forw | UGUAAUCCCAGCACUUUGGG | 442 |
| 759rev | CAAUUCUUGUGGGAGACUGC | 443 |
| 760forw | CCACCCCCAACCCUCCCAGC | 444 |
| 760rev | CUCAAGUGAUCCACCCGCUU | 445 |
| 766forw | AGCACUUUGGGAGGCCGAAG | 446 |
| 767forw | GCACUUUGGGAGGCCGAAGC | 447 |
| 769rev | AAAUCAGAGCCAAUUCUUGU | 448 |
| 76forw | GUUCAGGCCUUUCAGGCCGC | 449 |
| 770forw | CUUUGGGAGGCCGAAGCGGG | 450 |
| 770rev | GAAAUCAGAGCCAAUUCUUG | 451 |
| 780forw | CGGCAGUCUCCCACAAGAAU | 452 |
| 783rev | CAGGCUGGUCUCGAACGCCA | 453 |
| 784rev | CCAGGCUGGUCUCGAACGCC | 454 |
| 786forw | CGGGUGGAUCACUUGAGCCC | 455 |

TABLE 1-continued

Guide RNA sequences

| Seq Name | Sequence | Seq ID NO |
|---|---|---|
| 792rev | CCAUUAGCUUAUUUUCUUAA | 456 |
| 798rev | UUUCACCAUGUUGCCCAGGC | 457 |
| 802rev | GGGGUUUCACCAUGUUGCCC | 458 |
| 804forw | CCUGGCGUUCGAGACCAGCC | 459 |
| 805forw | CUGGCGUUCGAGACCAGCCU | 460 |
| 812forw | CCUUUAAGAAAAUAAGCUAA | 461 |
| 813forw | CGAGACCAGCCUGGGCAACA | 462 |
| 815rev | UUUGUUUCUUUCAACCUAGU | 463 |
| 816rev | GUUUGUUUCUUUCAACCUAG | 464 |
| 821forw | AAAUAAGCUAAUGGCCCACU | 465 |
| 821rev | UGUGUUUUUAGUAGAGACGG | 466 |
| 822rev | UUGUGUUUUUAGUAGAGACG | 467 |
| 823rev | UUUGUGUUUUUAGUAGAGAC | 468 |
| 824rev | UUUUGUGUUUUUAGUAGAGA | 469 |
| 82forw | GCCUUUCAGGCCGCAGGAAG | 470 |
| 839forw | CUAGGUUGAAAGAAACAAAC | 471 |
| 83forw | AGUGAAGGCCAGGGACUGAA | 472 |
| 842rev | GUCGUGAUAAGUGGGCAGAA | 473 |
| 850rev | AUUACCUUGUCGUGAUAAGU | 474 |
| 851rev | AAUUACCUUGUCGUGAUAAG | 475 |
| 853forw | CUAAAAACACAAAAACUAGC | 476 |
| 854forw | UAAAAACACAAAAACUAGCU | 477 |
| 859forw | ACACAAAAACUAGCUGGGCG | 478 |
| 862forw | CAAAAACUAGCUGGGCGUGG | 479 |
| 866forw | AACUAGCUGGGCGUGGUGGC | 480 |
| 866forw | UCUGCCCACUUAUCACGACA | 481 |
| 871rev | UCCUGAGUAGCUGGGGAUUAC | 482 |
| 874rev | UUGAAGGUAUGGAUUUGGGA | 483 |
| 878rev | GGAAUUGAAGGUAUGGAUUU | 484 |
| 879rev | UCUCAGCCUCCUGAGUAGCU | 485 |
| 879rev | AGGAAUUGAAGGUAUGGAUU | 486 |
| 87forw | UCAGGCCGCAGGAAGAGGAA | 487 |
| 880rev | GUCUCAGCCUCCUGAGUAGC | 488 |
| 885rev | AUCCUAAGGAAUUGAAGGUA | 489 |
| 890forw | GCCUGUAAUCCCAGCUACUC | 490 |
| 890rev | AGAUGAUCCUAAGGAAUUGA | 491 |
| 893forw | UGUAAUCCCAGCUACUCAGG | 492 |

TABLE 1-continued

Guide RNA sequences

| Seq Name | Sequence | Seq ID NO |
|---|---|---|
| 899rev | ACUACCCCCAGAUGAUCCUA | 493 |
| 903forw | AUCCAUACCUUCAAUUCCUU | 494 |
| 912forw | UUCAAUUCCUUAGGAUCAUC | 495 |
| 913forw | UCAAUUCCUUAGGAUCAUCU | 496 |
| 914forw | CAAUUCCUUAGGAUCAUCUG | 497 |
| 915forw | AAUUCCUUAGGAUCAUCUGG | 498 |
| 919rev | CACUGCAACCUCUGCCUCCC | 499 |
| 920rev | UCACUGCAACCUCUGCCUCC | 500 |
| 921forw | ACACGAGAAUCGCUUGAACC | 501 |
| 922forw | CACGAGAAUCGCUUGAACCC | 502 |
| 924rev | CCCCUGGCUGCUCUCUCUCU | 503 |
| 925forw | GAGAAUCGCUUGAACCCGGG | 504 |
| 931forw | CGCUUGAACCCGGGAGGCAG | 505 |
| 940rev | GGCCUUUAUAUACACACCCC | 506 |
| 942forw | UGCCAAGAGAGAGAGCAGCC | 507 |
| 943forw | GCCAAGAGAGAGAGCAGCCA | 508 |
| 944forw | CCAAGAGAGAGAGCAGCCAG | 509 |
| 944rev | GGAGUCUAGUGGCGUGAUCU | 510 |
| 955rev | CCAGGCUGGAUGGAGUCUAG | 511 |
| 958forw | AGCCAGGGGUGUGUAUAUAA | 512 |
| 961rev | CAGGCUAUCACCCUAAAGGU | 513 |
| 962rev | UCAGGCUAUCACCCUAAAGG | 514 |
| 965rev | GCUCUUUCGCCCAGGCUGGA | 515 |
| 965rev | GAUUCAGGCUAUCACCCUAA | 516 |
| 969rev | UCUUGCUCUUUCGCCCAGGC | 517 |
| 970forw | GUAUAUAAAGGCCCACCUUU | 518 |
| 971forw | UAUAUAAAGGCCCACCUUUA | 519 |
| 973rev | GGAGUCUUGCUCUUUCGCCC | 520 |
| 975forw | CCACUAGACUCCAUCCAGCC | 521 |
| 976forw | CACUAGACUCCAUCCAGCCU | 522 |
| 97rev | AGGGAAUCGCGCCGCGCGCG | 523 |
| 980rev | ACUUUCAAUCAUCAGGAUUC | 524 |
| 987rev | ACUUCUGACUUUCAAUCAUC | 525 |
| 98rev | CAGGGAAUCGCGCCGCGCGC | 526 |
| 994rev | AACGAUUUUUUUUUUUGAGA | 527 |
| 99rev | UCAGGGAAUCGCGCCGCGCG | 528 |

TABLE 2

Guide RNA sequences

| Seq Name | Sequence | Seq ID NO |
|---|---|---|
| 1420forw | GUGAACCGCGUCUGGUCUGCA | 529 |
| 1591rev | GCUGACUCUCGCGGCUCUCGU | 530 |
| 634forw | AACUCCACGGAGUUUAUCUAA | 531 |
| 640forw | ACGGAGUUUAUCUAACUGAAU | 532 |
| 1688forw | CCGGCAGCGCACCGGGUUGCG | 533 |
| 716forw | GGCCAUUAUAAAAAUUCGCGG | 534 |
| 1608forw | AGUGACUCUCACGAGAGCCGC | 535 |
| 1678forw | GCCGACUCGCCCGGCAGCGCA | 536 |
| 1728rev | GGCGCCUACGCCCUUCUCAGU | 537 |
| 620forw | GGACCGACAGCGACAACUCCA | 538 |
| 1239rev | CAGAAUCUUGUCUCGGCUCAG | 539 |
| 1229rev | UCUCGGCUCAGUGGGAUGCGU | 540 |
| 1584forw | CCCCCCAACCAGCCCGCCCGA | 541 |
| 481rev | GGUUGUAAAGUUUUUUACGGA | 542 |
| 1625rev | AAGGGAGCGGCCGCCGACCGC | 543 |
| 1896forw | CGCCCCUCCCGGGGACCUGCG | 544 |
| 1661rev | CGCAACCCGGUGCGCUGCCGG | 545 |
| 383forw | UGAGAUAAUGUGGGAUGCUAA | 546 |
| 472forw | AAGUGCAAUAGUGCUAAAAAC | 547 |
| 614rev | UAUUCAGUUAGAUAAACUCCG | 548 |
| 1376rev | UCACCUCGACUACCUUAAAAA | 549 |
| 166forw | CCAUAAGGAAACUAUGUUAUG | 550 |
| 409rev | AUAGAGUAGAUGCUAAAUGCU | 551 |
| 1170rev | UCUCCAGCCUCUCCUUGAGCA | 552 |
| 1122rev | CUACAUUAUUAAUCUUAAGGA | 553 |
| 1372forw | CUUAGGCCCUAAAAUCUUCCU | 554 |
| 268rev | AAAUUCCUAUUGCUUAUAAUC | 555 |
| 1836rev | GCUGACAUUUUUGUUUGCUC | 556 |
| 183forw | UAUGAUGAAUGUGAUAGUUUG | 557 |
| 1260rev | CCCAGGCAGCACUGACUACAG | 558 |
| 1034rev | GUCUUGAUGAGGUAAAAAGAG | 559 |
| 1027forw | AAAAAAUCGUUACAAUUUAUG | 560 |
| 287forw | GUACUCAAGAUUAUAAGCAAU | 561 |
| 101rev | UUAAUUUCUCUCCUUUGCAUA | 562 |
| 1201rev | CCUACCCUGCCCCCUUCUCCU | 563 |
| 1284forw | CUGCUGUAGUCAGUGCUGCCU | 564 |
| 429rev | CACUUAGCACAGUACCUUACA | 565 |
| 355forw | ACUUAGAUAUGAAGGGGAAAG | 566 |

TABLE 2-continued

Guide RNA sequences

| Seq Name | Sequence | Seq ID NO |
|---|---|---|
| 661rev | UGCAGUUUUACAUAUAAAUGA | 567 |
| 1703forw | GUUGCGGAGGGUGGGCCUGGG | 568 |
| 1332forw | AAAAAUGUGAUGAUCAAAACU | 569 |
| 1219forw | GGCAUUCUAAGGAGAAGGGGG | 570 |
| 372forw | AAAGAAGGGUUUGAGAUAAUG | 571 |
| 192forw | UGUGAUAGUUUGGAGAAUAAA | 572 |
| 531forw | GCAGAUGCUAUGAAAGAAAAA | 573 |
| 708rev | UAUGAGCCACCGCACCCGGCC | 574 |
| 741rev | CGCUUCGGCCUCCCAAAGUGC | 575 |
| 765forw | CCAGCACUUUGGGGAGGCCGAA | 576 |
| 769forw | CACUUUGGGGAGGCCGAAGCGG | 577 |
| 820rev | UUUUGUGUUUUUAGUAGAGAC | 578 |
| 877rev | UGUCUCAGCCUCCUGAGUAGC | 579 |
| 886rev | CGAUUCUCGUGUCUCAGCCUC | 580 |
| 905forw | CUACUCAGGAGGCUGAGACAC | 581 |
| 918rev | GCUCACUGCAACCUCUGCCUC | 582 |
| 962rev | UGCUCUUUCGCCCAGGCUGGA | 583 |
| 967rev | AGUCUUGCUCUUUCGCCCAGG | 584 |
| 991rev | UAACGAUUUUUUUUUUUGAGA | 585 |
| 94rev | GCCCAACUCUUCGCGGUGGCA | 586 |
| 302rev | CCCCAUUGCCGGCGAGGGGUG | 587 |
| 997rev | AACUACCCCCAGAUGAUCCUA | 588 |
| 237rev | ACUGCAUGUGUGAGCCGAGUC | 589 |
| 309rev | CACAAGCCCCCAUUGCCGGCG | 590 |
| 579forw | GAUCUCGACCAGUCCCCUCAA | 591 |
| 110forw | GAGGCACCCACUGCCACCGCG | 592 |
| 1082forw | GCCCACCUUUAGGGUGAUAGC | 593 |
| 456forw | GUUGCCUGGAGCCGUUCCUGC | 594 |
| 1391rev | AAAAAGCGAUCUUAGAUCACC | 595 |
| 414forw | GCACCUCCAAAGUCGGCCAAA | 596 |
| 1182forw | CUAUUACCUAAGUAGGUCCCC | 597 |
| 192forw | GGCCGCAGGAAGAGGAACGGA | 598 |
| 875forw | UCCCAGCCGGCAGUCUCCCAC | 599 |
| 1830forw | GGUGGUGCAGGGCCGUGAAGC | 600 |
| 214rev | GGGUGCACGUCCCACAGCUCA | 601 |
| 1724rev | CAUGCACUUGUCUGUAGUUCA | 602 |
| 1070forw | GUGUAUAUAAAGGCCCACCUU | 603 |

TABLE 2-continued

Guide RNA sequences

| Seq Name | Sequence | Seq ID NO |
|---|---|---|
| 337rev | CUGGCCCAGUCAGUCAGGUUU | 604 |
| 850rev | UUGUGGGAGACUGCCGGCUGG | 605 |
| 984rev | UGAUCCUAAGGAAUUGAAGGU | 606 |
| 1086rev | UGACUUCUGACUUUCAAUCAU | 607 |
| 843rev | AGACUGCCGGCUGGGAGGGUU | 608 |
| 1014forw | UUCAAUUCCUUAGGAUCAUCU | 609 |
| 1348forw | UGAUUUUGCCAAGAACUUGUC | 610 |
| 1703rev | AGGAGUCCCCGCCCUUGCAAA | 611 |
| 244rev | AAAGCGAACUGCAUGUGUGAG | 612 |
| 945rev | UACCUUGUCGUGAUAAGUGGG | 613 |
| 1847forw | AAGCAAGAAUGGCCACAGACU | 614 |
| 1043forw | UUGCCAAGAGAGAGCAGCC | 615 |
| 50rev | GGGCCGACCGCGGCCUCCAGG | 616 |
| 131forw | AAGAGUUGGGCUCUGUCAGCC | 617 |
| 1217forw | AGAUACAUUUCUUAGCACUAU | 618 |
| 1763rev | AGAAGCAAAAGUACCACUAGA | 619 |
| 431forw | CAAAAUGAAUGGGCAGUGAGC | 620 |
| 1322forw | GCAUGGUUUUGUGGAAAAGUA | 621 |
| 972rev | AUUGAAGGUAUGGAUUUGGGA | 622 |
| 629forw | UGAGAGAUCAUUUAACAUUUA | 623 |
| 1003forw | AAAUCCAUACCUUCAAUUCCU | 624 |
| 1244forw | UAAGAAAUGUAAAAAAACCUC | 625 |
| 836rev | CGGCUGGGAGGGUUGGGGGUG | 626 |
| 1462forw | UCCCACUCUGUCACCCAGAGC | 627 |
| 764rev | UUAUUGGAACGCUAAGCUUGU | 628 |
| 829rev | GAGGGUUGGGGGUGGGGGGUG | 629 |
| 1445rev | CUGCACUCCAGCUCUGGGUGA | 630 |
| 755forw | CUUGGCGAUGACCUUGAGCAG | 631 |
| 1436forw | UUUCUUCUCUUUCUUUUGAGA | 632 |
| 1453rev | UGGGGACACUGCACUCCAGCU | 633 |
| 1544forw | UUCUCUCAGCCUCCCAAGUAG | 634 |
| 1570rev | CUGAAAAUACAAAAAAAUCAG | 635 |
| 1621rev | GCGGGCGGAUCACCUGAGGUC | 636 |
| 1638rev | CACUUUGGGAGGCAGAAGCGG | 637 |
| 1666forw | CGCUUCUGCCUCCCAAAGUGC | 638 |

In some aspects, a guide RNA molecule can comprise a part of any sequence recited in Table 3 or Table 4. In some aspects, a guide RNA molecule can comprise the first about 20 nucleotides of any sequence recited in Table 3. In some aspects, a guide RNA molecule can comprise the first about 21 nucleotides of any sequence recited in Table 4.

TABLE 3

Guide RNA sequences

| Seq Name | Sequence | Seq ID NO |
|---|---|---|
| 1015rev | UGUUCAUAAAUUUACUGACAUGG | 639 |
| 1025forw | AAAAAAAUCGUUACAAUUUAUGG | 640 |
| 1028forw | AAAAUCGUUACAAUUUAUGGUGG | 641 |
| 1037rev | UCUUGAUGAGGUAAAAAGAGGGG | 642 |
| 1038rev | GUCUUGAUGAGGUAAAAAGAGGG | 643 |
| 1039rev | UGUCUUGAUGAGGUAAAAAGAGG | 644 |
| 103rev | AAUUUCUCUCCUUUGCAUAUUGG | 645 |
| 1049rev | AGUAGUGCUGUGUCUUGAUGAGG | 646 |
| 1059rev | AGGGGACCUACUUAGGUAAUAGG | 647 |
| 1066rev | CAAUUCCAGGGGACCUACUUAGG | 648 |
| 106forw | ACGGAGCGAGUCCCCGCGCGCGG | 649 |
| 1073forw | UUUUAACCUAUUACCUAAGUAGG | 650 |
| 1077rev | UAUCUGCUAGACAAUUCCAGGGG | 651 |
| 1078rev | GUAUCUGCUAGACAAUUCCAGGG | 652 |
| 1079rev | UGUAUCUGCUAGACAAUUCCAGG | 653 |
| 1081forw | UAUUACCUAAGUAGGUCCCCUGG | 654 |
| 1098rev | UCCCUUUUAUUAGGAAAGAAAGG | 655 |
| 1107rev | GACUGAAUCUCCCUUUUAUUAGG | 656 |
| 1116forw | CGCCUUUCUUUCCUAAUAAAAGG | 657 |
| 1117forw | GCCUUUCUUUCCUAAUAAAAGGG | 658 |
| 1129rev | CUACUACAUUAUUAAUCUUAAGG | 659 |
| 1139rev | CCAGCAACAGUGGACUCUAGAGG | 660 |
| 1149rev | GAGAACAUUACCAGCAACAGUGG | 661 |
| 114forw | GCUAAAUAUCCAAUAUGCAAAGG | 662 |
| 1159forw | CCUCUAGAGUCCACUGUUGCUGG | 663 |
| 1168rev | GCCUCUCCUUGAGCAGAGGAUGG | 664 |
| 116rev | GGUGCACGUCCCACAGCUCAGGG | 665 |
| 1172rev | UCCAGCCUCUCCUUGAGCAGAGG | 666 |
| 1178forw | CUGGUAAUGUUCUCUAAAUAAGG | 667 |
| 117rev | GGGUGCACGUCCCACAGCUCAGG | 668 |
| 1182forw | UUAAAGCCAUCCUCUGCUCAAGG | 669 |
| 1187forw | GCCAUCCUCUGCUCAAGGAGAGG | 670 |
| 1191forw | UCCUCUGCUCAAGGAGAGGCUGG | 671 |
| 1193rev | UUCCACAAAACCAUGCUGAUAGG | 672 |
| 1197forw | GCUCAAGGAGAGGCUGGAGAAGG | 673 |
| 1203forw | AAAUAUUUUUCCUAUCAGCAUGG | 674 |

TABLE 3-continued

| | Guide RNA sequences | |
|---|---|---|
| Seq Name | Sequence | Seq ID NO |
| 1207forw | AGGCUGGAGAAGGCAUUCUAAGG | 675 |
| 1211forw | UUCCUAUCAGCAUGGUUUUGUGG | 676 |
| 1213forw | GAGAAGGCAUUCUAAGGAGAAGG | 677 |
| 1214forw | AGAAGGCAUUCUAAGGAGAAGGG | 678 |
| 1215forw | GAAGGCAUUCUAAGGAGAAGGGG | 679 |
| 1216forw | AAGGCAUUCUAAGGAGAAGGGGG | 680 |
| 1220forw | CAUUCUAAGGAGAAGGGGGCAGG | 681 |
| 1221forw | AUUCUAAGGAGAAGGGGGCAGGG | 682 |
| 1221forw | CAUGGUUUUGUGGAAAAGUAAGG | 683 |
| 1225forw | UAAGGAGAAGGGGGCAGGGUAGG | 684 |
| 1232forw | AAGGGGGCAGGGUAGGAACUCGG | 685 |
| 1234rev | CAAGACUCUAGACAAGUUCUUGG | 686 |
| 1241rev | GAAUCUUGUCUCGGCUCAGUGGG | 687 |
| 1242rev | AGAAUCUUGUCUCGGCUCAGUGG | 688 |
| 1250rev | ACUACAGCAGAAUCUUGUCUCGG | 689 |
| 1257forw | AGAACUUGUCUAGAGUCUUGAGG | 690 |
| 126forw | CGGCGCGAUUCCCUGAGCUGUGG | 691 |
| 127forw | GGCGCGAUUCCCUGAGCUGUGGG | 692 |
| 1281rev | CUUUGUGAAAAUAGAUUCCCAGG | 693 |
| 1281rev | AGAUCACCUUGAGUAAACUGAGG | 694 |
| 1283forw | CUGCUGUAGUCAGUGCUGCCUGG | 695 |
| 1284forw | UGCUGUAGUCAGUGCUGCCUGGG | 696 |
| 1295forw | AGUAAGCCUCAGUUUACUCAAGG | 697 |
| 1308rev | GUUUUGAUCAUCACAUUUUUUGG | 698 |
| 1332forw | AAAAUGUGAUGAUCAAAACUAGG | 699 |
| 1335forw | UUCUUCUCUUUCUUUUGAGACGG | 700 |
| 1341rev | CCAGCUCUGGGUGACAGAGUGGG | 701 |
| 1342rev | UCCAGCUCUGGGUGACAGAGUGG | 702 |
| 1353rev | GGACACUGCACUCCAGCUCUGGG | 703 |
| 1354forw | GAAUUAGUGUUCUGUGUCUUAGG | 704 |
| 1354rev | GGGACACUGCACUCCAGCUCUGG | 705 |
| 1357rev | GAAUUCACAGGAAGAUUUUAGGG | 706 |
| 1358rev | GGAAUUCACAGGAAGAUUUUAGG | 707 |
| 1361forw | CCCACUCUGUCACCCAGAGCUGG | 708 |
| 1369rev | ACCUUAAAAAUGGAAUUCACAGG | 709 |
| 1374rev | GGUUGCAGUGAGCCAAGAUGGGG | 710 |
| 1375rev | AGGUUGCAGUGAGCCAAGAUGGG | 711 |

TABLE 3-continued

| | Guide RNA sequences | |
|---|---|---|
| Seq Name | Sequence | Seq ID NO |
| 1376rev | GAGGUUGCAGUGAGCCAAGAUGG | 712 |
| 1379rev | CACCUCGACUACCUUAAAAAUGG | 713 |
| 137rev | GCAUGUGUGAGCCGAGUCCUGGG | 714 |
| 1382forw | GGAGUGCAGUGUCCCCAUCUUGG | 715 |
| 1388forw | UCCUGUGAAUUCCAUUUUUAAGG | 716 |
| 138rev | UGCAUGUGUGAGCCGAGUCCUGG | 717 |
| 1395rev | GCUAGAAACCGAGGAGGCAGAGG | 718 |
| 1397forw | UUCCAUUUUUAAGGUAGUCGAGG | 719 |
| 1401rev | AAAAUCGCUAGAAACCGAGGAGG | 720 |
| 1404rev | UAUCCUCUGCAGACCAGACGCGG | 721 |
| 1404rev | GAGAAAAUCGCUAGAAACCGAGG | 722 |
| 1407forw | CACUGCAACCUCUGCCUCCUCGG | 723 |
| 140forw | GAAAUUAAAGAUUUAAAAGCAGG | 724 |
| 140forw | GAGCUGUGGGACGUGCACCCAGG | 725 |
| 1411forw | UAGUCGAGGUGAACCGCGUCUGG | 726 |
| 1421forw | GAACCGCGUCUGGUCUGCAGAGG | 727 |
| 1431rev | UGUAAACCCAGCUACUUGGGAGG | 728 |
| 1433forw | GUCUGCAGAGGAUAGAAAAAAGG | 729 |
| 1434rev | GCCUGUAAACCCAGCUACUUGGG | 730 |
| 1435rev | UGCCUGUAAACCCAGCUACUUGG | 731 |
| 1436rev | AACUAACUUGAGGUAUCAGAGGG | 732 |
| 1437rev | AAACUAACUUGAGGUAUCAGAGG | 733 |
| 1444forw | CUCUCAGCCUCCCAAGUAGCUGG | 734 |
| 1445forw | UCUCAGCCUCCCAAGUAGCUGGG | 735 |
| 1446rev | UUAAAGGUGAAACUAACUUGAGG | 736 |
| 1453forw | UCCCAAGUAGCUGGGUUUACAGG | 737 |
| 145rev | AUCAUAACAUAGUUUCCUUAUGG | 738 |
| 1462rev | UUACUUCCGACCUUCUUUAAAGG | 739 |
| 1462rev | AAAAAAUCAGCCGGGUAUGGUGG | 740 |
| 1465rev | ACAAAAAAAUCAGCCGGGUAUGG | 741 |
| 146forw | UGGGACGUGCACCCAGGACUCGG | 742 |
| 1470rev | AAAAUACAAAAAAAUCAGCCGGG | 743 |
| 1471rev | GAAAAUACAAAAAAAUCAGCCGG | 744 |
| 1472forw | GUUAGUUUCACCUUUAAAGAAGG | 745 |
| 1472forw | CAGGCACACACCACCAUACCCGG | 746 |
| 1476forw | GUUUCACCUUUAAAGAAGGUCGG | 747 |
| 1495rev | CCCUUCCGCACGUCCGGGAAAGG | 748 |
| 1500rev | CGUUGCCCUUCCGCACGUCCGGG | 749 |

TABLE 3-continued

Guide RNA sequences

| Seq Name | Sequence | Seq ID NO |
|---|---|---|
| 1501rev | ACGUUGCCCUUCCGCACGUCCGG | 750 |
| 1502forw | UAAAGACGCAAAGCCUUUCCCGG | 751 |
| 1502forw | UUUUGUAUUUUCAGUAAAGUUGG | 752 |
| 1503forw | UUUGUAUUUUCAGUAAAGUUGGG | 753 |
| 1507forw | UAUUUUCAGUAAAGUUGGGCAGG | 754 |
| 150forw | AUUUAAAAGCAGGAGCCAUAAGG | 755 |
| 1510forw | CAAAGCCUUUCCCGGACGUGCGG | 756 |
| 1511forw | UUCAGUAAAGUUGGGCAGGCUGG | 757 |
| 1514forw | GCCUUUCCCGGACGUGCGGAAGG | 758 |
| 1514rev | CACCUGAGGUCAGGAGUUCGAGG | 759 |
| 1515forw | CCUUUCCCGGACGUGCGGAAGGG | 760 |
| 1523rev | CGGGCGGAUCACCUGAGGUCAGG | 761 |
| 1524rev | UCCAUUUCCGGCCAUGAGGAAGG | 762 |
| 1528rev | AAGUUCCAUUUCCGGCCAUGAGG | 763 |
| 1528rev | AGAAGCGGGCGGAUCACCUGAGG | 764 |
| 1532forw | GGCCUCGAACUCCUGACCUCAGG | 765 |
| 1533forw | AAGGGCAACGUCCUUCCUCAUGG | 766 |
| 1536rev | GGAAAUUAAAGUUCCAUUUCCGG | 767 |
| 1537forw | GCAACGUCCUUCCUCAUGGCCGG | 768 |
| 1539rev | CUUUGGGAGGCAGAAGCGGGCGG | 769 |
| 1542rev | GCACUUUGGGAGGCAGAAGCGGG | 770 |
| 1543forw | UCCUUCCUCAUGGCCGGAAAUGG | 771 |
| 1543rev | AGCACUUUGGGAGGCAGAAGCGG | 772 |
| 1552rev | UGUAAUCCCAGCACUUUGGGAGG | 773 |
| 1555rev | GCCUGUAAUCCCAGCACUUUGGG | 774 |
| 1556rev | CGCCUGUAAUCCCAGCACUUUGG | 775 |
| 1557rev | GCGGGCUGGUUGGGGGGAACGGG | 776 |
| 1558rev | GGCGGGCUGGUUGGGGGGAACGG | 777 |
| 1563rev | UCUCGGGCGGGCUGGUUGGGGGG | 778 |
| 1564rev | CUCUCGGGCGGGCUGGUUGGGGG | 779 |
| 1565forw | GCUUCUGCCUCCCAAAGUGCUGG | 780 |
| 1565rev | UCUCUCGGGCGGGCUGGUUGGGG | 781 |
| 1566forw | CUUCUGCCUCCCAAAGUGCUGGG | 782 |
| 1566rev | CUCUCUCGGGCGGGCUGGUUGGG | 783 |
| 1567rev | ACUCUCUCGGGCGGGCUGGUUGG | 784 |
| 1571rev | AGUCACUCUCUCGGGCGGGCUGG | 785 |
| 1574forw | UCCCAAAGUGCUGGGAUUACAGG | 786 |

TABLE 3-continued

Guide RNA sequences

| Seq Name | Sequence | Seq ID NO |
|---|---|---|
| 1575rev | UGAGAGUCACUCUCUCGGGCGGG | 787 |
| 1576rev | GUGAGAGUCACUCUCUCGGGCGG | 788 |
| 1579rev | CUCGUGAGAGUCACUCUCUCGGG | 789 |
| 1580rev | UCUCGUGAGAGUCACUCUCUCGG | 790 |
| 1583rev | GGAUCUUAGUCCCCGCACGGUGG | 791 |
| 1586rev | AAGGGAUCUUAGUCCCCGCACGG | 792 |
| 1591forw | UACAGGCGUGAGCCACCGUGCGG | 793 |
| 1592forw | ACAGGCGUGAGCCACCGUGCGGG | 794 |
| 1593forw | CAGGCGUGAGCCACCGUGCGGGG | 795 |
| 1604rev | AUUGGCCAAGCUGACUCUCGCGG | 796 |
| 1604rev | GAGUCCCCGCCCUUGCAAAAGGG | 797 |
| 1605rev | GGAGUCCCCGCCCUUGCAAAAGG | 798 |
| 1614forw | GGACUAAGAUCCCUUUUGCAAGG | 799 |
| 1615forw | GACUAAGAUCCCUUUUGCAAGGG | 800 |
| 1618forw | UAAGAUCCCUUUUGCAAGGGCGG | 801 |
| 1619forw | GAGAGCCGCGAGAGUCAGCUUGG | 802 |
| 1619forw | AAGAUCCCUUUUGCAAGGGCGGG | 803 |
| 1620forw | AGAUCCCUUUUGCAAGGGCGGGG | 804 |
| 1622rev | CGGCCGCCGACCGCACGGAUUGG | 805 |
| 1626rev | AUGCACUUGUCUGUAGUUCAAGG | 806 |
| 1627rev | GGGAGCGGCCGCCGACCGCACGG | 807 |
| 1632forw | GUCAGCUUGGCCAAUCCGUGCGG | 808 |
| 1636forw | GCUUGGCCAAUCCGUGCGGUCGG | 809 |
| 1639forw | UGGCCAAUCCGUGCGGUCGGCGG | 810 |
| 1642rev | GAGUCGGCUUAUAAAGGGAGCGG | 811 |
| 1647rev | CGGGCGAGUCGGCUUAUAAAGGG | 812 |
| 1648rev | CCGGGCGAGUCGGCUUAUAAAGG | 813 |
| 1658rev | CGGUGCGCUGCCGGGCGAGUCGG | 814 |
| 1665rev | GAAGCAAAAGUACCACUAGAUGG | 815 |
| 1666rev | CCGCAACCCGGUGCGCUGCCGGG | 816 |
| 1667rev | UCCGCAACCCGGUGCGCUGCCGG | 817 |
| 1668forw | CCUUUAUAAGCCGACUCGCCCGG | 818 |
| 1673forw | UUUGUUCUUACUCCAUCUAGUGG | 819 |
| 1678rev | CAGGCCCACCCUCCGCAACCCGG | 820 |
| 1679forw | CGACUCGCCCGGCAGCGCACCGG | 821 |
| 1680forw | GACUCGCCCGGCAGCGCACCGGG | 822 |
| 1686forw | CCCGGCAGCGCACCGGGUUGCGG | 823 |
| 1689forw | GGCAGCGCACCGGGUUGCGGAGG | 824 |

TABLE 3-continued

Guide RNA sequences

| Seq Name | Sequence | Seq ID NO |
|---|---|---|
| 1689rev | CACCACAAAUGUUGUAAAUGUGG | 825 |
| 1690forw | GCAGCGCACCGGGUUGCGGAGGG | 826 |
| 1693forw | GCGCACCGGGUUGCGGAGGGUGG | 827 |
| 1694forw | CGCACCGGGUUGCGGAGGGUGGG | 828 |
| 1697rev | AAAUGGCCACCACCCCUCCCAGG | 829 |
| 1699forw | CGGGUUGCGGAGGGUGGGCCUGG | 830 |
| 1700forw | GGGUUGCGGAGGGUGGGCCUGGG | 831 |
| 1703forw | UUGCGGAGGGUGGGCCUGGGAGG | 832 |
| 1704forw | UGCGGAGGGUGGGCCUGGGAGGG | 833 |
| 1705forw | GCGGAGGGUGGGCCUGGGAGGGG | 834 |
| 1707forw | CUCCACAUUUACAACAUUUGUGG | 835 |
| 1708forw | GAGGGUGGGCCUGGGAGGGGUGG | 836 |
| 170rev | UCGGCGUUCCCCCCACCAACAGG | 837 |
| 1710forw | CACAUUUACAACAUUUGUGGUGG | 838 |
| 1711forw | GGUGGGCCUGGGAGGGGUGGUGG | 839 |
| 1714rev | AGUUAGGGUUAGACAAAAAAUGG | 840 |
| 1716forw | UACAACAUUUGUGGUGGUGCAGG | 841 |
| 1717forw | ACAACAUUUGUGGUGGUGCAGGG | 842 |
| 1720rev | CUGUGGCCAUUCUUGCUUCACGG | 843 |
| 1729rev | GCCUACGCCCUUCUCAGUUAGGG | 844 |
| 1730rev | CGCCUACGCCCUUCUCAGUUAGG | 845 |
| 1734forw | GCAGGGCCGUGAAGCAAGAAUGG | 846 |
| 1737rev | AGAAAAACAUUCCCAGUCUGUGG | 847 |
| 1741forw | UUGUCUAACCCUAACUGAGAAGG | 848 |
| 1742forw | UGUCUAACCCUAACUGAGAAGGG | 849 |
| 1745forw | AAGCAAGAAUGGCCACAGACUGG | 850 |
| 1746forw | AGCAAGAAUGGCCACAGACUGGG | 851 |
| 1748forw | ACCCUAACUGAGAAGGGCGUAGG | 852 |
| 1753rev | GCGCGCGGGGAGCAAAAGCACGG | 853 |
| 175forw | CAUGCAGUUCGCUUUCCUGUUGG | 854 |
| 1766rev | AGCGAGAAAAACAGCGCGCGGGG | 855 |
| 1767rev | CAGCGAGAAAAACAGCGCGCGGG | 856 |
| 1768rev | UCAGCGAGAAAAACAGCGCGCGG | 857 |
| 178forw | GCAGUUCGCUUUCCUGUUGGUGG | 858 |
| 1798forw | UUUUUCUCGCUGACUUUCAGCGG | 859 |
| 1799forw | UUUUCUCGCUGACUUUCAGCGGG | 860 |
| 179forw | CAGUUCGCUUUCCUGUUGGUGGG | 861 |

TABLE 3-continued

Guide RNA sequences

| Seq Name | Sequence | Seq ID NO |
|---|---|---|
| 1802forw | UCUCGCUGACUUUCAGCGGGCGG | 862 |
| 180forw | AGUUCGCUUUCCUGUUGGUGGGG | 863 |
| 1810rev | CGGUGGAAGGCGGCAGGCCGAGG | 864 |
| 1813forw | UUCAGCGGGCGGAAAAGCCUCGG | 865 |
| 1816rev | AAUGAACGGUGGAAGGCGGCAGG | 866 |
| 181forw | UUAUGAUGAAUGUGAUAGUUUGG | 867 |
| 181forw | GUUCGCUUUCCUGUUGGUGGGGG | 868 |
| 1820rev | CUAGAAUGAACGGUGGAAGGCGG | 869 |
| 1823rev | GCUCUAGAAUGAACGGUGGAAGG | 870 |
| 1827rev | GUUUGCUCUAGAAUGAACGGUGG | 871 |
| 182forw | UUCGCUUUCCUGUUGGUGGGGGG | 872 |
| 1830rev | UUUGUUUGCUCUAGAAUGAACGG | 873 |
| 1866forw | AAACAAAAAAUGUCAGCUGCUGG | 874 |
| 1869rev | GGUCCCCGGGAGGGGCGAACGGG | 875 |
| 1870rev | AGGUCCCCGGGAGGGGCGAACGG | 876 |
| 1877rev | CCGCCGCAGGUCCCCGGGAGGGG | 877 |
| 1878rev | CCCGCCGCAGGUCCCCGGGAGGG | 878 |
| 1879rev | ACCCGCCGCAGGUCCCCGGGAGG | 879 |
| 1882rev | GCGACCCGCCGCAGGUCCCCGGG | 880 |
| 1883rev | GGCGACCCGCCGCAGGUCCCCGG | 881 |
| 1884forw | GCUGGCCCGUUCGCCCCUCCCGG | 882 |
| 1885forw | CUGGCCCGUUCGCCCCUCCCGGG | 883 |
| 1886forw | UGGCCCGUUCGCCCCUCCCGGGG | 884 |
| 1890rev | CUGGGCAGGCGACCCGCCGCAGG | 885 |
| 1894forw | UCGCCCCUCCCGGGGACCUGCGG | 886 |
| 1897forw | CCCCUCCCGGGGACCUGCGGCGG | 887 |
| 1898forw | CCCUCCCGGGGACCUGCGGCGGG | 888 |
| 189rev | GGGUGACGGAUGCGCACGAUCGG | 889 |
| 1904rev | GCGGGGUUCGGGGGCUGGGCAGG | 890 |
| 1908rev | CCAGGCGGGGUUCGGGGGCUGGG | 891 |
| 1909rev | UCCAGGCGGGGUUCGGGGGCUGG | 892 |
| 1913rev | GGCCUCCAGGCGGGGUUCGGGGG | 893 |
| 1914rev | CGGCCUCCAGGCGGGGUUCGGGG | 894 |
| 1915rev | GCGGCCUCCAGGCGGGGUUCGGG | 895 |
| 1916rev | CGCGGCCUCCAGGCGGGGUUCGG | 896 |
| 1921rev | CCGACCGCGGCCUCCAGGCGGGG | 897 |
| 1922rev | GCCGACCGCGGCCUCCAGGCGGG | 898 |
| 1923rev | GGCCGACCGCGGCCUCCAGGCGG | 899 |

TABLE 3-continued

| Guide RNA sequences | | |
|---|---|---|
| Seq Name | Sequence | Seq ID NO |
| 1926rev | CCGGGCCGACCGCGGCCUCCAGG | 900 |
| 1928forw | CCCAGCCCCCGAACCCCGCCUGG | 901 |
| 1931forw | AGCCCCCGAACCCCGCCUGGAGG | 902 |
| 1934rev | GAGAAGCCCCGGGCCGACCGCGG | 903 |
| 1937forw | CGAACCCCGCCUGGAGGCCGCGG | 904 |
| 1941forw | CCCCGCCUGGAGGCCGCGGUCGG | 905 |
| 1944rev | GGUGCCUCCGGAGAAGCCCCGGG | 906 |
| 1945rev | GGGUGCCUCCGGAGAAGCCCCGG | 907 |
| 1946forw | CCUGGAGGCCGCGGUCGGCCCGG | 908 |
| 1947forw | CUGGAGGCCGCGGUCGGCCCGGG | 909 |
| 1948forw | UGGAGGCCGCGGUCGGCCCGGGG | 910 |
| 1956rev | GCGGUGGCAGUGGGUGCCUCCGG | 911 |
| 1957forw | CGGUCGGCCCGGGGCUUCUCCGG | 912 |
| 1960forw | UCGGCCCGGGGCUUCUCCGGAGG | 913 |
| 1965rev | CAACUCUUCGCGGUGGCAGUGGG | 914 |
| 1966rev | CCAACUCUUCGCGGUGGCAGUGG | 915 |
| 1986forw | CCACUGCCACCGCGAAGAGUUGG | 916 |
| 1987forw | CACUGCCACCGCGAAGAGUUGGG | 917 |
| 199forw | UUUGGAGAAUAAAUUGAAUGAGG | 918 |
| 1rev | CAGAGCCCAACUCUUCGCGGUGG | 919 |
| 203forw | GAGAAUAAAUUGAAUGAGGAAGG | 920 |
| 203rev | CCAUUGCCGGCGAGGGGUGACGG | 921 |
| 206rev | AACUGAUCACCAAAUCUCCAGGG | 922 |
| 207rev | UAACUGAUCACCAAAUCUCCAGG | 923 |
| 209forw | AAAUUGAAUGAGGAAGGCCCUGG | 924 |
| 209rev | AAGCCCCCAUUGCCGGCGAGGGG | 925 |
| 210rev | CAAGCCCCCAUUGCCGGCGAGGG | 926 |
| 211rev | ACAAGCCCCCAUUGCCGGCGAGG | 927 |
| 216rev | GGUUCACAAGCCCCCAUUGCCGG | 928 |
| 217forw | UGAGGAAGGCCCUGGAGAUUUGG | 929 |
| 217forw | GCGCAUCCGUCACCCCUCGCCGG | 930 |
| 223forw | CCGUCACCCCUCGCCGGCAAUGG | 931 |
| 224forw | CGUCACCCCUCGCCGGCAAUGGG | 932 |
| 225forw | GUCACCCCUCGCCGGCAAUGGGG | 933 |
| 226forw | UCACCCCUCGCCGGCAAUGGGGG | 934 |
| 237rev | GCCCAGUCAGUCAGGUUUGGGGG | 935 |
| 238rev | GGCCCAGUCAGUCAGGUUUGGGG | 936 |

TABLE 3-continued

| Guide RNA sequences | | |
|---|---|---|
| Seq Name | Sequence | Seq ID NO |
| 239rev | UGGCCCAGUCAGUCAGGUUUGGG | 937 |
| 240rev | CUGGCCCAGUCAGUCAGGUUUGG | 938 |
| 243rev | AAGACUUGGCACUUUAUAUGUGG | 939 |
| 245rev | GCACACUGGCCCAGUCAGUCAGG | 940 |
| 255forw | AACCCCCAAACCUGACUGACUGG | 941 |
| 256forw | ACCCCCAAACCUGACUGACUGGG | 942 |
| 257rev | AUAAUCUUGAGUACAAGACUUGG | 943 |
| 259rev | CCUGCCAAUUUGCAGCACACUGG | 944 |
| 275forw | UGGGCCAGUGUGCUGCAAAUUGG | 945 |
| 279forw | CCAGUGUGCUGCAAAUUGGCAGG | 946 |
| 287forw | UACUCAAGAUUAUAAGCAAUAGG | 947 |
| 28rev | CCUCGCCCCCGAGAGACCCGCGG | 948 |
| 290forw | CAAAUUGGCAGGAGACGUGAAGG | 949 |
| 295rev | UUCAUUUUGGCCGACUUUGGAGG | 950 |
| 298rev | CCAUUCAUUUUGGCCGACUUUGG | 951 |
| 305forw | CGUGAAGGCACCUCCAAAGUCGG | 952 |
| 308rev | GGCUCACUGCCCAUUCAUUUUGG | 953 |
| 318forw | CCAAAGUCGGCCAAAAUGAAUGG | 954 |
| 319forw | CAAAGUCGGCCAAAAUGAAUGGG | 955 |
| 31forw | GAGUUGGGCUCUGUCAGCCGCGG | 956 |
| 329rev | GGAACGGCUCCAGGCAACCCCGG | 957 |
| 32forw | AGUUGGGCUCUGUCAGCCGCGGG | 958 |
| 330forw | AAAAUGAAUGGGCAGUGAGCCGG | 959 |
| 331forw | AAAUGAAUGGGCAGUGAGCCGGG | 960 |
| 331rev | UUUCCCCUUCAUAUCUAAGUAGG | 961 |
| 332forw | AAUGAAUGGGCAGUGAGCCGGGG | 962 |
| 338rev | ACCCACGCAGGAACGGCUCCAGG | 963 |
| 340forw | GGCAGUGAGCCGGGGUUGCCUGG | 964 |
| 345rev | CGGGAGAACCCACGCAGGAACGG | 965 |
| 346forw | UAGUGCCUACUUAGAUAUGAAGG | 966 |
| 347forw | AGUGCCUACUUAGAUAUGAAGGG | 967 |
| 348forw | GUGCCUACUUAGAUAUGAAGGGG | 968 |
| 350rev | GAAGACGGGAGAACCCACGCAGG | 969 |
| 356forw | UUAGAUAUGAAGGGGAAAGAAGG | 970 |
| 356forw | UGCCUGGAGCCGUUCCUGCGUGG | 971 |
| 357forw | UAGAUAUGAAGGGGAAAGAAGGG | 972 |
| 357forw | GCCUGGAGCCGUUCCUGCGUGGG | 973 |
| 364rev | GGCAACAAAAAGCGGAAGACGGG | 974 |

TABLE 3-continued

| Guide RNA sequences | | |
|---|---|---|
| Seq Name | Sequence | Seq ID NO |
| 365rev | AGGCAACAAAAAGCGGAAGACGG | 975 |
| 372forw | AAGAAGGGUUUGAGAUAAUGUGG | 976 |
| 372rev | CCAUAAAAGGCAACAAAAAGCGG | 977 |
| 373forw | AGAAGGGUUUGAGAUAAUGUGGG | 978 |
| 385rev | AGUUGUAAUACAACCAUAAAAGG | 979 |
| 388forw | AAUGUGGGAUGCUAAGAGAAUGG | 980 |
| 391forw | GUGGGAUGCUAAGAGAAUGGUGG | 981 |
| 392forw | CCGCUUUUUGUUGCCUUUUAUGG | 982 |
| 40forw | UCUGUCAGCCGCGGGUCUCUCGG | 983 |
| 413rev | CUCAACAAAUCUGCAGAGCAGG | 984 |
| 41forw | CUGUCAGCCGCGGGUCUCUCGGG | 985 |
| 42forw | UGUCAGCCGCGGGUCUCUCGGGG | 986 |
| 434forw | CUGCUCUGCAGAUUUUGUUGAGG | 987 |
| 439forw | UUUAGCAUCUACUCUAUGUAAGG | 988 |
| 43forw | GUCAGCCGCGGGUCUCUCGGGGG | 989 |
| 448rev | GACUGGUCGAGAUCUACCUUGGG | 990 |
| 449rev | GGACUGGUCGAGAUCUACCUUGG | 991 |
| 452forw | UGAGGUUUUUGCUUCUCCCAAGG | 992 |
| 465rev | CCACACCCCGUUGAGGGGACUGG | 993 |
| 470rev | UUCUCCCACACCCCGUUGAGGGG | 994 |
| 471rev | GUUCUCCCACACCCGUUGAGGG | 995 |
| 472forw | AGUGCAAUAGUGCUAAAAACAGG | 996 |
| 472rev | UGUUCUCCCACACCCCGUUGAGG | 997 |
| 478forw | AUCUCGACCAGUCCCCUCAACGG | 998 |
| 479forw | UCUCGACCAGUCCCCUCAACGGG | 999 |
| 480forw | CUCGACCAGUCCCCUCAACGGGG | 1000 |
| 485forw | CCAGUCCCCUCAACGGGGUGUGG | 1001 |
| 486forw | CAGUCCCCUCAACGGGGUGUGGG | 1002 |
| 488rev | CCAGGUUGUAAAGUUUUUUACGG | 1003 |
| 48forw | CCGCGGGUCUCUCGGGGGCGAGG | 1004 |
| 49forw | CGCGGGUCUCUCGGGGGCGAGGG | 1005 |
| 4rev | UGACAGAGCCCAACUCUUCGCGG | 1006 |
| 506rev | UUUCUUUCAUAGCAUCUGCCAGG | 1007 |
| 508forw | CCGUAAAAAACUUUACAACCUGG | 1008 |
| 530forw | GCAGAUGCUAUGAAAGAAAAAGG | 1009 |
| 531forw | CAGAUGCUAUGAAAGAAAAAGGG | 1010 |
| 532forw | AGAUGCUAUGAAAGAAAAAGGGG | 1011 |

TABLE 3-continued

| Guide RNA sequences | | |
|---|---|---|
| Seq Name | Sequence | Seq ID NO |
| 536forw | GCUAUGAAAGAAAAAGGGGAUGG | 1012 |
| 537forw | CUAUGAAAGAAAAAGGGGAUGGG | 1013 |
| 549forw | AAGGGGAUGGGAGAGAGAGAAGG | 1014 |
| 54forw | GUCUCUCGGGGGCGAGGGCGAGG | 1015 |
| 552forw | GGGAUGGGAGAGAGAGAAGGAGG | 1016 |
| 553forw | GGAUGGGAGAGAGAGAAGGAGGG | 1017 |
| 561forw | UAGAAGAUCUAAAUGAACAUUGG | 1018 |
| 563forw | GAGAGAAGGAGGGAGAGAGAUGG | 1019 |
| 568forw | AAGGAGGGAGAGAGAUGGAGAGG | 1020 |
| 569forw | AGGAGGGAGAGAGAUGGAGAGGG | 1021 |
| 574rev | CAUAAACCGAUGACCAUUAAAGG | 1022 |
| 57forw | AACAAGCGCUAUGACUAGCAAGG | 1023 |
| 581forw | UGGAAAUUGUGUUCCUUUAAUGG | 1024 |
| 588forw | UGUGUUCCUUUAAUGGUCAUCGG | 1025 |
| 597rev | AAAAAGAAACUUCUAACCUCUGG | 1026 |
| 598forw | UUUACUUUUCUUUCAGAUCGAGG | 1027 |
| 601forw | UGGUCAUCGGUUUAUGCCAGAGG | 1028 |
| 602rev | CUCCGUGGAGUUGUCGCUGUCGG | 1029 |
| 60forw | CGGGGGCGAGGGCGAGGUUCAGG | 1030 |
| 617rev | AUUCAGUUAGAUAAACUCCGUGG | 1031 |
| 620forw | GACCGACAGCGACAACUCCACGG | 1032 |
| 632rev | ACUGCUCAAGGUCAUCGCCAAGG | 1033 |
| 635forw | UUUUUUGAAAAAUUAGACCUUGG | 1034 |
| 63rev | UCCUCUUCCUGCGGCCUGAAAGG | 1035 |
| 644rev | GGGUUUAUAUCCUACUGCUCAAGG | 1036 |
| 655forw | UGGCGAUGACCUUGAGCAGUAGG | 1037 |
| 663rev | CAGUUUUACAUAUAAAUGACAGG | 1038 |
| 664rev | UUGGAACGCUAAGCUUGUGGGGG | 1039 |
| 665rev | AUUGGAACGCUAAGCUUGUGGGG | 1040 |
| 666rev | UAUUGGAACGCUAAGCUUGUGGG | 1041 |
| 667rev | UUAUUGGAACGCUAAGCUUGUGG | 1042 |
| 683rev | UAUGCCUAGUGUUCCGUUAUUGG | 1043 |
| 68forw | UGACUAGCAAGGUUAAGUGAAGG | 1044 |
| 690forw | CAAGCUUAGCGUUCCAAUAACGG | 1045 |
| 694forw | UAUGUAAAACUGCACUAUACUGG | 1046 |
| 697rev | CCGGCCGCGAAUUUUUUAUAAUGG | 1047 |
| 699forw | CGUUCCAAUAACGGAACACUAGG | 1048 |
| 69forw | GGGCGAGGUUCAGGCCUUUCAGG | 1049 |

45

TABLE 3-continued

Guide RNA sequences

| Seq Name | Sequence | Seq ID NO |
|---|---|---|
| 713forw | CUGGCCAUUAUAAAAAUUCGCGG | 1050 |
| 714forw | ACACUAGGCAUAAUGAAAGACGG | 1051 |
| 716rev | CAGGUAUGAGCCACCGCACCCGG | 1052 |
| 717forw | CCAUUAUAAAAAUUCGCGGCCGG | 1053 |
| 718forw | CAUUAUAAAAAUUCGCGGCCGGG | 1054 |
| 71rev | ACUUUAAGCCUUUCAGUCCCUGG | 1055 |
| 723forw | UAAAAAUUCGCGGCCGGGUGCGG | 1056 |
| 726forw | AAAUUCGCGGCCGGGUGCGGUGG | 1057 |
| 72rev | UCGCUCCGUUCCUCUUCCUGCGG | 1058 |
| 731rev | AGGGUUGGGGGUGGGGGGUGUGG | 1059 |
| 735rev | UCCCAAAGUGCUGGGAUUACAGG | 1060 |
| 736rev | CUGGGAGGGUUGGGGGUGGGGGG | 1061 |
| 737rev | GCUGGGAGGGUUGGGGGUGGGGG | 1062 |
| 738rev | GGCUGGGAGGGUUGGGGGUGGGG | 1063 |
| 739rev | CGGCUGGGAGGGUUGGGGGUGGG | 1064 |
| 73forw | AGCAAGGUUAAGUGAAGGCCAGG | 1065 |
| 740rev | CCGGCUGGGAGGGUUGGGGGUGG | 1066 |
| 743rev | CUUCGGCCUCCCAAAGUGCUGGG | 1067 |
| 743rev | CUGCCGGCUGGGAGGGUUGGGGG | 1068 |
| 744rev | GCUUCGGCCUCCCAAAGUGCUGG | 1069 |
| 744rev | ACUGCCGGCUGGGAGGGUUGGGG | 1070 |
| 745rev | GACUGCCGGCUGGGAGGGUUGGG | 1071 |
| 746rev | AGACUGCCGGCUGGGAGGGUUGG | 1072 |
| 74forw | GCAAGGUUAAGUGAAGGCCAGGG | 1073 |
| 750rev | UGGGAGACUGCCGGCUGGGAGGG | 1074 |
| 751rev | GUGGGAGACUGCCGGCUGGGAGG | 1075 |
| 753forw | UACCUGUAAUCCCAGCACUUUGG | 1076 |
| 754forw | ACCUGUAAUCCCAGCACUUUGGG | 1077 |
| 754rev | CUUGUGGGAGACUGCCGGCUGG | 1078 |
| 755rev | UCUUGUGGGAGACUGCCGGCUGG | 1079 |
| 757forw | UGUAAUCCCAGCACUUUGGGAGG | 1080 |
| 759rev | CAAUUCUUGUGGGAGACUGCCGG | 1081 |
| 760forw | CCACCCCCAACCCUCCCAGCCGG | 1082 |
| 760rev | CUCAAGUGAUCCACCCGCUUCGG | 1083 |
| 766forw | AGCACUUUGGGAGGCCGAAGCGG | 1084 |
| 767forw | GCACUUUGGGAGGCCGAAGCGG | 1085 |
| 769rev | AAAUCAGAGCCAAUUCUUGUGGG | 1086 |

46

TABLE 3-continued

Guide RNA sequences

| Seq Name | Sequence | Seq ID NO |
|---|---|---|
| 76forw | GUUCAGGCCUUUCAGGCCGCAGG | 1087 |
| 770forw | CUUUGGGGAGGCCGAAGCGGGUGG | 1088 |
| 770rev | GAAAUCAGAGCCAAUUCUUGUGG | 1089 |
| 780forw | CGGCAGUCUCCCACAAGAAUUGG | 1090 |
| 783rev | CAGGCUGGUCUCGAACGCCAGGG | 1091 |
| 784rev | CCAGGCUGGUCUCGAACGCCAGG | 1092 |
| 786forw | CGGGUGGAUCACUUGAGCCCUGG | 1093 |
| 792rev | CCAUUAGCUUAUUUUCUUAAAGG | 1094 |
| 798rev | UUUCACCAUGUUGCCCAGGCUGG | 1095 |
| 802rev | GGGGUUUCACCAUGUUGCCCAGG | 1096 |
| 804forw | CCUGGCGUUCGAGACCAGCCUGG | 1097 |
| 805forw | CUGGCGUUCGAGACCAGCCUGGG | 1098 |
| 812forw | CCUUUAAGAAAAUAAGCUAAUGG | 1099 |
| 813forw | CGAGACCAGCCUGGGCAACAUGG | 1100 |
| 815rev | UUUGUUUCUUUCAACCUAGUGGG | 1101 |
| 816rev | GUUUGUUUCUUUCAACCUAGUGG | 1102 |
| 821forw | AAAUAAGCUAAUGGCCCACUAGG | 1103 |
| 821rev | UGUGUUUUUAGUAGAGACGGGGG | 1104 |
| 822rev | UUGUGUUUUUAGUAGAGACGGGG | 1105 |
| 823rev | UUUGUGUUUUUAGUAGAGACGGG | 1106 |
| 824rev | UUUUGUGUUUUUAGUAGAGACGG | 1107 |
| 82forw | GCCUUUCAGGCCGCAGGAAGAGG | 1108 |
| 839forw | CUAGGUUGAAAGAAACAAACAGG | 1109 |
| 83forw | AGUGAAGGCCAGGGACUGAAAGG | 1110 |
| 842rev | GUCGUGAUAAGUGGGCAGAAUGG | 1111 |
| 850rev | AUUACCUUGUCGUGAUAAGUGGG | 1112 |
| 851rev | AAUUACCUUGUCGUGAUAAGUGG | 1113 |
| 853forw | CUAAAAACACAAAAACUAGCUGG | 1114 |
| 854forw | UAAAAACACAAAAACUAGCUGGG | 1115 |
| 859forw | ACACAAAAACUAGCUGGGCGUGG | 1116 |
| 862forw | CAAAAACUAGCUGGGCGUGGUGG | 1117 |
| 866forw | AACUAGCUGGGCGUGGUGGCAGG | 1118 |
| 866forw | UCUGCCCACUUAUCACGACAAGG | 1119 |
| 871rev | UCCUGAGUAGCUGGGAUUACAGG | 1120 |
| 874rev | UUGAAGGUAUGGAUUUGGGACGG | 1121 |
| 878rev | GGAAUUGAAGGUAUGGAUUUGGG | 1122 |
| 879rev | UCUCAGCCUCCUGAGUAGCUGGG | 1123 |
| 879rev | AGGAAUUGAAGGUAUGGAUUUGG | 1124 |

TABLE 3-continued

Guide RNA sequences

| Seq Name | Sequence | Seq ID NO |
|---|---|---|
| 87forw | UCAGGCCGCAGGAAGAGGAACGG | 1125 |
| 880rev | GUCUCAGCCUCCUGAGUAGCUGG | 1126 |
| 885rev | AUCCUAAGGAAUUGAAGGUAUGG | 1127 |
| 890forw | GCCUGUAAUCCCAGCUACUCAGG | 1128 |
| 890rev | AGAUGAUCCUAAGGAAUUGAAGG | 1129 |
| 893forw | UGUAAUCCCAGCUACUCAGGAGG | 1130 |
| 899rev | ACUACCCCCAGAUGAUCCUAAGG | 1131 |
| 903forw | AUCCAUACCUUCAAUUCCUUAGG | 1132 |
| 912forw | UUCAAUUCCUUAGGAUCAUCUGG | 1133 |
| 913forw | UCAAUUCCUUAGGAUCAUCUGGG | 1134 |
| 914forw | CAAUUCCUUAGGAUCAUCUGGGG | 1135 |
| 915forw | AAUUCCUUAGGAUCAUCUGGGGG | 1136 |
| 919rev | CACUGCAACCUCUGCCUCCCGGG | 1137 |
| 920rev | UCACUGCAACCUCUGCCUCCCGG | 1138 |
| 921forw | ACACGAGAAUCGCUUGAACCCGG | 1139 |
| 922forw | CACGAGAAUCGCUUGAACCCGGG | 1140 |
| 924rev | CCCCUGGCUGCUCUCUCUCUUGG | 1141 |
| 925forw | GAGAAUCGCUUGAACCCGGGAGG | 1142 |
| 931forw | CGCUUGAACCCGGGAGGCAGAGG | 1143 |
| 940rev | GGCCUUUAUAUACACACCCCUGG | 1144 |
| 942forw | UGCCAAGAGAGAGAGCAGCCAGG | 1145 |
| 943forw | GCCAAGAGAGAGAGCAGCCAGGG | 1146 |
| 944forw | CCAAGAGAGAGAGCAGCCAGGGG | 1147 |
| 944rev | GGAGUCUAGUGGCGUGAUCUCGG | 1148 |
| 955rev | CCAGGCUGGAUGGAGUCUAGUGG | 1149 |
| 958forw | AGCCAGGGGUGUGUAUAUAAAGG | 1150 |
| 961rev | CAGGCUAUCACCCUAAAGGUGGG | 1151 |
| 962rev | UCAGGCUAUCACCCUAAAGGUGG | 1152 |
| 965rev | GCUCUUUCGCCCAGGCUGGAUGG | 1153 |
| 965rev | GAUUCAGGCUAUCACCCUAAAGG | 1154 |
| 969rev | UCUUGCUCUUUCGCCCAGGCUGG | 1155 |
| 970forw | GUAUAUAAAGGCCCACCUUUAGG | 1156 |
| 971forw | UAUAUAAAGGCCCACCUUUAGGG | 1157 |
| 973rev | GGAGUCUUGCUCUUUCGCCCAGG | 1158 |
| 975forw | CCACUAGACUCCAUCCAGCCUGG | 1159 |
| 976forw | CACUAGACUCCAUCCAGCCUGGG | 1160 |
| 97rev | AGGGAAUCGCGCCGCGCGCGGGG | 1161 |

TABLE 3-continued

Guide RNA sequences

| Seq Name | Sequence | Seq ID NO |
|---|---|---|
| 980rev | ACUUUCAAUCAUCAGGAUUCAGG | 1162 |
| 987rev | ACUUCUGACUUUCAAUCAUCAGG | 1163 |
| 98rev | CAGGGAAUCGCGCCGCGCGCGGG | 1164 |
| 994rev | AACGAUUUUUUUUUUUUGAGACGG | 1165 |
| 99rev | UCAGGGAAUCGCGCCGCGCGCGG | 1166 |

TABLE 4

Guide RNA sequences

| Seq Name | Sequence | Seq ID NO |
|---|---|---|
| 1420forw | GUGAACCGCGUCUGGUCUGCAGAGGAU | 1167 |
| 1591rev | GCUGACUCUCGCGGCUCUCGUGAGAGU | 1168 |
| 634forw | AACUCCACGGAGUUUAUCUAACUGAAU | 1169 |
| 640forw | ACGGAGUUUAUCUAACUGAAUACGAGU | 1170 |
| 1688forw | CCGGCAGCGCACCGGGUUGCGGAGGGU | 1171 |
| 716forw | GGCCAUUAUAAAAAUUCGCGGCCGGGU | 1172 |
| 1608forw | AGUGACUCUCACGAGAGCCGCGAGAGU | 1173 |
| 1678forw | GCCGACUCGCCCGGCAGCGCACCGGGU | 1174 |
| 1728rev | GGCGCCUACGCCCUUCUCAGUUAGGGU | 1175 |
| 620forw | GGACCGACAGCGACAACUCCACGGAGU | 1176 |
| 1239rev | CAGAAUCUUGUCUCGGCUCAGUGGGAU | 1177 |
| 1229rev | UCUCGGCUCAGUGGGGAUGCGUCCGAGU | 1178 |
| 1584forw | CCCCCCAACCAGCCCGCCCGAGAGAGU | 1179 |
| 481rev | GGUUGUAAAGUUUUUUACGGACAGAAU | 1180 |
| 1625rev | AAGGGAGCGGCCGCCGACCGCACGGAU | 1181 |
| 1896forw | CGCCCCUCCCGGGGACCUGCGGCGGGU | 1182 |
| 1661rev | CGCAACCCGGUGCGCUGCCGGGCGAGU | 1183 |
| 383forw | UGAGAUAAUGUGGGGAUGCUAAGAGAAU | 1184 |
| 472forw | AAGUGCAAUAGUGCUAAAAACAGGAGU | 1185 |
| 614rev | UAUUCAGUUAGAUAAACUCCGUGGAGU | 1186 |
| 1376rev | UCACCUCGACUACCUUAAAAAUGGAAU | 1187 |
| 166forw | CCAUAAGGAAACUAUGUUAUGAUGAAU | 1188 |
| 409rev | AUAGAGUAGAUGCUAAAUGCUUUGAGU | 1189 |
| 1170rev | UCUCCAGCCUCUCCUUGAGCAGAGGAU | 1190 |
| 1122rev | CUACAUUAUUAAUCUUAAGGACUGAAU | 1191 |
| 1372forw | CUUAGGCCCUAAAAAUCUUCCUGUGAAU | 1192 |
| 268rev | AAAUUCCUAUUGCUUAUAAUCUUGAGU | 1193 |
| 1836rev | GCUGACAUUUUUUGUUUGCUCUAGAAU | 1194 |

TABLE 4-continued

| Guide RNA sequences | | |
|---|---|---|
| Seq Name | Sequence | Seq ID NO |
| 183forw | UAUGAUGAAUGUGAUAGUUUGGAGAAU | 1195 |
| 1260rev | CCCAGGCAGCACUGACUACAGCAGAAU | 1196 |
| 1034rev | GUCUUGAUGAGGUAAAAAGAGGGGAGU | 1197 |
| 1027forw | AAAAAAUCGUUACAAUUUAUGGUGGAU | 1198 |
| 287forw | GUACUCAAGAUUAUAAGCAAUAGGAAU | 1199 |
| 101rev | UUAAUUUCUCUCCUUUGCAUAUUGGAU | 1200 |
| 1201rev | CCUACCCUGCCCCCUUCUCCUUAGAAU | 1201 |
| 1284forw | CUGCUGUAGUCAGUGCUGCCUGGGAAU | 1202 |
| 429rev | CACUUAGCACAGUACCUUACAUAGAGU | 1203 |
| 355forw | ACUUAGAUAUGAAGGGGAAAGAAGGGU | 1204 |
| 661rev | UGCAGUUUUACAUAUAAAUGACAGGAU | 1205 |
| 1703forw | GUUGCGGAGGGUGGGCCUGGGAGGGGU | 1206 |
| 1332forw | AAAAAUGUGAUGAUCAAAACUAGGAAU | 1207 |
| 1219forw | GGCAUUCUAAGGAGAAGGGGGCAGGGU | 1208 |
| 372forw | AAAGAAGGGUUUGAGAUAAUGUGGGAU | 1209 |
| 192forw | UGUGAUAGUUUGGAGAAUAAAUUGAAU | 1210 |
| 531forw | GCAGAUGCUAUGAAAGAAAAAGGGGAU | 1211 |
| 708rev | UAUGAGCCACCGCACCCGGCCGCGAAU | 1212 |
| 741rev | CGCUUCGGCCUCCCAAAGUGCUGGGAU | 1213 |
| 765forw | CCAGCACUUUGGGGAGGCCGAAGCGGGU | 1214 |
| 769forw | CACUUUGGGGAGGCCGAAGCGGGUGGAU | 1215 |
| 820rev | UUUUGUGUUUUUAGUAGAGACGGGGGU | 1216 |
| 877rev | UGUCUCAGCCUCCUGAGUAGCUGGGAU | 1217 |
| 886rev | CGAUUCUCGUGUCUCAGCCUCCUGAGU | 1218 |
| 905forw | CUACUCAGGAGGCUGAGACACGAGAAU | 1219 |
| 918rev | GCUCACUGCAACCUCUGCCUCCCGGGU | 1220 |
| 962rev | UGCUCUUUCGCCCAGGCUGGAUGGAGU | 1221 |
| 967rev | AGUCUUGCUCUUUCGCCCAGGCUGGAU | 1222 |
| 991rev | UAACGAUUUUUUUUUUGAGACGGAGU | 1223 |
| 94rev | GCCCAACUCUUCGCGGUGGCAGUGGGU | 1224 |
| 302rev | CCCCAUUGCCGGCGAGGGGUGACGGAU | 1225 |
| 997rev | AACUACCCCCAGAUGAUCCUAAGGAAU | 1226 |
| 237rev | ACUGCAUGUGUGAGCCGAGUCCUGGGU | 1227 |
| 309rev | CACAAGCCCCAUUGCCGGCGAGGGGGU | 1228 |
| 579forw | GAUCUCGACCAGUCCCCUCAACGGGGU | 1229 |
| 110forw | GAGGCACCCACUGCCACCGCGAAGAGU | 1230 |
| 1082forw | GCCCACCUUUAGGGUGAUAGCCUGAAU | 1231 |

TABLE 4-continued

| Guide RNA sequences | | |
|---|---|---|
| Seq Name | Sequence | Seq ID NO |
| 456forw | GUUGCCUGGAGCCGUUCCUGCGUGGGU | 1232 |
| 1391rev | AAAAAGCGAUCUUAGAUCACCUUGAGU | 1233 |
| 414forw | GCACCUCCAAAGUCGGCCAAAAUGAAU | 1234 |
| 1182forw | CUAUUACCUAAGUAGGUCCCCUGGAAU | 1235 |
| 192forw | GGCCGCAGGAAGAGGAACGGAGCGAGU | 1236 |
| 875forw | UCCCAGCCGGCAGUCUCCCACAAGAAU | 1237 |
| 1830forw | GGUGGUGCAGGGCCGUGAAGCAAGAAU | 1238 |
| 214rev | GGGUGCACGUCCCACAGCUCAGGGAAU | 1239 |
| 1724rev | CAUGCACUUGUCUGUAGUUCAAGGAGU | 1240 |
| 1070forw | GUGUAUAUAAAGGCCCACCUUUAGGGU | 1241 |
| 337rev | CUGGCCCAGUCAGUCAGGUUUGGGGGU | 1242 |
| 850rev | UUGUGGGAGACUGCCGGCUGGGGAGGGU | 1243 |
| 984rev | UGAUCCUAAGGAAUUGAAGGUAUGGAU | 1244 |
| 1086rev | UGACUUCUGACUUUCAAUCAUCAGGAU | 1245 |
| 843rev | AGACUGCCGGCUGGGAGGGUUGGGGGU | 1246 |
| 1014forw | UUCAAUUCCUUAGGAUCAUCUGGGGGU | 1247 |
| 1348forw | UGAUUUUGCCAAGAACUUGUCUAGAGU | 1248 |
| 1703rev | AGGAGUCCCCGCCCUUGCAAAAGGGAU | 1249 |
| 244rev | AAAGCGAACUGCAUGUGUGAGCCGAGU | 1250 |
| 945rev | UACCUUGUCGUGAUAAGUGGGCAGAAU | 1251 |
| 1847forw | AAGCAAGAAUGGCCACAGACUGGGAAU | 1252 |
| 1043forw | UUGCCAAGAGAGAGCAGCCAGGGGU | 1253 |
| 50rev | GGGCCGACCGCGGCCUCCAGGCGGGGU | 1254 |
| 131forw | AAGAGUUGGGCUCUGUCAGCCGCGGGU | 1255 |
| 1217forw | AGAUACAUUUCUUAGCACUAUUAGAAU | 1256 |
| 1763rev | AGAAGCAAAAGUACCACUAGAUGGAGU | 1257 |
| 431forw | CAAAAUGAAUGGGCAGUGAGCCGGGGU | 1258 |
| 1322forw | GCAUGGUUUUGUGGAAAAGUAAGGAAU | 1259 |
| 972rev | AUUGAAGGUAUGGAUUUGGGACGGAAU | 1260 |
| 629forw | UGAGAGAUCAUUUAACAUUUAAUGAAU | 1261 |
| 1003forw | AAAUCCAUACCUUCAAUUCCUUAGGAU | 1262 |
| 1244forw | UAAGAAAUGUAAAAAAACCUCUAGAGU | 1263 |
| 836rev | CGGCUGGGAGGGUUGGGGGUGGGGGGU | 1264 |
| 1462forw | UCCCACUCUGUCACCCAGAGCUGGAGU | 1265 |
| 764rev | UUAUUGGAACGCUAAGCUUGUGGGGGU | 1266 |
| 829rev | GAGGGUUGGGGGUGGGGGGUGUGGGAU | 1267 |
| 1445rev | CUGCACUCCAGCUCUGGGUGACAGAGU | 1268 |
| 755forw | CUUGGCGAUGACCUUGAGCAGUAGGAU | 1269 |

TABLE 4-continued

Guide RNA sequences

| Seq Name | Sequence | Seq ID NO |
|---|---|---|
| 1436forw | UUUCUUCUCUUUCUUUUGAGACGGAGU | 1270 |
| 1453rev | UGGGGACACUGCACUCCAGCUCUGGGU | 1271 |
| 1544forw | UUCUCUCAGCCUCCCAAGUAGCUGGGU | 1272 |
| 1570rev | CUGAAAAUACAAAAAAAUCAGCCGGGU | 1273 |
| 1621rev | GCGGGCGGAUCACCUGAGGUCAGGAGU | 1274 |
| 1638rev | CACUUUGGGAGGCAGAAGCGGGCGGAU | 1275 |
| 1666forw | CGCUUCUGCCUCCCAAAGUGCUGGGAU | 1276 |

In some aspects, a guide RNA molecule can be chemically synthesized using methods standard in the art. In some aspects, a guide RNA molecule can be chemically synthesized such that the guide RNA molecule comprises at least one chemical modification. In some aspects, a guide RNA molecule can be produced by in vitro transcription methods standard in the art, including, but not limited to, in vitro transcription using a plasmid template, in vitro transcription using a PCR-based template. In some aspects, in vitro transcription methods can be performed such that the produced guide RNA molecules comprise at least one chemical modification.

In some aspects, any of the compositions of the present disclosure can further comprise at least one mRNA and/or polynucleotide encoding a fusion protein comprising at least a portion of the MS2 coat protein (MCP) and at least one transactivation molecule. In some aspects, the at least one polynucleotide can be a plasmid comprising a nucleic acid encoding a fusion protein comprising at least a portion of the MS2 coat protein (MCP) and at least one transactivation molecule operably linked to at least one promoter sufficient to drive expression of the fusion protein.

In some aspects, any of the compositions of the present disclosure can further comprise at least one mRNA and/or polynucleotide encoding a fusion protein comprising at least a portion of MS2 coat protein (MCP) and at least one VP64 transactivation molecule. In some aspects, the at least one polynucleotide can be a plasmid comprising a nucleic acid encoding a fusion protein comprising at least a portion of MS2 coat protein (MCP) and at least one VP64 transactivation molecule operably linked to at least one promoter sufficient to drive expression of the fusion protein.

In some aspects, any of the compositions of the present disclosure can further comprise at least one mRNA and/or polynucleotide encoding a fusion protein comprising at least a portion of MS2 coat protein (MCP) and at least one P65-HSF transactivation molecule. In some aspects, the at least one polynucleotide can be a plasmid comprising a nucleic acid encoding a fusion protein comprising at least a portion of MS2 coat protein (MCP) and at least one P65-HSF transactivation molecule operably linked to at least one promoter sufficient to drive expression of the fusion protein.

In some aspects, any of the compositions of the present disclosure can further comprise at least one mRNA and/or polynucleotide encoding a fusion protein comprising at least one antibody that binds to the SunTag peptide and at least one transactivation molecule. In some aspects, the at least one polynucleotide can be a plasmid comprising a nucleic acid encoding a fusion protein comprising at least one antibody that binds to the SunTag peptide and at least one transactivation molecule operably linked to at least one promoter sufficient to drive expression of the fusion protein.

In some aspects, any of the compositions of the present disclosure can further comprise at least one mRNA and/or polynucleotide encoding a fusion protein comprising at least one antibody that binds to the SunTag peptide and at least one P65-HSF transactivation molecule. In some aspects, the at least one polynucleotide can be a plasmid comprising a nucleic acid encoding a fusion protein comprising at least one antibody that binds to the SunTag peptide and at least one P65-HSF transactivation molecule operably linked to at least one promoter sufficient to drive expression of the fusion protein.

In some aspects, any of the compositions of the present disclosure can further comprise at least one mRNA and/or polynucleotide encoding a fusion protein comprising at least one antibody that binds to the SunTag peptide and at least one VP64 transactivation molecule. In some aspects, the at least one polynucleotide can be a plasmid comprising a nucleic acid encoding a fusion protein comprising at least one antibody that binds to the SunTag peptide and at least one VP64 transactivation molecule operably linked to at least one promoter sufficient to drive expression of the fusion protein.

In some aspects, any composition of the present disclosure can further comprise at least one mRNA and/or polynucleotide encoding at least one rejuvenating factor. In some aspects, the at least one polynucleotide can be a plasmid comprising a nucleic acid encoding at least one rejuvenating factor operably linked to at least one promoter sufficient to drive expression of the at least one rejuvenating factor. A rejuvenating factor can comprise telomerase RNA component (TERC), telomerase associated reverse-transcriptase (TERT), protection of telomeres 1 (POT1), insulin-like growth factor 1 (IGF1), WD repeat containing antisense to TP53 (WRAP53), nuclear protein family A, member 3 (NOP3), heterogeneous nuclear ribonucleoprotein A1 (hnRNPA1), shelterin complex subunit and telomerase recruitment factor (ACD/TPP1), TRF-1 interacting ankyrin-related ADP-ribose polymerase (TNKS), telomeric repeat binding factor 1 (TRF-1), telomeric repeat binding factor 2 (TRF-2), TERF1 interacting nuclear factor 2 (TIN2), telomeric repeat binding factor 2 (Rap1), Dyskerin Pseudouridine Synthase 1 (DKC1), ribonucleoprotein NHP2 or any combination thereof.

The compositions of the present disclosure can be diluted in at least one cell culture medium. In some aspects, the at least one cell culture medium can comprise adjusted Opti-MEM (Opti-MEM with the pH adjusted to 8.2 or Opti-MEM with the pH adjusted to any value in the range between 7.4 and 8.6), non-adjusted Opti-MEM, human serum, fetal bovine serum (FBS), 1× phosphate-buffered saline (PBS) with the pH in the range between of 7.0 and 8.6 or any combination thereof.

In some aspects, any composition of the present disclosure can be packaged into any cellular delivery system known in the art. Cellular delivery systems can include, but are not limited to, adeno-associated virus (AAV; all serotypes, pseudotypes and hybrids), adenovirus, lentivirus, foamy-virus, herpes simplex virus (HSV) particle, retrovirus particle, alphavirus particle, flavivirus particle, rhabdovirus particle, measle virus particle, Newcastle disease virus particle, poxvirus particle, picornavirus particle, nanoparticles, exosomes and any combination thereof.

In some aspects, adeno-associate virus can include, but are not limited to AAV1, AAV2, AAV3, AAV4, AAV5, AAV6, AAV7, AAV8, AAV9, AAV10, AAV11, AAV12, AAV2/1, AAV2/2, AAV2/3, AAV2/4, AAV2/5, AAV2/6, AAV2/7, AAV2/8, AAV2/9, AAV-DJ, AAV-DJ8 or any combination thereof.

The present disclosure provides at least one viral particle, wherein the at least one viral particle comprises any composition of the present disclosure. In some aspects, an at least one viral particle can be an adeno-associated virus (AAV) particle. In some aspects, the at least one viral particle can be an AAV1, AAV2, AAV3, AAV4, AAV5, AAV6, AAV7, AAV8, AAV9, AAV10, AAV11, AAV12, AAV2/1, AAV2/2, AAV2/3, AAV2/4, AAV2/5, AAV2/6, AAV2/7, AAV2/8, AAV2/9, AAV-DJ, or AAV-DJ8 particle. In some aspects, the at least one viral particle can be an adenovirus particle. In some aspects, the at least one viral particle can be a foamy-virus particle. In some aspects, the at least one viral particle can be a lentivirus particle. A retrovirus particle can be MMSV or MSCV particle. A lentivirus particle can be HIV-1 or HIV-2 particle. An alphavirus particle can be SFV, SIN, VEE, or M1 particle. A flavivirus particle can be Kunjin virus, West Nile virus, or Dengue virus particle.

The present disclosure provides at least one exosome, microvesicle or liposome, wherein the at least one exosome, microvesicle or liposome comprises any composition of the present disclosure.

The present disclosure provides at least one nanoparticle, wherein the at least one nanoparticle comprises any composition of the present disclosure. In some aspects, a nanoparticle can comprise a liposome, a micelle, a polymer-based nanoparticle, a lipid-polymer based nanoparticle, a metal based nanoparticle, a nanocrystal, a carbon nanotube based nanoparticle or a polymeric micelle. In some aspects, a polymer-based nanoparticle can comprise a multiblock copolymer, a diblock copolymer, a polymeric micelle or a hyperbranched macromolecule. In some aspects, a polymer-based nanoparticle can comprise a multiblock copolymer a diblock copolymer. In some aspects, a polymer-based nanoparticle comprises a poly(lactic-co-glycolic acid) PLGA polymer.

In some aspects, the present disclosure provides a composition comprising: a) at least one modified mRNA molecule comprising a nucleic acid sequence encoding at least a portion of human telomerase reverse transcriptase (hTERT); b) at least one modified mRNA molecule comprising a nucleic acid sequence encoding at least a portion of at least one DNA targeting polypeptide, wherein the at least one DNA targeting polypeptide comprises dCas9 and a VP64-P65-Rta (VPR) molecule; and c) a plurality of guide RNA (gRNA) molecules, wherein at least one gRNA in the plurality is complementary to a nucleic acid sequence located upstream of the endogenous hTERC gene.

Kits

In some aspects, the present disclosure provides a kit comprising any composition of the present disclosure. In some aspects, the present disclosure provides a kit comprising any portion of any composition of the present disclosure. In some aspects, any kit of the present disclosure can be used in any method of the present disclosure.

In a non-limiting example, the present disclosure provides a kit comprising a) at least one first polynucleotide molecule comprising a nucleic acid sequence encoding at least a portion of telomerase reverse transcriptase (TERT); and b) at least one second polynucleotide molecule comprising a nucleic acid sequence encoding at least a portion of at least one DNA targeting polypeptide, wherein the DNA targeting polypeptide increases transcription of telomerase RNA component (TERC).

Rejuvenation Methods of the Present Disclosure

The present disclosure provides a method of rejuvenating at least one cell, the method comprising contacting the at least one cell with at least one composition of the present disclosure. The method can further comprise expanding the at least one cell contacted with the at least one composition of the present disclosure to produce a plurality of rejuvenated cells.

Thus, the present disclosure provides a method of rejuvenating at least one cell, the method comprising contacting the at least one cell with a composition comprising a) at least one first polynucleotide molecule comprising a nucleic acid sequence encoding at least a portion of telomerase reverse transcriptase (TERT); and b) at least one second polynucleotide molecule comprising a nucleic acid sequence encoding at least a portion of at least one DNA targeting polypeptide, wherein the DNA targeting polypeptide increases transcription of telomerase RNA component (TERC).

The present disclosure provides a method of treating and/or preventing a disease in a subject comprising: a) contacting at least one cell with at least one composition of the present disclosure; b) expanding the at least one cell contacted with the at least one composition of the present disclosure to produce a plurality of rejuvenated cells; and c) administering the plurality of rejuvenated cells to the subject.

The present disclosure provides a method of treating and/or preventing a disease in a subject comprising: a) contacting at least one cell with at least one composition of the present disclosure; b) expanding the at least one cell contacted with the at least one composition of the present disclosure to produce a plurality of rejuvenated cells; c) culturing the plurality of rejuvenated cells under conditions sufficient to transform the plurality of rejuvenated cells into at least one tissue or organ; and d) administering the at least one tissue or organ to the subject.

The present disclosure provides a method of producing an in vitro tissue or organ comprising: a) contacting at least one cell with a composition of the present disclosure; b) expanding the at least one cell contacted with the at least one composition of the present disclosure to produce a plurality of rejuvenated cells; c) culturing the plurality of rejuvenated cells under conditions sufficient to transform the plurality of rejuvenated cells into at least one tissue or organ. The at least one tissue or organ can be used for further in vitro testing, including, but not limited to the testing or drugs and/or therapeutic compounds.

The present disclosure provides a method of producing a plurality of rejuvenated cells comprising: a) contacting at least one cell with at least one composition of the present disclosure; b) expanding the at least one cell contacted with the at least one composition of the present disclosure to produce a plurality of rejuvenated cells.

The present disclosure provides a method of producing a plurality of rejuvenated edited cells comprising: a) contacting a plurality of cells with a gene editing system such that at least one gene in the genome of at least one cell in the plurality is edited, thereby producing at least one edited cell; b) isolating the at least one edited cell; c) contacting the isolated at least one edited cell with at least one composition of the present disclosure; and d) expanding the at least one cell contacted with the at least one composition of the present disclosure to produce a plurality of rejuvenated edited cell.

The present disclosure provides a method of treating and/or preventing a disease in a subject comprising: a) contacting a plurality of cells with a gene editing system such that at least one gene in the genome of at least one cell in the plurality is edited, thereby producing at least one edited cell; b) isolating the at least one edited cell; c) contacting the isolated at least one edited cell with at least one composition of the present disclosure; d) expanding the at least one cell contacted with the at least one composition of the present disclosure to produce a plurality of rejuvenated edited cells; and e) administering to the subject the plurality of rejuvenated edited cells.

In some aspects, the present disclosure provides a method of treating epidermolysis bullosa (EB) in a subject comprising: a) contacting a plurality of cells comprising keratinocytes, dermal fibroblasts, mesenchymal stem/stromal cells or any combination thereof with a gene editing system such that at least one gene in the genome of at least one cell in the plurality is edited, thereby producing at least one edited cell; b) isolating the at least one edited cell; c) contacting the isolated at least one edited cell with at least one composition of the present disclosure; d) expanding the at least one cell contacted with the at least one composition of the present disclosure to produce a plurality of rejuvenated edited cells; and e) administering to the subject the plurality of rejuvenated edited cells.

In some aspects, the present disclosure provides a method of rejuvenating at least one cell in a subject comprising administering to the subject at least one therapeutically effective amount of at least one composition of the present disclosure. In some aspects, the present disclosure provides a method of rejuvenating at least one cell in a subject comprising administering to the subject at least one therapeutically effective amount of at least one portion of at least one composition of the present disclosure.

In some aspects, the present disclosure provides a method of rejuvenating at least one subject comprising administering at least one therapeutically effective amount of at least one composition of the present disclosure. In some aspects, the present disclosure provides a method of rejuvenating at least one subject comprising administering at least one therapeutically effective amount of at least one portion of at least one composition of the present disclosure.

In some aspects of the methods of the present disclosure, contacting at least one cell with at least one composition of the present disclosure can comprise contacting the at least one cell with a first portion of the at least one composition of the present disclosure and then contacting the at least one cell with a second portion of the least one composition of the present disclosure at least about 1 hour, or at least about 2 hours, or at least about 3 hours, or at least about 4 hours, or at least about 5 hours, or at least about 6 hours, or at least about 7 hours, or at least about 8 hours, or at least about 9 hours, or at least about 10 hours, or at least about 11 hours, or at least about 12 hours, or at least about 16 hours, or at least about 20 hours, or at least about 24 hours, or at least about 28 hours, or at least about 32 hours, or at least about 36 hours, or at least about 40 hours, or at least about 44 hours, or at least about 48 hours, or at least about 52 hours, or at least about 56 hours, or at least about 60 hours, or at least about 64 hours, or at least about 68 hours, or at least about 72 hours, or at least about 76 hours, or at least about 80 hours, or at least about 84 hours, or at least about 88 hours, or at least about 92 hours, or at least about 96 hours after contacting the at least one cell with the first portion of the at least one composition of the present disclosure.

Thus, contacting at least one cell with at least one composition of the present disclosure can comprise: a) contacting the at least one cell with at least one first polynucleotide molecule comprising a nucleic acid sequence encoding at least a portion of telomerase reverse transcriptase (TERT); and b) contacting the at least one cell with at least one second polynucleotide molecule comprising a nucleic acid sequence encoding at least a portion of at least one DNA targeting polypeptide, wherein the DNA targeting polypeptide increases transcription of telomerase RNA component (TERC), at least about 24 hours after step (a). Optionally, steps (a) and step (b) can be repeated about every 1, or about every 2, or about every 3, or about every 4, or about every 5, or about every 6, or about every 7, or about every 8, or about every 9, or about every 10 days.

In some aspects of the methods of the present disclosure, contacting at least one cell with at least one composition of the present disclosure can further comprise pretreating the at least one cell. In some aspects, pretreating a cell can comprise contacting the at least one cell with at least one first polynucleotide molecule comprising a nucleic acid sequence encoding at least a portion of telomerase reverse transcriptase (TERT) once about every 4 hours, or about every 8 hours, or about every 12 hours, or about every 16 hours, or about every 20 hours, or about every 24 hours, or about every 28 hours, or about every 32 hours, or about every 36 hours, or about every 40 hours, or about every 44 hours, or about every 48 hours. In some aspects, the at least one cell can be pretreated for at least about 2, or at least about 4, or at least about 6, or at least about 8, or at least about 10 days.

In some aspects, contacting at least one cell with at least one composition of the present disclosure can comprise: a) contacting the at least one cell with at least one first polynucleotide molecule comprising a nucleic acid sequence encoding at least a portion of telomerase reverse transcriptase (TERT) and at least one second polynucleotide molecule comprising a nucleic acid sequence encoding at least a portion of at least one DNA targeting polypeptide, wherein the DNA targeting polypeptide increases transcription of telomerase RNA component (TERC); and b) repeating step (a) about every 1, or about every 2, or about every 3, or about every 4, or about every 5, or about every 6, or about every 7, or about every 8, or about every 9, or about every 10 days.

Figure 8:
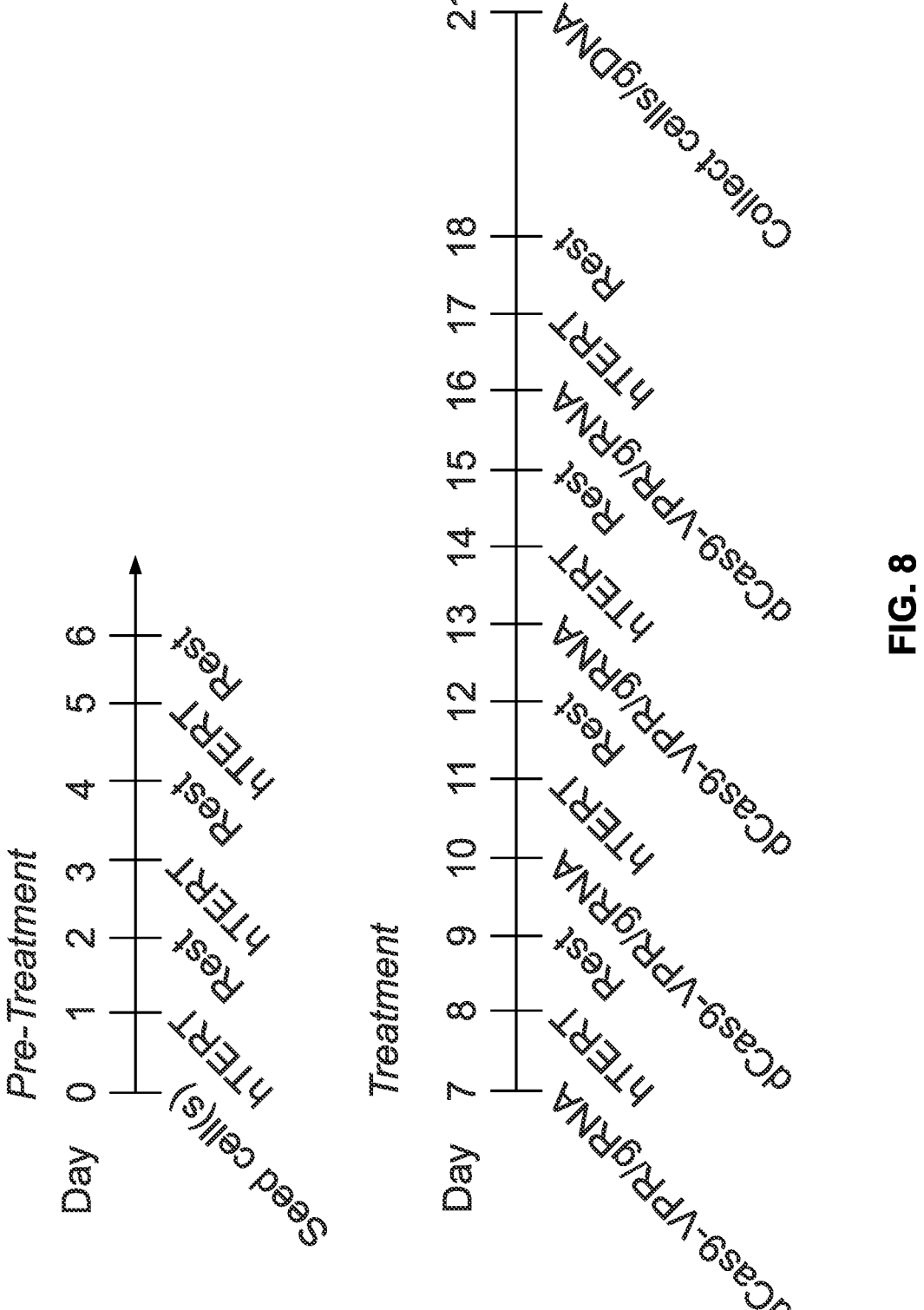
FIG. 8 is schematic overview of one of the transfection regimes of the present disclosure.
Figure 10:
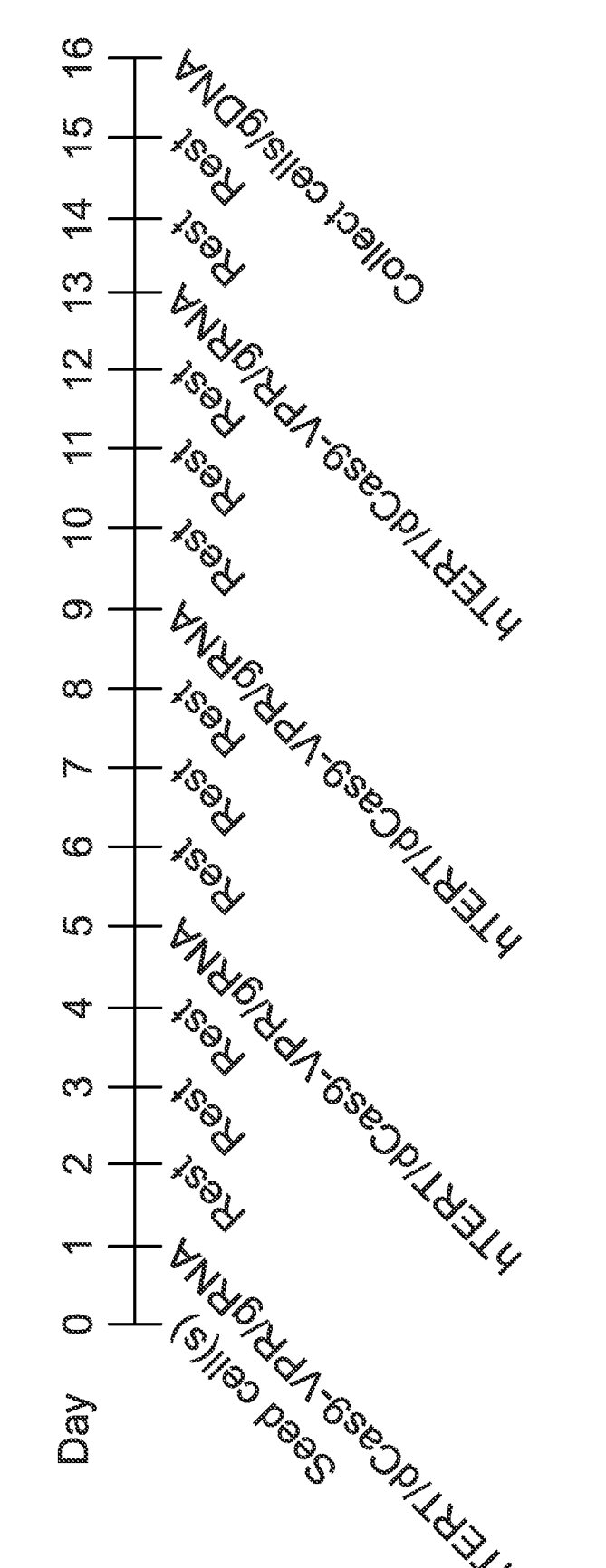
FIG. 10 is a schematic overview of an alternative transfection regime of the present disclosure.
Figure 11:
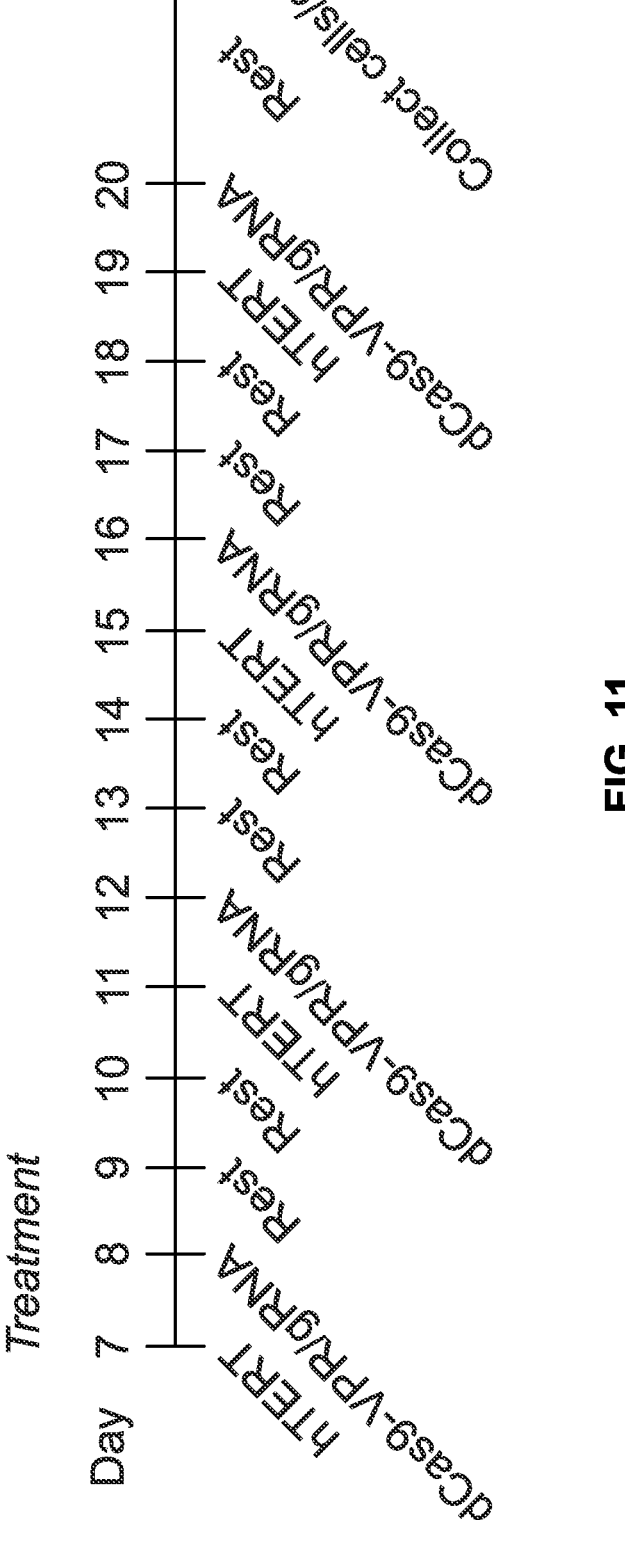
FIG. 11 is a schematic overview of another transfection regime of the present disclosure.

Exemplary transfection regimes are shown in FIGS. 8, 10 and 11.

In some aspects of the methods of the present disclosure, contacting at least one cell with a composition of the present disclosure can comprise transfection. In some aspects, transfection can comprise the use of lipofectamine. In some aspects, transfection can comprise any standard transfection method known in the art. In some aspects of the methods of the present disclosure, contacting at least one cell with a composition of the present disclosure can comprise electroporation.

In some aspects of the methods of the present disclosure, contacting at least one cell can comprise transfection, transduction, electroporation, nucleofection, at least one cell-penetrating peptide or any combination thereof.

In some aspects of the methods of the present disclosure, contacting at least one cell with a composition of the present disclosure can comprise nucleofection. In some aspects, nucleofection can comprise any standard nucleofection method known in the art.

In some aspects of the methods of the present disclosure, contacting at least one cell with a composition of the present disclosure can comprise contacting the cell with at least one cell-penetrating peptides. In some aspects, a cell-penetrating peptide can be an HIV-derived TAT protein. In some aspects, a cell-penetrating peptide can comprise polyarginine. Without wishing to be bound by theory, the at least one cell-penetrating peptide can aid in the delivery of a protein or a RNP complex of the present disclosure to the cytoplasm of a target cell.

In some aspects, at least one composition or at least one portion of at least one composition of the present disclosure can be administered to a subject orally, nasally, transdermally, pulmonary, inhalationally, buccally, sublingually, intraperitoneally, subcutaneously, intramuscularly, intravenously, rectally, intrapleurally, intrathecally and/or parenterally.

In some aspects of the methods of the present disclosure, expanding at least one cell can comprise culturing the at least one cell using adjusted Opti-MEM, non-adjusted Opti-MEM, human serum, fetal bovine serum (FBS) or any combination thereof.

In some aspect of the methods of the present disclosure, rejuvenating at least one cell can comprise increasing the expression of TERC in the at least one cell. In some aspects, rejuvenating at least one cell can comprise increasing the expression of TERC by at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%, or at least about 150%, or at least about 200%, or at least about 250%, or at least about 300%, or at least about 350%, or at least about 400%, or at least about 450%, or at least about 500%, or at least about 550%, or at least about 600%, or at least about 650%, or at least about 700%, or at least about 750%, or at least about 800%, or at least about 850%, or at least about 900%, or at least about 950%, or at least about 1000%, or at least about 10,000%, or at least about 100,000%, or at least about 1,000,000%, or at least about 10,000,000%, or at least about 100,000,000%. In some aspects, rejuvenating at least one cell can comprise increasing the expression of TERC in the at least one cell such that the expression level of TERC after contacting the at least one cell with at least one composition of the present disclosure is at least about 0.5 times, or at least about 1.0 times, or at least about 1.5 times, or at least about 2.0 times, or at least about 2.5 times, or at least about 3.0 times, or at least about 3.5 times, or at least about 4.0 times, or at least about 4.5 times, or at least about 5.0 times, or at least about 5.5 times, or at least about 6.0 times, or at least about 6.5 times, or at least about 7.0 times, or at least about 7.5 times, or at least about 8.0 times, or at least about 8.5 times, or at least about 9.0 times, or at least about 9.5 times, or at least about 10.0 times, or at least about 25 times, or at least about 50 times, or at least about 75 times, or at least about 100 times, or at least about 1000 times, or at least about 10,000 times, or at least about 20,000 times, or at least about 30,000 times, or at least about 40,000 times, or at least about 50,000 times, or at least about 60,000 times, or at least about 70,000 times, or at least about 80,000 times, or at least about 90,000, or at least about 100,000 times greater as compared to the expression level of TERC prior to contacting the at least one cell with the at least one composition of the present disclosure.

In some aspects of the methods of the present disclosure, rejuvenating at least one cell can comprise increasing the expression of TERC in the at least one cell such that the expression level of TERC is at least about the same as, or at least about 1.5 times, or at least about 2.0 times, or at least about 2.5 times, or at least about 3.0 times, or at least about 3.5 times, or at least about 4.0 times, or at least about 4.5 times, or at least about 5.0 times, or at least about 5.5 times, or at least about 6.0 times, or at least about 6.5 times, or at least about 7.0 times, or at least about 7.5 times, or at least about 8.0 times, or at least about 8.5 times, or at least about 9.0 times, or at least about 9.5 times, or at least about 10.0 times, or at least about 25 times, or at least about 50 times, or at least about 75 times, or at least about 100 times, or at least about 1000 times, or at least about 10,000 times, or at least about 20,000 times, or at least about 30,000 times, or at least about 40,000 times, or at least about 50,000 times, or at least about 60,000 times, or at least about 70,000 times, or at least about 80,000 times, or at least about 90,000, or at least about 100,000 times the expression of TERC in a control cell.

In some aspect of the methods of the present disclosure, rejuvenating at least one cell can comprise increasing the expression of TERT in the at least one cell. In some aspects, rejuvenating at least one cell can comprise increasing the expression of TERT by at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%, or at least about 150%, or at least about 200%, or at least about 250%, or at least about 300%, or at least about 350%, or at least about 400%, or at least about 450%, or at least about 500%, or at least about 550%, or at least about 600%, or at least about 650%, or at least about 700%, or at least about 750%, or at least about 800%, or at least about 850%, or at least about 900%, or at least about 950%, or at least about 1000% or at least about 10,000%, or at least about 100,000%, or at least about 1,000,000%, or at least about 10,000,000%, or at least about 100,000,000%. In some aspects, rejuvenating at least one cell can comprise increasing the expression of TERT in the at least one cell such that the expression level of TERT after contacting the at least one cell with at least one composition of the present disclosure is at least about 0.5 times, or at least about 1.0 times, or at least about 1.5 times, or at least about 2.0 times, or at least about 2.5 times, or at least about 3.0 times, or at least about 3.5 times, or at least about 4.0 times, or at least about 4.5 times, or at least about 5.0 times, or at least about 5.5 times, or at least about 6.0 times, or at least about 6.5 times, or at least about 7.0 times, or at least about 7.5 times, or at least about 8.0 times, or at least about 8.5 times, or at least about 9.0 times, or at least about 9.5 times, or at least about 10.0 times, or at least about 25 times, or at least about 50 times, or at least about 75 times, or at least about 100 times, or at least about 1000 times, or at least about 10,000 times, or at least about 20,000 times, or at least about 30,000 times, or at least about 40,000 times, or at least about 50,000 times, or at least about 60,000 times, or at least about 70,000 times, or at least about 80,000 times, or at least about 90,000, or at least about 100,000 times greater as compared to the expression level of TERT prior to contacting the at least one cell with the at least one composition of the present disclosure.

In some aspects of the methods of the present disclosure, rejuvenating at least one cell can comprise increasing the expression of TERT in the at least one cell such that the expression level of TERT is at least about the same as, or at least about 1.5 times, or at least about 2.0 times, or at least about 2.5 times, or at least about 3.0 times, or at least about 3.5 times, or at least about 4.0 times, or at least about 4.5 times, or at least about 5.0 times, or at least about 5.5 times, or at least about 6.0 times, or at least about 6.5 times, or at least about 7.0 times, or at least about 7.5 times, or at least about 8.0 times, or at least about 8.5 times, or at least about 9.0 times, or at least about 9.5 times, or at least about 10.0 times, or at least about 25 times, or at least about 50 times, or at least about 75 times, or at least about 100 times, or at least about 1000 times, or at least about 10,000 times, or at least about 20,000 times, or at least about 30,000 times, or at least about 40,000 times, or at least about 50,000 times, or at least about 60,000 times, or at least about 70,000 times, or at least about 80,000 times, or at least about 90,000, or at least about 100,000 times the expression of TERT in a control cell.

In some aspects of the methods of the present disclosure, rejuvenating at least one cell can comprise increasing the total number of population doublings exhibited by the at least one cell. In some aspects, rejuvenating at least one cell can comprise increasing the total number of population doublings exhibited by the at least one cell by at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%, or at least about 150%, or at least about 200%, or at least about 250%, or at least about 300%, or at least about 350%, or at least about 400%, or at least about 450%, or at least about 500%, or at least about 550%, or at least about 600%, or at least about 650%, or at least about 700%, or at least about 750%, or at least about 800%, or at least about 850%, or at least about 900%, or at least about 950%, or at least about 1,000%, or at least about 2,000%, or at least about 3,000%, or at least about 4,000%, or at least about 5,000%, or at least about 6,000%, or at least about 7,000%, or at least about 8,000%, or at least about 9,000%, or at least about 10,000%, or at least about 20,000%, or at least about 30,000%, or at least about 40,000%, or at least about 50,000%, or at least about 60,000%, or at least about 70,000%, or at least about 80,000%, or at least about 90,000%, or at least about 100,000%.

In some aspects, rejuvenating at least one cell can comprise increasing the total number of population doublings such that the number of population doublings exhibited by the at least one cell is at least about 1.5 times, or at least about 2.0 times, or at least about 2.5 times, or at least about 3.0 times, or at least about 3.5 times, or at least about 4.0 times, or at least about 4.5 times, or at least about 5.0 times, or at least about 5.5 times, or at least about 6.0 times, or at least about 6.5 times, or at least about 7.0 times, or at least about 7.5 times, or at least about 8.0 times, or at least about 8.5 times, or at least about 9.0 times, or at least about 9.5 times, or at least about 10.0 times, or at least about 25 times, or at least about 50 times, or at least about 75 times, or at least about 100 times, or at least about 200 times, or at least about 300 times, or at least about 400 times, or at least about 500 times, or at least about 600 times, or at least about 700 times or at least about 800 times, or at least about 900 times, or at least about 1,000 times the total number of population doublings exhibited by at least one control cell.

In some aspects of the methods of the present disclosure, rejuvenating at least one cell can comprise increasing the length of telomeres in the at least one cell. In some aspects, rejuvenating at least one cell can comprising increasing the length of telomeres in the at least one cell by at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%, or at least about 150%, or at least about 200%, or at least about 250%, or at least about 300%, or at least about 350%, or at least about 400%, or at least about 450%, or at least about 500%, or at least about 550%, or at least about 600%, or at least about 650%, or at least about 700%, or at least about 750%, or at least about 800%, or at least about 850%, or at least about 900%, or at least about 950%, or at least about 1000%, or at least about 2000%, or at least about 3000%, or at least about 4000%, or at least about 5000%, or at least about 6000%, or at least about 7000%, or at least about 8,000%, or at least about 9,000%, or at least about 10,000%, or at least about 20,000%, or at least about 30,000%, or at least about 40,000%, or at least about 50,000%, or at least about 60,000%, or at least about 70,000%, or at least about 80,000%, or at least about 90,000%, or at least about 100,000%.

In some aspects, rejuvenating at least one cell can comprise increasing the length of telomeres in the at least one cell such that the length of the telomeres in the at least one cell is the same as, or at least about 1.5 times, or at least about 2.0 times, or at least about 2.5 times, or at least about 3.0 times, or at least about 3.5 times, or at least about 4.0 times, or at least about 4.5 times, or at least about 5.0 times, or at least about 5.5 times, or at least about 6.0 times, or at least about 6.5 times, or at least about 7.0 times, or at least about 7.5 times, or at least about 8.0 times, or at least about 8.5 times, or at least about 9.0 times, or at least about 9.5 times, or at least about 10.0 times, or at least about 25 times, or at least about 50 times, or at least about 75 times, or at least about 100 times, or at least about 200 times, or at least about 300 times, or at least about 400 times, or at least about 500 times, or at least about 600 times, or at least about 700 times, or at least about 800 times, or at least about 900 times or at least about 1,000 times the length of telomeres in at least one control cell.

In some aspects of the methods of the present disclosure, rejuvenating at least one cell can comprise increasing the mitochondrial DNA copy number in the at least one cell. In some aspects, rejuvenating at least one cell can comprise increasing the mitochondrial DNA copy number in the at least one cell by a at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%, or at least about 150%, or at least about 200%, or at least about 250%, or at least about 300%, or at least about 350%, or at least about 400%, or at least about 450%, or at least about 500%, or at least about 550%, or at least about 600%, or at least about 650%, or at least about 700%, or at least about 750%, or at least about 800%, or at least about 850%, or at least about 900%, or at least about 950%, or at least about 1,000%, or at least about 2,000%, or at least about 3,000%, or at least about 4,000%, or at least about 5,000%, or at least about 6,000%, or at least about 7,000%, or at least about 8,000%, or at least about 9,000%, or at least about 10,000%, or at least about 20,000%, or at least about 30,000%, or at least about 40,000%, or at least about 50,000%, or at least about 60,000%, or at least about 70,000%, or at least about 80,000%, or at least about 90,000%, or at least about 100,000%.

In some aspects, rejuvenating at least one cell can comprise increasing the mitochondrial DNA copy number in the at least one cell such that the mitochondrial DNA copy number is the same as, or at least about 1.5 times, or at least about 2.0 times, or at least about 2.5 times, or at least about 3.0 times, or at least about 3.5 times, or at least about 4.0 times, or at least about 4.5 times, or at least about 5.0 times, or at least about 5.5 times, or at least about 6.0 times, or at least about 6.5 times, or at least about 7.0 times, or at least about 7.5 times, or at least about 8.0 times, or at least about 8.5 times, or at least about 9.0 times, or at least about 9.5 times, or at least about 10.0 times, or at least about 25 times, or at least about 50 times, or at least about 75 times, or at least about 100 times, or at least about 200 times, or at least about 300 times, or at least about 400 times, or at least about 500 times, or at least about 600 times, or at least about 700 times, or at least about 800 times, or at least about 900 times, or at least about 1000 times the mitochondrial DNA copy number in at least one control cell.

In some aspects of the methods of the present disclosure, rejuvenating at least one cell can comprise increasing the amount of mitochondrial DNA in the at least one cell. In some aspects, rejuvenating at least one cell can comprise increasing the amount of mitochondrial DNA in the at least one cell by at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%, or at least about 150%, or at least about 200%, or at least about 250%, or at least about 300%, or at least about 350%, or at least about 400%, or at least about 450%, or at least about 500%, or at least about 550%, or at least about 600%, or at least about 650%, or at least about 700%, or at least about 750%, or at least about 800%, or at least about 850%, or at least about 900%, or at least about 950%, or at least about 1,000%, or at least about 2,000%, or at least about 3,000%, or at least about 4,000%, or at least about 5,000%, or at least about 6,000%, or at least about 7,000%, or at least about 8,000%, or at least about 9,000%, or at least about 10,000%, or at least about 20,000%, or at least about 30,000%, or at least about 40,000%, or at least about 50,000%, or at least about 60,000%, or at least about 70,000%, or at least about 80,000%, or at least about 90,000%, or at least about 100,000%.

In some aspects, rejuvenating at least one cell can comprise increasing the amount of mitochondrial DNA in the at least one cell such that the amount of mitochondrial DNA in the at least one cell is the same as, or at least about 1.5 times, or at least about 2.0 times, or at least about 2.5 times, or at least about 3.0 times, or at least about 3.5 times, or at least about 4.0 times, or at least about 4.5 times, or at least about 5.0 times, or at least about 5.5 times, or at least about 6.0 times, or at least about 6.5 times, or at least about 7.0 times, or at least about 7.5 times, or at least about 8.0 times, or at least about 8.5 times, or at least about 9.0 times, or at least about 9.5 times, or at least about 10.0 times, or at least about 25 times, or at least about 50 times, or at least about 75 times, or at least about 100 times, or at least about 200 times, or at least about 300 times, or at least about 400 times, or at least about 500 times, or at least about 600 times, or at least about 700 times, or at least about 800 times, or at least about 900 times, or at least about 1000 times the amount of mitochondrial DNA in at least one control cell.

In some aspects of the methods of the present disclosure, rejuvenating at least one cell can comprise increasing the number of mitochondria in the at least one cell. In some aspects, rejuvenating at least one cell can comprise increasing the number of mitochondria in the at least one cell by at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%, or at least about 150%, or at least about 200%, or at least about 250%, or at least about 300%, or at least about 350%, or at least about 400%, or at least about 450%, or at least about 500%, or at least about 550%, or at least about 600%, or at least about 650%, or at least about 700%, or at least about 750%, or at least about 800%, or at least about 850%, or at least about 900%, or at least about 950%, or at least about 1,000%, or at least about 2,000%, or at least about 3,000%, or at least about 4,000%, or at least about 5,000%, or at least about 6,000%, or at least about 7,000%, or at least about 8,000%, or at least about 9,000%, or at least about 10,000%, or at least about 20,000%, or at least about 30,000%, or at least about 40,000%, or at least about 50,000%, or at least about 60,000%, or at least about 70,000%, or at least about 80,000%, or at least about 90,000%, or at least about 100,000%.

In some aspects, rejuvenating at least one cell can comprise increasing the number of mitochondria in the at least one cell such that the number of mitochondria is the same as, or at least about 1.5 times, or at least about 2.0 times, or at least about 2.5 times, or at least about 3.5 times, or at least about 4.0 times, or at least about 4.5 times, or at least about 5.0 times, or at least about 5.5 times, or at least about 6.0 times, or at least about 6.5 times, or at least about 7.0 times, or at least about 7.5 times, or at least about 8.0 times, or at least about 8.5 times, or at least about 9.0 times, or at least about 9.5 times, or at least about 10.0 times, or at least about 25 times, or at least about 50 times, or at least about 75 times, or at least about 100 times, or at least about 200 times, or at least about 300 times, or at least about 400 times, or at least about 500 times, or at least about 600 times, or at least about 700 times, or at least about 800 times, or at least about 900 times, or at least about 1,000 times the amount of mitochondria in at least one control cell.

In some aspects of the methods of the present disclosure, rejuvenating at least one cell can comprise increasing the migration activity of the at least one cell. In some aspects, rejuvenating at least one cell can comprise increasing the migration activity of the at least one cell by at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%, or at least about 150%, or at least about 200%, or at least about 250%, or at least about 300%, or at least about 350%, or at least about 400%, or at least about 450%, or at least about 500%, or at least about 550%, or at least about 600%, or at least about 650%, or at least about 700%, or at least about 750%, or at least about 800%, or at least about 850%, or at least about 900%, or at least about 950%, or at least about 1,000%, or at least about 2,000%, or at least about 3,000%, or at least about 4,000%, or at least about 5,000%, or at least about 6,000%, or at least about 7,000%, or at least about 8,000%, or at least about 9,000%, or at least about 10,000%, or at least about 20,000%, or at least about 30,000%, or at least about 40,000%, or at least about 50,000%, or at least about 60,000%, or at least about 70,000%, or at least about 80,000%, or at least about 90,000%, or at least about 100,000%.

In some aspects, rejuvenating at least one cell can comprise increasing the migration activity of the at least one cell such that the migration activity of the at least one cell is the same as, or at least 1.5 times, or at least about 2.0 times, or at least about 2.5 times, or at least about 3.5 times, or at least about 4.0 times, or at least about 4.5 times, or at least about 5.0 times, or at least about 5.5 times, or at least about 6.0 times, or at least about 6.5 times, or at least about 7.0 times, or at least about 7.5 times, or at least about 8.0 times, or at least about 8.5 times, or at least about 9.0 times, or at least about 9.5 times, or at least about 10.0 times, or at least about 25 times, or at least about 50 times, or at least about 75 times, or at least about 100 times, or at least about 200 times, or at least about 300 times, or at least about 400 times, or at least about 500 times, or at least about 600 times, or at least about 700 times, or at least about 800 times, or at least about 900 times, or at least about 1000 times the migration activity of at least one control cell.

In some aspects, rejuvenating at least one cell can comprise restoring the young-like state of thiol group oxidation on at least one protein in the at least one cell. In a non-limiting example, rejuvenating can comprise increasing the thiol group oxidation of at least one protein in the at least one cell such that the thiol group oxidation of the at least one protein in the at least one cell is comparable to the thiol group oxidation of the same protein in a young cell. In a non-limiting example, rejuvenating can comprise decreasing the thiol group oxidation of at least one protein in the at least one cell such that the thiol group oxidation of the at least one protein in the at least one cell is comparable to the thiol group oxidation of the same protein in a young cell.

In some aspects, rejuvenating at least one cell can comprise decreasing the thiol group oxidation of at least one protein in the at least one cell by at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%. In some aspects, the at least one protein can be EIF2S1, TM9F3 or USP14.

In some aspects, rejuvenating at least one cell can comprise increasing the thiol group oxidation of at least one protein in the at least one cell by at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%, or at least about 150%, or at least about 200%, or at least about 250%, or at least about 300%, or at least about 350%, or at least about 400%, or at least about 450%, or at least about 500%, or at least about 550%, or at least about 600%, or at least about 650%, or at least about 700%, or at least about 750%, or at least about 800%, or at least about 850%, or at least about 900%, or at least about 950%, or at least about 1,000%, or at least about 2,000%, or at least about 3,000%, or at least about 4,000%, or at least about 5,000%, or at least about 6,000%, or at least about 7,000%, or at least about 8,000%, or at least about 9,000%, or at least about 10,000%, or at least about 20,000%, or at least about 30,000%, or at least about 40,000%, or at least about 50,000%, or at least about 60,000%, or at least about 70,000%, or at least about 80,000%, or at least about 90,000%, or at least abouat 100,000%. In some aspects, the at least one protein can be IGFB5.

In some aspects of the methods of the present disclosure, rejuvenating at least one cell can comprise reducing senescence-associated DNA methylation in the at least one cell. In some aspects, reducing senescence-associated DNA methylation in the at least one cell can comprise reducing DNA methylation at least one genomic location which is associated with senescence-related methylation. In some aspects, the at least one genomic location can be cg09780241, cg05099537, cg24541426, cg04316624, cg13180312, cg13316854, cg15726154, cg21507095, cg01697719 or any combination thereof.

In some aspects, rejuvenating at least one cell can comprise reducing DNA methylation at least one genomic location by at least about 1%, or at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 100%.

In some aspects, an at least one control cell can comprise a cell that has not been contacted with a composition of the present disclosure. In some aspects, an at least one control cell can comprise a cell that has not been contacted with a composition of the present disclosure but has otherwise been grown under the same conditions as at least one cell contacted with a composition of the present disclosure. In some aspects, an at least one control cell can be a dermal fibroblast isolated from a human subject that is 50 years old. In some aspects, an at least one control cell can be a neonatal human epidermal keratinocyte (HEKn). In some aspects, an at least one control cell can be an induced pluripotent stem cell (iPSC).

In some aspects, editing at least one cell can comprise the correction of at least one gene in the at least one cell, the knockout of at least one gene in the at least one cell, the insertion of at least one DNA sequence into the genome of the at least one cell, the deletion of at least one DNA sequence in the genome of the at least one cell or any combination thereof. In some aspects, a gene editing system can comprise any system known in the art for modifying the genome of a target cell, including, but not limited to CRISPR methods, viral methods, etc.

An at least one cell can be obtained and/or isolated from a subject. In some aspects, an at least one cell can be any somatic cell. In some aspects, an at least one cell can be a fibroblast, a keratinocyte, a mesenchymal stem/stromal cell, a peripheral blood mononuclear cell, a chimeric antigen receptor T cell (CAR-T cell), an endothelial cell, a chondrocyte, a muscle stem cell, a neural stem cell, a hepatocyte, a limbal stem cell, a retinal pigmented epithelial cell, a hematopoietic stem cell, a macrophage, a cardiomyocyte, a pancreatic cell, a β-cell or any combination thereof.

In some aspects, an at least one cell can be an Exocrine secretory epithelial cell, a Brunner's gland cell, an insulated goblet cell of the respiratory and digestive tracts, a stomach foveolar cell, a chief cell, a parietal cell, a pancreatic acinar cell, a paneth cell of small intestine, a Type II pneumocyte of lung, a club cell of lung, a barrier cell, a type I pneumocyte, a gall bladder epithelial cell, a centroacinar cell, an intercalated duct cell, an intestinal brush border cell, a hormone-secreting cell, an enteroendocrine cell, a K cell, an L cell, an I cell, a G cell, an Enterochromaffin cell, an Enterochromaffin-like cell, an N cell, an S cell, a D cell, a Mo cell (or M cell), a Thyroid gland cell, a Thyroid epithelial cell, a Parafollicular cell, a Parathyroid gland cell, a Parathyroid chief cell, an Oxyphil cell, a Pancreatic islets (islets of Langerhans), an Alpha cell, a Beta cell, a Delta cell, an Epsilon cell, a PP cell (gamma cell), an Exocrine secretory epithelial cell, a Salivary gland mucous cell, a Salivary gland serous cell, a Von Ebner's gland cell, a Mammary gland cell, a Lacrimal gland cell, a Ceruminous gland cell, an Eccrine sweat gland dark cell, a Eccrine sweat gland clear cell, an Apocrine sweat gland cell, a Gland of Moll cell, a Sebaceous gland cell, a Bowman's gland cell, an Anterior/Intermediate pituitary cell, a Corticotrope, a Gonadotrope, a Lactotrope, a Melanotrope, a Somatotrope, a thyrotrope, a magnocellular neurosecretory cell, a Parvocellular neurosecretory cell, a Chromaffin cell, an Epithelial cell, a Keratinocyte, an Epidermal basal cell, a Melanocyte, a Trichocyte, a hair shaft cell, a Cortical hair shaft cell, a Cuticular hair shaft cell, a Huxley's layer hair root sheath cell, a Henle's layer hair root sheath cell, an Outer root sheath hair cell, a Surface epithelial cell, a basal cell (stem cell), an Intercalated duct cell, a Striated duct cell, a Lactiferous duct cell, an Ameloblast, an Oral cell, an Odontoblast, a Cementoblast, a neuron, an Auditory inner hair cell, an auditory outer hair cell, a Basal cell of olfactory epithelium cell, a Cold-sensitive primary sensory neuron, a Heat-sensitive primary sensory neuron, a Merkel cell, a Olfactory receptor neuron, a Pain-sensitive primary sensory neuron, a Photoreceptor cell, a Photoreceptor rod cell, a Photoreceptor blue-sensitive cone cell, a Photoreceptor green-sensitive cone cell, a Photoreceptor red-sensitive cone cell, a Proprioceptive primary sensory neuron, a Touch-sensitive primary sensory neuron, a Chemoreceptor glomus cell, an Outer hair cell, an Inner hair cell, a Taste receptor cell, an autonomic neuron, a Cholinergic neuron, a Adrenergic neural cell, a Peptidergic neural cell, an Inner pillar cell, an Outer pillar cell, an Inner phalangeal cell, an Outer phalangeal cell, a Border cell, a Hensen's cell, a Vestibular apparatus supporting cell, a Taste bud supporting cell, a Olfactory epithelium supporting cell, a Schwann cell, a Satellite glial cell, a Enteric glial cell, a glial cell, an interneuron, a Basket cell, a Cartwheel cell, a Stellate cell, a Golgi cell, a Granule cell, a Lugaro cell, a Unipolar brush cell, a Martinotti cell, a Chandelier cell, a Cajal-Retzius cell, a Double-bouquet cell, a Neurogliaform cell, a Retina horizontal cell, an Amacrine cell, a Spinal interneuron, a Renshaw cell, a principal cell, a Spindle neuron, a Fork neuron, a Pyramidal cell, a Place cell, a Grid cell, a Speed cell, a Head direction cell, a Betz cell, a Stellate cell, a Boundary cell, a Bushy cell, a Purkinje cell, a Medium spiny neuron, a Astrocyte (various types), a Oligodendrocyte, a Ependymal cell, a Tanycytes, a Pituicyte, a Lens cell, an Anterior lens epithelial cell, a Crystallin-containing lens fiber cell, a Adipocytes: White fat cell, a Brown fat cell, a Liver lipocyte, a Theca interna cell, a Corpus luteum cell, a Granulosa lutein cell, a Theca lutein cell, a Leydig cell of testes secreting testosterone, a Seminal vesicle cell, a Prostate gland cell, a Bulbourethral gland cell, a Bartholin's gland cell, a Gland of Littre cell, a Uterus endometrium cell, a Juxtaglomerular cell, a Macula densa cell of kidney, a Peripolar cell of kidney, a Mesangial cell of kidney, a barrier cell, a Parietal epithelial cell, a Podocyte, a Proximal tubule brush border cell, a Loop of Henle thin segment cell, a Kidney distal tubule cell, a Kidney collecting duct cell Principal cell, a Intercalated cell, a Transitional epithelium, a Duct cell, a Efferent ducts cell, a Epididymal principal cell, a Epididymal basal cell, a Endothelial cell, a Planum semilunatum epithelial cell, a interdental epithelial cell, a Corneal fibroblasts, a Tendon fibroblasts, a Bone marrow reticular tissue fibroblasts, an Other nonepithelial fibroblasts, a Pericyte Hepatic stellate cell (Ito cell), a Nucleus pulposus cell of intervertebral disc, a Hyaline cartilage chondrocyte, a Fibrocartilage chondrocyte, an Elastic cartilage chondrocyte, a Osteoblast/osteocyte, a Osteoprogenitor cell, a Hyalocyte of vitreous body of eye, a Stellate cell of perilymphatic space of ear, a Pancreatic stellate cell, a Skeletal muscle cell, a Red skeletal muscle cell, a White skeletal muscle cell, an Intermediate skeletal muscle cell, a Nuclear bag cell of muscle spindle, a Nuclear chain cell of muscle spindle, a Myosatellite cell, a Cardiac muscle cell, a Cardiac muscle cell, a SA node cell, a Purkinje fiber cell, a Smooth muscle cell, a Myoepithelial cell, a Erythrocyte, a Megakaryocyte, a Platelets, a Monocyte, a Connective tissue macrophage, a Epidermal Langerhans cell, a Osteoclast, a Dendritic cell, a Microglial cell, a Neutrophil granulocyte, a myeloblast, a promyelocyte, a myelocyte, a metamyelocyte, a Eosinophil granulocyte, a Basophil granulocyte, a Mast cell, a Helper T cell, a Suppressor T cell, a Cytotoxic T cell, a Natural killer T cell, a B cell, a Plasma cell, a Natural killer cell, a Hematopoietic stem cell, a Germ cell, a Oogonium/Oocyte, a Spermatid, a Spermatocyte, a Spermatogonium cell, a Spermatozoon, a Nurse cell, a Granulosa cell, a Sertoli cell, a Epithelial reticular cell, a Interstitial cell, a Interstitial kidney cell or any combination thereof.

In some aspects, a disease can comprise inflammatory disorder, an autoimmune disease, a degenerative disease, cardiovascular disease, ischemic disease, cancer, a genetic disease, a metabolic disorder, idiopathic disorder or any combination thereof. In some aspects, a disease can comprise any medical disorder, including, but not limited to those medical disorders initiated by direct tissue injury (e.g., burns, trauma, decubitus ulcers, etc.), ischemic/vascular events (e.g., myocardial infarct, stroke, shock, hemorrhage, coagulopathy, etc.), infections (e.g., cellulitis, pneumonia, meningitis, SIRS, etc.), neoplasia (e.g., breast cancer, lung cancer, lymphoma, etc.), immunologic/autoimmune conditions (e.g., graft vs. host disease, multiple sclerosis, diabetes, inflammatory bowel disease, lupus erythematosus, rheumatoid arthritis, psoriasis, etc.), degenerative diseases (e.g., osteoporosis, osteoarthritis, Alzheimer's disease, etc.), congenital/genetic diseases (e.g., epidermolysis bullosa, osteogenesis imperfecta, muscular dystrophies, lysosomal storage diseases, Huntington's disease, etc.), adverse drug effects (e.g., drug-induced hepatitis, drug-induced cardiac injury, etc.), toxic injuries (e.g., radiation exposure(s), chemical exposure(s), alcoholic hepatitis, alcoholic pancreatitis, alcoholic cardiomyopathy, cocaine cardiomyopathy, etc.), metabolic derangements (e.g., uremic pericarditis, metabolic acidosis, etc.), iatrogenic conditions (e.g., radiation-induced tissue injury, surgery-related complications, etc.), and/or idiopathic processes (e.g., amyotrophic lateral sclerosis, Parsonnage-Turner Syndrome, etc.) or any combination thereof. In some aspects, a disease can comprise graft-vs-host diseases (GvHD), Epidermolysis Bullosa (EB), junctional EB (JEB), EB simplex (EBS), congenital ichthyosis, congenital dyskeratosis, Recessive Dystrophic form of EB (RDEB), macular degeneration, Alzheimer's disease, aging, Type II diabetes, heart disease, osteoporosis, chronic skin wounds, diabetes-associated ulcers/wounds, connective tissue diseases such as Ehlers-Danlos Syndrome (EDS) or Marfan syndrome, cancer, or any combination thereof. In some aspects, a disease can also comprise an injury. An injury can comprise a burn, a broken bone, a concussion, a contusion, a fractured bone, a ruptured tendon, a torn ligament, punctured, scarped and/or cut skin, or any other injury known in the art. In some aspects, a disease can be Ehlers-Danlos Syndrome.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "preventing," "prevent," or "protecting against" describes reducing or eliminating the onset of the symptoms or complications of such disease, condition or disorder.

As used herein, the terms "ameliorate", "ameliorating" and grammatical variations thereof mean to decrease the severity of the symptoms of a disease in a subject.

The terms "effective amount" and "therapeutically effective amount" of an agent or compound are used in the broadest sense to refer to a nontoxic but sufficient amount of an active agent or compound to provide the desired effect or benefit.

The term "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

In any method, composition or kit of the present disclosure, TERT can be human TERT (hTERT).

In any method, composition or kit of the present disclosure, TERC can be human TERC (hTERC).

As used herein, a "subject" includes a mammal. The mammal can be any mammal, e.g., a human, a primate, a mouse, a rat, a dog, a cat, a cow, a horse, a goat, a camel, a sheep, a pig or any other mammal. In some aspects, a mammal can be a human. The subject can be a male or a female.

EXAMPLES

Figure 4:
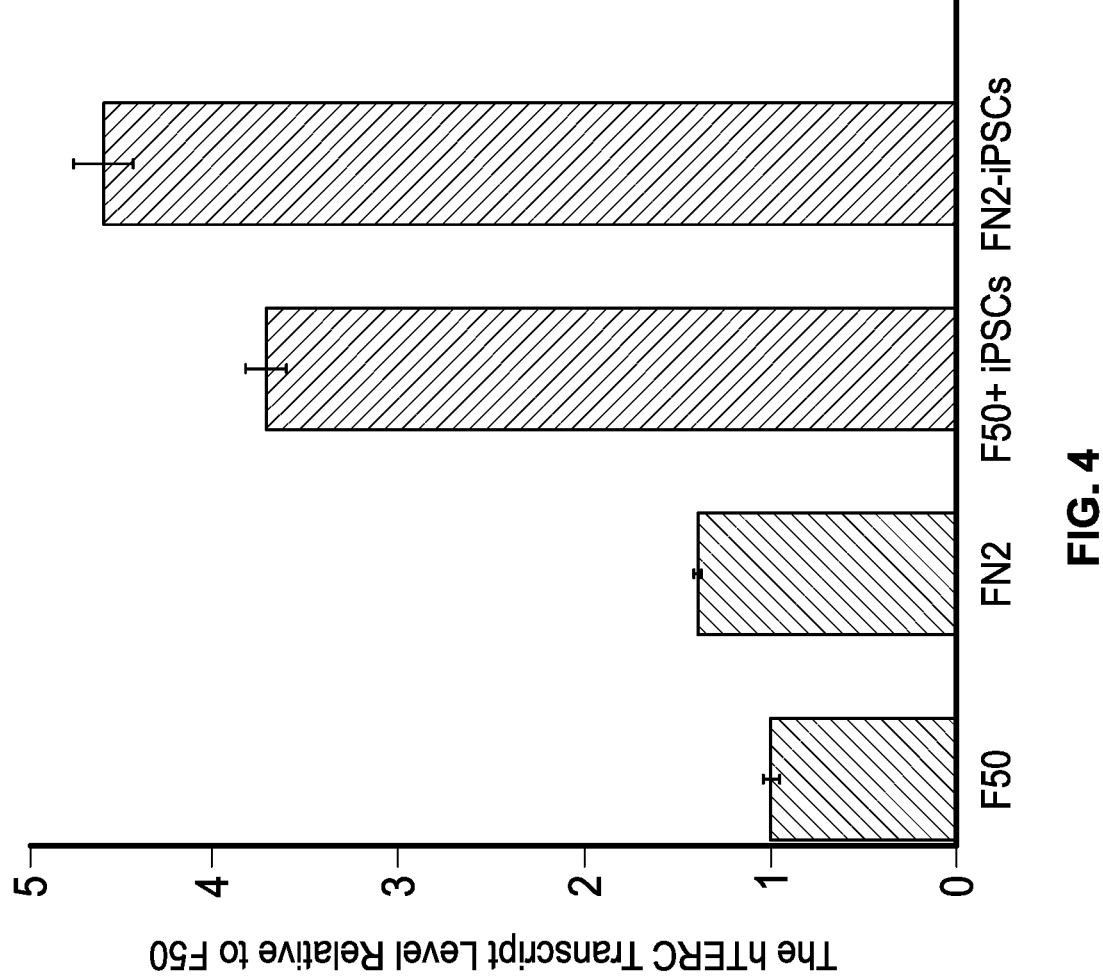
FIG. 4 is a chart showing the hTERC transcript level in various cell types.

Example 1—Levels of hTERC Transcripts are Higher in Induced Pluripotent Stem Cells as Compared to Fibroblasts The levels of human telomerase RNA component (hTERC) transcripts in fibroblasts (FBs), induced pluripotent stem cells (iPSCs) were measured using the NanoString nCounter Gene Expression Assay. An approximately 2.4-4.6-fold upregulation of hTERC in iPSCs as compared to the parental F50 (human dermal fibroblast derived from a 50 year old individual) and FN2 (neonatal fibroblasts) lines, as shown in FIG. 4.

Example 2—Contacting Somatic Cells with Compositions of the Present Disclosure Increases the Level Of hTERC in the Somatic Cells In this example, various cell lines were transfected with various compositions of the present disclosure.

Human dermal fibroblasts derived from a 50 year old individual (F50), neonatal human epidermal keratinocytes (HEKn) and GFP-expressing human mesenchymal stem/stromal cells (hMSC-GFP) were subjected to one transfection with 500 ng modified mRNA (mod-mRNA) encoding dCas9-VPR and 500 ng hTERC guide RNA (gRNA) (either independently or as a mix of 4 guides at a 1:1:1:1 ratio) using Lipofectamine® RNAiMAX™ (RNAiMAX) (Thermo Fisher Scientific). Cells were collected 24 post-transfection. Real time quantitative PCR reactions for human TERC RNA expression were then carried out using the Bio-Rad CFX Connect System. Data was analyzed using the ΔΔCt method.

Figure 5:
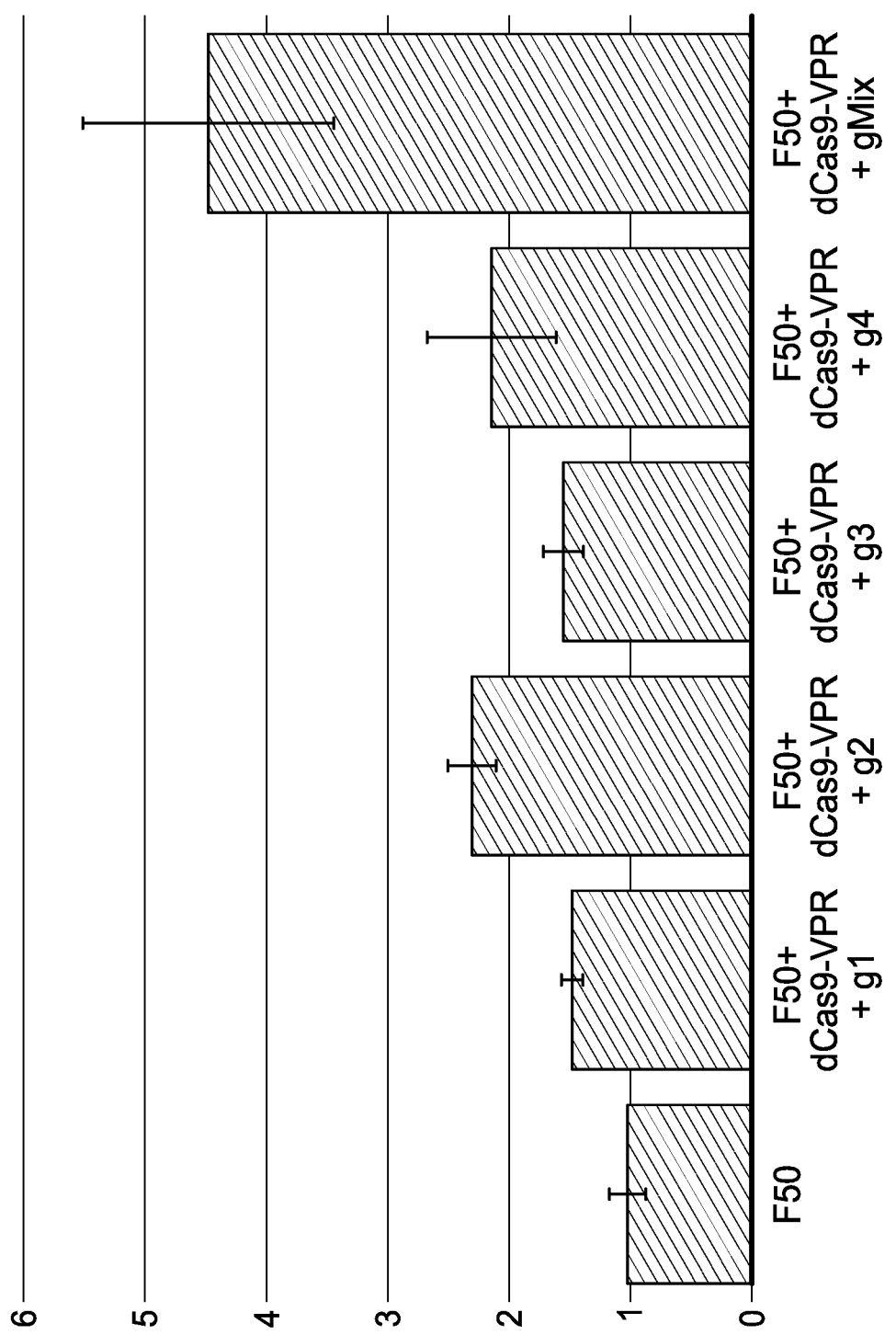
FIG. 5 is a chart showing the level of human TERC RNA in F50 cells transfected with compositions of the present disclosure.

To test the activation of the endogenous hTERC transcript, F50 cells were transfected with either 1 separate individual gRNA (g1, g2, g3, and g4) plus mod-mRNA encoding dCas9-VPR or a mix of all 4 guides at a 1:1:1:1 ratio (gmix) plus mod-mRNA encoding dCas9-VPR. Levels of hTERC transcript were quantified using quantitative reverse transcription PCR. As shown in FIG. 5, the results indicate that even as little as only 1 single guide is sufficient to activate endogenous hTERC (g2, g4) to levels comparable to those achieved by the mix of 4 gRNAs. Transfection with the mix of 4 gRNAs and mod-mRNA encoding dCas9-VPR displayed the greatest increase in expression of hTERC, as shown in FIG. 5.

Figure 6:
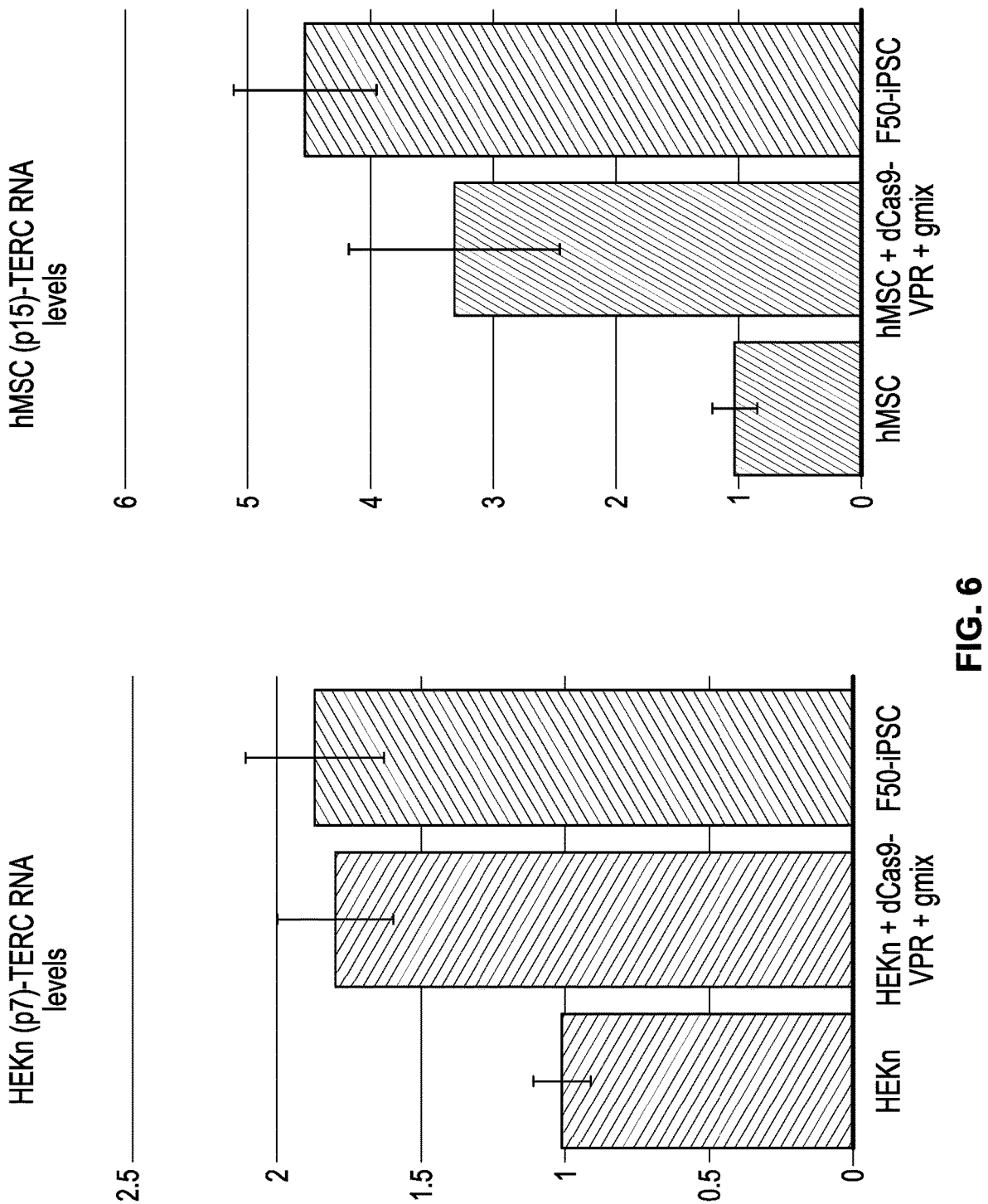
FIG. 6 is a series of charts showing the level of human TERC RNA in HEKn cells (left) and human Mesenchymal Stem/Stromal Cells (hMSCs) (right) transfected with compositions of the present disclosure (+dCas9–VPR+gmix) as compared to non-transfected HEKn cells, non-transfected hMSC cells and F50-derived induced pluripotent stem cells.

To monitor endogenous hTERC activation by dCas9-VPR across other cell lines, HEKn and hMSC-GFP cell lines were transfected with a mix of all 4 gRNAs plus mod-mRNA encoding dCas9-VPR. The expression of hTERC was then measured using quantitative reverse transcription PCR. The results are shown in FIG. 6. As shown in FIG. 6, the level of hTERC activation observed in all tested cells lines was comparable to that observed in iPSCs.

Example 2 Methods

Cell lines: 50 year-old human dermal fibroblast (F50, at passage 5), and neonatal human epidermal keratinocytes (HEKn, at passage 7) lines were obtained from ATCC. Human mesenchymal stem/stromal cells with GFP fluorescence (hMSC-GFP, at passage 15) were obtained from Cyagen. The F50 line was cultured in fibroblast expansion medium (FEM) comprised of DMEM/F12 supplemented with 5% human serum, 1× MEM non-essential amino acids solution, 55 μM of 2-mercaptoethanol (β-ME), 1× Gluta-MAX™ supplement, plus antibiotics (all from Thermo Fisher Scientific), with 50 ug/ml ascorbic acid, 1 ng/ml hydrocortisone (both from Sigma), 12 ng/ml basic FGF (Gibco) and 5 ng/ml human EGF (Invitrogen). HEKn cells were cultured in EpiLife medium supplemented with EDGS and antibiotics (all from ThermoFisher). hMSCs were cultured in mesenchymal stem cell growth medium (MSCGM) (prepared as a kit from Cyagen).

Transfections: All transfections of fibroblasts and keratinocytes were performed using Opti-MEM®I Reduced Serum Medium (Opti-MEM) (Thermo Fisher Scientific) as a complexation buffer, while transfections of human mesenchymal stem/stromal cells (hMSCs) was performed using Opti-MEM with the pH adjusted to 8.2 (Opti-MEM-pH 8.2) as described in Kogut et al. *Nature Communications, 2018.* One transfection with 500 ng mod-mRNA encoding dCas9-VPR and 500 ng hTERC guide RNA (gRNA) (either individual (g1, g2, g3, g4) or a mix of 4 guides (gmix) at a 1:1:1:1 ratio) or 500 ng modified mRNA encoding dCas9-VPR alone was performed using Lipofectamine® RNAiMAX™ (RNAiMAX) (Thermo Fisher Scientific). RNA and RNAiMAX were first diluted in either Opti-MEM for keratinocyte and fibroblast transfections, or Opti-MEM-pH 8.2 for hMSC transfections. For mod-mRNA and/or gRNA transfections, 100 ng/μl RNA was diluted 5×, and 5 μl of RNAiMAX per microgram of mod-mRNAs and/or gRNA was diluted 10× using either Opti-MEM (for keratinocytes and fibroblasts) or Opti-MEM-pH 8.2 (for hMSCs). After dilution, these components were combined together and incubated for 15 min at room temperature (RT). After incubation at RT, transfection mixtures of mod-RNA mix and/or gRNA and RNAiMAX were applied to the cell cultures, in their respective media supplemented with 200 ng/ml B18R (eBioscience).

PCR: F50, HEKn, and hMSC-GFP cells collected 24 hours post-transfection. RNA was extracted using the RNeasy Plus Minikit (Qiagen). cDNA was synthesized using the iScript™ cDNA Synthesis Kit (BioRad). Quantitative PCR (QPCR) reactions for human TERC RNA were performed using SsoAdvanced™ Universal SYBR® Green Supermix. Data was analyzed using the ΔΔCt method.

Summary of Example 2: transfecting somatic cells with compositions of the present disclosure, more specifically a mod-mRNA encoding dCas9-VPR in combination with a plurality of gRNAs comprising 1 or more different gRNA species, can increase the expression of hTERC in the transfected cells, including to levels that are comparable to induced pluripotent stem cells.

Example 3—Transfecting Mod-RNA Encoding dCas9-VPR Alone does not Induce hTERC Expression in Target Cells In this example, various cell lines were transfected with various compositions of the present disclosure, specifically a composition comprising only a mod-RNA encoding dCas9-VPR.

Figure 7:
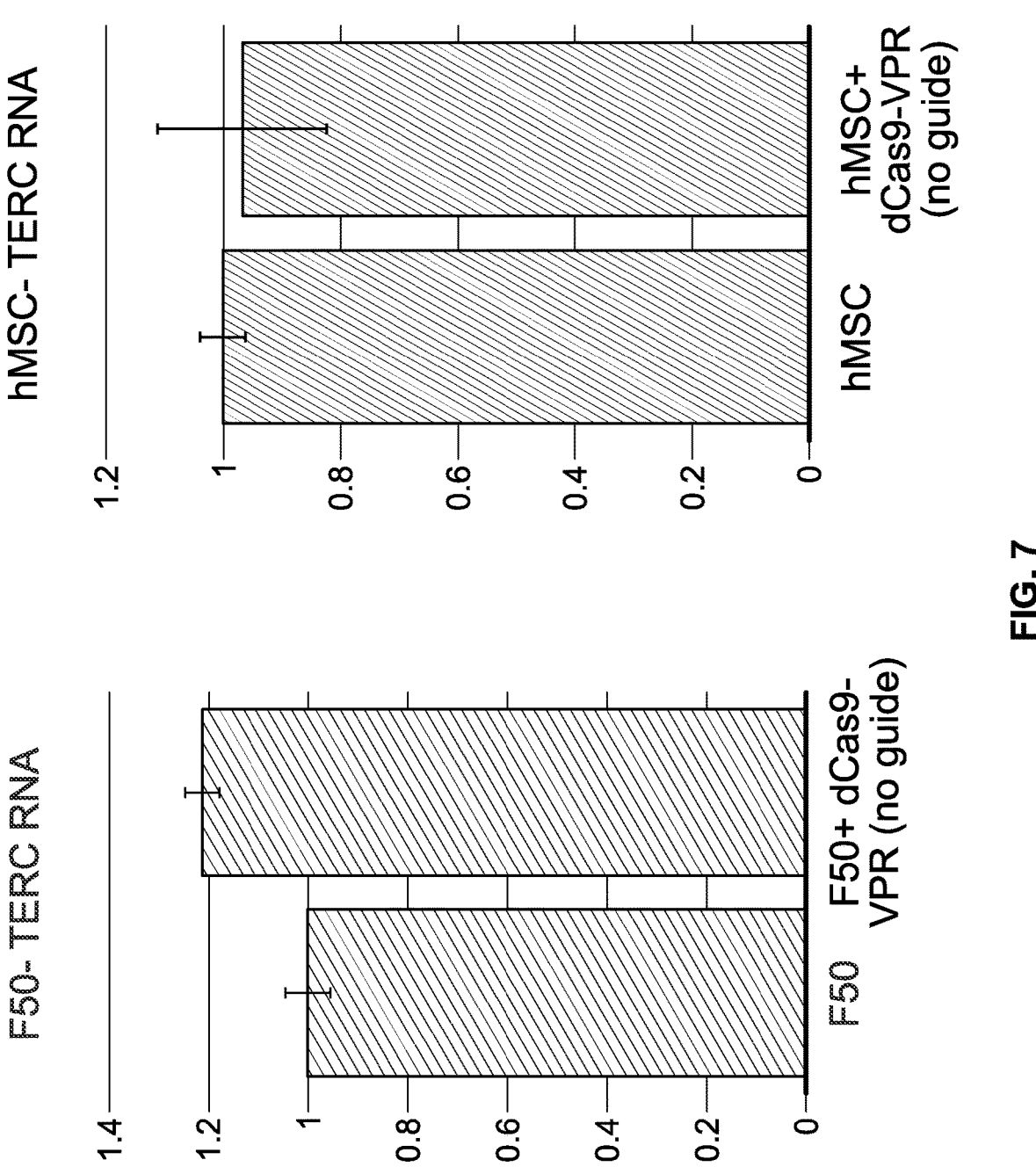
FIG. 7 is a series of charts showing the level of human TERC RNA in F50 cells (left) and hMSCs (right) transfected with compositions of the present disclosure lacking guide RNA (+dCas9–VPR (no guide)).

50 year-old human dermal fibroblasts (F50), and GFP-expressing human mesenchymal stem/stromal cells (hMSC-GFP) were subjected to one transfection with 500 ng mod-mRNA encoding dCas9-VPR using Lipofectamine® RNAiMAX™ (RNAiMAX) (Thermo Fisher Scientific). Cells were collected 24 hours (F50, hMSC-GFP) post-transfection. Quantitative reverse transcription PCR reactions for human TERC RNA expression were carried out using the Bio-Rad CFX Connect System and data was analyzed using the ΔΔCt method. The results are shown in FIG. 7. As shown in FIG. 7, the expression levels of hTERC does not increase when only a mod-RNA encoding dCas9-VPR is transfected into a target cell in the absence of any guide RNA.

Example 3 Methods

Cell lines: 50 year-old human dermal fibroblast (F50, at passage 5) were obtained from ATCC. Human mesenchymal stem/stromal cells with GFP fluorescence (hMSC-GFP, at passage p11) were obtained from Cyagen. F50 line was cultured in fibroblast expansion medium (FEM) comprised of DMEM/F12 supplemented with 5% human serum, 1× MEM non-essential amino acids solution, 55 μM of 2-mercaptoethanol (β-ME), 1× GlutaMAX™ supplement, plus antibiotics (all from Thermo Fisher Scientific), with 50 ug/ml ascorbic acid, 1 ng/ml hydrocortisone (both from Sigma), 12 ng/ml basic FGF (Gibco) and 5 ng/ml human EGF (Invitrogen). hMSCs were cultured in mesenchymal stem cell growth medium (MSCGM) (prepared as a kit from Cyagen).

Transfections: All transfections of fibroblasts were performed using Opti-MEM as a complexation buffer, while transfections of human mesenchymal stem/stromal cells (hMSCs) was performed Opti-MEM-pH 8.2 One transfection with 500 ng mod-mRNA encoding dCas9-VPR alone was performed using Lipofectamine® RNAiMAX™ (RNAiMAX) (Thermo Fisher Scientific). RNA and RNAiMAX were first diluted in appropriate Opti-MEM. For mod-mRNA transfections, 100 ng/μl RNA was diluted 5×, and 5 μl of RNAiMAX per microgram of mod-mRNAs was diluted 10× using appropriate Opti-MEM. After dilution, these components were combined together and incubated for 15 min at RT. After incubation at RT, transfection mixtures of mod-RNA mix and RNAiMAX were applied to the cell cultures, in their respective media supplemented with 200 ng/ml B18R (eBioscience).

PCR: F50 and hMSC-GFP cells were collected 24 hours post-transfection. RNA was extracted using the RNeasy Plus Minikit (Qiagen). cDNA was synthesized using the iScript™ cDNA Synthesis Kit (BioRad). QPCR reactions for human TERC RNA were performed using SsoAdvanced™ Universal SYBR® Green Supermix. Data was analyzed using the Δ66 Ct method. P values were calculated using a paired, two-tailed Student's t-test. *P≤0.05, P≤0.01, *P≤0.001.

Example 3 summary: Increases in hTERC expression using the methods and the compositions of the present disclosure are dependent on specific targeting of a DNA-targeting molecule comprising a transactivation domain, for example through the co-administration of at least one guide RNA.

Example 4—The Methods and Compositions of the Present Disclosure Cause an Increase in Population Doubling (PD) of Senescent Fibroblast Cells In this example, senescent fibroblast cells were contacted with compositions of the present disclosure using methods of the present disclosure.

50 year-old human dermal fibroblast (F50) line was obtained from ATCC, and subsequently cultured until 90% of cells displayed the senescent phenotype as previously described in Kogut et al, *Nature Communications, 2018.* Briefly, the senescent phenotype can include an enlargement of cellular morphology and upwards of about 90% positivity for senescence-associated β-galactosidase. The F50 line was thawed (F50S, at passage 15, 32.5 PD) and cultured in FEM: DMEM/F12 supplemented with 5% human serum, 1× MEM non-essential amino acids solution, 55 μM of 2-mercapto-ethanol (β-ME), 1× GlutaMAX™ supplement, plus antibiotics (all from Thermo Fisher Scientific), with 50 ug/ml ascorbic acid, 1 ng/ml hydrocortisone (both from Sigma), 12 ng/ml basic FGF (Gibco) and 5 ng/ml human EGF (Invitrogen). Initially, 10 k fibroblasts (F50S p15, 32.5 PD) were seeded, per well.

FIG. 8 shows a schematic of the transfection regimen of fibroblasts using rejuvenating compositions of the present disclosure. Initially, 10 k senescent fibroblasts (F50S, p15, 32.5 PD) were seeded, per well. The cells were first pre-treated with three sequential transfections with 500 ng mod-mRNA encoding hTERT. After pretreatment, four sequential transfection series with 500 ng mod-mRNA encoding hTERT followed by 500 ng mod-mRNA encoding dCas9-VPR and 500 ng human TERC guide RNA (gRNA) (4 guides, 1:1:1:1 ratio) the next day were performed using Lipofectamine® RNAiMAX™ (RNAiMAX) (Thermo Fisher Scientific). RNA and RNAiMAX were first diluted in Opti-MEM®I Reduced Serum Medium (Opti-MEM). For mod-mRNA and/or gRNA transfections, 100 ng/μl RNA was diluted 5×, and 5 μl of RNAiMAX per microgram of mod-mRNAs and/or gRNA were diluted 10× using Opti-MEM. After dilution, these components were combined together and incubated for 15 min at RT. After incubation at RT, transfection mixtures of mod-RNA mix and/or gRNA and RNAiMAX were applied to the cell culture, in FEM supplemented with 200 ng/ml B18R (eBioscience). The medium was changed after overnight incubation after each transfection.

Figure 9:
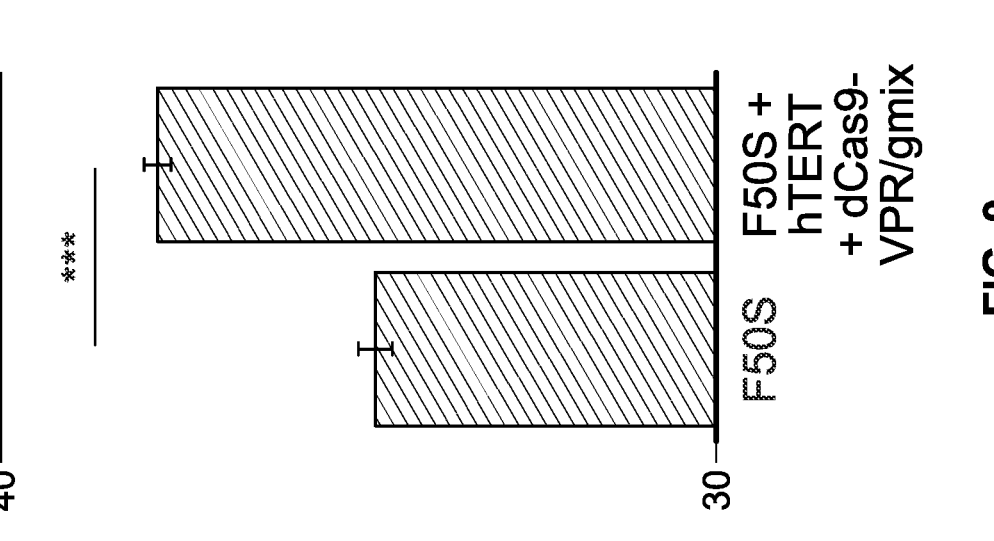
FIG. 9 is a chart showing the total population doubling of senescent F50S cells transfected with compositions of the present disclosure.

The cumulative population doubling of non-treated senescent fibroblasts (F50S, p15, 32.5 starting PD) and the same cells treated with the rejuvenating composition (using the regimen put forth in FIG. 8) was measured. When cells reached 70-80% confluence, they were typsinized, counted using a hemocytometer, and passaged. PD was calculated as the log of the ratio of the final count (N) to the starting (baseline) count (X$_0$) divided by the log of 2; that is: PD=[log(N ÷X$_0$)]÷log 2. P values were calculated using a paired, two-tailed Student's t-test. *P≤0.05, P≤0.01, *P≤0.001. The results are shown in FIG. 9. As shown in FIG. 9, the treatment with the rejuvenating composition of the present disclosure results in the increased population doubling.

Example 4 summary: The compositions and methods of the present disclosure can be used to rejuvenate senescent cells, including senescent fibroblasts, leading to an increase in the total number of population doublings exhibited by the treated cells.

Example 5—the Methods and Compositions of the Present Disclosure Increase Telomere Length and Mitochondrial DNA Amount in Transfected Target Cells In this example, various cell lines (low passage and senescent 50 year-old human dermal fibroblasts (F50 and F50S respectively), human mesenchymal stem/stromal cells (hMSCs) and human keratinocytes) were transfected with various compositions of the present disclosure using various methods of the present disclosure. Changes in telomere length in each cell line were then measured.

Low passage and senescent 50 year-old human dermal fibroblasts: 50 year-old human dermal fibroblast (F50) lines were obtained from ATCC, and subsequently cultured until 90% of cells displayed the senescent phenotype as previously described in Kogut et al, *Nature Communications, 2018.* Breifly, the senescent phenotype can include an enlargement of cellular morphology and upwards of about 90% positivity for senescence-associated β-galactosidase. The F50 lined was thawed (F50S, at passage 15, 32.5 PD) and cultured in FEM: DMEM/F12 supplemented with 5% human serum, 1× MEM non-essential amino acids solution, 55 μM of 2-mercaptoethanol (β-ME), 1× GlutaMAX™ supplement, plus antibiotics (all from Thermo Fisher Scientific), with 50 ug/ml ascorbic acid, 1 ng/ml hydrocortisone (both from Sigma), 12 ng/ml basic FGF (Gibco) and 5 ng/ml human EGF (Invitrogen). Initially, 10 k fibroblasts (F50 p3-4 or F50S p15, 32.5 PD) were seeded, per well.

FIG. 8 shows a schematic of a transfection regimen of fibroblasts using a rejuvenating composition of the present disclosure. Initially, 10 k senescent fibroblasts (F50S, p15, 32.5 PD) were seeded, per well. The cells were first pre-treated with three sequential transfections with 500 ng mod-mRNA encoding hTERT. After pretreatment, four sequential transfection series with 500 ng mod-mRNA encoding hTERT followed by 500 ng mod-mRNA encoding dCas9-VPR and 500 ng human TERC guide RNA (gRNA) (4 guides, 1:1:1:1 ratio) the next day were performed using Lipofectamine® RNAiMAX™ (RNAiMAX) (Thermo Fisher Scientific). RNA and RNAiMAX were first diluted in Opti-MEM®I Reduced Serum Medium (Opti-MEM). For mod-mRNA and/or gRNA transfections, 100 ng/μl RNA was diluted 5×, and 5 μl of RNAiMAX per microgram of mod-mRNAs and/or gRNA were diluted 10× using Opti-MEM. After dilution, these components were combined together and incubated for 15 min at RT. After incubation at RT, transfection mixtures of mod-RNA mix and/or gRNA and RNAiMAX were applied to the cell culture, in FEM supplemented with 200 ng/ml B18R (eBioscience). The medium was changed after overnight incubation after each transfection.

FIG. 10 shows a schematic of an alternative transfection regimen of fibroblasts using a rejuvenating composition of the present disclosure. F50 fibroblasts were plated in FEM at 15K cells per well of a 6-well format dish. Four transfection series with 500 ng mod-mRNA encoding hTERT together with 200 ng mod-mRNA encoding dCas9-VPR and 500 ng hTERC guide RNA (gRNA) (1 selected guide) were performed every 4 days using Lipofectamine® RNAiMAX™ (RNAiMAX) (Thermo Fisher Scientific). RNA and RNAiMAX were first diluted in Opti-MEM®I Reduced Serum Medium (Opti-MEM). For mod-mRNA and/or gRNA transfections, 100 ng/μl RNA was diluted 5×, and 5 μl of RNAiMAX per microgram of mod-mRNAs and/or gRNA were diluted 10× using Opti-MEM. After dilution, these components were combined together and incubated for 15 min at RT. After incubation at RT, transfection mixtures of mod-RNA mix and/or gRNA and RNAiMAX were applied to the cell culture, in FEM supplemented with 200 ng/ml B18R (eBioscience). The medium was changed after overnight incubation after each transfection.

Human mesenchymal stem/stromal cells: Human mesenchymal stem/stromal cells (hMSCs) were cultured in mesenchymal stem cell growth medium (MSCGM) (prepared as a kit from Cyagen) under low $O_2$ (5%). All transfections of hMSCs were performed using Opti-MEM with the pH adjusted to 8.2 (Opti-MEM-pH 8.2) as described in Kogut et al. *Nature Communications*, 2018.

FIG. 11 shows a schematic of the transfection regimen of hMSCs using rejuvenating compositions of the present disclosure. A pre-treatment of 3 transfections with 500 ng mod-mRNA encoding human TERT was performed using Lipofectamine® RNAiMAX™ (RNAiMAX) (Thermo Fisher Scientific). Following pre-treatment with hTERT mod-mRNA transfections, four sequential transfection series with 500 ng mod-mRNA encoding hTERT followed by 500 ng mod-mRNA encoding dCas9-VPR and 500 ng human TERC guide RNA (gRNA) (4 guides, 1:1:1:1 ratio) the next day were performed using Lipofectamine® RNAiMAX™ (RNAiMAX) (Thermo Fisher Scientific). RNA and RNAiMAX were first diluted in Opti-MEM-pH 8.2. For mod-mRNA transfections, 100 ng/μl RNA was diluted 5×, and 5 μl of RNAiMAX per microgram of mod-mRNAs was diluted 10× using Opti-MEM-pH 8.2. After dilution, these components were combined together and incubated for 15 min at RT. After incubation at RT, transfection mixtures of mod-RNA mix and RNAiMAX were applied to the cell culture, in respective media supplemented with 200 ng/ml B18R. The medium was changed after overnight incubation after each transfection.

Human keratinocytes: Human neonatal epidermal keratinocytes (HEKn) were cultured in EpiLife medium supplemented with EDGS and antibiotics (all from ThermoFisher). All transfections of HEKs were performed using Opti-MEM with no pH adjustment.

FIG. 11 shows a schematic of the transfection regimen of HEKn using rejuvenating compositions of the present disclosure. A pre-treatment of 3 transfections with 100 ng mod-mRNA encoding human human TERT was performed using Lipofectamine® RNAiMAX™ (RNAiMAX) (Thermo Fisher Scientific). RNA and RNAiMAX were first diluted in Opti-MEM®I Reduced Serum Medium (Opti-MEM) (Thermo Fisher Scientific). For mod-mRNA transfections, 100 ng/μl RNA was diluted 5×, and 5 μl of RNAiMAX per microgram of mod-mRNAs was diluted 10× using Opti-MEM. After dilution, these components were combined together and incubated for 15 min at RT. After incubation at RT, transfection mixtures of mod-RNA mix and RNAiMAX were applied to the cell culture, in EpiLife medium supplemented with 200 ng/ml B18R (eBioscience). Following pre-treatment of the HEKn cell line, 4 sequential transfection series with 100 ng mod-mRNA encoding hTERT followed by 100 ng mod-mRNA encoding dCas9-VPR+100 ng gRNA mix the next day were performed using Lipofectamine®RNAiMAX™ (RNAiMAX) (Thermo Fisher Scientific). RNA and RNAiMAX were first diluted in Opti-MEM (Thermo Fisher Scientific). For mod-mRNA and/or gRNA transfections, 100 ng/μl RNA was diluted 5×, and 5 μl of RNAiMAX per microgram of mod-mRNAs and/or gRNA were diluted 10× using Opti-MEM. After dilution, these components were combined together and incubated for 15 min at RT. After incubation at RT, transfection mixtures of mod-RNA mix and/or gRNA and RNAiMAX were applied to the cell culture, in EpiLife supplemented with 200 ng/ml B18R (eBioscience). The medium was changed after overnight incubation after each transfection.

The F5OS cells were collected 3 days after the last transfection. Genomic DNA (gDNA) was extracted using the DNeasy® Blood and Tissue Kit (Qiagen). Quantitative PCR reactions for relative telomere length in treated and untreated cells were performed using SsoAdvanced™ Universal SYBR® Green Supermix. The results are shown in FIG. 12.

The F50 cells were collected 3 days after the last transfection. Genomic DNA (gDNA) was extracted using the Quick-DNA™ Miniprep Kit (Zymo Research). Quantitative PCR was used to determine changes in average telomere length in treated and untreated cells based on ScienCell's Absolute Human Telomere Length Quantification and Mitochondrial DNA Copy Number qPCR Assay Kit (#8958). The telomere primer set recognizes and amplifies telomere length by comparing samples to reference genomic DNA containing a 100 base pair (bp) telomere sequence located on human chromosome 17 (provided by kit). Primer-probe real-time PCR was performed using BioRad's CFX96 Real-Time System (BioRad, Hercules, CA). The results are shown in FIG. 13.

The hMSCs and HEKn cells were collected 3 days after the last transfection. Genomic DNA (gDNA) was extracted using the DNeasy® Blood and Tissue Kit (Qiagen). Quantitative PCR was used to determine changes in average telomere length in treated and untreated cells based on ScienCell's Absolute Human Telomere Length Quantification and Mitochondrial DNA Copy Number qPCR Assay Kit (#8958). The telomere primer set recognizes and amplifies telomere length by comparing samples to reference genomic DNA containing a 100 base pair (bp) telomere sequence located on human chromosome 17 (provided by kit). Primer-probe real-time PCR was performed using BioRad's CFX96 Real-Time System (BioRad, Hercules, CA). The results are shown in FIG. 14.

Figure 12:
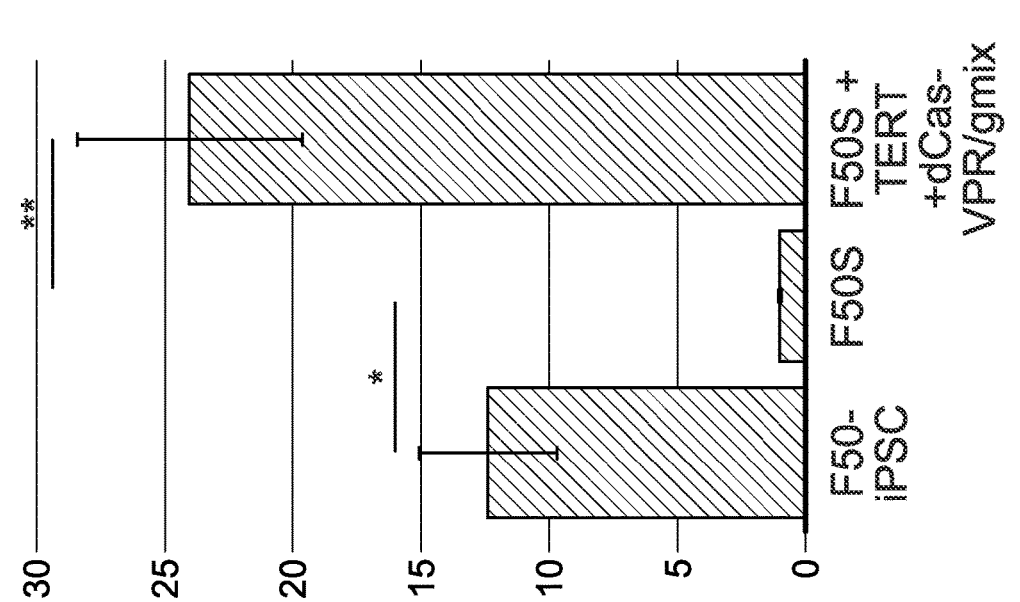
FIG. 12 is a chart showing the relative telomere length in senescent F50S cells transfected with compositions of the present disclosure (+TERT+dCas9–VPR/gmix) as compared to non-transfected F50S cells and F50-derived induced pluripotent stem cells.
Figure 13:
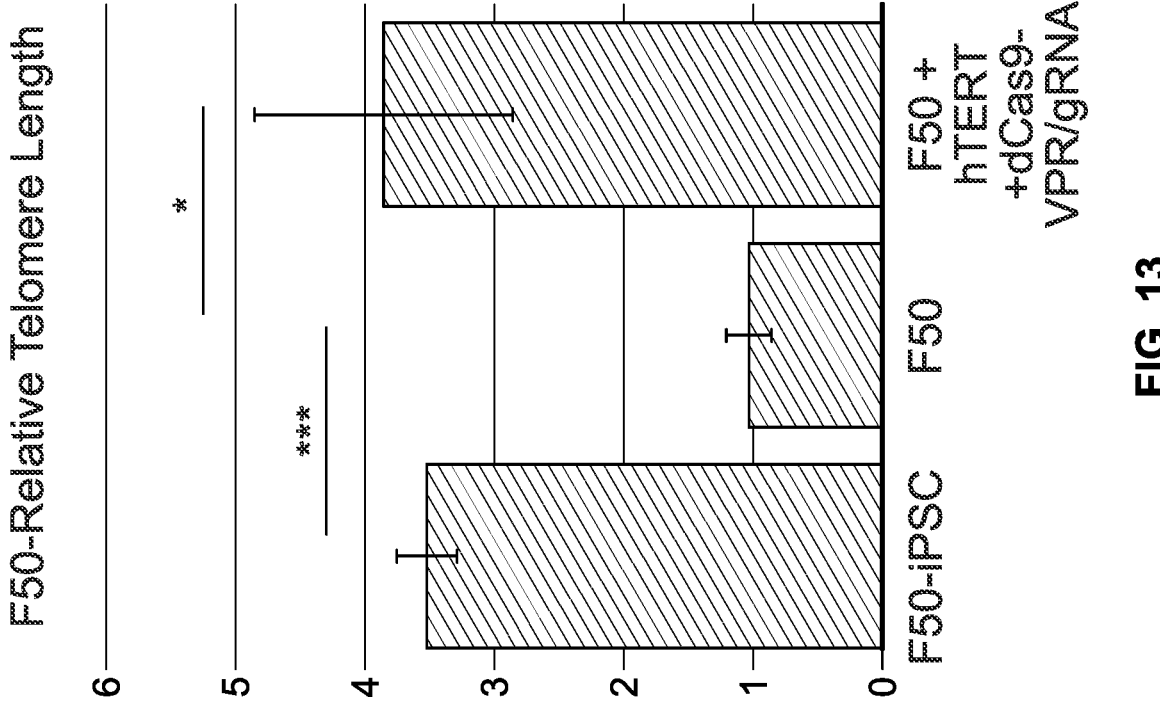
FIG. 13 is a chart showing the relative telomere length in F50 cells transfected with compositions of the present disclosure (+hTERT+dCas9–VPR/gmix) as compared to non-transfected F50 cells and F50-derived induced pluripotent stem cells.
Figure 14:
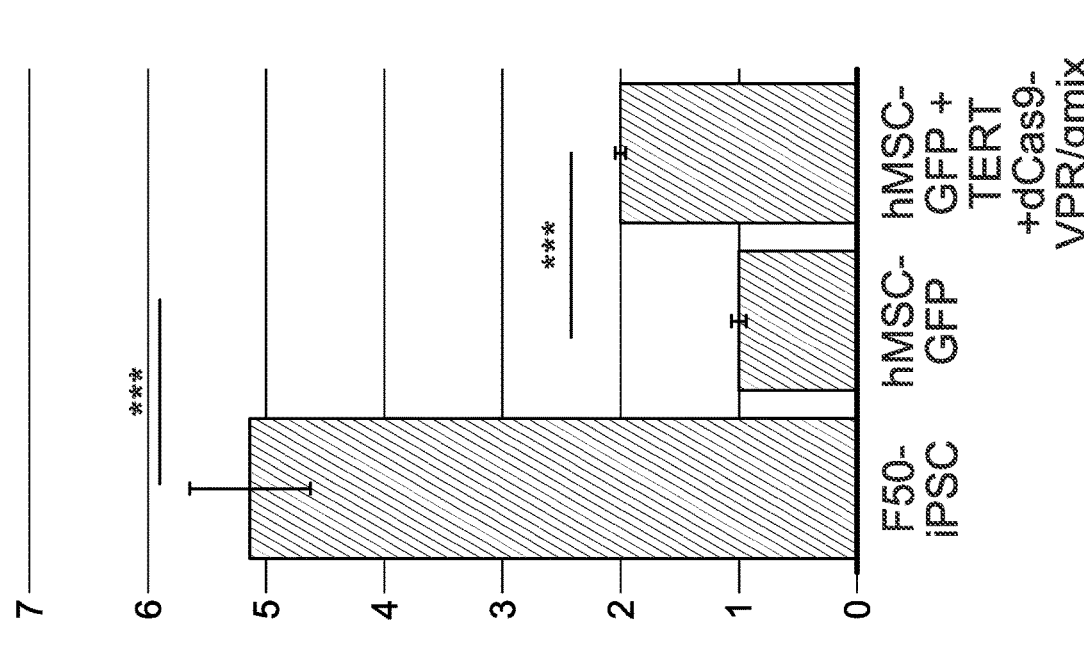
FIG. 14 is a series of charts showing the relative telomere length in HEKn cells (left) and hMSCs (right) transfected with compositions of the present disclosure (+TERT+dCas9–VPR/gmix) as compared to non-transfected HEKn cells, non-transfected hMSCs and F50-derived induced pluripotent stem cells.
Figure 14:
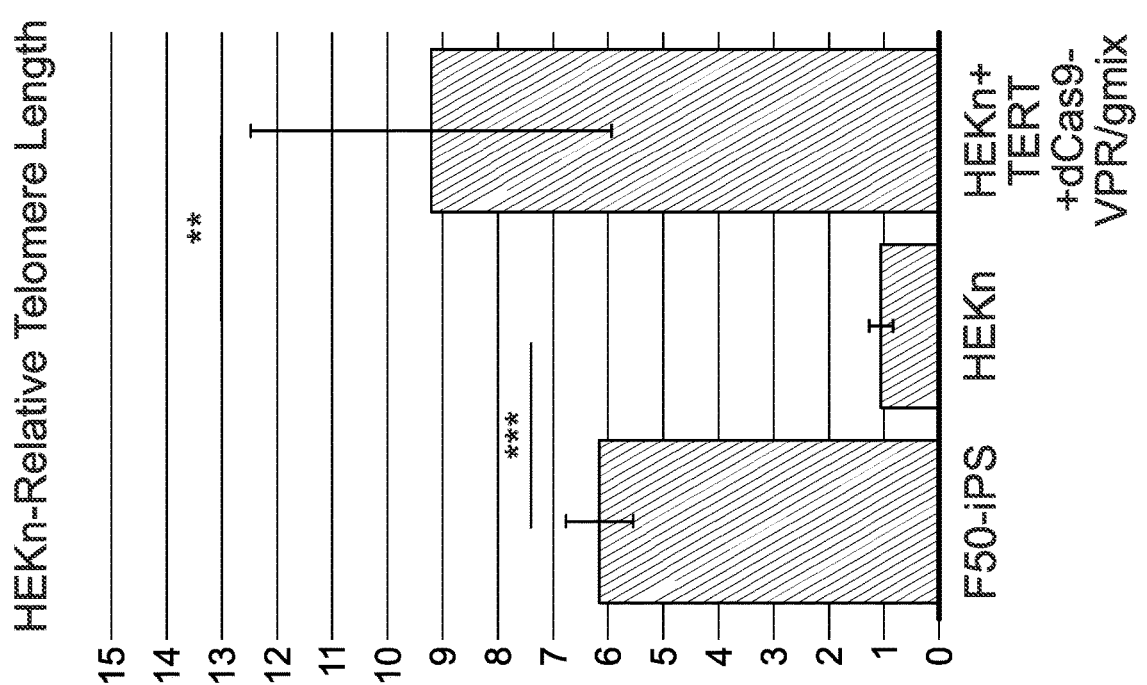

As shown in FIG. 12, FIG. 13 and FIG. 14, F50S, F50, hMSCs and HEKn cells treated with the rejuvenating compositions of the present disclosure displayed increased telomere length as compared to untreated control cells. Moreover, in the case of the treated F50S and HEKn cells, the telomere lengths exceeded the telomere lengths measured in F50-derived induced pluripotent stem cells (F50-iPSCs).

Figure 15:
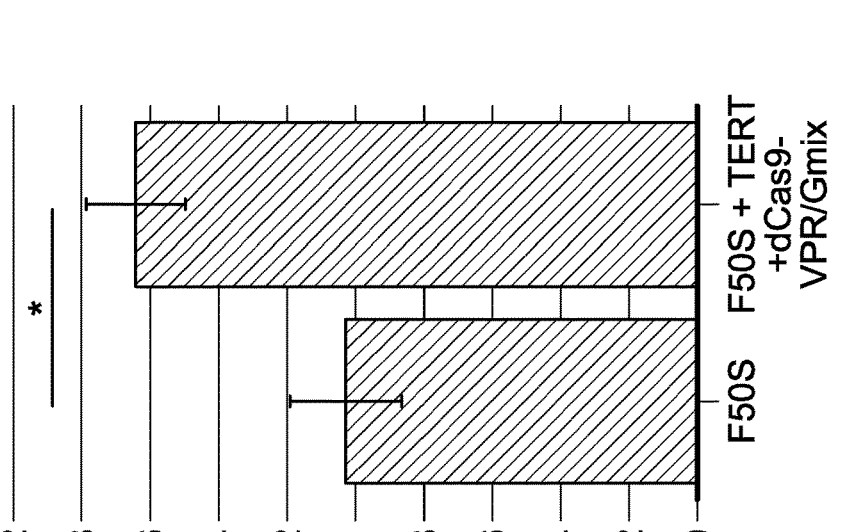
FIG. 15 is a series of charts showing the relative amount of mitochondrial DNA in F50 cells (left), HEKn cells (middle) and hMSCs (right) transfected with compositions of the present disclosure (+TERT+dCas9–VPR/gmix) as compared to non-transfected F50 cells, non-transfected HEKn cells and non-transfected hMSCs.

Quantitative PCR was used to determine changes in mitochondrial DNA copy number using ScienCell's Absolute Human Telomere Length Quantification and Mitochondrial DNA Copy Number Dual Quantification qPCR Assay Kit (#8958). The mtDNA primer set recognizes and amplifies one of the most conserved regions on human mtDNA and will not amplify any off-target sequence on nuclear genomic DNA. The single copy reference (SCR) primer set recognizes and amplifies a 100 bp-long region on human chromosome 17 and serves as reference for data normalization. Primer-probe real-time PCR was performed using BioRad's CFX96 Real-Time System (BioRad, Hercules, CA). The results are shown in FIG. 15. As shown in FIG. 15, F50S, hMSCs and HEKn cells treated with the rejuvenating compositions of the present disclosure displayed increased mitochondrial DNA copy number as compared to untreated cells.

Summary of Example 5: the compositions and methods of the present disclosure can be used to rejuvenate various cell types, including low passage and senescent fibroblasts, human mesenchymal stem/stromal cells and human epidermal keratinocytes, leading to an increase in telomere length and mitochondrial DNA amount in treated cells.

Example 6—the Methods and Compositions of the Present Disclosure Reactivate Telomerase Activity in Fibroblasts In this example, 50 year-old human fibroblasts (F50) were transfected with various compositions of the present disclosure. The telomerase activity in the transfected target cells, as well as control cells, was analyzed.

Fifty year-old human dermal fibroblast (F50 passage 6) were cultured in fibroblast expansion medium (FEM) comprised of DMEM/F12 supplemented with 5% human serum, 1× MEM non-essential amino acids solution, 55 µM of 2-mercaptoethanol (β-ME), 1× GlutaMAX™ supplement, plus antibiotics (all from Thermo Fisher Scientific), with 50 ug/ml ascorbic acid, 1 ng/ml hydrocortisone (both from Sigma), 12 ng/ml basic FGF (Gibco) and 5 ng/ml human EGF (Invitrogen). As untreated control lines, the F50-iPSC line was cultured in mTeSR™1 Media supplemented with 1× mTeSR™1 supplement (StemCell Technologies) plus antibiotics (Thermo Fisher Scientific) on plates coated with Matrigel coating matrix (Corning).

Two sequential transfections with either 3 ug mod-mRNA encoding hTERT or 3 ug mod-mRNA encoding hTERT with 3 ug mod-mRNA encoding dCas9-VPR+500 ng gRNA mix were performed using Lipofectamine® RNAiMAX™ (RNAiMAX) (Thermo Fisher Scientific). RNA and RNAiMAX were first diluted in Opti-MEM®I Reduced Serum Medium (Opti-MEM) (Thermo Fisher Scientific). For mod-mRNA transfections, 100 ng/µl RNA was diluted 5×, and 5 µl of RNAiMAX per microgram of mod-mRNAs was diluted 10× using Opti-MEM. After dilution, these components were combined together and incubated for 15 min at RT. After incubation at RT, transfection mixtures of mod-RNA and/or gRNA and RNAiMAX were applied to the cell culture, in FEM supplemented with 200 ng/ml B18R (eBioscience). The medium was changed after overnight incubation after each transfection.

Telomerase activity was measured with the TRAPeze® Telomerase Detection Kit (Millipore) according to the manufacturer's instructions. CHAPS (1×) lysis buffer was used to obtain extracts from, positive control cells (kit provided), an iPSC line derived from F50 (F50-iPSC), fibroblasts (F50), and fibroblasts (F50) treated with two sequential transfections of 3 ug hTERT only or 3 ug hTERT with 3 ug dCas9-VPR+3 ug gRNA mix. About 10,000 cells were assayed for each telomeric repeat amplification protocol assay, and 1,500 cell equivalents were loaded into each well of a 15% non-denaturing TBE (Tris borate, EDTA)-Urea polyacrylamide gel. Each sample was heat inactivated for 10 min at 85° C. to assess the background of the assay.

Figure 16:
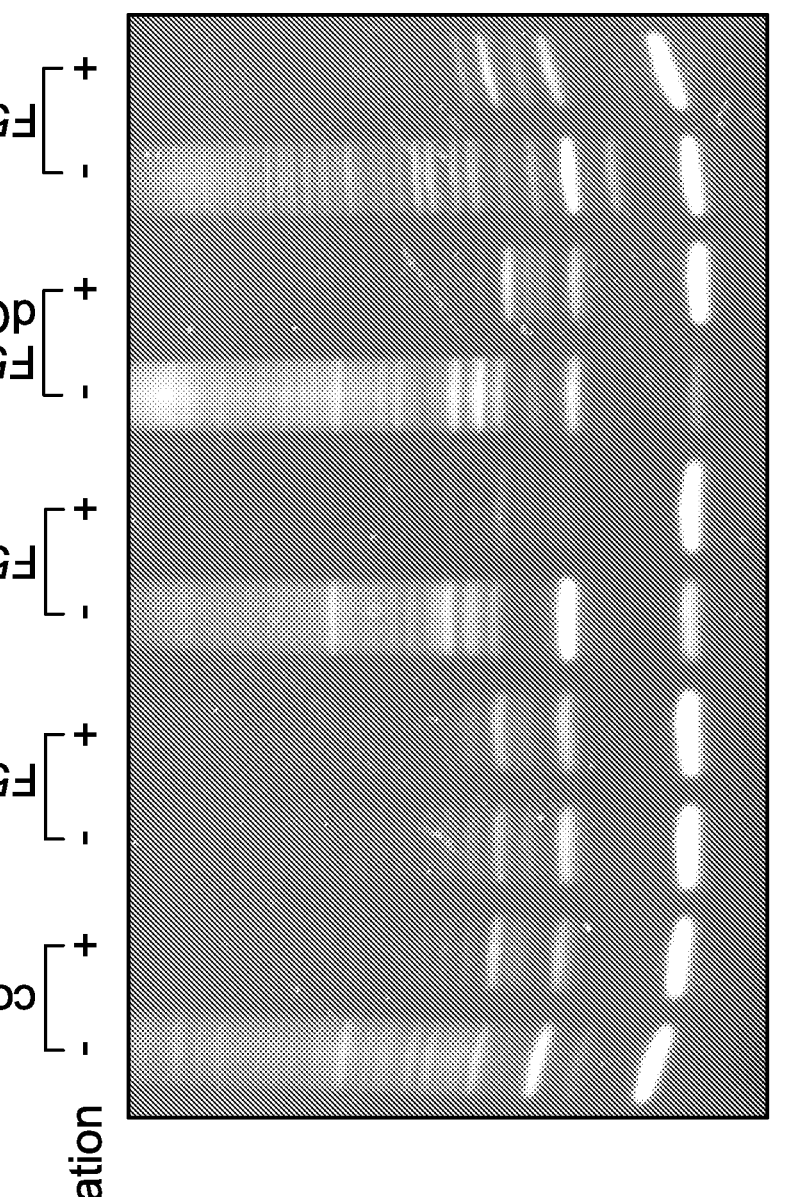
FIG. 16 is a gel image of the results of a telomerase activity assay in F50 cells transfected with various compositions of the present disclosure (F50+TERT and F50+TERT+dCas9–VPR/gmix) as well as non-transfected F50 cells and F50-derived induced pluripotent stem cells.

The results of the telomerase activity assay are shown in FIG. 16. Brighter products are indicative of higher activity. As show in in FIG. 16, the combined treatment with mod-mRNA encoding hTERT, mod-mRNA encoding dCas9-VPR and hTERC-specific gRNAs resulted in a higher level of telomerase activity as compared to untreated iPSCs or F50 cells transfected with only mod-mRNA encoding hTERT treatment alone.

Example 6 summary: The compositions and methods of the present disclosure can reactivate and increase telomerase activity in target cells, thereby rejuvenating the target cells.

Example 7—the Compositions of The Present Disclosure Facilitate Single Cell Expansion In this example, primary human adult fibroblasts were transfected with compositions of the present disclosure to determine if the methods and compositions of the present disclosure could support the expansion from a single cell.

Primary human adult fibroblasts were obtained from a skin biopsy. Adult fibroblasts were cultured in fibroblast expansion medium (FEM) comprised of DMEM/F12 supplemented with 5% human serum, 1× MEM non-essential amino acids solution, 55 µM of 2-mercaptoethanol (β-ME), 1× GlutaMAX™ supplement, plus antibiotics (all from Thermo Fisher Scientific), with 50 ug/ml ascorbic acid, 1 ng/ml hydrocortisone (both from Sigma), 12 ng/ml basic FGF (Gibco) and 5 ng/ml human EGF (Invitrogen). Individual patient-derived fibroblasts were plated and single cells selected using a (10×10 mm) PYREX® cloning cylinder.

FIG. 11 shows a schematic of the transfection regimen of the select, single fibroblasts using rejuvenating compositions of the present disclosure, with adjustments made for the reduced tissue culture surface area. The cells were first pre-treated with three sequential transfections with 50 ng mod-mRNA encoding hTERT. After pretreatment, four sequential transfection series with 50 ng mod-mRNA encoding hTERT followed by 50 ng mod-mRNA encoding dCas9-VPR and 50 ng hTERC guide RNA (gRNA) (4 guides, 1:1:1:1 ratio) the next day were performed using Lipofectamine® RNAiMAX™ (RNAiMAX) (Thermo Fisher Scientific). RNA and RNAiMAX were first diluted in Opti-MEM®I Reduced Serum Medium (Opti-MEM). For mod-mRNA and/or gRNA transfections, 100 ng/µl RNA was diluted 5×, and 5 µl of RNAiMAX per microgram of mod-mRNAs and/or gRNA were diluted 10× using Opti-MEM. After dilution, these components were combined together and incubated for 15 min at RT. After incubation at RT, transfection mixtures of mod-RNA mix and/or gRNA and RNAiMAX were applied to the cell culture, in FEM supplemented with 200 ng/ml B18R (eBioscience). The medium was changed after overnight incubation after each transfection.

Figure 17:
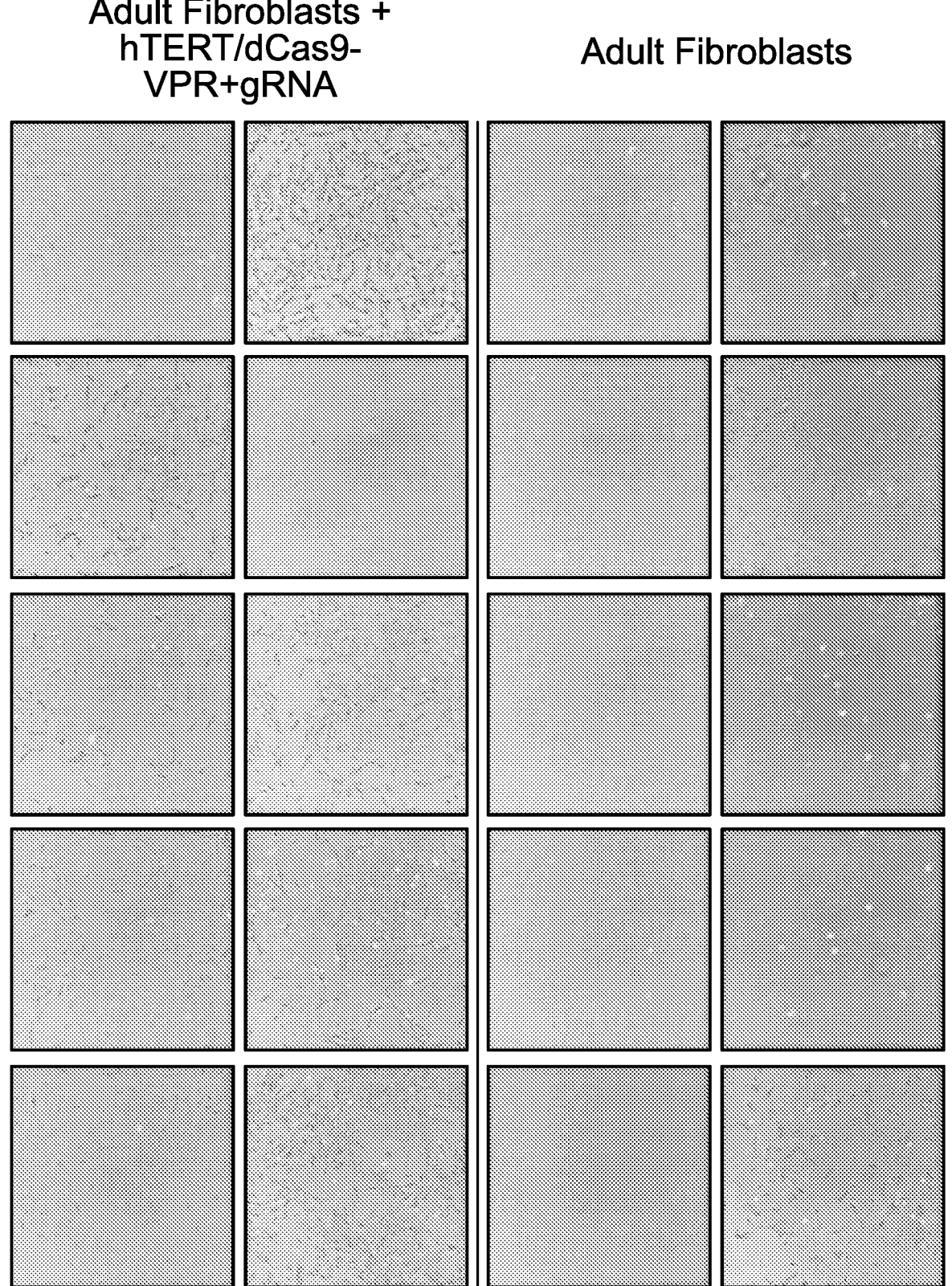
FIG. 17 is a series of representative microscopy images of adult human primary fibroblasts expanded from single cells that were not transfected (top two rows) or transfected with compositions of the present disclosure (+hTERT/dCas9–VPR+gRNA; bottom two rows).

Following the transfection regimen, each well was trypsinized and cells were transferred into one well of a 6-well tissue culture plate for further expansion in FEM. As shown in FIG. 17, one week after the last transfection, 2/10 wells of untreated cells expanded successfully and were able to be collected for gDNA extraction while 9/10 wells of treated fibroblasts expanded and collected.

Summary of Example 7: The compositions and methods of the present disclosure can facilitate the expansion of even single cells.

Example 8—the Compositions and Methods of the Present Disclosure Increase The Migration Activity of High Passage Human Mesenchymal Stem/Stromal Cells (hMSCs)

In this example, human mesenchymal stem/stromal cells (hMSCs) were transfected with compositions of the present disclosure to determine if the compositions and methods of the present disclosure can increase the migration activity of high passage hMSCs.

Figure 18:
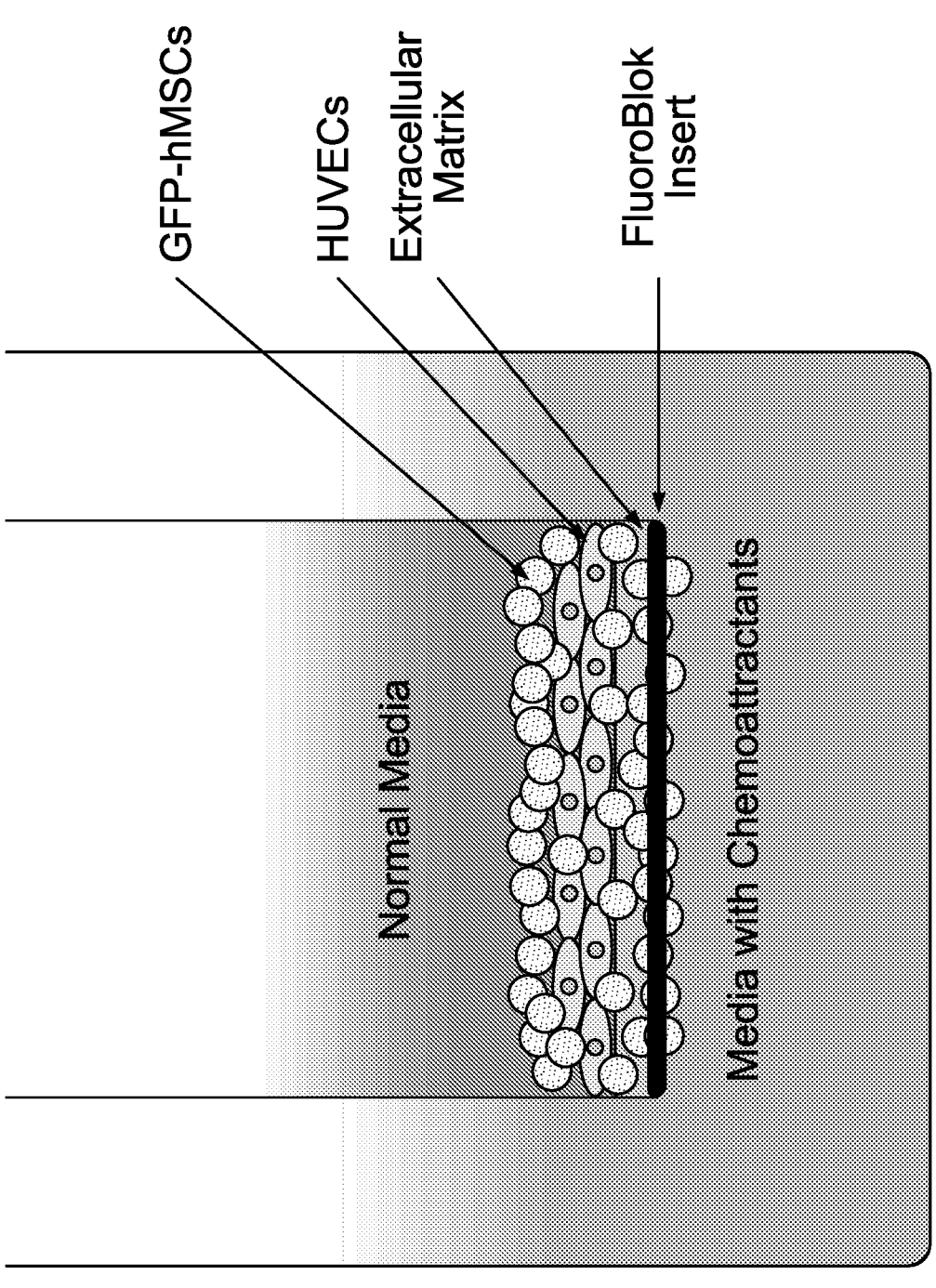
FIG. 18 is a schematic overview of the transendothelial migration (TEM) assay.

To measure migration activity of treated and untreated hMSCs, a Transendothelial Migration (TEM) assay was used. A schematic of the TEM assay is shown in FIG. 18. Briefly, Corning FluoroBlok cell culture inserts were pre-seeded with human endothelial cells (HUVEC). GFP+ hMSCs are plated, and their migration through the HUVEC layer and pores of the FluoroBlok membrane was quantified over time via bottom-reading fluorescence microscopes such as the CellInsight CX7 High-Content Screening (HCS) Platform.

24-well Corning FluoroBlok™ Inserts were coated with collagen. After coating, human umbilical vein endothelial cells (HUVECs) were plated at 80K/cm² in ECM-2MV BulletKit™ media (Lonza) and allowed to attach in 5% CO2 incubation overnight. Following overnight incubation and successful attachment, media in the basal chamber was changed to Human Mesenchymal Stem Cell Growth Medium (Cyagen) supplemented with human recombinant EGF [10 ng/mL] (Stemcell Technologies). Human Mesenchymal Stem/Stromal Cells labeled with Green Fluorescent Protein (GFP) purchased from Cyagen were cultured for twelve passages (P12) and treated with the rejuvenating compositions of the present disclosure as described in FIG. 11 and Example 5, while control hMSCs were cultured without mRNA treatment. The rejuvenation procedure lasted for two passages bringing the passage number to P14. A portion of the rejuvenated hMSCs were frozen in a CoolCell LX™ overnight at −80° while the remaining cells were allowed to remain in culture. After two passages, the frozen cells were thawed and allowed to culture for further two passages.

Figure 19:
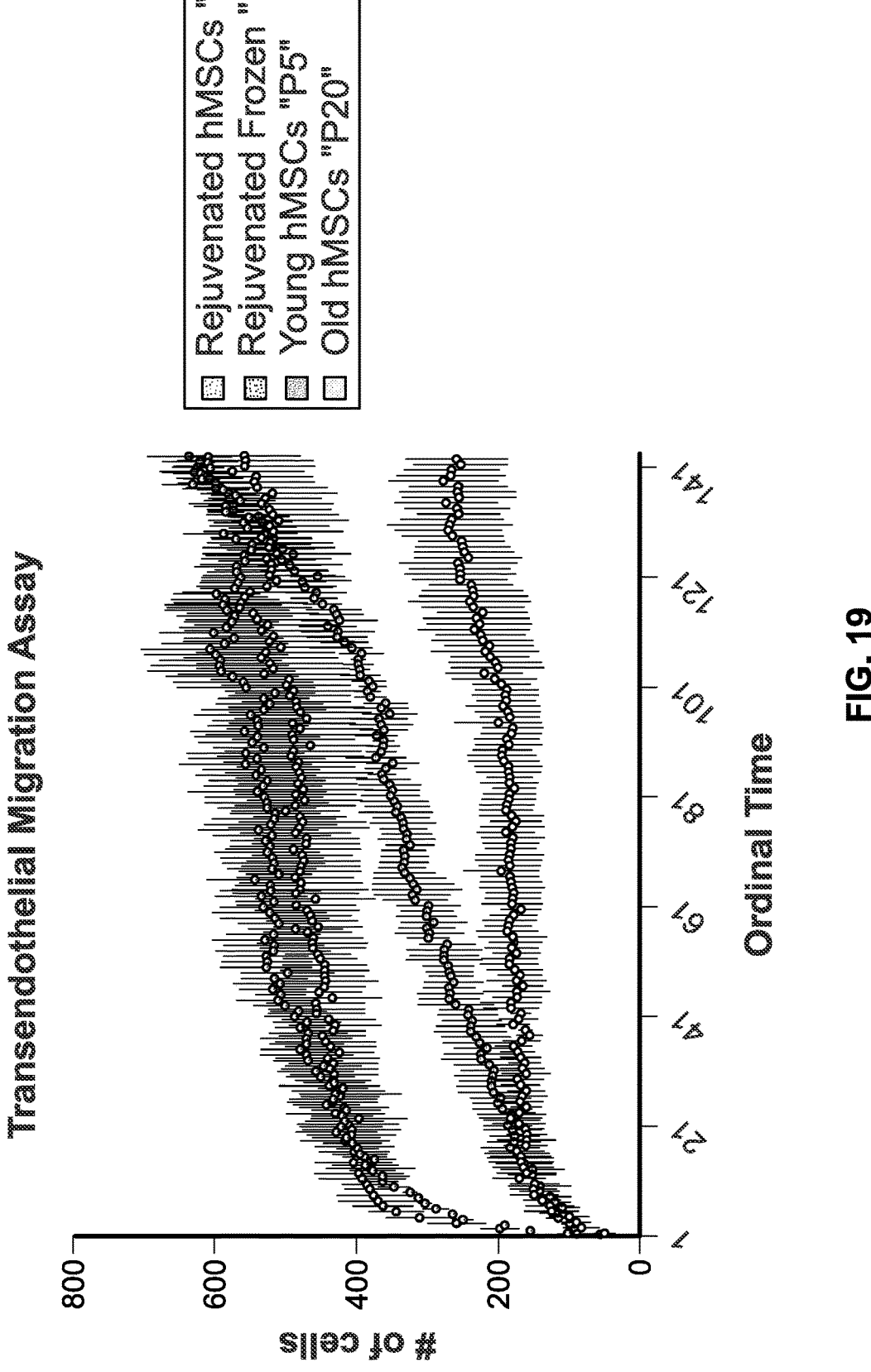
FIG. 19 is chart showing the migration activity of hMSCs transfected with compositions of the present disclosure as measured using the TEM assay.

The four conditions were as follows; Old high passage hMSCs (P20) were never rejuvenated or frozen; Young low passage hMSCs (P5) were a fresh vial of GFP labeled hMSCs (Cyagen) that was thawed allowed to attached overnight then lifted and run on the Transendothelial Migration Assay, frozen rejuvenated hMSCs (P17) that were frozen at P15 then thawed and allowed to culture for two passages and rejuvenated hMSCs that were never frozen but underwent five passages following the rejuvenation protocol. These four conditions were then added to the apical chamber of the FluoroBlok on top of the layer of attached HUVECs. Four fields of view from three replicates were obtained on ThermoScientific's CellInsight CX7 LED High-Content Screening (HCS) Platform. The CX7 HCS is designed to use brightfield, widefield and confocal microscopy for the entire fluorescence spectrum to rapidly capture and quantify high content data such as the kinetic analysis performed on Transendothelial Migration Assays (TEM). As shown in FIG. 19, the rejuvenated high passage hMSCs reached the saturation point significantly faster than untreated young hMSCs (40-50 ordinal time vs 130 ordinal time), while old high passage hMSCs (P20) showed poor migratory ability. A one-way ANOVA analysis exhibited significance of $p<0.0001$ between young and both groups rejuvenated hMSCs as compared to high passage hMSCs.

Example 8 summary: The compositions and methods of the present disclosure can rejuvenate hMSCs as evidenced by the increase in the migration activity of high passage hMSCs treated using the compositions and methods of the present disclosure.

Example 9—the Compositions and Methods of the Present Disclosure Restore the Level of Thiol Group Oxidation of Proteins in High Passage Senescent Human Mesenchymal Stem/Stromal Cells (hMSCs) to that Observed in Young Low Passage hMSCs In this example, senescent high passage human mesenchymal stem/stromal cells (hMSCs) were transfected with compositions of the present disclosure to determine if the compositions and methods of the present disclosure can restore the level of thiol group oxidation of proteins in high passage senescent human mesenchymal stem/stromal cells (hMSCs) to that observed in young low passage hMSCs. Among amino acids, the sulphur-containing cysteine (Cys) is particularly prone to oxidation. This is due to the presence of the thiol moiety (—SH) in the side chain of Cys, which can easily form disulfide bonds with a different thiol moiety in response to oxidation. Reversible oxidation of Cys thiols regulate the activity of enzymes and ligand binding, as well as participate in redox signaling, which deregulation plays an essential role in the development of many human disease and aging.

Human mesenchymal stem/stromal cells (hMSCs) were cultured in mesenchymal stem cell growth medium (MSCGM) (prepared as a kit from Cyagen) under low $O_2$ (5%). The three conditions were as follows: Senescent high passage hMSCs (P14) were never rejuvenated; Young low passage hMSCs (P5) were a fresh vial of hMSCs that were thawed allowed to attached overnight then lifted and processed for the peptide analysis; Senescent high passage hMSCs treated at passage 12 with the rejuvenating compositions of the present disclosure. The rejuvenation procedure lasted for two passages bringing the passage number of treated senescent hMSCs to P14 before the peptide analysis was performed, matching untreated senescent hMSCs.

For hMSCS, a pre-treatment of 3 transfections with 500 ng mod-mRNA encoding human TERT was performed using Lipofectamine® RNAiMAX™ (RNAiMAX) (Thermo Fisher Scientific). Following pre-treatment with hTERT mod-mRNA transfections, three sequential transfection series with 500 ng mod-mRNA encoding hTERT followed by 500 ng mod-mRNA encoding dCas9-VPR and 500 ng hTERC guide RNA (gRNA) (1 selected guide) the next day were performed using Lipofectamine® RNAiMAX™ (RNAiMAX) (Thermo Fisher Scientific). RNA and RNAiMAX were first diluted in Opti-MEM-pH 8.2. For mod-mRNA transfections, 100 ng/µl RNA was diluted 5×, and 5 µl of RNAiMAX per microgram of mod-mRNAs was diluted 10× using Opti-MEM-pH 8.2. After dilution, these components were combined together and incubated for 15 min at RT. After incubation at RT, transfection mixtures of mod-RNA mix and RNAiMAX were applied to the cell culture, in respective media supplemented with 200 ng/ml B18R. The medium was changed after overnight incubation after each transfection.

Transfected senescent and un-transfected senescent and low passage young hMSCs were processed using iodoTMTsixplex Isobaric Mass Tag Labeling Kit (Thermo-Scientific). Resulted iodoTMT labeled peptide mix was analyzed by QExactive HF Orbitrap mass spectrometer with an Easy nLC 1000 UPLC system (Thermo Fischer Scientific). Peptide identifications were performed using Max-Quant program. Each MS/MS spectrum was analyzed against a human specific database (Uniprot). After this analysis, data files were exported and additionally analyzed with Perseus software for data of interest. Each experiment was repeated twice. MaxQuant and Perseus software were downloaded from Max Planck Institute of Biochemistry website.

Figure 20:
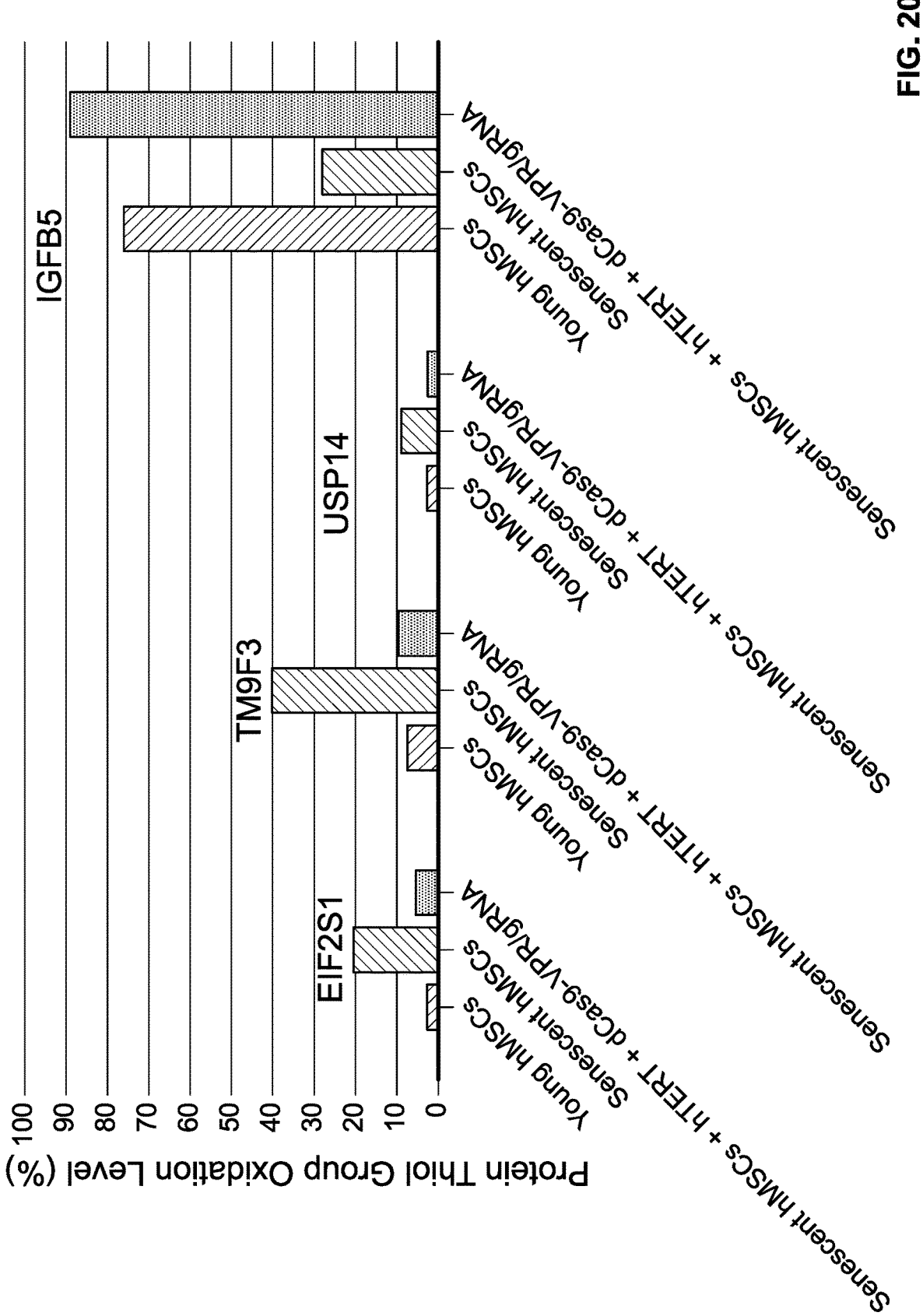
FIG. 20 is series chart showing the oxidation level of thiol groups detected in selected proteins in senescent hMSCs transfected with compositions of the present disclosure as compared to non-transfected young low passage and senescent high passage hMSCs.

The level of thiol group oxidation in senescent high passage hMSCs increased in 88 proteins and decreased in 31 proteins as compared to young hMSCs. The transfection of senescent hMSCs with rejuvenating compositions of the present disclosure resulted in the restoration of thiol group oxidation levels in approximately 90% of target proteins to the level observed in young cells. FIG. 20 shows representative results of the thiol group analysis in proteins whose thiol group oxidation levels increased (EIF2S1, TM9F3and USP14) and decreased (IGFB5) in senescent high passage hMSCs and the reversion of these thiol group oxidation levels to the young-like state in response to the treatment with the rejuvenating composition.

Example 9 summary: The compositions and methods of the present disclosure can rejuvenate hMSCs as evidenced by the restoration of the young-like level of protein thiol group oxidation in high passage hMSCs treated using the compositions and methods of the present disclosure.

Example 10—the Compositions and Methods of the Present Disclosure Reduce Senescence-Associated DNA Methylation in High Passage Senescent Human Mesenchymal Stem/Stromal Cells (hMSCs) and Human Neonatal Epidermal Keratinocytes (HEKn)

In this example, senescent high passage human mesenchymal stem/stromal cells (hMSCs) and senescent high passage human neonatal epidermal keratinocytes (HEKn) were transfected with compositions of the present disclosure to determine if the compositions and methods of the present disclosure can reduce the level of senescence-associated DNA methylation in these cells. Changes in DNA methylation have been recognized as one of the most common molecular alterations in aging and cellular senescence.

Human fibroblasts of different origin were cultured in FEM; human keratinocytes of different origin were cultured in EpiLife medium supplemented with EDGS and hMSCs were cultured in mesenchymal stem cell growth medium (MSCGM). The following cell types used for DNA methylation analysis were not treated with rejuvenating compositions: young low passage neonatal fibroblasts (P3), young low passage adult F50 fibroblasts (P3), young low passage neonatal keratinocytes HEKn (P3), young low passage fetal keratinocyte (P2), young low passage adult keratinocytes (P3), young umbilical cord-derived hMSCs (P2), senescent high passage F50S fibroblasts (P15), senescent high passage hMSCs (P13) and senescent high passage HEKn (P10). The treated group included senescent high passage HEKn and senescent high passage hMSCs treated with rejuvenating compositions as described in FIG. 11 and Example 5. After completing the treatment with compositions, the treated cells were expanded for additional 6 days. Genomic DNA (gDNA) was extracted from each cell culture using the Quick-DNA™ Miniprep Kit (Zymo Research) and subjected to DNA methylation analysis using the Illumina Infinium MathylationEPIC BeadChip Kit.

The DNA methylation data generated for cells of different types were analyzed using the R package "IlluminaHumanMethylationEPICanno.ilm10b2. hg19" and combined into three groups as follows: young cells, senescent (high passage) cells and senescent cells treated with rejuvenating compositions of the present disclosure. The young group included young low passage neonatal fibroblasts (P3), young low passage adult fibroblasts (P3), young low passage neonatal keratinocytes (P3), young low passage fetal keratinocyte (P2), young low passage adult keratinocytes (P3) and young umbilical cord-derived hMSCs (P2). The senescent group included senescent high passage F50S fibroblasts (P15), senescent high passage hMSCs (P13) and senescent high passage HEKn (P10). The treated group included senescent high passage HEKn and senescent high passage hMSCs treated with rejuvenating compositions. Cells of different type and origin were combined based on their senescence state to eliminate cell type-specific methylation differences among groups. The groups were compared using the 2-tailed t-test for two groups with unequal variance, and the degree of methylation was calculated as a fraction of methylated nucleotides at a site of interest, ranging from 0 to 1. Differential methylation sites were selected based on the largest difference in the degree of methylation for each group, and 9 DNA methylation sites were identified as the most methylated in senescent high passage cells irrespectively of the cell type of origin.

Figure 21:
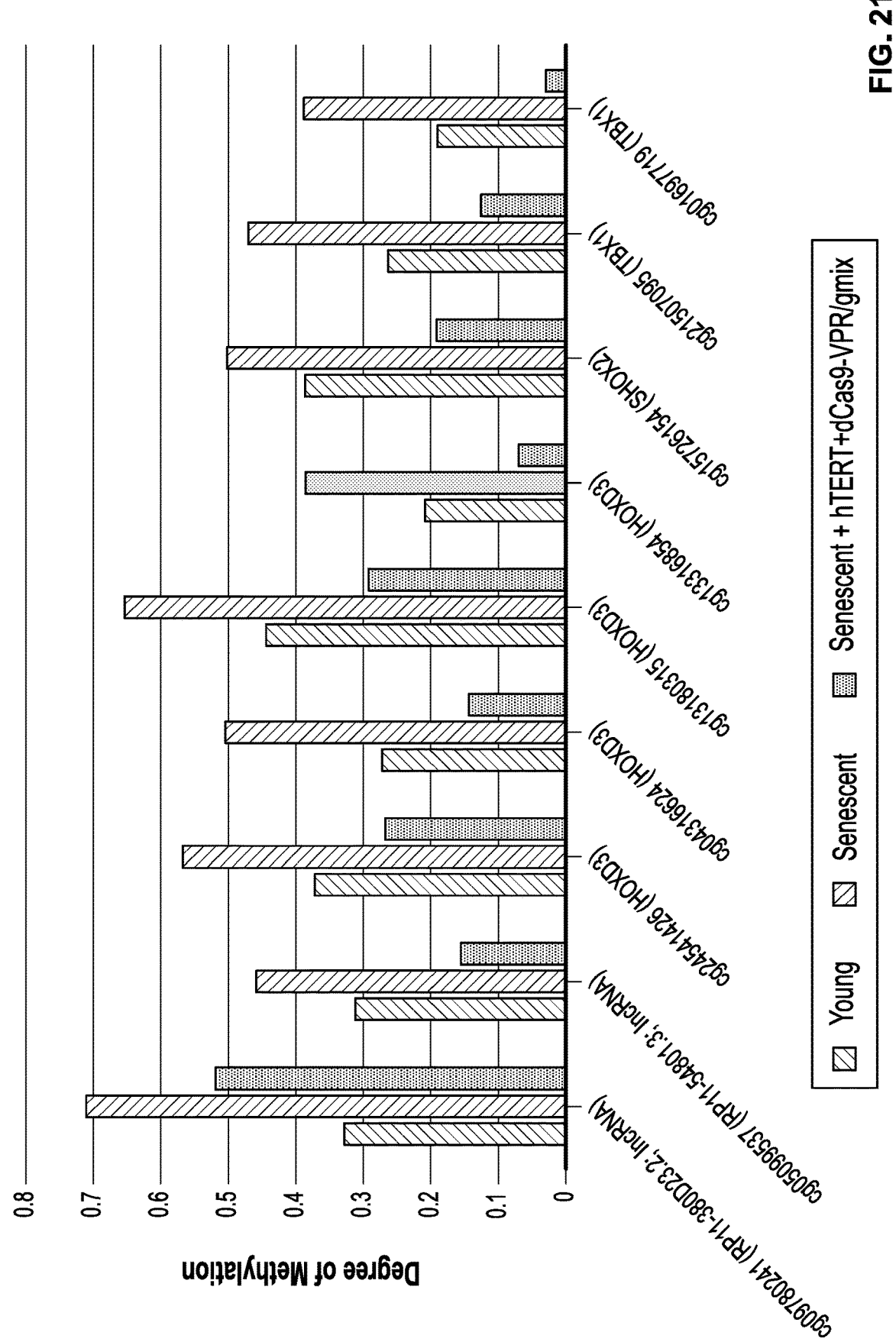
FIG. 21 is a series chart showing the degree of methylation at 9 senescence-associated DNA methylation sites in senescent cells of different types transfected with compositions of the present disclosure as compared to non-transfected young low passage and senescent high passage cells.

FIG. 21 depicts the location of 9 identified senescence-associated DNA marks and their associated genomic loci. All 9 sites showed an increase in DNA methylation levels in the senescence high passage group. The treatment of the cells from the senescent group with rejuvenating compositions of the present disclosure reduced the level of DNA methylation at all 9 sites to the level similar to that of the young cell group.

Example 10 summary: the compositions and methods of the present disclosure can be used to rejuvenate various cell types, including senescent human mesenchymal stem/stromal cells and human epidermal keratinocytes, leading to a reduction in senescence-association DNA methylation in treated cells.

What is claimed is:

1. A composition comprising:
a) at least one first polynucleotide molecule comprising a nucleic acid sequence encoding at least a biologically active exogenous human telomerase reverse transcriptase (TERT) having telomere elongation activity; and
b) at least one second polynucleotide molecule comprising a nucleic acid sequence encoding at least a portion of at least one DNA targeting polypeptide, wherein the at least a portion of the at least one DNA targeting polypeptide increases transcription of endogenous human telomerase RNA component (TERC) compared to untreated cells wherein none of the DNA-targeting polypeptides target an endogenous TERT gene, wherein the DNA-targeting polypeptide does not target an endogenous TERT gene, and wherein the combination of a) and b) increases telomere length compared to untreated cells.

2. The composition of claim 1, wherein the at least one first polynucleotide molecule comprises:
i) an mRNA molecule encoding at least a biologically active human TERT having elongation activity; or
ii) a plasmid comprising a nucleic acid sequence encoding at least a biologically active human TERT operably linked to at least one promoter to drive detectable expression of the at least one biologically active human TERT.

3. The composition of claim 1, wherein the at least one second polynucleotide molecule comprises: i) an mRNA molecule encoding at least a portion of at least one DNA targeting polypeptide; or ii) a plasmid comprising a nucleic acid sequence encoding at least a portion of at least one DNA targeting polypeptide operably linked to at least one promoter to drive detectable expression of the at least one portion of the at least one DNA targeting polypeptide.

4. The composition of claim 1, wherein the DNA targeting polypeptide comprises at least one CRISPR-associated protein 9 (Cas9) molecule, at least one Cas9 variant that remains functionally active, or at least one Cas9 ortholog thereof that remains functionally active, at least one Transcription Activator-Like Effector (TALE) molecule, at least one zinc-finger molecule, at least one meganuclease molecule or any combination thereof.

5. The composition of claim 1, wherein the DNA targeting polypeptide comprises at least one transactivation molecule.

6. The composition of claim 1, wherein when the DNA targeting polypeptide comprises at least one Cas9 molecule, at least one Cas9 variant that remains functionally active, or at least one Cas9 ortholog thereof, the composition further comprises at least one guide RNA (gRNA).

7. The composition of claim 5, wherein the transactivation molecule comprises at least one single guide RNA MS2 bacteriophage (sgRNA-MS2) molecule, wherein the at least one sgRNA-MS2 molecule comprises a nucleic acid sequence complementary to a nucleic acid sequence located upstream, within, or downstream of the endogenous TERC gene and at least one MS2 RNA aptamer.

8. The composition of claim 1, further comprising: i) a plurality of guide RNA (gRNA) molecules, wherein at least one gRNA in the plurality is complementary to a nucleic acid sequence located upstream, within, or downstream of the endogenous TERC gene; or ii) at least one plasmid comprising at least one nucleic acid sequence encoding at least one gRNA operably linked to at least one promoter to drive detectable expression of the at least one species gRNA.

9. The composition of claim 1, wherein the nucleic acid sequence encoding at least a portion of the at least one DNA targeting polypeptide in b) comprises at least one modified mRNA molecule and wherein the at least one DNA targeting polypeptide comprises dCas9 and a VP64-P65-Rta (VPR) molecule; and further comprising:

c) a plurality of guide RNA (gRNA) molecules, wherein at least one gRNA is selected from the group consisting of SEQ ID nos. 1-1276.

10. The composition of claim 1, further comprising at least one polynucleotide encoding at least one rejuvenating factor.

11. The composition of claim 1, wherein the composition is packaged or encoded in at least one viral particle, at least one exosome, at least one microvesicle, at least one liposome, or at least one nanoparticle.

12. A method of rejuvenating at least one cell, the method comprising contacting the at least one cell in need of rejuvenation with the composition of claim 1.

13. A method of treating, reducing the risk of onset of, or preventing a health condition in a subject comprising: a) contacting at least one cell in vitro with the composition of claim 1; b) expanding the at least one cell in vitro to produce a plurality of rejuvenated cells; and c) administering a therapeutically effective amount of the plurality of rejuvenated cells to the subject in need of cell therapy and treating, reducing onset of, or preventing the health condition in the subject.

14. A method for rejuvenating at least one cell in a subject comprising administering to the subject a therapeutically effective amount of the composition of claim 1.

15. The composition of claim 1, further comprising a pharmaceutically acceptable excipient.

16. A kit comprising the composition of claim 1, and at least one container.

17. A method for preparing a composition of claim 1 comprising combining a) and b) into a medium.

18. The composition of claim 1, wherein the DNA targeting polypeptide comprises at least one Cas9 molecule, at least one Cas9 variant that remains functionally active, or the at least one Cas9 ortholog molecule thereof that remains functionally active and the at least one Cas9 molecule, the at least one Cas9 variant, or the at least one Cas9 ortholog molecule thereof comprises at least one of eSpCas9 (K855A), eSpCas9 (1.0), eSpCas9 (1.1), SpCas9-HF1 (VP12), HypaCas9, xCas9, SpyFi Cas9, iSpy Cas9, iSpy-Mac, Cas9 (VQR), Cas9 (EQR), Cas9 (VRER), Cas9 (D11 35E), Cas9 (QQR1), SaCas9 (KKH, Nme1Cas9, Nme2Cas9, Nme3Cas9, Streptococcus pyogenes Cas9 (spCas9), Francisella novicida Cas9 (FnCas9), Staphylococcus aureus Cas9 (SaCas9), Neisseria meningitidis Cas9 (NmCas9; NmeCas9), Streptococcus thermophilus CRISPR1-Cas9 (St1Cas9), Streptococcus thermophilus CRISPR3-Cas9 (St3Cas9), Campylobacter jejuni Cas9 (CjCas9), Acidaminococcus sp. BV3L6 Cpf1 (AsCpf1), Lachnospiraceae bacterium ND2006 Cpf1 (LbCpf1), Streptococcus canis Cas9 (ScCas9), Treponema denticola Cas9 (TdCas9), Streptococcus macacae Cas9 (SmacCas9), Casφ (Cas12j), Francisella tularensis subsp. novicida Cas9, Pasteurella multocida Cas9, Campylobacter lari CF89-12 Cas9, Mycoplasma gallisepticum str. F Cas9, Nitratifractor salsuginis str DSM 16511 Cas9, Parvibaculum lavamentivorans Cas9, Roseburia intestinalis Cas9, Neisseria cinerea Cas9, Gluconacetobacter diazotrophicus Cas9, Azospirillum B510 Cas9, Sphaerochaeta globus str. Buddy Cas9, Flavobacterium columnare Cas9, Fluviicola taffensis Cas9, Bacteroides coprophilus Cas9, Mycoplasma mobile Cas9, Lactobacillus farciminis Cas9, Streptococcus pasteurianus Cas9, Lactobacillus johnsonii Cas9, Staphylococcus pseudintermedius Cas9, Filifactor alocis Cas9, Legionella pneumophila str. Paris Cas9, Sutterella wadsworthensis Cas9, Corynebacter diphtheriae Cas9 or any combination thereof.

19. The composition of claim 4, wherein the DNA targeting polypeptide comprises at least one Cas9 molecule, at least one Cas9 variant, or the at least one Cas9 ortholog molecule thereof and the at least one Cas9 molecule, the at least one Cas9 variant, or the at least one Cas9 ortholog molecule thereof comprises at least one of SpCas9, SaCas9, SpyFi Cas9, Cpf1 and xCas9, or variant or ortholog molecule thereof.

* * * * *

SEQUENCE LISTING

<160> NUMBER OF SEQ ID NOS: 1276

<210> SEQ ID NO 1
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 1
uguucauaaa uuuacugaca                                              20

<210> SEQ ID NO 2
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 2
aaaaaaaucg uuacaauuua                                              20

```
<210> SEQ ID NO 3
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 3
aaaaucguua caauuuaugg                                          20

<210> SEQ ID NO 4
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 4
ucuugaugag guaaaaagag                                          20

<210> SEQ ID NO 5
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 5
gucuugauga gguaaaaaga                                          20

<210> SEQ ID NO 6
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 6
ugucuugaug agguaaaaag                                          20

<210> SEQ ID NO 7
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 7
aauuucucuc cuuugcauau                                          20

<210> SEQ ID NO 8
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 8
aguagugcug ugucuugaug                                          20

<210> SEQ ID NO 9
<211> LENGTH: 20
<212> TYPE: RNA
<213> ORGANISM: Artificial Sequence
<220> FEATURE:
<223> OTHER INFORMATION: Synthetic Sequence
```

-continued

```
<400> SEQUENCE: 9
aggggaccua cuuagguaau                                              20

<210> SEQ ID NO 10
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 10
caauuccagg ggaccuacuu                                             20

<210> SEQ ID NO 11
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 11
acggagcgag uccccgcgcg                                             20

<210> SEQ ID NO 12
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 12
uuuuaaccua uuaccuaagu                                             20

<210> SEQ ID NO 13
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 13
uaucugcuag acaauuccag                                             20

<210> SEQ ID NO 14
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 14
guaucugcua gacaauucca                                             20

<210> SEQ ID NO 15
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 15
uguaucugcu agacaauucc                                             20

<210> SEQ ID NO 16
<211> LENGTH: 20
```

```
<212> TYPE: RNA
<213> ORGANISM: Artificial Sequence
<220> FEATURE:
<223> OTHER INFORMATION: Synthetic Sequence

<400> SEQUENCE: 16
uauuaccuaa guaggucccc                                             20

<210> SEQ ID NO 17
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 17
ucccuuuuau uaggaaagaa                                             20

<210> SEQ ID NO 18
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 18
gacugaaucu cccuuuuauu                                             20

<210> SEQ ID NO 19
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 19
cgccuuucuu uccuaauaaa                                             20

<210> SEQ ID NO 20
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 20
gccuuucuuu ccuaauaaaa                                             20

<210> SEQ ID NO 21
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 21
cuacuacauu auuaaucuua                                             20

<210> SEQ ID NO 22
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 22
```
ccagcaacag uggacucuag                                          20

<210> SEQ ID NO 23
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 23
gagaacauua ccagcaacag                                          20

<210> SEQ ID NO 24
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 24
gcuaaauauc caauaugcaa                                          20

<210> SEQ ID NO 25
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 25
ccucuagagu ccacguuugc                                          20

<210> SEQ ID NO 26
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 26
gccucuccuu gagcagagga                                          20

<210> SEQ ID NO 27
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 27
ggugcacguc ccacagcuca                                          20

<210> SEQ ID NO 28
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 28
uccagccucu ccuugagcag                                          20

<210> SEQ ID NO 29
<211> LENGTH: 20
<212> TYPE: RNA
<213> ORGANISM: Artificial Sequence -continued

```
<220> FEATURE:
<223> OTHER INFORMATION: Synthetic Sequence

<400> SEQUENCE: 29
cugguaaugu ucucuaaaua                                              20

<210> SEQ ID NO 30
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 30
gggugcacgu cccacagcuc                                              20

<210> SEQ ID NO 31
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 31
uuaaagccau ccucugcuca                                              20

<210> SEQ ID NO 32
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 32
gccauccucu gcucaaggag                                              20

<210> SEQ ID NO 33
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 33
uccucugcuc aaggagaggc                                              20

<210> SEQ ID NO 34
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 34
uuccacaaaa ccaugcugau                                              20

<210> SEQ ID NO 35
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 35
gcucaaggag aggcuggaga                                              20
```

```
<210> SEQ ID NO 36
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 36
aaauauuuuu ccuaucagca                                                    20

<210> SEQ ID NO 37
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 37
aggcuggaga aggcauucua                                                    20

<210> SEQ ID NO 38
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 38
uuccuaucag caugguuuug                                                    20

<210> SEQ ID NO 39
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 39
gagaaggcau ucuaaggaga                                                    20

<210> SEQ ID NO 40
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 40
agaaggcauu cuaaggagaa                                                    20

<210> SEQ ID NO 41
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 41
gaaggcauuc uaaggagaag                                                    20

<210> SEQ ID NO 42
<211> LENGTH: 20
<212> TYPE: RNA
<213> ORGANISM: Artificial Sequence
<220> FEATURE:
<223> OTHER INFORMATION: Synthetic Sequence
```

-continued

```
<400> SEQUENCE: 42
aaggcauucu aaggagaagg                                        20

<210> SEQ ID NO 43
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 43
cauucuaagg agaaggggc                                         20

<210> SEQ ID NO 44
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 44
auucuaagga gaagggggca                                        20

<210> SEQ ID NO 45
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 45
caugguuuug uggaaaagua                                        20

<210> SEQ ID NO 46
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 46
uaaggagaag ggggcagggu                                        20

<210> SEQ ID NO 47
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 47
aagggggcag gguaggaacu                                        20

<210> SEQ ID NO 48
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 48
caagacucua gacaaguucu                                        20

<210> SEQ ID NO 49
```

-continued

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 49
gaaucuuguc ucggcucagu                                                    20

<210> SEQ ID NO 50
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 50
agaaucuugu cucggcucag                                                    20

<210> SEQ ID NO 51
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 51
acuacagcag aaucuugucu                                                    20

<210> SEQ ID NO 52
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 52
agaacuuguc uagagucuug                                                    20

<210> SEQ ID NO 53
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 53
cggcgcgauu cccugagcug                                                    20

<210> SEQ ID NO 54
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 54
ggcgcgauuc ccugagcugu                                                    20

<210> SEQ ID NO 55
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 55
```

-continued cuuugugaaa auagauuccc                                                            20

<210> SEQ ID NO 56
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 56
agaucaccuu gaguaaacug                                                            20

<210> SEQ ID NO 57
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 57
cugcuguagu cagugcugcc                                                            20

<210> SEQ ID NO 58
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 58
ugcuguaguc agugcugccu                                                            20

<210> SEQ ID NO 59
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 59
aguaagccuc aguuuacuca                                                            20

<210> SEQ ID NO 60
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 60
guuuugauca ucacauuuuu                                                            20

<210> SEQ ID NO 61
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 61
aaaaugugau gaucaaaacu                                                            20

<210> SEQ ID NO 62
<211> LENGTH: 20
<212> TYPE: RNA

-continued

```
<213> ORGANISM: Artificial Sequence
<220> FEATURE:
<223> OTHER INFORMATION: Synthetic Sequence

<400> SEQUENCE: 62
uucuucucuu ucuuuugaga                                                            20

<210> SEQ ID NO 63
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 63
ccagcucugg gugacagagu                                                            20

<210> SEQ ID NO 64
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 64
uccagcucug ggugacagag                                                            20

<210> SEQ ID NO 65
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 65
ggacacugca cuccagcucu                                                            20

<210> SEQ ID NO 66
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 66
gaauuagugu ucugugucuu                                                            20

<210> SEQ ID NO 67
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 67
gggacacugc acuccagcuc                                                            20

<210> SEQ ID NO 68
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 68
gaauucacag gaagauuuua                                                            20
```

```
<210> SEQ ID NO 69
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 69
ggaauucaca ggaagauuuu                                        20

<210> SEQ ID NO 70
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 70
cccacucugu cacccagagc                                        20

<210> SEQ ID NO 71
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 71
accuuaaaaa uggaauucac                                        20

<210> SEQ ID NO 72
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 72
gguugcagug agccaagaug                                        20

<210> SEQ ID NO 73
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 73
agguugcagu gagccaagau                                        20

<210> SEQ ID NO 74
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 74
gagguugcag ugagccaaga                                        20

<210> SEQ ID NO 75
<211> LENGTH: 20
<212> TYPE: RNA
<213> ORGANISM: Artificial Sequence
<220> FEATURE:
```

-continued

<223> OTHER INFORMATION: Synthetic Sequence

<400> SEQUENCE: 75
caccucgacu accuuaaaaa                                              20

<210> SEQ ID NO 76
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 76
gcauguguga gccgaguccu                                              20

<210> SEQ ID NO 77
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 77
ggagugcagu guccccaucu                                              20

<210> SEQ ID NO 78
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 78
uccugugaau uccauuuuua                                              20

<210> SEQ ID NO 79
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 79
ugcaugugug agccgagucc                                              20

<210> SEQ ID NO 80
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 80
gcuagaaacc gaggaggcag                                              20

<210> SEQ ID NO 81
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 81
uuccauuuuu aagguagucg                                              20

-continued

```
<210> SEQ ID NO 82
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 82
aaaaucgcua gaaaccgagg                                                        20

<210> SEQ ID NO 83
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 83
uauccucugc agaccagacg                                                        20

<210> SEQ ID NO 84
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 84
gagaaaaucg cuagaaaccg                                                        20

<210> SEQ ID NO 85
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 85
cacugcaacc ucugccuccu                                                        20

<210> SEQ ID NO 86
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 86
gaaauuaaag auuuaaaagc                                                        20

<210> SEQ ID NO 87
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 87
gagcuguggg acgugcaccc                                                        20

<210> SEQ ID NO 88
<211> LENGTH: 20
<212> TYPE: RNA
<213> ORGANISM: Artificial Sequence
<220> FEATURE:
<223> OTHER INFORMATION: Synthetic Sequence
```

-continued

<400> SEQUENCE: 88
uagucgaggu gaaccgcguc                                                                    20

<210> SEQ ID NO 89
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 89
gaaccgcguc uggucugcag                                                                    20

<210> SEQ ID NO 90
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 90
uguaaaccca gcuacuuggg                                                                    20

<210> SEQ ID NO 91
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 91
gucugcagag gauagaaaaa                                                                    20

<210> SEQ ID NO 92
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 92
gccuguaaac ccagcuacuu                                                                    20

<210> SEQ ID NO 93
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 93
ugccuguaaa cccagcuacu                                                                    20

<210> SEQ ID NO 94
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 94
aacuaacuug agguaucaga                                                                    20

<210> SEQ ID NO 95
<211> LENGTH: 20

-continued

<212> TYPE: RNA
<213> ORGANISM: Artificial Sequence
<220> FEATURE:
<223> OTHER INFORMATION: Synthetic Sequence

<400> SEQUENCE: 95
aaacuaacuu gagguaucag                                                    20

<210> SEQ ID NO 96
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 96
cucucagccu cccaaguagc                                                    20

<210> SEQ ID NO 97
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 97
ucucagccuc ccaaguagcu                                                    20

<210> SEQ ID NO 98
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 98
uuaaagguga aacuaacuug                                                    20

<210> SEQ ID NO 99
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 99
ucccaaguag cuggguuuac                                                    20

<210> SEQ ID NO 100
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 100
aucauaacau aguuuccuua                                                    20

<210> SEQ ID NO 101
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 101

```
uuacuuccga ccuucuuuaa                                                    20

<210> SEQ ID NO 102
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 102
aaaaaaucag ccggguaugg                                                    20

<210> SEQ ID NO 103
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 103
acaaaaaaau cagccgggua                                                    20

<210> SEQ ID NO 104
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 104
ugggacgugc acccaggacu                                                    20

<210> SEQ ID NO 105
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 105
aaaauacaaa aaaaucagcc                                                    20

<210> SEQ ID NO 106
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 106
gaaaauacaa aaaaucagc                                                     20

<210> SEQ ID NO 107
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 107
guuaguuuca ccuuuaaaga                                                    20

<210> SEQ ID NO 108
<211> LENGTH: 20
<212> TYPE: RNA
<213> ORGANISM: Artificial Sequence
```

<220> FEATURE:
<223> OTHER INFORMATION: Synthetic Sequence

<400> SEQUENCE: 108
caggcacaca ccaccauacc                                                          20

<210> SEQ ID NO 109
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 109
guuucaccuu uaaagaaggu                                                          20

<210> SEQ ID NO 110
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 110
cccuuccgca cguccgggaa                                                          20

<210> SEQ ID NO 111
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 111
cguugcccuu ccgcacgucc                                                          20

<210> SEQ ID NO 112
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 112
acguugcccu uccgcacguc                                                          20

<210> SEQ ID NO 113
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 113
uaaagacgca aagccuuucc                                                          20

<210> SEQ ID NO 114
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 114
uuuuguauuu ucaguaaagu                                                          20

<210> SEQ ID NO 115
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 115
uuuguauuuu caguaaaguu                                                                    20

<210> SEQ ID NO 116
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 116
uauuuucagu aaaguugggc                                                                    20

<210> SEQ ID NO 117
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 117
auuuaaaagc aggagccaua                                                                    20

<210> SEQ ID NO 118
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 118
caaagccuuu cccggacgug                                                                    20

<210> SEQ ID NO 119
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 119
uucaguaaag uugggcaggc                                                                    20

<210> SEQ ID NO 120
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 120
gccuuucccg gacgugcgga                                                                    20

<210> SEQ ID NO 121
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 121
caccugaggu caggaguucg                                                      20

<210> SEQ ID NO 122
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 122
ccuuucccgg acgugcggaa                                                      20

<210> SEQ ID NO 123
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 123
cgggcggauc accugagguc                                                      20

<210> SEQ ID NO 124
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 124
uccauuuccg gccaugagga                                                      20

<210> SEQ ID NO 125
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 125
aaguuccauu uccggccaug                                                      20

<210> SEQ ID NO 126
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 126
agaagcgggc ggaucaccug                                                      20

<210> SEQ ID NO 127
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 127
ggccucgaac uccugaccuc                                                      20

<210> SEQ ID NO 128

-continued

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 128
aagggcaacg uccuuccuca                                              20

<210> SEQ ID NO 129
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 129
ggaaauuaaa guuccauuuc                                              20

<210> SEQ ID NO 130
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 130
gcaacguccu uccucauggc                                              20

<210> SEQ ID NO 131
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 131
cuuugggagg cagaagcggg                                              20

<210> SEQ ID NO 132
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 132
gcacuuuggg aggcagaagc                                              20

<210> SEQ ID NO 133
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 133
uccuuccuca uggccggaaa                                              20

<210> SEQ ID NO 134
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 134
```

-continued agcacuuugg gaggcagaag                                                                                20

<210> SEQ ID NO 135
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 135
uguaauccca gcacuuuggg                                                                                20

<210> SEQ ID NO 136
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 136
gccuguaauc ccagcacuuu                                                                                20

<210> SEQ ID NO 137
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 137
cgccuguaau cccagcacuu                                                                                20

<210> SEQ ID NO 138
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 138
gcgggcuggu uggggggaac                                                                                20

<210> SEQ ID NO 139
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 139
ggcgggcugg uuggggggaa                                                                                20

<210> SEQ ID NO 140
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 140
ucucgggcgg gcugguuggg                                                                                20

<210> SEQ ID NO 141
<211> LENGTH: 20
<212> TYPE: RNA

<213> ORGANISM: Artificial Sequence
<220> FEATURE:
<223> OTHER INFORMATION: Synthetic Sequence

<400> SEQUENCE: 141
cucucgggcg ggcugguugg                                                        20

<210> SEQ ID NO 142
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 142
gcuucugccu cccaaagugc                                                        20

<210> SEQ ID NO 143
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 143
ucucucgggc gggcugguug                                                        20

<210> SEQ ID NO 144
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 144
cuucugccuc ccaaagugcu                                                        20

<210> SEQ ID NO 145
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 145
cucucucggg cgggcugguu                                                        20

<210> SEQ ID NO 146
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 146
acucucucgg gcgggcuggu                                                        20

<210> SEQ ID NO 147
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 147
agucacucuc ucgggcgggc                                                        20

```
<210> SEQ ID NO 148
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 148
ucccaaagug cugggauuac                                              20

<210> SEQ ID NO 149
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 149
ugagagucac ucucucgggc                                              20

<210> SEQ ID NO 150
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 150
gugagaguca cucucucggg                                              20

<210> SEQ ID NO 151
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 151
cucgugagag ucacucucuc                                              20

<210> SEQ ID NO 152
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 152
ucucgugaga gucacucucu                                              20

<210> SEQ ID NO 153
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 153
ggaucuuagu ccccgcacgg                                              20

<210> SEQ ID NO 154
<211> LENGTH: 20
<212> TYPE: RNA
<213> ORGANISM: Artificial Sequence
<220> FEATURE:
```

-continued

```
<223> OTHER INFORMATION: Synthetic Sequence

<400> SEQUENCE: 154
aagggaucuu aguccccgca                                                 20

<210> SEQ ID NO 155
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 155
uacaggcgug agccaccgug                                                 20

<210> SEQ ID NO 156
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 156
acaggcguga gccaccgugc                                                 20

<210> SEQ ID NO 157
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 157
caggcgugag ccaccgugcg                                                 20

<210> SEQ ID NO 158
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 158
auuggccaag cugacucucg                                                 20

<210> SEQ ID NO 159
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 159
gaguccccgc ccuugcaaaa                                                 20

<210> SEQ ID NO 160
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 160
ggaguccccg cccuugcaaa                                                 20
```

-continued

```
<210> SEQ ID NO 161
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 161
ggacuaagau cccuuuugca                                                          20

<210> SEQ ID NO 162
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 162
gacuaagauc ccuuuugcaa                                                          20

<210> SEQ ID NO 163
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 163
uaagaucccu uuugcaaggg                                                          20

<210> SEQ ID NO 164
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 164
gagagccgcg agagucagcu                                                          20

<210> SEQ ID NO 165
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 165
aagaucccuu uugcaagggc                                                          20

<210> SEQ ID NO 166
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 166
agaucccuuu ugcaagggcg                                                          20

<210> SEQ ID NO 167
<211> LENGTH: 20
<212> TYPE: RNA
<213> ORGANISM: Artificial Sequence
<220> FEATURE:
<223> OTHER INFORMATION: Synthetic Sequence
```

<400> SEQUENCE: 167
cggccgccga ccgcacggau                                             20

<210> SEQ ID NO 168
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 168
augcacuugu cuguaguuca                                             20

<210> SEQ ID NO 169
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 169
gggagcggcc gccgaccgca                                             20

<210> SEQ ID NO 170
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 170
gucagcuugg ccaauccgug                                             20

<210> SEQ ID NO 171
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 171
gcuuggccaa uccgugcggu                                             20

<210> SEQ ID NO 172
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 172
uggccaaucc gugcggucgg                                             20

<210> SEQ ID NO 173
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 173
gagucggcuu auaaagggag                                             20

<210> SEQ ID NO 174
<211> LENGTH: 20

```
<212> TYPE: RNA
<213> ORGANISM: Artificial Sequence
<220> FEATURE:
<223> OTHER INFORMATION: Synthetic Sequence

<400> SEQUENCE: 174
cgggcgaguc ggcuuauaaa                                                 20

<210> SEQ ID NO 175
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 175
ccgggcgagu cggcuuauaa                                                 20

<210> SEQ ID NO 176
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 176
cggugcgcug ccgggcgagu                                                 20

<210> SEQ ID NO 177
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 177
gaagcaaaag uaccacuaga                                                 20

<210> SEQ ID NO 178
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 178
ccgcaacccg gugcgcugcc                                                 20

<210> SEQ ID NO 179
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 179
uccgcaaccc ggugcgcugc                                                 20

<210> SEQ ID NO 180
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 180
```
ccuuuauaag ccgacucgcc                                                     20

<210> SEQ ID NO 181
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 181
uuuguucuua cuccaucuag                                                     20

<210> SEQ ID NO 182
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 182
caggcccacc cuccgcaacc                                                     20

<210> SEQ ID NO 183
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 183
cgacucgccc ggcagcgcac                                                     20

<210> SEQ ID NO 184
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 184
gacucgcccg gcagcgcacc                                                     20

<210> SEQ ID NO 185
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 185
cccggcagcg caccggguug                                                     20

<210> SEQ ID NO 186
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 186
ggcagcgcac cggguugcgg                                                     20

<210> SEQ ID NO 187
<211> LENGTH: 20
<212> TYPE: RNA
<213> ORGANISM: Artificial Sequence -continued

```
<220> FEATURE:
<223> OTHER INFORMATION: Synthetic Sequence

<400> SEQUENCE: 187
caccacaaau guuguaaaug                                              20

<210> SEQ ID NO 188
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 188
gcagcgcacc ggguugcgga                                              20

<210> SEQ ID NO 189
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 189
gcgcaccggg uugcggaggg                                              20

<210> SEQ ID NO 190
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 190
cgcaccgggu ugcggagggu                                              20

<210> SEQ ID NO 191
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 191
aaauggccac caccccuccc                                              20

<210> SEQ ID NO 192
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 192
cggguugcgg aggguggccc                                              20

<210> SEQ ID NO 193
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 193
ggguugcgga ggguggccu                                               20
```

```
<210> SEQ ID NO 194
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 194 uugcggagggg ugggccuggg                                                    20

<210> SEQ ID NO 195
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 195
ugcggagggu gggccuggga                                                     20

<210> SEQ ID NO 196
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 196
gcggagggug ggccugggag                                                     20

<210> SEQ ID NO 197
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 197
cuccacauuu acaacauuug                                                     20

<210> SEQ ID NO 198
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 198
gagggugggc cugggagggg                                                     20

<210> SEQ ID NO 199
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 199
ucggcguucc ccccaccaac                                                     20

<210> SEQ ID NO 200
<211> LENGTH: 20
<212> TYPE: RNA
<213> ORGANISM: Artificial Sequence
<220> FEATURE:
<223> OTHER INFORMATION: Synthetic Sequence
```

-continued

<400> SEQUENCE: 200
cacauuuaca acauuugugg                                                                20

<210> SEQ ID NO 201
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 201 gguggggccug ggaggggugg                                                               20

<210> SEQ ID NO 202
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 202 aguuagggguu agacaaaaaa                                                               20

<210> SEQ ID NO 203
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 203
uacaacauuu gugguggugc                                                                20

<210> SEQ ID NO 204
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 204
acaacauuug uggguggugca                                                               20

<210> SEQ ID NO 205
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 205
cuguggccau ucuugcuuca                                                                20

<210> SEQ ID NO 206
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 206
gccuacgccc uucucaguua                                                                20

<210> SEQ ID NO 207

-continued

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 207
cgccuacgcc cuucucaguu                                                20

<210> SEQ ID NO 208
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 208
gcagggccgu gaagcaagaa                                                20

<210> SEQ ID NO 209
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 209
agaaaaacau ucccagucug                                                20

<210> SEQ ID NO 210
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 210
uugucuaacc cuaacugaga                                                20

<210> SEQ ID NO 211
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 211
ugucuaaccc uaacugagaa                                                20

<210> SEQ ID NO 212
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 212
aagcaagaau ggccacagac                                                20

<210> SEQ ID NO 213
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 213
```
agcaagaaug gccacagacu                                            20

<210> SEQ ID NO 214
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 214
acccuaacug agaagggcgu                                            20

<210> SEQ ID NO 215
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 215
gcgcgcgggg agcaaaagca                                            20

<210> SEQ ID NO 216
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 216
caugcaguuc gcuuuccugu                                            20

<210> SEQ ID NO 217
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 217
agcgagaaaa acagcgcgcg                                            20

<210> SEQ ID NO 218
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 218
cagcgagaaa aacagcgcgc                                            20

<210> SEQ ID NO 219
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 219
ucagcgagaa aaacagcgcg                                            20

<210> SEQ ID NO 220
<211> LENGTH: 20
<212> TYPE: RNA

-continued

```
<213> ORGANISM: Artificial Sequence
<220> FEATURE:
<223> OTHER INFORMATION: Synthetic Sequence

<400> SEQUENCE: 220
gcaguucgcu uuccuguugg                                                    20

<210> SEQ ID NO 221
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 221
uuuuucucgc ugacuuucag                                                    20

<210> SEQ ID NO 222
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 222
uuuucucgcu gacuuucagc                                                    20

<210> SEQ ID NO 223
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 223
caguucgcuu uccuguuggu                                                    20

<210> SEQ ID NO 224
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 224
ucucgcugac uuucagcggg                                                    20

<210> SEQ ID NO 225
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 225
aguucgcuuu ccuguuggug                                                    20

<210> SEQ ID NO 226
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 226
cgguggaagg cggcaggccg                                                    20
```

```
<210> SEQ ID NO 227
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 227
uucagcgggc ggaaaagccu                                              20

<210> SEQ ID NO 228
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 228
aaugaacggu ggaaggcggc                                              20

<210> SEQ ID NO 229
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 229
uuaugaugaa ugugauaguu                                              20

<210> SEQ ID NO 230
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 230
guucgcuuuc cuguuggugg                                              20

<210> SEQ ID NO 231
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 231
cuagaaugaa cgguggaagg                                              20

<210> SEQ ID NO 232
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 232
gcucuagaau gaacggugga                                              20

<210> SEQ ID NO 233
<211> LENGTH: 20
<212> TYPE: RNA
<213> ORGANISM: Artificial Sequence
<220> FEATURE:
```

-continued

<223> OTHER INFORMATION: Synthetic Sequence

<400> SEQUENCE: 233
guuugcucua gaaugaacgg                                             20

<210> SEQ ID NO 234
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 234
uucgcuuucc uguugguggg                                             20

<210> SEQ ID NO 235
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 235
uuuguuugcu cuagaaugaa                                             20

<210> SEQ ID NO 236
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 236
aaacaaaaaa ugucagcugc                                             20

<210> SEQ ID NO 237
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 237
gguccccggg aggggcgaac                                             20

<210> SEQ ID NO 238
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 238
agguccccgg gaggggcgaa                                             20

<210> SEQ ID NO 239
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 239
ccgccgcagg uccccgggag                                             20

-continued

```
<210> SEQ ID NO 240
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 240
cccgccgcag guccccggga                                                    20

<210> SEQ ID NO 241
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 241
acccgccgca gguccccggg                                                    20

<210> SEQ ID NO 242
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 242
gcgacccgcc gcaggucccc                                                    20

<210> SEQ ID NO 243
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 243
ggcgacccgc cgcagguccc                                                    20

<210> SEQ ID NO 244
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 244
gcuggcccgu ucgccccucc                                                    20

<210> SEQ ID NO 245
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 245
cuggcccguu cgccccuccc                                                    20

<210> SEQ ID NO 246
<211> LENGTH: 20
<212> TYPE: RNA
<213> ORGANISM: Artificial Sequence
<220> FEATURE:
<223> OTHER INFORMATION: Synthetic Sequence
```

-continued

<400> SEQUENCE: 246
uggcccguuc gccccucccg                                                    20

<210> SEQ ID NO 247
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 247
cugggcaggc gacccgccgc                                                    20

<210> SEQ ID NO 248
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 248 ucgcccucc cggggaccug                                                     20

<210> SEQ ID NO 249
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 249
ccccucccgg ggaccugcgg                                                    20

<210> SEQ ID NO 250
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 250
cccucccggg gaccugcggc                                                    20

<210> SEQ ID NO 251
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 251
gggugacgga ugcgcacgau                                                    20

<210> SEQ ID NO 252
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 252
gcgggguucg ggggcugggc                                                    20

<210> SEQ ID NO 253
<211> LENGTH: 20

-continued

```
<212> TYPE: RNA
<213> ORGANISM: Artificial Sequence
<220> FEATURE:
<223> OTHER INFORMATION: Synthetic Sequence

<400> SEQUENCE: 253
ccaggcgggg uucgggggcu                                              20

<210> SEQ ID NO 254
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 254
uccaggcggg guucgggggc                                              20

<210> SEQ ID NO 255
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 255
ggccuccagg cgggguucgg                                              20

<210> SEQ ID NO 256
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 256
cggccuccag gcgggguucg                                              20

<210> SEQ ID NO 257
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 257
gcggccucca ggcgggguuc                                              20

<210> SEQ ID NO 258
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 258
cgcggccucc aggcgggguu                                              20

<210> SEQ ID NO 259
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 259
```

-continued ccgaccgcgg ccuccaggcg                                                    20

<210> SEQ ID NO 260
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 260
gccgaccgcg gccuccaggc                                                    20

<210> SEQ ID NO 261
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 261
ggccgaccgc ggccuccagg                                                    20

<210> SEQ ID NO 262
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 262
ccgggccgac cgcggccucc                                                    20

<210> SEQ ID NO 263
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 263
cccagccccc gaaccccgcc                                                    20

<210> SEQ ID NO 264
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 264
agcccccgaa ccccgccugg                                                    20

<210> SEQ ID NO 265
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 265
gagaagcccc gggccgaccg                                                    20

<210> SEQ ID NO 266
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 266
cgaaccccgc cuggaggccg                                                              20

<210> SEQ ID NO 267
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 267
ccccgccugg aggccgcggu                                                              20

<210> SEQ ID NO 268
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 268
ggugccuccg gagaagcccc                                                              20

<210> SEQ ID NO 269
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 269
gggugccucc ggagaagccc                                                              20

<210> SEQ ID NO 270
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 270
ccuggaggcc gcggucggcc                                                              20

<210> SEQ ID NO 271
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 271
cuggaggccg cggucggccc                                                              20

<210> SEQ ID NO 272
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 272
uggaggccgc ggucggcccg                                                              20

<210> SEQ ID NO 273
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 273
gcgguggcag ugggugccuc                                                                              20

<210> SEQ ID NO 274
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 274
cggucggccc ggggcuucuc                                                                              20

<210> SEQ ID NO 275
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 275
ucggcccggg gcuucuccgg                                                                              20

<210> SEQ ID NO 276
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 276
caacucuucg cgguggcagu                                                                              20

<210> SEQ ID NO 277
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 277
ccaacucuuc gcgguggcag                                                                              20

<210> SEQ ID NO 278
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 278
ccacugccac cgcgaagagu                                                                              20

<210> SEQ ID NO 279
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 279
cacugccacc gcgaagaguu                                                                    20

<210> SEQ ID NO 280
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 280
uuuggagaau aaauugaaug                                                                    20

<210> SEQ ID NO 281
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 281
cagagcccaa cucuucgcgg                                                                    20

<210> SEQ ID NO 282
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 282
gagaauaaau ugaaugagga                                                                    20

<210> SEQ ID NO 283
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 283
ccauugccgg cgagggguga                                                                    20

<210> SEQ ID NO 284
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 284
aacugaucac caaaucucca                                                                    20

<210> SEQ ID NO 285
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 285
uaacugauca ccaaaucucc                                                                    20

<210> SEQ ID NO 286

<211> LENGTH: 20
<212> TYPE: RNA
<213> ORGANISM: Artificial Sequence
<220> FEATURE:
<223> OTHER INFORMATION: Synthetic Sequence

<400> SEQUENCE: 286
aaauugaaug aggaaggccc                                                              20

<210> SEQ ID NO 287
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 287
aagcccccau ugccggcgag                                                              20

<210> SEQ ID NO 288
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 288 caagcccccca uugccggcga                                                             20

<210> SEQ ID NO 289
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 289
acaagccccc auugccggcg                                                              20

<210> SEQ ID NO 290
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 290
gguucacaag cccccauugc                                                              20

<210> SEQ ID NO 291
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 291
ugaggaaggc ccuggagauu                                                              20

<210> SEQ ID NO 292
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 292
gcgcauccgu caccccucgc                                                    20

<210> SEQ ID NO 293
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 293
ccgucacccc ucgccggcaa                                                    20

<210> SEQ ID NO 294
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 294 cgucacccu cgccggcaau                                                     20

<210> SEQ ID NO 295
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 295
gucaccccuc gccggcaaug                                                    20

<210> SEQ ID NO 296
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 296
ucaccccucg ccggcaaugg                                                    20

<210> SEQ ID NO 297
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 297
gcccagucag ucagguuugg                                                    20

<210> SEQ ID NO 298
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 298
ggcccaguca gucagguuug                                                    20

<210> SEQ ID NO 299
<211> LENGTH: 20
<212> TYPE: RNA

-continued

<213> ORGANISM: Artificial Sequence
<220> FEATURE:
<223> OTHER INFORMATION: Synthetic Sequence

<400> SEQUENCE: 299
uggcccaguc agucaggutu                                                                     20

<210> SEQ ID NO 300
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 300
cuggcccagu cagucagguu                                                                     20

<210> SEQ ID NO 301
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 301
aagacuuggc acuuuauaug                                                                     20

<210> SEQ ID NO 302
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 302
gcacacuggc ccagucaguc                                                                     20

<210> SEQ ID NO 303
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 303
aacccccaaa ccugacugac                                                                     20

<210> SEQ ID NO 304
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 304
acccccaaac cugacugacu                                                                     20

<210> SEQ ID NO 305
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 305
auaaucuuga guacaagacu                                                                     20

-continued

```
<210> SEQ ID NO 306
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 306
ccugccaauu ugcagcacac                                              20

<210> SEQ ID NO 307
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 307
ugggccagug ugcugcaaau                                              20

<210> SEQ ID NO 308
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 308
ccagugugcu gcaaauuggc                                              20

<210> SEQ ID NO 309
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 309
uacucaagau uauaagcaau                                              20

<210> SEQ ID NO 310
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 310
ccucgccccc gagagacccg                                              20

<210> SEQ ID NO 311
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 311
caaauuggca ggagacguga                                              20

<210> SEQ ID NO 312
<211> LENGTH: 20
<212> TYPE: RNA
<213> ORGANISM: Artificial Sequence
<220> FEATURE:
```

-continued

<223> OTHER INFORMATION: Synthetic Sequence

<400> SEQUENCE: 312
uucauuuugg ccgacuuugg                                               20

<210> SEQ ID NO 313
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 313
ccauucauuu uggccgacuu                                               20

<210> SEQ ID NO 314
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 314
cgugaaggca ccuccaaagu                                               20

<210> SEQ ID NO 315
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 315
ggcucacugc ccauucauuu                                               20

<210> SEQ ID NO 316
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 316
ccaaagucgg ccaaaaugaa                                               20

<210> SEQ ID NO 317
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 317
caaagucggc caaaaugaau                                               20

<210> SEQ ID NO 318
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 318
gaguugggcu cugucagccg                                               20

-continued

```
<210> SEQ ID NO 319
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 319
ggaacggcuc caggcaaccc                                                20

<210> SEQ ID NO 320
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 320
aguugggcuc ugucagccgc                                                20

<210> SEQ ID NO 321
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 321
aaaaugaaug ggcagugagc                                                20

<210> SEQ ID NO 322
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 322
aaaugaaugg gcagugagcc                                                20

<210> SEQ ID NO 323
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 323
uuuccccuuc auaucuaagu                                                20

<210> SEQ ID NO 324
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 324
aaugaauggg cagugagccg                                                20

<210> SEQ ID NO 325
<211> LENGTH: 20
<212> TYPE: RNA
<213> ORGANISM: Artificial Sequence
<220> FEATURE:
<223> OTHER INFORMATION: Synthetic Sequence
```

-continued

```
<400> SEQUENCE: 325
acccacgcag gaacggcucc                                                          20

<210> SEQ ID NO 326
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 326
ggcagugagc cgggguugcc                                                          20

<210> SEQ ID NO 327
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 327
cgggagaacc cacgcaggaa                                                          20

<210> SEQ ID NO 328
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 328
uagugccuac uuagauauga                                                          20

<210> SEQ ID NO 329
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 329
agugccuacu uagauaugaa                                                          20

<210> SEQ ID NO 330
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 330
gugccuacuu agauaugaag                                                          20

<210> SEQ ID NO 331
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 331
gaagacggga gaacccacgc                                                          20

<210> SEQ ID NO 332
<211> LENGTH: 20
```

```
<212> TYPE: RNA
<213> ORGANISM: Artificial Sequence
<220> FEATURE:
<223> OTHER INFORMATION: Synthetic Sequence

<400> SEQUENCE: 332
uuagauauga aggggaaaga                                                          20

<210> SEQ ID NO 333
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 333
ugccuggagc cguuccugcg                                                          20

<210> SEQ ID NO 334
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 334
uagauaugaa ggggaaagaa                                                          20

<210> SEQ ID NO 335
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 335
gccuggagcc guuccugcgu                                                          20

<210> SEQ ID NO 336
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 336
ggcaacaaaa agcggaagac                                                          20

<210> SEQ ID NO 337
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 337
aggcaacaaa aagcggaaga                                                          20

<210> SEQ ID NO 338
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 338
``` aagaagggutu ugagauaaug                                              20

<210> SEQ ID NO 339
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 339
ccauaaaagg caacaaaaag                                               20

<210> SEQ ID NO 340
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 340 agaaggguu gagauaaugu                                                20

<210> SEQ ID NO 341
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 341
aguuguaaua caaccauaaa                                               20

<210> SEQ ID NO 342
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 342
aaugugggau gcuaagagaa                                               20

<210> SEQ ID NO 343
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 343
gugggaugcu aagagaaugg                                               20

<210> SEQ ID NO 344
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 344
ccgcuuuuug uugccuuuua                                               20

<210> SEQ ID NO 345
<211> LENGTH: 20
<212> TYPE: RNA
<213> ORGANISM: Artificial Sequence -continued
<220> FEATURE:
<223> OTHER INFORMATION: Synthetic Sequence

<400> SEQUENCE: 345
ucugucagcc gcgggucucu                                                        20

<210> SEQ ID NO 346
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 346
cucaacaaaa ucugcagagc                                                        20

<210> SEQ ID NO 347
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 347
cugucagccg cgggucucuc                                                        20

<210> SEQ ID NO 348
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 348
ugucagccgc gggucucucg                                                        20

<210> SEQ ID NO 349
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 349
cugcucugca gauuuuguug                                                        20

<210> SEQ ID NO 350
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 350
uuuagcaucu acucuaugua                                                        20

<210> SEQ ID NO 351
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 351
gucagccgcg ggucucucgg                                                        20

-continued

```
<210> SEQ ID NO 352
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 352
gacuggucga gaucuaccuu                                                     20

<210> SEQ ID NO 353
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 353
ggacuggucg agaucuaccu                                                     20

<210> SEQ ID NO 354
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 354
ugagguuuuu gcuucuccca                                                     20

<210> SEQ ID NO 355
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 355
ccacaccccg uugaggggac                                                     20

<210> SEQ ID NO 356
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 356
uucucccaca ccccguugag                                                     20

<210> SEQ ID NO 357
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 357
guucucccac accccguuga                                                     20

<210> SEQ ID NO 358
<211> LENGTH: 20
<212> TYPE: RNA
<213> ORGANISM: Artificial Sequence
<220> FEATURE:
<223> OTHER INFORMATION: Synthetic Sequence
```

-continued

<400> SEQUENCE: 358
agugcaauag ugcuaaaaac                                                    20

<210> SEQ ID NO 359
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 359
uguucuccca caccccguug                                                    20

<210> SEQ ID NO 360
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 360
aucucgacca gucccucaa                                                     20

<210> SEQ ID NO 361
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 361
ucucgaccag uccccucaac                                                    20

<210> SEQ ID NO 362
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 362
cucgaccagu ccccucaacg                                                    20

<210> SEQ ID NO 363
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 363 ccagucccu caacggggug                                                     20

<210> SEQ ID NO 364
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 364 cagucccuc aacggggugu                                                     20

<210> SEQ ID NO 365

-continued

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 365
ccagguugua aaguuuuuua                                                    20

<210> SEQ ID NO 366
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 366
ccgcgggucu cucgggggcg                                                    20

<210> SEQ ID NO 367
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 367
cgcgggcucu ucgggggcga                                                    20

<210> SEQ ID NO 368
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 368
ugacagagcc caacucuucg                                                    20

<210> SEQ ID NO 369
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 369
uuucuuucau agcaucugcc                                                    20

<210> SEQ ID NO 370
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 370
ccguaaaaaa cuuuacaacc                                                    20

<210> SEQ ID NO 371
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 371
```

-continued

```
gcagaugcua ugaaagaaaa                                              20

<210> SEQ ID NO 372
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 372
cagaugcuau gaaagaaaaa                                              20

<210> SEQ ID NO 373
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 373
agaugcuaug aaagaaaaag                                              20

<210> SEQ ID NO 374
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 374
gcuaugaaag aaaaaggggga                                             20

<210> SEQ ID NO 375
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 375
cuaugaaaga aaaggggau                                               20

<210> SEQ ID NO 376
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 376
aaggggaugg gagagagaga                                              20

<210> SEQ ID NO 377
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 377
gucucucggg ggcgagggcg                                             20

<210> SEQ ID NO 378
<211> LENGTH: 20
<212> TYPE: RNA
```

-continued

<213> ORGANISM: Artificial Sequence
<220> FEATURE:
<223> OTHER INFORMATION: Synthetic Sequence

<400> SEQUENCE: 378
gggaugggag agagagaagg                                                          20

<210> SEQ ID NO 379
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 379
ggaugggaga gagagaagga                                                          20

<210> SEQ ID NO 380
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 380
uagaagaucu aaaugaacau                                                          20

<210> SEQ ID NO 381
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 381
gagagaagga gggagagaga                                                          20

<210> SEQ ID NO 382
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 382
aaggagggag agagauggag                                                          20

<210> SEQ ID NO 383
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 383
aggagggaga gagauggaga                                                          20

<210> SEQ ID NO 384
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 384
cauaaaccga ugaccauuaa                                                          20

```
<210> SEQ ID NO 385
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 385
aacaagcgcu augacuagca                                                        20

<210> SEQ ID NO 386
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 386
uggaaauugu guuccuuuaa                                                        20

<210> SEQ ID NO 387
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 387
uguguuccuu uaauggcau                                                         20

<210> SEQ ID NO 388
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 388
aaaaagaaac uucuaaccuc                                                        20

<210> SEQ ID NO 389
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 389
uuuacuuuuc uuucagaucg                                                        20

<210> SEQ ID NO 390
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 390
uggucaucgg uuuaugccag                                                        20

<210> SEQ ID NO 391
<211> LENGTH: 20
<212> TYPE: RNA
<213> ORGANISM: Artificial Sequence
<220> FEATURE:
```

-continued

<223> OTHER INFORMATION: Synthetic Sequence

<400> SEQUENCE: 391
cuccguggag uugucgcugu                                                    20

<210> SEQ ID NO 392
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 392 cggggggcgag ggcgagguuc                                                   20

<210> SEQ ID NO 393
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 393
auucaguuag auaaacuccg                                                    20

<210> SEQ ID NO 394
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 394
gaccgacagc gacaacucca                                                    20

<210> SEQ ID NO 395
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 395
acugcucaag gucaucgcca                                                    20

<210> SEQ ID NO 396
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 396
uuuuuugaaa aauuagaccu                                                    20

<210> SEQ ID NO 397
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 397
uccucuuccu gcggccugaa                                                    20

-continued

```
<210> SEQ ID NO 398
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 398
ggguuauauc cuacugcuca                                                20

<210> SEQ ID NO 399
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 399
uggcgaugac cuugagcagu                                                20

<210> SEQ ID NO 400
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 400
caguuuuaca uauaaaugac                                                20

<210> SEQ ID NO 401
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 401
uuggaacgcu aagcuugugg                                                20

<210> SEQ ID NO 402
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 402
auuggaacgc uaagcuugug                                                20

<210> SEQ ID NO 403
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 403
uauuggaacg cuaagcuugu                                                20

<210> SEQ ID NO 404
<211> LENGTH: 20
<212> TYPE: RNA
<213> ORGANISM: Artificial Sequence
<220> FEATURE:
<223> OTHER INFORMATION: Synthetic Sequence
```

<400> SEQUENCE: 404
uuauuggaac gcuaagcuug                                                    20

<210> SEQ ID NO 405
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 405
uaugccuagu guuccguuau                                                    20

<210> SEQ ID NO 406
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 406
ugacuagcaa gguuaaguga                                                    20

<210> SEQ ID NO 407
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 407
caagcuuagc guuccaauaa                                                    20

<210> SEQ ID NO 408
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 408
uauguaaaac ugcacuauac                                                    20

<210> SEQ ID NO 409
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 409
ccggccgcga auuuuauaa                                                     20

<210> SEQ ID NO 410
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 410
cguuccaaua acggaacacu                                                    20

<210> SEQ ID NO 411
<211> LENGTH: 20

-continued

```
<212> TYPE: RNA
<213> ORGANISM: Artificial Sequence
<220> FEATURE:
<223> OTHER INFORMATION: Synthetic Sequence

<400> SEQUENCE: 411
gggcgagguu caggccuuuc                                          20

<210> SEQ ID NO 412
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 412
cuggccauua uaaaaauucg                                          20

<210> SEQ ID NO 413
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 413
acacuaggca uaaugaaaga                                          20

<210> SEQ ID NO 414
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 414
cagguaugag ccaccgcacc                                          20

<210> SEQ ID NO 415
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 415
ccauuauaaa aauucgcggc                                          20

<210> SEQ ID NO 416
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 416
cauuauaaaa auucgcggcc                                          20

<210> SEQ ID NO 417
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 417
```
acuuuaagcc uuucaguccc                                            20

<210> SEQ ID NO 418
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 418
uaaaaauucg cggccggglug                                          20

<210> SEQ ID NO 419
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 419
aaauucgcgg ccgggugcgg                                           20

<210> SEQ ID NO 420
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 420
ucgcuccguu ccucuuccug                                           20

<210> SEQ ID NO 421
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 421
aggguugggg gugggggggug                                          20

<210> SEQ ID NO 422
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 422
ucccaaagug cugggauuac                                           20

<210> SEQ ID NO 423
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 423
cugggagggu uggggugggg                                           20

<210> SEQ ID NO 424
<211> LENGTH: 20
<212> TYPE: RNA
<213> ORGANISM: Artificial Sequence -continued

```
<220> FEATURE:
<223> OTHER INFORMATION: Synthetic Sequence

<400> SEQUENCE: 424
gcugggaggg uuggggugg                                          20

<210> SEQ ID NO 425
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 425
ggcugggagg guuggggug                                          20

<210> SEQ ID NO 426
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 426
cggcugggag gguuggggu                                          20

<210> SEQ ID NO 427
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 427
agcaagguua agugaaggcc                                         20

<210> SEQ ID NO 428
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 428
ccggcuggga gguugggg                                           20

<210> SEQ ID NO 429
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 429
cuucggccuc ccaaagugcu                                         20

<210> SEQ ID NO 430
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 430
cugccggcug ggaggguugg                                         20
```

-continued

<210> SEQ ID NO 431
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 431
gcuucggccu cccaaagugc                                                             20

<210> SEQ ID NO 432
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 432
acugccggcu gggaggguug                                                             20

<210> SEQ ID NO 433
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 433
gacugccggc ugggaggguu                                                             20

<210> SEQ ID NO 434
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 434
agacugccgg cugggagggu                                                             20

<210> SEQ ID NO 435
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 435
gcaagguuaa gugaaggcca                                                             20

<210> SEQ ID NO 436
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 436
ugggagacug ccggcuggga                                                             20

<210> SEQ ID NO 437
<211> LENGTH: 20
<212> TYPE: RNA
<213> ORGANISM: Artificial Sequence
<220> FEATURE:
<223> OTHER INFORMATION: Synthetic Sequence -continued

<400> SEQUENCE: 437
gugggagacu gccggcuggg                                                        20

<210> SEQ ID NO 438
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 438
uaccuguaau cccagcacuu                                                        20

<210> SEQ ID NO 439
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 439
accuguaauc ccagcacuuu                                                        20

<210> SEQ ID NO 440
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 440
cuugugggag acugccggcu                                                        20

<210> SEQ ID NO 441
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 441
ucuuguggga gacugccggc                                                        20

<210> SEQ ID NO 442
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 442
uguaauccca gcacuuuggg                                                        20

<210> SEQ ID NO 443
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 443
caauucuugu gggagacugc                                                        20

<210> SEQ ID NO 444

-continued

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 444
ccacccccaa cccucccagc                                              20

<210> SEQ ID NO 445
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 445
cucaagugau ccacccgcuu                                              20

<210> SEQ ID NO 446
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 446
agcacuuugg gaggccgaag                                              20

<210> SEQ ID NO 447
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 447
gcacuuuggg aggccgaagc                                              20

<210> SEQ ID NO 448
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 448
aaaucagagc caauucuugu                                              20

<210> SEQ ID NO 449
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 449
guucaggccu uucaggccgc                                              20

<210> SEQ ID NO 450
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 450
```

-continued cuuugggagg ccgaagcggg                                                                          20

<210> SEQ ID NO 451
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 451
gaaaucagag ccaauucuug                                                                          20

<210> SEQ ID NO 452
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 452
cggcagucuc ccacaagaau                                                                          20

<210> SEQ ID NO 453
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 453
caggcugguc ucgaacgcca                                                                          20

<210> SEQ ID NO 454
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 454
ccaggcuggu cucgaacgcc                                                                          20

<210> SEQ ID NO 455
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 455
cggguggauc acuugagccc                                                                          20

<210> SEQ ID NO 456
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 456
ccauuagcuu auuuucuuaa                                                                          20

<210> SEQ ID NO 457
<211> LENGTH: 20
<212> TYPE: RNA

-continued

<213> ORGANISM: Artificial Sequence
<220> FEATURE:
<223> OTHER INFORMATION: Synthetic Sequence

<400> SEQUENCE: 457
uuucaccaug uugcccaggc                                                                20

<210> SEQ ID NO 458
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 458
gggguuucac cauguugccc                                                                20

<210> SEQ ID NO 459
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 459
ccuggcguuc gagaccagcc                                                                20

<210> SEQ ID NO 460
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 460
cuggcguucg agaccagccu                                                                20

<210> SEQ ID NO 461
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 461
ccuuuaagaa aauaagcuaa                                                                20

<210> SEQ ID NO 462
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 462
cgagaccagc cugggcaaca                                                                20

<210> SEQ ID NO 463
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 463
uuuguuucuu ucaaccuagu                                                                20

```
<210> SEQ ID NO 464
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 464
guuuguuucu uucaaccuag                                              20

<210> SEQ ID NO 465
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 465
aaauaagcua auggcccacu                                              20

<210> SEQ ID NO 466
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 466
uguguuuuua guagagacgg                                              20

<210> SEQ ID NO 467
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 467
uuguguuuuu aguagagacg                                              20

<210> SEQ ID NO 468
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 468
uuuguguuuu uaguagagac                                              20

<210> SEQ ID NO 469
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 469
uuuuguguuu uuaguagaga                                              20

<210> SEQ ID NO 470
<211> LENGTH: 20
<212> TYPE: RNA
<213> ORGANISM: Artificial Sequence
<220> FEATURE:
```

<223> OTHER INFORMATION: Synthetic Sequence

<400> SEQUENCE: 470
gccuuucagg ccgcaggaag                                                20

<210> SEQ ID NO 471
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 471
cuagguugaa agaaacaaac                                                20

<210> SEQ ID NO 472
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 472
agugaaggcc agggacugaa                                                20

<210> SEQ ID NO 473
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 473
gucgugauaa gugggcagaa                                                20

<210> SEQ ID NO 474
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 474
auuaccuugu cgugauaagu                                                20

<210> SEQ ID NO 475
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 475
aauuaccuug ucgugauaag                                                20

<210> SEQ ID NO 476
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 476
cuaaaaacac aaaaacuagc                                                20

-continued

```
<210> SEQ ID NO 477
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 477
uaaaaacaca aaaacuagcu                                             20

<210> SEQ ID NO 478
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 478
acacaaaaac uagcugggcg                                             20

<210> SEQ ID NO 479
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 479
caaaaacuag cugggcgugg                                             20

<210> SEQ ID NO 480
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 480
aacuagcugg gcgugguggc                                             20

<210> SEQ ID NO 481
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 481
ucugcccacu uaucacgaca                                             20

<210> SEQ ID NO 482
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 482
uccugaguag cugggauuac                                             20

<210> SEQ ID NO 483
<211> LENGTH: 20
<212> TYPE: RNA
<213> ORGANISM: Artificial Sequence
<220> FEATURE:
<223> OTHER INFORMATION: Synthetic Sequence
```

-continued

```
<400> SEQUENCE: 483
uugaagguau ggauuuggga                                                    20

<210> SEQ ID NO 484
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 484
ggaauugaag guauggauuu                                                    20

<210> SEQ ID NO 485
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 485
ucucagccuc cugaguagcu                                                    20

<210> SEQ ID NO 486
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 486
aggaauugaa gguauggauu                                                    20

<210> SEQ ID NO 487
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 487
ucaggccgca ggaagaggaa                                                    20

<210> SEQ ID NO 488
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 488
gucucagccu ccgaguagc                                                     20

<210> SEQ ID NO 489
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 489
auccuaagga auugaaggua                                                    20

<210> SEQ ID NO 490
<211> LENGTH: 20
```

-continued

```
<212> TYPE: RNA
<213> ORGANISM: Artificial Sequence
<220> FEATURE:
<223> OTHER INFORMATION: Synthetic Sequence

<400> SEQUENCE: 490
gccuguaauc ccagcuacuc                                              20

<210> SEQ ID NO 491
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 491
agaugauccu aaggaauuga                                              20

<210> SEQ ID NO 492
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 492
uguaauccca gcuacucagg                                              20

<210> SEQ ID NO 493
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 493
acuaccccca gaugauccua                                              20

<210> SEQ ID NO 494
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 494
auccauaccu ucaauuccuu                                              20

<210> SEQ ID NO 495
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 495
uucaauuccu uaggaucauc                                              20

<210> SEQ ID NO 496
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 496
```

-continued

```
ucaauuccuu aggaucaucu                                          20

<210> SEQ ID NO 497
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 497
caauuccuua ggaucaucug                                          20

<210> SEQ ID NO 498
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 498
aauuccuuag gaucaucugg                                          20

<210> SEQ ID NO 499
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 499
cacugcaacc ucugccuccc                                          20

<210> SEQ ID NO 500
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 500
ucacugcaac cucugccucc                                          20

<210> SEQ ID NO 501
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 501
acacgagaau cgcuugaacc                                          20

<210> SEQ ID NO 502
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 502
cacgagaauc gcuugaaccc                                          20

<210> SEQ ID NO 503
<211> LENGTH: 20
<212> TYPE: RNA
<213> ORGANISM: Artificial Sequence
```

-continued

<220> FEATURE:
<223> OTHER INFORMATION: Synthetic Sequence

<400> SEQUENCE: 503
ccccuggcug cucucucucu                                                    20

<210> SEQ ID NO 504
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 504
gagaaucgcu ugaacccggg                                                    20

<210> SEQ ID NO 505
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 505
cgcuugaacc cgggaggcag                                                    20

<210> SEQ ID NO 506
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 506
ggccuuuaua uacacacccc                                                    20

<210> SEQ ID NO 507
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 507
ugccaagaga gagagcagcc                                                    20

<210> SEQ ID NO 508
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 508
gccaagagag agagcagcca                                                    20

<210> SEQ ID NO 509
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 509
ccaagagaga gagcagccag                                                    20

<210> SEQ ID NO 510
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 510
ggagucuagu ggcgugaucu                                                              20

<210> SEQ ID NO 511
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 511
ccaggcugga uggagucuag                                                              20

<210> SEQ ID NO 512
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 512
agccaggggu guguauauaa                                                              20

<210> SEQ ID NO 513
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 513
caggcuauca cccuaaaggu                                                              20

<210> SEQ ID NO 514
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 514
ucaggcuauc acccuaaagg                                                              20

<210> SEQ ID NO 515
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 515
gcucuuucgc ccaggcugga                                                              20

<210> SEQ ID NO 516
<211> LENGTH: 20
<212> TYPE: RNA
<213> ORGANISM: Artificial Sequence
<220> FEATURE:
<223> OTHER INFORMATION: Synthetic Sequence -continued

<400> SEQUENCE: 516
gauucaggcu aucacccuaa                                              20

<210> SEQ ID NO 517
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 517
ucuugcucuu ucgcccaggc                                              20

<210> SEQ ID NO 518
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 518
guauauaaag gcccaccuuu                                              20

<210> SEQ ID NO 519
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 519
uauauaaagg cccaccuuua                                              20

<210> SEQ ID NO 520
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 520
ggagucuugc ucuuucgccc                                              20

<210> SEQ ID NO 521
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 521
ccacuagacu ccauccagcc                                              20

<210> SEQ ID NO 522
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 522
cacuagacuc cauccagccu                                              20

<210> SEQ ID NO 523

-continued

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 523
agggaaucgc gccgcgcgcg                                          20

<210> SEQ ID NO 524
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 524
acuuucaauc aucaggauuc                                          20

<210> SEQ ID NO 525
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 525
acuucugacu uucaaucauc                                          20

<210> SEQ ID NO 526
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 526
cagggaaucg cgccgcgcgc                                          20

<210> SEQ ID NO 527
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 527
aacgauuuuu uuuuuugaga                                          20

<210> SEQ ID NO 528
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 528
ucagggaauc gcgccgcgcg                                          20

<210> SEQ ID NO 529
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 529
```

-continued gugaaccgcg ucuggucugc a                                                          21

<210> SEQ ID NO 530
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 530
gcugacucuc gcggcucucg u                                                          21

<210> SEQ ID NO 531
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 531
aacuccacgg aguuuaucua a                                                          21

<210> SEQ ID NO 532
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 532
acggaguuua ucuaacugaa u                                                          21

<210> SEQ ID NO 533
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 533
ccggcagcgc accggguugc g                                                          21

<210> SEQ ID NO 534
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 534
ggccauuaua aaaauucgcg g                                                          21

<210> SEQ ID NO 535
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 535
agugacucuc acgagagccg c                                                          21

<210> SEQ ID NO 536
<211> LENGTH: 21
<212> TYPE: RNA

-continued

<213> ORGANISM: Artificial Sequence
<220> FEATURE:
<223> OTHER INFORMATION: Synthetic Sequence

<400> SEQUENCE: 536
gccgacucgc ccggcagcgc a                                                                          21

<210> SEQ ID NO 537
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 537
ggcgccuacg cccuucucag u                                                                          21

<210> SEQ ID NO 538
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 538
ggaccgacag cgacaacucc a                                                                          21

<210> SEQ ID NO 539
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 539
cagaaucuug ucucggcuca g                                                                          21

<210> SEQ ID NO 540
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 540
ucucggcuca gugggaugcg u                                                                          21

<210> SEQ ID NO 541
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 541
ccccccaacc agcccgcccg a                                                                          21

<210> SEQ ID NO 542
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 542
gguuguaaag uuuuuuacgg a                                                                          21

<210> SEQ ID NO 543
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 543
aagggagcgg ccgccgaccg c                                                                                21

<210> SEQ ID NO 544
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 544
cgccccuccc ggggaccugc g                                                                                21

<210> SEQ ID NO 545
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 545
cgcaacccgg ugcgcugccg g                                                                                21

<210> SEQ ID NO 546
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 546
ugagauaaug ugggaugcua a                                                                                21

<210> SEQ ID NO 547
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 547
aagugcaaua gugcuaaaaa c                                                                                21

<210> SEQ ID NO 548
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 548
uauucaguua gauaaacucc g                                                                                21

<210> SEQ ID NO 549
<211> LENGTH: 21
<212> TYPE: RNA
<213> ORGANISM: Artificial Sequence
<220> FEATURE:

<223> OTHER INFORMATION: Synthetic Sequence

<400> SEQUENCE: 549
ucaccucgac uaccuuaaaa a                                            21

<210> SEQ ID NO 550
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 550
ccauaaggaa acuauguuau g                                            21

<210> SEQ ID NO 551
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 551
auagaguaga ugcuaaaugc u                                            21

<210> SEQ ID NO 552
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 552
ucuccagccu cuccuugagc a                                            21

<210> SEQ ID NO 553
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 553
cuacauuauu aaucuuaagg a                                            21

<210> SEQ ID NO 554
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 554
cuuaggcccu aaaacuucc u                                             21

<210> SEQ ID NO 555
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 555
aaauuccuau ugcuuauaau c                                            21

-continued

```
<210> SEQ ID NO 556
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 556
gcugacauuu uuuguuugcu c                                              21

<210> SEQ ID NO 557
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 557
uaugaugaau gugauaguuu g                                             21

<210> SEQ ID NO 558
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 558
cccaggcagc acugacuaca g                                             21

<210> SEQ ID NO 559
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 559
gucuugauga gguaaaaaga g                                             21

<210> SEQ ID NO 560
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 560
aaaaaaucgu uacaauuuau g                                             21

<210> SEQ ID NO 561
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 561
guacucaaga uuauaagcaa u                                             21

<210> SEQ ID NO 562
<211> LENGTH: 21
<212> TYPE: RNA
<213> ORGANISM: Artificial Sequence
<220> FEATURE:
<223> OTHER INFORMATION: Synthetic Sequence
```

-continued

<400> SEQUENCE: 562
uuaauuucuc uccuuugcau a                                                    21

<210> SEQ ID NO 563
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 563
ccuacccugc ccccuucucc u                                                    21

<210> SEQ ID NO 564
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 564
cugcuguagu cagugcugcc u                                                    21

<210> SEQ ID NO 565
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 565
cacuuagcac aguaccuuac a                                                    21

<210> SEQ ID NO 566
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 566
acuuagauau gaaggggaaa g                                                    21

<210> SEQ ID NO 567
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 567
ugcaguuuua cauauaaaug a                                                    21

<210> SEQ ID NO 568
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 568
guugcggagg gugggccugg g                                                    21

<210> SEQ ID NO 569
<211> LENGTH: 21

-continued

<212> TYPE: RNA
<213> ORGANISM: Artificial Sequence
<220> FEATURE:
<223> OTHER INFORMATION: Synthetic Sequence

<400> SEQUENCE: 569
aaaaauguga ugaucaaaac u                                              21

<210> SEQ ID NO 570
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 570
ggcauucuaa ggagaagggg g                                              21

<210> SEQ ID NO 571
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 571
aaagaagggu uugagauaau g                                              21

<210> SEQ ID NO 572
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 572
ugugauaguu uggagaauaa a                                              21

<210> SEQ ID NO 573
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 573
gcagaugcua ugaaagaaaa a                                              21

<210> SEQ ID NO 574
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 574
uaugagccac cgcacccggc c                                              21

<210> SEQ ID NO 575
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 575

-continued cgcuucggcc ucccaaagug c                                                            21

<210> SEQ ID NO 576
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 576
ccagcacuuu gggaggccga a                                                            21

<210> SEQ ID NO 577
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 577
cacuuuggga ggccgaagcg g                                                            21

<210> SEQ ID NO 578
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 578
uuuuguguuu uuaguagaga c                                                            21

<210> SEQ ID NO 579
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 579
ugucucagcc uccugaguag c                                                            21

<210> SEQ ID NO 580
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 580
cgauucucgu gucucagccu c                                                            21

<210> SEQ ID NO 581
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 581
cuacucagga ggcugagaca c                                                            21

<210> SEQ ID NO 582
<211> LENGTH: 21
<212> TYPE: RNA
<213> ORGANISM: Artificial Sequence -continued

```
<220> FEATURE:
<223> OTHER INFORMATION: Synthetic Sequence

<400> SEQUENCE: 582
gcucacugca accucugccu c                                                          21

<210> SEQ ID NO 583
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 583
ugcucuuucg cccaggcugg a                                                          21

<210> SEQ ID NO 584
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 584
agucuugcuc uuucgcccag g                                                          21

<210> SEQ ID NO 585
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 585
uaacgauuuu uuuuuuugag a                                                          21

<210> SEQ ID NO 586
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 586
gcccaacucu ucgcgguggc a                                                          21

<210> SEQ ID NO 587
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 587
ccccauugcc ggcgaggggu g                                                          21

<210> SEQ ID NO 588
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 588
aacuaccccc agaugauccu a                                                          21
```

```
<210> SEQ ID NO 589
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 589
acugcaugug ugagccgagu c                                              21

<210> SEQ ID NO 590
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 590
cacaagcccc cauugccggc g                                              21

<210> SEQ ID NO 591
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 591
gaucucgacc aguccccuca a                                              21

<210> SEQ ID NO 592
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 592
gaggcaccca cugccaccgc g                                              21

<210> SEQ ID NO 593
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 593
gcccaccuuu agggugauag c                                              21

<210> SEQ ID NO 594
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 594
guugccugga gccguuccug c                                              21

<210> SEQ ID NO 595
<211> LENGTH: 21
<212> TYPE: RNA
<213> ORGANISM: Artificial Sequence
<220> FEATURE:
<223> OTHER INFORMATION: Synthetic Sequence
```

<400> SEQUENCE: 595
aaaaagcgau cuuagaucac c                                          21

<210> SEQ ID NO 596
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 596
gcaccuccaa agucggccaa a                                          21

<210> SEQ ID NO 597
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 597
cuauuaccua aguagguccc c                                          21

<210> SEQ ID NO 598
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 598
ggccgcagga agaggaacgg a                                          21

<210> SEQ ID NO 599
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 599
ucccagccgg cagucuccca c                                          21

<210> SEQ ID NO 600
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 600
gguggugcag ggccgugaag c                                          21

<210> SEQ ID NO 601
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 601
gggugcacgu cccacagcuc a                                          21

<210> SEQ ID NO 602

```
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 602
caugcacuug ucuguaguuc a                                        21

<210> SEQ ID NO 603
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 603
guguauauaa aggcccaccu u                                        21

<210> SEQ ID NO 604
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 604
cuggcccagu cagucagguu u                                        21

<210> SEQ ID NO 605
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 605 uuguggggaga cugccggcug g                                       21

<210> SEQ ID NO 606
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 606
ugauccuaag gaauugaagg u                                        21

<210> SEQ ID NO 607
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 607
ugacuucuga cuuucaauca u                                        21

<210> SEQ ID NO 608
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 608
```
agacugccgg cugggagggu u                                                    21

<210> SEQ ID NO 609
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 609
uucaauuccu uaggaucauc u                                                    21

<210> SEQ ID NO 610
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 610
ugauuuugcc aagaacuugu c                                                    21

<210> SEQ ID NO 611
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 611 aggaguccc gcccuugcaa a                                                     21

<210> SEQ ID NO 612
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 612
aaagcgaacu gcauguguga g                                                    21

<210> SEQ ID NO 613
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 613
uaccuugucg ugauaagugg g                                                    21

<210> SEQ ID NO 614
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 614
aagcaagaau ggccacagac u                                                    21

<210> SEQ ID NO 615
<211> LENGTH: 21
<212> TYPE: RNA

-continued

```
<213> ORGANISM: Artificial Sequence
<220> FEATURE:
<223> OTHER INFORMATION: Synthetic Sequence

<400> SEQUENCE: 615
uugccaagag agagagcagc c                                              21

<210> SEQ ID NO 616
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 616
gggccgaccg cggccuccag g                                              21

<210> SEQ ID NO 617
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 617
aagaguuggg cucugucagc c                                              21

<210> SEQ ID NO 618
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 618
agauacauuu cuuagcacua u                                              21

<210> SEQ ID NO 619
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 619
agaagcaaaa guaccacuag a                                              21

<210> SEQ ID NO 620
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 620
caaaaugaau gggcagugag c                                              21

<210> SEQ ID NO 621
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 621
gcaugguuuu guggaaaagu a                                              21
```

<210> SEQ ID NO 622
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 622
auugaaggua uggauuuggg a                                              21

<210> SEQ ID NO 623
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 623
ugagagauca uuuaacauuu a                                              21

<210> SEQ ID NO 624
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 624
aaauccauac cuucaauucc u                                              21

<210> SEQ ID NO 625
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 625
uaagaaaugu aaaaaaaccu c                                              21

<210> SEQ ID NO 626
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 626
cggcugggag gguuggggu g                                               21

<210> SEQ ID NO 627
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 627
ucccacucug ucacccagag c                                              21

<210> SEQ ID NO 628
<211> LENGTH: 21
<212> TYPE: RNA
<213> ORGANISM: Artificial Sequence
<220> FEATURE:

-continued

<223> OTHER INFORMATION: Synthetic Sequence

<400> SEQUENCE: 628
uuauuggaac gcuaagcuug u                                        21

<210> SEQ ID NO 629
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 629
gaggguuggg ggugggggu g                                         21

<210> SEQ ID NO 630
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 630
cugcacucca gcucugggug a                                        21

<210> SEQ ID NO 631
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 631
cuuggcgaug accuugagca g                                        21

<210> SEQ ID NO 632
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 632
uuucuucucu ucuuuugag a                                         21

<210> SEQ ID NO 633
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 633
uggggacacu gcacuccagc u                                        21

<210> SEQ ID NO 634
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 634
uucucucagc cucccaagua g                                        21

-continued

```
<210> SEQ ID NO 635
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 635
cugaaaauac aaaaaaauca g                                                21

<210> SEQ ID NO 636
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 636
gcgggcggau caccugaggu c                                                21

<210> SEQ ID NO 637
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 637
cacuuuggga ggcagaagcg g                                                21

<210> SEQ ID NO 638
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 638
cgcuucugcc ucccaaagug c                                                21

<210> SEQ ID NO 639
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 639
uguucauaaa uuuacugaca ugg                                              23

<210> SEQ ID NO 640
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 640
aaaaaaaucg uuacaauuua ugg                                              23

<210> SEQ ID NO 641
<211> LENGTH: 23
<212> TYPE: RNA
<213> ORGANISM: Artificial Sequence
<220> FEATURE:
<223> OTHER INFORMATION: Synthetic Sequence
```

<400> SEQUENCE: 641
aaaaucguua caauuuaugg ugg                                            23

<210> SEQ ID NO 642
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 642
ucuugaugag guaaaaagag ggg                                            23

<210> SEQ ID NO 643
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 643
gucuugauga gguaaaaaga ggg                                            23

<210> SEQ ID NO 644
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 644
ugucuugaug agguaaaaag agg                                            23

<210> SEQ ID NO 645
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 645
aauuucucuc cuuugcauau ugg                                            23

<210> SEQ ID NO 646
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 646
aguagugcug ugucuugaug agg                                            23

<210> SEQ ID NO 647
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 647
aggggaccua cuuagguaau agg                                            23

<210> SEQ ID NO 648
<211> LENGTH: 23

-continued

<212> TYPE: RNA
<213> ORGANISM: Artificial Sequence
<220> FEATURE:
<223> OTHER INFORMATION: Synthetic Sequence

<400> SEQUENCE: 648
caauuccagg ggaccuacuu agg                                                                    23

<210> SEQ ID NO 649
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 649
acggagcgag uccccgcgcg cgg                                                                    23

<210> SEQ ID NO 650
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 650
uuuuaaccua uuaccuaagu agg                                                                    23

<210> SEQ ID NO 651
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 651
uaucugcuag acaauuccag ggg                                                                    23

<210> SEQ ID NO 652
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 652
guaucugcua gacaauucca ggg                                                                    23

<210> SEQ ID NO 653
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 653
uguaucugcu agacaauucc agg                                                                    23

<210> SEQ ID NO 654
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 654

-continued uauuaccuaa guagguccc ugg                                             23

<210> SEQ ID NO 655
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 655
ucccuuuuau uaggaaagaa agg                                            23

<210> SEQ ID NO 656
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 656
gacugaaucu cccuuuuauu agg                                            23

<210> SEQ ID NO 657
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 657
cgccuuucuu uccaauaaa agg                                             23

<210> SEQ ID NO 658
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 658
gccuuucuuu ccaauaaaa ggg                                             23

<210> SEQ ID NO 659
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 659
cuacuacauu auuaaucuua agg                                            23

<210> SEQ ID NO 660
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 660
ccagcaacag uggacucuag agg                                            23

<210> SEQ ID NO 661
<211> LENGTH: 23
<212> TYPE: RNA
<213> ORGANISM: Artificial Sequence -continued
<220> FEATURE:
<223> OTHER INFORMATION: Synthetic Sequence
<400> SEQUENCE: 661
gagaacauua ccagcaacag ugg                                                            23

<210> SEQ ID NO 662
<211> LENGTH: 23
<212> TYPE: RNA
<213> ORGANISM: Artificial Sequence
<220> FEATURE:
<223> OTHER INFORMATION: Synthetic Sequence
<400> SEQUENCE: 662
gcuaaauauc caauaugcaa agg                                                            23

<210> SEQ ID NO 663
<211> LENGTH: 23
<212> TYPE: RNA
<213> ORGANISM: Artificial Sequence
<220> FEATURE:
<223> OTHER INFORMATION: Synthetic Sequence
<400> SEQUENCE: 663
ccucuagagu ccacuguugc ugg                                                            23

<210> SEQ ID NO 664
<211> LENGTH: 23
<212> TYPE: RNA
<213> ORGANISM: Artificial Sequence
<220> FEATURE:
<223> OTHER INFORMATION: Synthetic Sequence
<400> SEQUENCE: 664
gccucuccuu gagcagagga ugg                                                            23

<210> SEQ ID NO 665
<211> LENGTH: 23
<212> TYPE: RNA
<213> ORGANISM: Artificial Sequence
<220> FEATURE:
<223> OTHER INFORMATION: Synthetic Sequence
<400> SEQUENCE: 665
ggugcacguc ccacagcuca ggg                                                            23

<210> SEQ ID NO 666
<211> LENGTH: 23
<212> TYPE: RNA
<213> ORGANISM: Artificial Sequence
<220> FEATURE:
<223> OTHER INFORMATION: Synthetic Sequence
<400> SEQUENCE: 666
uccagccucu ccuugagcag agg                                                            23

<210> SEQ ID NO 667
<211> LENGTH: 23
<212> TYPE: RNA
<213> ORGANISM: Artificial Sequence
<220> FEATURE:
<223> OTHER INFORMATION: Synthetic Sequence
<400> SEQUENCE: 667
cugguaaugu ucucuaaaua agg                                                            23

-continued

```
<210> SEQ ID NO 668
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 668
gggugcacgu cccacagcuc agg                                                23

<210> SEQ ID NO 669
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 669
uuaaagccau ccucugcuca agg                                                23

<210> SEQ ID NO 670
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 670
gccauccucu gcucaaggag agg                                                23

<210> SEQ ID NO 671
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 671
uccucugcuc aaggagaggc ugg                                                23

<210> SEQ ID NO 672
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 672
uuccacaaaa ccaugcugau agg                                                23

<210> SEQ ID NO 673
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 673
gcucaaggag aggcuggaga agg                                                23

<210> SEQ ID NO 674
<211> LENGTH: 23
<212> TYPE: RNA
<213> ORGANISM: Artificial Sequence
<220> FEATURE:
<223> OTHER INFORMATION: Synthetic Sequence
```

<400> SEQUENCE: 674
aaauauuuuu ccuaucagca ugg                                          23

<210> SEQ ID NO 675
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 675
aggcuggaga aggcauucua agg                                          23

<210> SEQ ID NO 676
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 676
uuccuaucag caugguuuug ugg                                          23

<210> SEQ ID NO 677
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 677
gagaaggcau ucuaaggaga agg                                          23

<210> SEQ ID NO 678
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 678
agaaggcauu cuaaggagaa ggg                                          23

<210> SEQ ID NO 679
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 679
gaaggcauuc uaaggagaag ggg                                          23

<210> SEQ ID NO 680
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 680
aaggcauucu aaggagaagg ggg                                          23

<210> SEQ ID NO 681

-continued

```
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 681
cauucuaagg agaaggggc agg                                              23

<210> SEQ ID NO 682
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 682
auucuaagga gaaggggca ggg                                              23

<210> SEQ ID NO 683
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 683
caugguuuug uggaaaagua agg                                             23

<210> SEQ ID NO 684
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 684
uaaggagaag ggggcagggu agg                                             23

<210> SEQ ID NO 685
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 685 aaggggggcag gguaggaacu cgg                                            23

<210> SEQ ID NO 686
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 686
caagacucua gacaaguucu ugg                                             23

<210> SEQ ID NO 687
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 687
```

-continued

```
gaaucuuguc ucggcucagu ggg                                              23

<210> SEQ ID NO 688
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 688
agaaucuugu cucggcucag ugg                                              23

<210> SEQ ID NO 689
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 689
acuacagcag aaucuugucu cgg                                              23

<210> SEQ ID NO 690
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 690
agaacuuguc uagagucuug agg                                              23

<210> SEQ ID NO 691
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 691
cggcgcgauu cccugagcug ugg                                              23

<210> SEQ ID NO 692
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 692
ggcgcgauuc ccugagcugu ggg                                              23

<210> SEQ ID NO 693
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 693
cuuugugaaa auagauuccc agg                                              23

<210> SEQ ID NO 694
<211> LENGTH: 23
<212> TYPE: RNA
```

-continued

<213> ORGANISM: Artificial Sequence
<220> FEATURE:
<223> OTHER INFORMATION: Synthetic Sequence

<400> SEQUENCE: 694
agaucaccuu gaguaaacug agg                                                    23

<210> SEQ ID NO 695
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 695
cugcuguagu cagugcugcc ugg                                                    23

<210> SEQ ID NO 696
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 696
ugcuguaguc agugcugccu ggg                                                    23

<210> SEQ ID NO 697
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 697
aguaagccuc aguuuacuca agg                                                    23

<210> SEQ ID NO 698
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 698
guuuugauca ucacauuuuu ugg                                                    23

<210> SEQ ID NO 699
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 699
aaaaugugau gaucaaaacu agg                                                    23

<210> SEQ ID NO 700
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 700
uucuucucuu ucuuuugaga cgg                                                    23

-continued

```
<210> SEQ ID NO 701
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 701
ccagcucugg gugacagagu ggg                                              23

<210> SEQ ID NO 702
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 702
uccagcucug ggugacagag ugg                                              23

<210> SEQ ID NO 703
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 703
ggacacugca cuccagcucu ggg                                              23

<210> SEQ ID NO 704
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 704
gaauuagugu ucugugucuu agg                                              23

<210> SEQ ID NO 705
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 705
gggacacugc acuccagcuc ugg                                              23

<210> SEQ ID NO 706
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 706
gaauucacag gaagauuuua ggg                                              23

<210> SEQ ID NO 707
<211> LENGTH: 23
<212> TYPE: RNA
<213> ORGANISM: Artificial Sequence
<220> FEATURE:
```

<223> OTHER INFORMATION: Synthetic Sequence

<400> SEQUENCE: 707
ggaauucaca ggaagauuuu agg                                    23

<210> SEQ ID NO 708
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 708
cccacucugu cacccagagc ugg                                    23

<210> SEQ ID NO 709
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 709
accuuaaaaa uggaauucac agg                                    23

<210> SEQ ID NO 710
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 710
gguugcagug agccaagaug ggg                                    23

<210> SEQ ID NO 711
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 711
agguugcagu gagccaagau ggg                                    23

<210> SEQ ID NO 712
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 712
gagguugcag ugagccaaga ugg                                    23

<210> SEQ ID NO 713
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 713
caccucgacu accuuaaaaa ugg                                    23

<210> SEQ ID NO 714
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 714
gcauguguga gccgaguccu ggg                                                    23

<210> SEQ ID NO 715
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 715
ggagugcagu guccccaucu ugg                                                    23

<210> SEQ ID NO 716
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 716
uccugugaau uccauuuuua agg                                                    23

<210> SEQ ID NO 717
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 717
ugcaugugug agccgagucc ugg                                                    23

<210> SEQ ID NO 718
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 718
gcuagaaacc gaggaggcag agg                                                    23

<210> SEQ ID NO 719
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 719
uuccauuuuu aagguagucg agg                                                    23

<210> SEQ ID NO 720
<211> LENGTH: 23
<212> TYPE: RNA
<213> ORGANISM: Artificial Sequence
<220> FEATURE:
<223> OTHER INFORMATION: Synthetic Sequence -continued

<400> SEQUENCE: 720
aaaaucgcua gaaaccgagg agg                                                          23

<210> SEQ ID NO 721
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 721
uauccucugc agaccagacg cgg                                                          23

<210> SEQ ID NO 722
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 722
gagaaaaucg cuagaaaccg agg                                                          23

<210> SEQ ID NO 723
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 723
cacugcaacc ucugccuccu cgg                                                          23

<210> SEQ ID NO 724
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 724
gaaauuaaag auuuaaaagc agg                                                          23

<210> SEQ ID NO 725
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 725
gagcuguggg acgugcaccc agg                                                          23

<210> SEQ ID NO 726
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 726
uagucgaggu gaaccgcguc ugg                                                          23

<210> SEQ ID NO 727
<211> LENGTH: 23

<212> TYPE: RNA
<213> ORGANISM: Artificial Sequence
<220> FEATURE:
<223> OTHER INFORMATION: Synthetic Sequence

<400> SEQUENCE: 727
gaaccgcguc uggucugcag agg                                                                    23

<210> SEQ ID NO 728
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 728
uguaaaccca gcuacuuggg agg                                                                    23

<210> SEQ ID NO 729
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 729
gucugcagag gauagaaaaa agg                                                                    23

<210> SEQ ID NO 730
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 730
gccuguaaac ccagcuacuu ggg                                                                    23

<210> SEQ ID NO 731
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 731
ugccuguaaa cccagcuacu ugg                                                                    23

<210> SEQ ID NO 732
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 732
aacuaacuug agguaucaga ggg                                                                    23

<210> SEQ ID NO 733
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 733
aaacuaacuu gagguaucag agg                                        23

<210> SEQ ID NO 734
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 734
cucucagccu cccaaguagc ugg                                        23

<210> SEQ ID NO 735
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 735
ucucagccuc ccaaguagcu ggg                                        23

<210> SEQ ID NO 736
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 736
uuaaagguga aacuaacuug agg                                        23

<210> SEQ ID NO 737
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 737
ucccaaguag cuggguuuac agg                                        23

<210> SEQ ID NO 738
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 738
aucauaacau aguuuccuua ugg                                        23

<210> SEQ ID NO 739
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 739
uuacuuccga ccuucuuuaa agg                                        23

<210> SEQ ID NO 740
<211> LENGTH: 23
<212> TYPE: RNA
<213> ORGANISM: Artificial Sequence -continued
<220> FEATURE:
<223> OTHER INFORMATION: Synthetic Sequence

<400> SEQUENCE: 740
aaaaaaucag ccggguaugg ugg                                          23

<210> SEQ ID NO 741
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 741
acaaaaaaau cagccgggua ugg                                          23

<210> SEQ ID NO 742
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 742
ugggacgugc acccaggacu cgg                                          23

<210> SEQ ID NO 743
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 743
aaaauacaaa aaaucagcc ggg                                           23

<210> SEQ ID NO 744
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 744
gaaaauacaa aaaaucagc cgg                                           23

<210> SEQ ID NO 745
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 745
guuaguuuca ccuuuaaaga agg                                          23

<210> SEQ ID NO 746
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 746
caggcacaca ccaccauacc cgg                                          23

-continued

```
<210> SEQ ID NO 747
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 747
guuucaccuu uaaagaaggu cgg                                              23

<210> SEQ ID NO 748
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 748
cccuuccgca cguccgggaa agg                                              23

<210> SEQ ID NO 749
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 749
cguugcccuu ccgcacgucc ggg                                              23

<210> SEQ ID NO 750
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 750
acguugcccu uccgcacguc cgg                                              23

<210> SEQ ID NO 751
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 751
uaaagacgca aagccuuucc cgg                                              23

<210> SEQ ID NO 752
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 752
uuuuguauuu ucaguaaagu ugg                                              23

<210> SEQ ID NO 753
<211> LENGTH: 23
<212> TYPE: RNA
<213> ORGANISM: Artificial Sequence
<220> FEATURE:
<223> OTHER INFORMATION: Synthetic Sequence
```

<400> SEQUENCE: 753
uuuguauuuu caguaaaguu ggg                                          23

<210> SEQ ID NO 754
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 754
uauuuucagu aaaguugggc agg                                          23

<210> SEQ ID NO 755
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 755
auuuaaaagc aggagccaua agg                                          23

<210> SEQ ID NO 756
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 756
caaagccuuu cccggacgug cgg                                          23

<210> SEQ ID NO 757
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 757
uucaguaaag uugggcaggc ugg                                          23

<210> SEQ ID NO 758
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 758
gccuuucccg gacgugcgga agg                                          23

<210> SEQ ID NO 759
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 759
caccugaggu caggaguucg agg                                          23

<210> SEQ ID NO 760

-continued

```
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 760
ccuuucccgg acgugcggaa ggg                                                       23

<210> SEQ ID NO 761
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 761
cgggcggauc accugagguc agg                                                       23

<210> SEQ ID NO 762
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 762
uccauuuccg gccaugagga agg                                                       23

<210> SEQ ID NO 763
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 763
aaguuccauu uccggccaug agg                                                       23

<210> SEQ ID NO 764
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 764
agaagcgggc ggaucaccug agg                                                       23

<210> SEQ ID NO 765
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 765
ggccucgaac uccugaccuc agg                                                       23

<210> SEQ ID NO 766
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 766
```
aagggcaacg uccuuccuca ugg            23

<210> SEQ ID NO 767
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 767
ggaaauuaaa guuccauuuc cgg            23

<210> SEQ ID NO 768
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 768
gcaacguccu uccucauggc cgg            23

<210> SEQ ID NO 769
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 769
cuuugggagg cagaagcggg cgg            23

<210> SEQ ID NO 770
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 770
gcacuuuggg aggcagaagc ggg            23

<210> SEQ ID NO 771
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 771
uccuuccuca uggccggaaa ugg            23

<210> SEQ ID NO 772
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 772
agcacuuugg gaggcagaag cgg            23

<210> SEQ ID NO 773
<211> LENGTH: 23
<212> TYPE: RNA

-continued

<213> ORGANISM: Artificial Sequence
<220> FEATURE:
<223> OTHER INFORMATION: Synthetic Sequence

<400> SEQUENCE: 773
uguaauccca gcacuuuggg agg                                                                    23

<210> SEQ ID NO 774
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 774
gccuguaauc ccagcacuuu ggg                                                                    23

<210> SEQ ID NO 775
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 775
cgccuguaau cccagcacuu ugg                                                                    23

<210> SEQ ID NO 776
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 776
gcgggcuggu ugggggaac ggg                                                                     23

<210> SEQ ID NO 777
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 777
ggcgggcugg uugggggaa cgg                                                                     23

<210> SEQ ID NO 778
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 778
ucucgggcgg gcugguuggg ggg                                                                    23

<210> SEQ ID NO 779
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 779
cucucgggcg ggcugguugg ggg                                                                    23

<210> SEQ ID NO 780
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 780
gcuucugccu cccaaagugc ugg                                                    23

<210> SEQ ID NO 781
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 781
ucucucgggc gggcugguug ggg                                                    23

<210> SEQ ID NO 782
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 782
cuucugccuc ccaaagugcu ggg                                                    23

<210> SEQ ID NO 783
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 783
cucucucggg cgggcugguu ggg                                                    23

<210> SEQ ID NO 784
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 784
acucucucgg gcgggcuggu ugg                                                    23

<210> SEQ ID NO 785
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 785
agucacucuc ucgggcgggc ugg                                                    23

<210> SEQ ID NO 786
<211> LENGTH: 23
<212> TYPE: RNA
<213> ORGANISM: Artificial Sequence
<220> FEATURE:

-continued

<223> OTHER INFORMATION: Synthetic Sequence

<400> SEQUENCE: 786
ucccaaagug cugggauuac agg                                                                                    23

<210> SEQ ID NO 787
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 787
ugagagucac ucucucgggc ggg                                                                                    23

<210> SEQ ID NO 788
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 788
gugagaguca cucucucggg cgg                                                                                    23

<210> SEQ ID NO 789
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 789
cucgugagag ucacucucuc ggg                                                                                    23

<210> SEQ ID NO 790
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 790
ucucgugaga gucacucucu cgg                                                                                    23

<210> SEQ ID NO 791
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 791
ggaucuuagu ccccgcacgg ugg                                                                                    23

<210> SEQ ID NO 792
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 792
aagggaucuu aguccccgca cgg                                                                                    23

-continued

```
<210> SEQ ID NO 793
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 793
uacaggcgug agccaccgug cgg                                                    23

<210> SEQ ID NO 794
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 794
acaggcguga gccaccgugc ggg                                                    23

<210> SEQ ID NO 795
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 795
caggcgugag ccaccgugcg ggg                                                    23

<210> SEQ ID NO 796
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 796
auuggccaag cugacucucg cgg                                                    23

<210> SEQ ID NO 797
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 797
gaguccccgc ccuugcaaaa ggg                                                    23

<210> SEQ ID NO 798
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 798
ggaguccccg cccuugcaaa agg                                                    23

<210> SEQ ID NO 799
<211> LENGTH: 23
<212> TYPE: RNA
<213> ORGANISM: Artificial Sequence
<220> FEATURE:
<223> OTHER INFORMATION: Synthetic Sequence
```

-continued

<400> SEQUENCE: 799
ggacuaagau cccuuuugca agg                                                    23

<210> SEQ ID NO 800
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 800
gacuaagauc ccuuuugcaa ggg                                                    23

<210> SEQ ID NO 801
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 801
uaagaucccu uuugcaaggg cgg                                                    23

<210> SEQ ID NO 802
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 802
gagagccgcg agagucagcu ugg                                                    23

<210> SEQ ID NO 803
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 803
aagaucccuu uugcaagggc ggg                                                    23

<210> SEQ ID NO 804
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 804
agaucccuuu ugcaagggcg ggg                                                    23

<210> SEQ ID NO 805
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 805
cggccgccga ccgcacggau ugg                                                    23

<210> SEQ ID NO 806
<211> LENGTH: 23

-continued

```
<212> TYPE: RNA
<213> ORGANISM: Artificial Sequence
<220> FEATURE:
<223> OTHER INFORMATION: Synthetic Sequence

<400> SEQUENCE: 806
augcacuugu cuguaguuca agg                                              23

<210> SEQ ID NO 807
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 807
gggagcggcc gccgaccgca cgg                                              23

<210> SEQ ID NO 808
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 808
gucagcuugg ccaauccgug cgg                                              23

<210> SEQ ID NO 809
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 809
gcuuggccaa uccgugcggu cgg                                              23

<210> SEQ ID NO 810
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 810
uggccaaucc gugcggucgg cgg                                              23

<210> SEQ ID NO 811
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 811
gagucggcuu auaaagggag cgg                                              23

<210> SEQ ID NO 812
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 812
```

-continued cgggcgaguc ggcuuauaaa ggg                                                                    23

<210> SEQ ID NO 813
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 813
ccgggcgagu cggcuuauaa agg                                                                    23

<210> SEQ ID NO 814
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 814
cggugcgcug ccgggcgagu cgg                                                                    23

<210> SEQ ID NO 815
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 815
gaagcaaaag uaccacuaga ugg                                                                    23

<210> SEQ ID NO 816
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 816
ccgcaacccg gugcgcugcc ggg                                                                    23

<210> SEQ ID NO 817
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 817 uccgcaacccc ggugcgcugc cgg                                                                    23

<210> SEQ ID NO 818
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 818
ccuuuauaag ccgacucgcc cgg                                                                    23

<210> SEQ ID NO 819
<211> LENGTH: 23
<212> TYPE: RNA
<213> ORGANISM: Artificial Sequence -continued
<220> FEATURE:
<223> OTHER INFORMATION: Synthetic Sequence

<400> SEQUENCE: 819
uuuguucuua cuccaucuag ugg                                                    23

<210> SEQ ID NO 820
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 820
caggcccacc cuccgcaacc cgg                                                    23

<210> SEQ ID NO 821
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 821
cgacucgccc ggcagcgcac cgg                                                    23

<210> SEQ ID NO 822
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 822
gacucgcccg gcagcgcacc ggg                                                    23

<210> SEQ ID NO 823
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 823
cccggcagcg caccggguug cgg                                                    23

<210> SEQ ID NO 824
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 824
ggcagcgcac cggguugcgg agg                                                    23

<210> SEQ ID NO 825
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 825
caccacaaau guuguaaaug ugg                                                    23

-continued

```
<210> SEQ ID NO 826
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 826
gcagcgcacc ggguugcgga ggg                                          23

<210> SEQ ID NO 827
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 827
gcgcaccggg uugcggaggg ugg                                          23

<210> SEQ ID NO 828
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 828
cgcaccgggu ugcggagggu ggg                                          23

<210> SEQ ID NO 829
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 829
aaauggccac cacccucccc agg                                          23

<210> SEQ ID NO 830
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 830
cggguugcgg aggguggggcc ugg                                         23

<210> SEQ ID NO 831
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 831
ggguugcgga gggugggccu ggg                                          23

<210> SEQ ID NO 832
<211> LENGTH: 23
<212> TYPE: RNA
<213> ORGANISM: Artificial Sequence
<220> FEATURE:
<223> OTHER INFORMATION: Synthetic Sequence
```

-continued

<400> SEQUENCE: 832
uugcggaggg ugggccuggg agg                                                        23

<210> SEQ ID NO 833
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 833 ugcggaggu gggccuggga ggg                                                         23

<210> SEQ ID NO 834
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 834 gcggaggug ggccugggag ggg                                                         23

<210> SEQ ID NO 835
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 835
cuccacauuu acaacauuug ugg                                                        23

<210> SEQ ID NO 836
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 836
gagggugggc cugggagggg ugg                                                        23

<210> SEQ ID NO 837
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 837
ucggcguucc ccccaccaac agg                                                        23

<210> SEQ ID NO 838
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 838
cacauuuaca acauuugugg ugg                                                        23

<210> SEQ ID NO 839

-continued

```
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 839
ggugggccug ggaggggugg ugg                                              23

<210> SEQ ID NO 840
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 840
aguuaggguu agacaaaaaa ugg                                              23

<210> SEQ ID NO 841
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 841
uacaacauuu gugguggugc agg                                              23

<210> SEQ ID NO 842
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 842
acaacauuug ugguggugca ggg                                              23

<210> SEQ ID NO 843
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 843
cuguggccau ucuugcuuca cgg                                              23

<210> SEQ ID NO 844
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 844
gccuacgccc uucucaguua ggg                                              23

<210> SEQ ID NO 845
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 845
```

-continued

--- cgccuacgcc cuucucaguu agg                                                    23

<210> SEQ ID NO 846
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 846
gcagggccgu gaagcaagaa ugg                                                    23

<210> SEQ ID NO 847
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 847
agaaaaacau ucccagucug ugg                                                    23

<210> SEQ ID NO 848
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 848
uugucuaacc cuaacugaga agg                                                    23

<210> SEQ ID NO 849
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 849
ugucuaaccc uaacugagaa ggg                                                    23

<210> SEQ ID NO 850
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 850
aagcaagaau ggccacagac ugg                                                    23

<210> SEQ ID NO 851
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 851
agcaagaaug gccacagacu ggg                                                    23

<210> SEQ ID NO 852
<211> LENGTH: 23
<212> TYPE: RNA

-continued

<213> ORGANISM: Artificial Sequence
<220> FEATURE:
<223> OTHER INFORMATION: Synthetic Sequence

<400> SEQUENCE: 852
acccuaacug agaagggcgu agg                                                             23

<210> SEQ ID NO 853
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 853
gcgcgcgggg agcaaaagca cgg                                                             23

<210> SEQ ID NO 854
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 854
caugcaguuc gcuuuccugu ugg                                                             23

<210> SEQ ID NO 855
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 855
agcgagaaaa acagcgcgcg ggg                                                             23

<210> SEQ ID NO 856
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 856
cagcgagaaa aacagcgcgc ggg                                                             23

<210> SEQ ID NO 857
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 857
ucagcgagaa aaacagcgcg cgg                                                             23

<210> SEQ ID NO 858
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 858
gcaguucgcu uuccuguugg ugg                                                             23

<210> SEQ ID NO 859
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 859
uuuuucucgc ugacuuucag cgg                                                                    23

<210> SEQ ID NO 860
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 860
uuuucucgcu gacuuucagc ggg                                                                    23

<210> SEQ ID NO 861
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 861
caguucgcuu uccuguuggu ggg                                                                    23

<210> SEQ ID NO 862
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 862
ucucgcugac uuucagcggg cgg                                                                    23

<210> SEQ ID NO 863
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 863
aguucgcuuu ccuguuggug ggg                                                                    23

<210> SEQ ID NO 864
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 864
cgguggaagg cggcaggccg agg                                                                    23

<210> SEQ ID NO 865
<211> LENGTH: 23
<212> TYPE: RNA
<213> ORGANISM: Artificial Sequence
<220> FEATURE:

-continued

<223> OTHER INFORMATION: Synthetic Sequence

<400> SEQUENCE: 865
uucagcgggc ggaaaagccu cgg                                                    23

<210> SEQ ID NO 866
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 866
aaugaacggu ggaaggcggc agg                                                    23

<210> SEQ ID NO 867
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 867
uuaugaugaa ugugauaguu ugg                                                    23

<210> SEQ ID NO 868
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 868
guucgcuuuc cguuggugg ggg                                                     23

<210> SEQ ID NO 869
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 869
cuagaaugaa cgguggaagg cgg                                                    23

<210> SEQ ID NO 870
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 870
gcucuagaau gaacggugga agg                                                    23

<210> SEQ ID NO 871
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 871
guuugcucua gaaugaacgg ugg                                                    23

<210> SEQ ID NO 872
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 872
uucgcuuucc uguuggugggg ggg                                              23

<210> SEQ ID NO 873
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 873
uuuguuugcu cuagaaugaa cgg                                               23

<210> SEQ ID NO 874
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 874
aaacaaaaaa ugucagcugc ugg                                              23

<210> SEQ ID NO 875
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 875
gguccccggg aggggcgaac ggg                                              23

<210> SEQ ID NO 876
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 876
agguccccgg gaggggcgaa cgg                                              23

<210> SEQ ID NO 877
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 877
ccgccgcagg uccccgggag ggg                                              23

<210> SEQ ID NO 878
<211> LENGTH: 23
<212> TYPE: RNA
<213> ORGANISM: Artificial Sequence
<220> FEATURE:
<223> OTHER INFORMATION: Synthetic Sequence -continued

<400> SEQUENCE: 878
cccgccgcag gucccgggga ggg                                                              23

<210> SEQ ID NO 879
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 879
acccgccgca gguccccggg agg                                                              23

<210> SEQ ID NO 880
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 880
gcgacccgcc gcagguccc ggg                                                               23

<210> SEQ ID NO 881
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 881
ggcgacccgc cgcagguccc cgg                                                              23

<210> SEQ ID NO 882
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 882
gcuggcccgu ucgccccucc cgg                                                              23

<210> SEQ ID NO 883
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 883
cuggcccguu cgccccuccc ggg                                                              23

<210> SEQ ID NO 884
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 884
uggcccguuc gccccucccg ggg                                                              23

<210> SEQ ID NO 885
<211> LENGTH: 23

-continued

```
<212> TYPE: RNA
<213> ORGANISM: Artificial Sequence
<220> FEATURE:
<223> OTHER INFORMATION: Synthetic Sequence

<400> SEQUENCE: 885
cugggcaggc gacccgccgc agg                                       23

<210> SEQ ID NO 886
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 886 ucgcccucc cggggaccug cgg                                        23

<210> SEQ ID NO 887
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 887
ccccucccgg ggaccugcgg cgg                                       23

<210> SEQ ID NO 888
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 888
cccucccggg gaccugcggc ggg                                       23

<210> SEQ ID NO 889
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 889
gggugacgga ugcgcacgau cgg                                       23

<210> SEQ ID NO 890
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 890
gcgggguucg ggggcugggc agg                                       23

<210> SEQ ID NO 891
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 891
```

-continued

```
ccaggcgggg uucgggggcu ggg                                              23

<210> SEQ ID NO 892
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 892
uccaggcggg guucgggggc ugg                                              23

<210> SEQ ID NO 893
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 893
ggccuccagg cgggguucgg ggg                                              23

<210> SEQ ID NO 894
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 894
cggccuccag gcgggguucg ggg                                              23

<210> SEQ ID NO 895
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 895
gcggccucca ggcgggguuc ggg                                              23

<210> SEQ ID NO 896
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 896
cgcggccucc aggcgggguu cgg                                              23

<210> SEQ ID NO 897
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 897
ccgaccgcgg ccuccaggcg ggg                                              23

<210> SEQ ID NO 898
<211> LENGTH: 23
<212> TYPE: RNA
<213> ORGANISM: Artificial Sequence
```

-continued

<220> FEATURE:
<223> OTHER INFORMATION: Synthetic Sequence

<400> SEQUENCE: 898
gccgaccgcg gccuccaggc ggg                                                     23

<210> SEQ ID NO 899
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 899
ggccgaccgc ggccuccagg cgg                                                     23

<210> SEQ ID NO 900
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 900
ccgggccgac cgcggccucc agg                                                     23

<210> SEQ ID NO 901
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 901
cccagccccc gaaccccgcc ugg                                                     23

<210> SEQ ID NO 902
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 902
agcccccgaa ccccgccugg agg                                                     23

<210> SEQ ID NO 903
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 903
gagaagcccc gggccgaccg cgg                                                     23

<210> SEQ ID NO 904
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 904
cgaaccccgc cuggaggccg cgg                                                     23

-continued

```
<210> SEQ ID NO 905
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 905
ccccgccugg aggccgcggu cgg                                          23

<210> SEQ ID NO 906
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 906
ggugccuccg gagaagcccc ggg                                          23

<210> SEQ ID NO 907
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 907
gggugccucc ggagaagccc cgg                                          23

<210> SEQ ID NO 908
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 908
ccuggaggcc gcggucggcc cgg                                          23

<210> SEQ ID NO 909
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 909
cuggaggccg cggucggccc ggg                                          23

<210> SEQ ID NO 910
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 910
uggaggccgc ggucggcccg ggg                                          23

<210> SEQ ID NO 911
<211> LENGTH: 23
<212> TYPE: RNA
<213> ORGANISM: Artificial Sequence
<220> FEATURE:
<223> OTHER INFORMATION: Synthetic Sequence
```

-continued

<400> SEQUENCE: 911
gcgguggcag ugggugccuc cgg                                                          23

<210> SEQ ID NO 912
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 912
cggucggccc ggggcuucuc cgg                                                          23

<210> SEQ ID NO 913
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 913
ucggcccggg gcuucuccgg agg                                                          23

<210> SEQ ID NO 914
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 914
caacucuucg cgguggcagu ggg                                                          23

<210> SEQ ID NO 915
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 915
ccaacucuuc gcgguggcag ugg                                                          23

<210> SEQ ID NO 916
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 916
ccacugccac cgcgaagagu ugg                                                          23

<210> SEQ ID NO 917
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 917
cacugccacc gcgaagaguu ggg                                                          23

<210> SEQ ID NO 918

-continued

```
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 918
uuuggagaau aaauugaaug agg                                          23

<210> SEQ ID NO 919
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 919
cagagcccaa cucuucgcgg ugg                                          23

<210> SEQ ID NO 920
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 920
gagaauaaau ugaaugagga agg                                          23

<210> SEQ ID NO 921
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 921
ccauugccgg cgagggguga cgg                                          23

<210> SEQ ID NO 922
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 922
aacugaucac caaaucucca ggg                                          23

<210> SEQ ID NO 923
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 923
uaacugauca ccaaaucucc agg                                          23

<210> SEQ ID NO 924
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 924
```
aaauugaaug aggaaggccc ugg                                    23

<210> SEQ ID NO 925
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 925 aagccccau ugccggcgag ggg                                     23

<210> SEQ ID NO 926
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 926
caagccccca uugccggcga ggg                                    23

<210> SEQ ID NO 927
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 927
acaagccccc auugccggcg agg                                    23

<210> SEQ ID NO 928
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 928
gguucacaag cccccauugc cgg                                    23

<210> SEQ ID NO 929
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 929
ugaggaaggc ccuggagauu ugg                                    23

<210> SEQ ID NO 930
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 930
gcgcauccgu caccccucgc cgg                                    23

<210> SEQ ID NO 931
<211> LENGTH: 23
<212> TYPE: RNA

-continued

```
<213> ORGANISM: Artificial Sequence
<220> FEATURE:
<223> OTHER INFORMATION: Synthetic Sequence

<400> SEQUENCE: 931
ccgucacccc ucgccggcaa ugg                                                  23

<210> SEQ ID NO 932
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 932
cgucaccccu cgccggcaau ggg                                                  23

<210> SEQ ID NO 933
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 933
gucaccccuc gccggcaaug ggg                                                  23

<210> SEQ ID NO 934
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 934
ucaccccucg ccggcaaugg ggg                                                  23

<210> SEQ ID NO 935
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 935
gcccagucag ucagguuugg ggg                                                  23

<210> SEQ ID NO 936
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 936
ggcccaguca gucagguuug ggg                                                  23

<210> SEQ ID NO 937
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 937
uggcccaguc agucagguuu ggg                                                  23
```

<210> SEQ ID NO 938
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 938
cuggcccagu cagucagguu ugg                                          23

<210> SEQ ID NO 939
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 939
aagacuuggc acuuuauaug ugg                                          23

<210> SEQ ID NO 940
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 940
gcacacuggc ccagucaguc agg                                          23

<210> SEQ ID NO 941
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 941
aacccccaaa ccugacugac ugg                                          23

<210> SEQ ID NO 942
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 942
acccccaaac cugacugacu ggg                                          23

<210> SEQ ID NO 943
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 943
auaaucuuga guacaagacu ugg                                          23

<210> SEQ ID NO 944
<211> LENGTH: 23
<212> TYPE: RNA
<213> ORGANISM: Artificial Sequence
<220> FEATURE:

-continued

```
<223> OTHER INFORMATION: Synthetic Sequence

<400> SEQUENCE: 944
ccugccaauu ugcagcacac ugg                                            23

<210> SEQ ID NO 945
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 945
ugggccagug ugcugcaaau ugg                                            23

<210> SEQ ID NO 946
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 946
ccagugugcu gcaaauuggc agg                                            23

<210> SEQ ID NO 947
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 947
uacucaagau uauaagcaau agg                                            23

<210> SEQ ID NO 948
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 948
ccucgccccc gagagacccg cgg                                            23

<210> SEQ ID NO 949
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 949
caaauuggca ggagacguga agg                                            23

<210> SEQ ID NO 950
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 950
uucauuuugg ccgacuuugg agg                                            23
```

<210> SEQ ID NO 951
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 951
ccauucauuu uggccgacuu ugg                                                                          23

<210> SEQ ID NO 952
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 952
cgugaaggca ccuccaaagu cgg                                                                          23

<210> SEQ ID NO 953
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 953
ggcucacugc ccauucauuu ugg                                                                          23

<210> SEQ ID NO 954
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 954
ccaaagucgg ccaaaaugaa ugg                                                                          23

<210> SEQ ID NO 955
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 955
caaagucggc caaaaugaau ggg                                                                          23

<210> SEQ ID NO 956
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 956
gaguugggcu cugucagccg cgg                                                                          23

<210> SEQ ID NO 957
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 957
ggaacggcuc caggcaaccc cgg                                                     23

<210> SEQ ID NO 958
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 958
aguugggcuc ugucagccgc ggg                                                     23

<210> SEQ ID NO 959
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 959
aaaaugaaug ggcagugagc cgg                                                     23

<210> SEQ ID NO 960
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 960
aaaugaaugg gcagugagcc ggg                                                     23

<210> SEQ ID NO 961
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 961
uuuccccuuc auaucuaagu agg                                                     23

<210> SEQ ID NO 962
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 962
aaugaauggg cagugagccg ggg                                                     23

<210> SEQ ID NO 963
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 963
acccacgcag gaacggcucc agg                                                     23

<210> SEQ ID NO 964
<211> LENGTH: 23

-continued

```
<212> TYPE: RNA
<213> ORGANISM: Artificial Sequence
<220> FEATURE:
<223> OTHER INFORMATION: Synthetic Sequence

<400> SEQUENCE: 964
ggcagugagc cgggguugcc ugg                                              23

<210> SEQ ID NO 965
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 965
cgggagaacc cacgcaggaa cgg                                              23

<210> SEQ ID NO 966
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 966
uagugccuac uuagauauga agg                                              23

<210> SEQ ID NO 967
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 967
agugccuacu uagauaugaa ggg                                              23

<210> SEQ ID NO 968
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 968
gugccuacuu agauaugaag ggg                                              23

<210> SEQ ID NO 969
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 969
gaagacggga gaacccacgc agg                                              23

<210> SEQ ID NO 970
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 970
```
uuagauauga aggggaaaga agg                                                    23

<210> SEQ ID NO 971
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 971
ugccuggagc cguuccugcg ugg                                                    23

<210> SEQ ID NO 972
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 972
uagauaugaa gggggaaagaa ggg                                                   23

<210> SEQ ID NO 973
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 973
gccuggagcc guuccugcgu ggg                                                    23

<210> SEQ ID NO 974
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 974
ggcaacaaaa agcggaagac ggg                                                    23

<210> SEQ ID NO 975
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 975
aggcaacaaa aagcggaaga cgg                                                    23

<210> SEQ ID NO 976
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 976
aagaaggguu ugagauaaug ugg                                                    23

<210> SEQ ID NO 977
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 977
ccauaaaagg caacaaaaag cgg                                                                     23

<210> SEQ ID NO 978
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 978
agaaggguuu gagauaaugu ggg                                                                     23

<210> SEQ ID NO 979
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 979
aguuguaaua caaccauaaa agg                                                                     23

<210> SEQ ID NO 980
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 980
aaugugggau gcuaagagaa ugg                                                                     23

<210> SEQ ID NO 981
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 981
gugggaugcu aagagaaugg ugg                                                                     23

<210> SEQ ID NO 982
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 982
ccgcuuuuug uugccuuuua ugg                                                                     23

<210> SEQ ID NO 983
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 983
ucugucagcc gcgggucucu cgg                                                                     23

-continued

```
<210> SEQ ID NO 984
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 984
cucaacaaaa ucugcagagc agg                                              23

<210> SEQ ID NO 985
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 985
cugucagccg cgggucucuc ggg                                              23

<210> SEQ ID NO 986
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 986
ugucagccgc gggucucucg ggg                                              23

<210> SEQ ID NO 987
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 987
cugcucugca gauuuuguug agg                                              23

<210> SEQ ID NO 988
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 988
uuuagcaucu acucuaugua agg                                              23

<210> SEQ ID NO 989
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 989
gucagccgcg ggucucucgg ggg                                              23

<210> SEQ ID NO 990
<211> LENGTH: 23
<212> TYPE: RNA
<213> ORGANISM: Artificial Sequence
<220> FEATURE:
<223> OTHER INFORMATION: Synthetic Sequence
```

<400> SEQUENCE: 990
gacuggucga gaucuaccuu ggg                                          23

<210> SEQ ID NO 991
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 991
ggacuggucg agaucuaccu ugg                                          23

<210> SEQ ID NO 992
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 992
ugagguuuuu gcuucuccca agg                                          23

<210> SEQ ID NO 993
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 993
ccacaccccg uugaggggac ugg                                          23

<210> SEQ ID NO 994
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 994
uucucccaca ccccguugag ggg                                          23

<210> SEQ ID NO 995
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 995
guucucccac accccguuga ggg                                          23

<210> SEQ ID NO 996
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 996
agugcaauag ugcuaaaaac agg                                          23

<210> SEQ ID NO 997

```
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 997
uguucuccca caccccguug agg                                                    23

<210> SEQ ID NO 998
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 998
aucucgacca gucccucaa cgg                                                     23

<210> SEQ ID NO 999
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 999
ucucgaccag uccccucaac ggg                                                    23

<210> SEQ ID NO 1000
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1000
cucgaccagu ccccucaacg ggg                                                    23

<210> SEQ ID NO 1001
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1001
ccaguccccu caacggggug ugg                                                    23

<210> SEQ ID NO 1002
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1002
caguccccuc aacgggugu ggg                                                     23

<210> SEQ ID NO 1003
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1003
```

-continued

```
ccagguugua aaguuuuuua cgg                                              23

<210> SEQ ID NO 1004
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1004
ccgcgggucu cucgggggcg agg                                              23

<210> SEQ ID NO 1005
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1005
cgcgggucuc ucgggggcga ggg                                              23

<210> SEQ ID NO 1006
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1006
ugacagagcc caacucuucg cgg                                              23

<210> SEQ ID NO 1007
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1007
uuucuuucau agcaucugcc agg                                              23

<210> SEQ ID NO 1008
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1008
ccguaaaaaa cuuuacaacc ugg                                              23

<210> SEQ ID NO 1009
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1009
gcagaugcua ugaaagaaaa agg                                              23

<210> SEQ ID NO 1010
<211> LENGTH: 23
<212> TYPE: RNA
```

-continued

```
<213> ORGANISM: Artificial Sequence
<220> FEATURE:
<223> OTHER INFORMATION: Synthetic Sequence

<400> SEQUENCE: 1010
cagaugcuau gaaagaaaaa ggg                                            23

<210> SEQ ID NO 1011
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1011
agaugcuaug aaagaaaaag ggg                                            23

<210> SEQ ID NO 1012
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1012
gcuaugaaag aaaaagggga ugg                                            23

<210> SEQ ID NO 1013
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1013
cuaugaaaga aaaggggau ggg                                             23

<210> SEQ ID NO 1014
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1014
aaggggaugg gagagagaga agg                                            23

<210> SEQ ID NO 1015
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1015
gucucucggg ggcgagggcg agg                                            23

<210> SEQ ID NO 1016
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1016
gggaugggag agagagaagg agg                                            23
```

<210> SEQ ID NO 1017
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1017
ggaugggaga gagagaagga ggg                                                                            23

<210> SEQ ID NO 1018
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1018
uagaagaucu aaaugaacau ugg                                                                            23

<210> SEQ ID NO 1019
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1019
gagagaagga gggagagaga ugg                                                                            23

<210> SEQ ID NO 1020
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1020
aaggagggag agagauggag agg                                                                            23

<210> SEQ ID NO 1021
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1021
aggagggaga gagauggaga ggg                                                                            23

<210> SEQ ID NO 1022
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1022
cauaaaccga ugaccauuaa agg                                                                            23

<210> SEQ ID NO 1023
<211> LENGTH: 23
<212> TYPE: RNA
<213> ORGANISM: Artificial Sequence
<220> FEATURE:

-continued

<223> OTHER INFORMATION: Synthetic Sequence

<400> SEQUENCE: 1023
aacaagcgcu augacuagca agg                                                            23

<210> SEQ ID NO 1024
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1024
uggaaauugu guuccuuuaa ugg                                                            23

<210> SEQ ID NO 1025
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1025
uguguuccuu uaauggucau cgg                                                            23

<210> SEQ ID NO 1026
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1026
aaaaagaaac uucuaaccuc ugg                                                            23

<210> SEQ ID NO 1027
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1027
uuuacuuuuc uuucagaucg agg                                                            23

<210> SEQ ID NO 1028
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1028
uggucaucgg uuuaugccag agg                                                            23

<210> SEQ ID NO 1029
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1029
cuccguggag uugucgcugu cgg                                                            23

-continued

```
<210> SEQ ID NO 1030
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1030 cggggggcgag ggcgagguuc agg                                          23

<210> SEQ ID NO 1031
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1031
auucaguuag auaaacuccg ugg                                          23

<210> SEQ ID NO 1032
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1032
gaccgacagc gacaacucca cgg                                          23

<210> SEQ ID NO 1033
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1033
acugcucaag gucaucgcca agg                                          23

<210> SEQ ID NO 1034
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1034
uuuuuugaaa aauuagaccu ugg                                          23

<210> SEQ ID NO 1035
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1035
uccucuuccu gcggccugaa agg                                          23

<210> SEQ ID NO 1036
<211> LENGTH: 23
<212> TYPE: RNA
<213> ORGANISM: Artificial Sequence
<220> FEATURE:
<223> OTHER INFORMATION: Synthetic Sequence
```

-continued

```
<400> SEQUENCE: 1036
ggguuauauc cuacugcuca agg                                              23

<210> SEQ ID NO 1037
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1037
uggcgaugac cuugagcagu agg                                              23

<210> SEQ ID NO 1038
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1038
caguuuuaca uauaaaugac agg                                              23

<210> SEQ ID NO 1039
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1039
uuggaacgcu aagcuugugg ggg                                              23

<210> SEQ ID NO 1040
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1040
auuggaacgc uaagcuugug ggg                                              23

<210> SEQ ID NO 1041
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1041
uauuggaacg cuaagcuugu ggg                                              23

<210> SEQ ID NO 1042
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1042
uuauuggaac gcuaagcuug ugg                                              23

<210> SEQ ID NO 1043
<211> LENGTH: 23
```

-continued

```
<212> TYPE: RNA
<213> ORGANISM: Artificial Sequence
<220> FEATURE:
<223> OTHER INFORMATION: Synthetic Sequence

<400> SEQUENCE: 1043
uaugccuagu guuccguuau ugg                                              23

<210> SEQ ID NO 1044
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1044
ugacuagcaa gguuaaguga agg                                              23

<210> SEQ ID NO 1045
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1045
caagcuuagc guuccaauaa cgg                                              23

<210> SEQ ID NO 1046
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1046
uauguaaaac ugcacuauac ugg                                              23

<210> SEQ ID NO 1047
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1047
ccggccgcga auuuuauaa ugg                                               23

<210> SEQ ID NO 1048
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1048
cguuccaaua acggaacacu agg                                              23

<210> SEQ ID NO 1049
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1049
```

-continued gggcgagguu caggccuuuc agg                                              23

<210> SEQ ID NO 1050
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1050
cuggccauua uaaaaauucg cgg                                              23

<210> SEQ ID NO 1051
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1051
acacuaggca uaugaaaga cgg                                               23

<210> SEQ ID NO 1052
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1052
cagguaugag ccaccgcacc cgg                                              23

<210> SEQ ID NO 1053
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1053
ccauuauaaa aauucgcggc cgg                                              23

<210> SEQ ID NO 1054
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1054
cauuauaaaa auucgcggcc ggg                                              23

<210> SEQ ID NO 1055
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1055
acuuuaagcc uuucaguccc ugg                                             23

<210> SEQ ID NO 1056
<211> LENGTH: 23
<212> TYPE: RNA
<213> ORGANISM: Artificial Sequence -continued
<220> FEATURE:
<223> OTHER INFORMATION: Synthetic Sequence

<400> SEQUENCE: 1056
uaaaaauucg cggccggug cgg                                                          23

<210> SEQ ID NO 1057
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1057
aaauucgcgg ccgggugcgg ugg                                                         23

<210> SEQ ID NO 1058
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1058
ucgcuccguu ccucuuccug cgg                                                         23

<210> SEQ ID NO 1059
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1059
aggguugggg gugggggug ugg                                                          23

<210> SEQ ID NO 1060
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1060
ucccaaagug cugggauuac agg                                                         23

<210> SEQ ID NO 1061
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1061
cugggagggu ugggggugg ggg                                                          23

<210> SEQ ID NO 1062
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1062
gcugggaggg uugggggugg ggg                                                         23

-continued

<210> SEQ ID NO 1063
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1063
ggcugggagg guuggggug ggg                                                                                    23

<210> SEQ ID NO 1064
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1064
cggcugggag gguuggggu ggg                                                                                    23

<210> SEQ ID NO 1065
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1065
agcaagguua agugaaggcc agg                                                                                   23

<210> SEQ ID NO 1066
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1066
ccggcuggga ggguugggg ugg                                                                                    23

<210> SEQ ID NO 1067
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1067
cuucggccuc ccaaagugcu ggg                                                                                   23

<210> SEQ ID NO 1068
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1068
cugccggcug ggaggguugg ggg                                                                                   23

<210> SEQ ID NO 1069
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1069
gcuucggccu cccaaagugc ugg                                              23

<210> SEQ ID NO 1070
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1070
acugccggcu gggaggguug ggg                                              23

<210> SEQ ID NO 1071
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1071
gacugccggc ugggaggguu ggg                                              23

<210> SEQ ID NO 1072
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1072
agacugccgg cugggagggu ugg                                              23

<210> SEQ ID NO 1073
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1073
gcaagguuaa gugaaggcca ggg                                              23

<210> SEQ ID NO 1074
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1074
ugggagacug ccggcuggga ggg                                              23

<210> SEQ ID NO 1075
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1075
gugggagacu gccggcuggg agg                                              23

<210> SEQ ID NO 1076

```
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1076
uaccuguaau cccagcacuu ugg                                          23

<210> SEQ ID NO 1077
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1077
accuguaauc ccagcacuuu ggg                                          23

<210> SEQ ID NO 1078
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1078
cuugugggag acugccggcu ggg                                          23

<210> SEQ ID NO 1079
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1079
ucuuguggga gacugccggc ugg                                          23

<210> SEQ ID NO 1080
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1080
uguaauccca gcacuuuggg agg                                          23

<210> SEQ ID NO 1081
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1081
caauucuugu gggagacugc cgg                                          23

<210> SEQ ID NO 1082
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1082
```
ccacccccaa cccucccagc cgg                                                                                                        23

<210> SEQ ID NO 1083
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1083
cucaagugau ccacccgcuu cgg                                                                                                        23

<210> SEQ ID NO 1084
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1084
agcacuuugg gaggccgaag cgg                                                                                                        23

<210> SEQ ID NO 1085
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1085
gcacuuuggg aggccgaagc ggg                                                                                                        23

<210> SEQ ID NO 1086
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1086
aaaucagagc caauucuugu ggg                                                                                                        23

<210> SEQ ID NO 1087
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1087
guucaggccu uucaggccgc agg                                                                                                        23

<210> SEQ ID NO 1088
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1088
cuuugggagg ccgaagcggg ugg                                                                                                        23

<210> SEQ ID NO 1089
<211> LENGTH: 23
<212> TYPE: RNA

<213> ORGANISM: Artificial Sequence
<220> FEATURE:
<223> OTHER INFORMATION: Synthetic Sequence

<400> SEQUENCE: 1089
gaaaucagag ccaauucuug ugg                                                    23

<210> SEQ ID NO 1090
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1090
cggcagucuc ccacaagaau ugg                                                    23

<210> SEQ ID NO 1091
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1091
caggcugguc ucgaacgcca ggg                                                    23

<210> SEQ ID NO 1092
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1092
ccaggcuggu cucgaacgcc agg                                                    23

<210> SEQ ID NO 1093
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1093
cggguggauc acuugagccc ugg                                                    23

<210> SEQ ID NO 1094
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1094
ccauuagcuu auuuucuuaa agg                                                    23

<210> SEQ ID NO 1095
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1095
uuucaccaug uugcccaggc ugg                                                    23

<210> SEQ ID NO 1096
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1096
gggguuucac cauguugccc agg                                              23

<210> SEQ ID NO 1097
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1097
ccuggcguuc gagaccagcc ugg                                              23

<210> SEQ ID NO 1098
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1098
cuggcguucg agaccagccu ggg                                              23

<210> SEQ ID NO 1099
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1099
ccuuuaagaa aauaagcuaa ugg                                              23

<210> SEQ ID NO 1100
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1100
cgagaccagc cugggcaaca ugg                                              23

<210> SEQ ID NO 1101
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1101
uuuguuucuu ucaaccuagu ggg                                              23

<210> SEQ ID NO 1102
<211> LENGTH: 23
<212> TYPE: RNA
<213> ORGANISM: Artificial Sequence
<220> FEATURE:

-continued

<223> OTHER INFORMATION: Synthetic Sequence

<400> SEQUENCE: 1102
guuuguuucu uucaaccuag ugg                                    23

<210> SEQ ID NO 1103
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1103
aaauaagcua auggcccacu agg                                    23

<210> SEQ ID NO 1104
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1104
uguguuuuua guagagacgg ggg                                    23

<210> SEQ ID NO 1105
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1105
uuguguuuuu aguagagacg ggg                                    23

<210> SEQ ID NO 1106
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1106
uuuguguuuu uaguagagac ggg                                    23

<210> SEQ ID NO 1107
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1107
uuuuguguuu uuaguagaga cgg                                    23

<210> SEQ ID NO 1108
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1108
gccuuucagg ccgcaggaag agg                                    23

-continued

```
<210> SEQ ID NO 1109
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1109
cuagguugaa agaaacaaac agg                                          23

<210> SEQ ID NO 1110
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1110
agugaaggcc agggacugaa agg                                          23

<210> SEQ ID NO 1111
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1111
gucgugauaa gugggcagaa ugg                                          23

<210> SEQ ID NO 1112
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1112
auuaccuugu cgugauaagu ggg                                          23

<210> SEQ ID NO 1113
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1113
aauuaccuug ucgugauaag ugg                                          23

<210> SEQ ID NO 1114
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1114
cuaaaaacac aaaaacuagc ugg                                          23

<210> SEQ ID NO 1115
<211> LENGTH: 23
<212> TYPE: RNA
<213> ORGANISM: Artificial Sequence
<220> FEATURE:
<223> OTHER INFORMATION: Synthetic Sequence
```

-continued

<400> SEQUENCE: 1115
uaaaaacaca aaaacuagcu ggg                                        23

<210> SEQ ID NO 1116
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1116
acacaaaaac uagcugggcg ugg                                        23

<210> SEQ ID NO 1117
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1117
caaaaacuag cugggcgugg ugg                                        23

<210> SEQ ID NO 1118
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1118
aacuagcugg gcgugguggc agg                                        23

<210> SEQ ID NO 1119
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1119
ucugcccacu uaucacgaca agg                                        23

<210> SEQ ID NO 1120
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1120
uccugaguag cugggauuac agg                                        23

<210> SEQ ID NO 1121
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1121
uugaagguau ggauuuggga cgg                                        23

<210> SEQ ID NO 1122
<211> LENGTH: 23

```
<212> TYPE: RNA
<213> ORGANISM: Artificial Sequence
<220> FEATURE:
<223> OTHER INFORMATION: Synthetic Sequence

<400> SEQUENCE: 1122
ggaauugaag guauggauuu ggg                                                    23

<210> SEQ ID NO 1123
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1123
ucucagccuc cugaguagcu ggg                                                    23

<210> SEQ ID NO 1124
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1124
aggaauugaa gguauggauu ugg                                                    23

<210> SEQ ID NO 1125
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1125
ucaggccgca ggaagaggaa cgg                                                    23

<210> SEQ ID NO 1126
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1126
gucucagccu ccgaguagc ugg                                                     23

<210> SEQ ID NO 1127
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1127
auccuaagga auugaaggua ugg                                                    23

<210> SEQ ID NO 1128
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1128
```
gccuguaauc ccagcuacuc agg                                                    23

<210> SEQ ID NO 1129
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1129
agaugauccu aaggaauuga agg                                                    23

<210> SEQ ID NO 1130
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1130
uguaauccca gcuacucagg agg                                                    23

<210> SEQ ID NO 1131
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1131
acuaccccca gaugauccua agg                                                    23

<210> SEQ ID NO 1132
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1132
auccauaccu ucaauuccuu agg                                                    23

<210> SEQ ID NO 1133
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1133
uucaauuccu uaggaucauc ugg                                                    23

<210> SEQ ID NO 1134
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1134
ucaauuccuu aggaucaucu ggg                                                    23

<210> SEQ ID NO 1135
<211> LENGTH: 23
<212> TYPE: RNA
<213> ORGANISM: Artificial Sequence -continued
<220> FEATURE:
<223> OTHER INFORMATION: Synthetic Sequence

<400> SEQUENCE: 1135
caauuccuua ggaucaucug ggg                                              23

<210> SEQ ID NO 1136
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1136
aauuccuuag gaucaucugg ggg                                              23

<210> SEQ ID NO 1137
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1137
cacugcaacc ucugccuccc ggg                                              23

<210> SEQ ID NO 1138
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1138
ucacugcaac cucugccucc cgg                                              23

<210> SEQ ID NO 1139
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1139
acacgagaau cgcuugaacc cgg                                              23

<210> SEQ ID NO 1140
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1140
cacgagaauc gcuugaaccc ggg                                              23

<210> SEQ ID NO 1141
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1141
ccccuggcug cucucucucu ugg                                              23

-continued

```
<210> SEQ ID NO 1142
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1142
gagaaucgcu ugaacccggg agg                                                    23

<210> SEQ ID NO 1143
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1143
cgcuugaacc cgggaggcag agg                                                    23

<210> SEQ ID NO 1144
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1144
ggccuuuaua uacacacccc ugg                                                    23

<210> SEQ ID NO 1145
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1145
ugccaagaga gagagcagcc agg                                                    23

<210> SEQ ID NO 1146
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1146
gccaagagag agagcagcca ggg                                                    23

<210> SEQ ID NO 1147
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1147
ccaagagaga gagcagccag ggg                                                    23

<210> SEQ ID NO 1148
<211> LENGTH: 23
<212> TYPE: RNA
<213> ORGANISM: Artificial Sequence
<220> FEATURE:
<223> OTHER INFORMATION: Synthetic Sequence
```

-continued

<400> SEQUENCE: 1148
ggagucuagu ggcgugaucu cgg                                            23

<210> SEQ ID NO 1149
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1149
ccaggcugga uggagucuag ugg                                            23

<210> SEQ ID NO 1150
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1150
agccaggggu guguauauaa agg                                            23

<210> SEQ ID NO 1151
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1151
caggcuauca cccuaaaggu ggg                                            23

<210> SEQ ID NO 1152
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1152
ucaggcuauc acccuaaagg ugg                                            23

<210> SEQ ID NO 1153
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1153
gcucuuucgc ccaggcugga ugg                                            23

<210> SEQ ID NO 1154
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1154
gauucaggcu aucacccuaa agg                                            23

<210> SEQ ID NO 1155

-continued

```
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1155
ucuugcucuu ucgcccaggc ugg                                              23

<210> SEQ ID NO 1156
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1156
guauauaaag gcccaccuuu agg                                              23

<210> SEQ ID NO 1157
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1157
uauauaaagg cccaccuuua ggg                                              23

<210> SEQ ID NO 1158
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1158
ggagucuugc ucuuucgccc agg                                              23

<210> SEQ ID NO 1159
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1159
ccacuagacu ccauccagcc ugg                                              23

<210> SEQ ID NO 1160
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1160
cacuagacuc cauccagccu ggg                                              23

<210> SEQ ID NO 1161
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1161
```

-continued agggaaucgc gccgcgcgcg ggg                                                        23

<210> SEQ ID NO 1162
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1162
acuuucaauc aucaggauuc agg                                                        23

<210> SEQ ID NO 1163
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1163
acuucugacu uucaaucauc agg                                                        23

<210> SEQ ID NO 1164
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1164
cagggaaucg cgccgcgcgc ggg                                                        23

<210> SEQ ID NO 1165
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1165
aacgauuuuu uuuuugaga cgg                                                         23

<210> SEQ ID NO 1166
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 1166
ucagggaauc gcgccgcgcg cgg                                                        23

<210> SEQ ID NO 1167
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1167
gugaaccgcg ucuggucugc agaggau                                                    27

<210> SEQ ID NO 1168
<211> LENGTH: 27
<212> TYPE: RNA

-continued

```
<213> ORGANISM: Artificial Sequence
<220> FEATURE:
<223> OTHER INFORMATION: Synthetic Sequence

<400> SEQUENCE: 1168
gcugacucuc gcggcucucg ugagagu                                    27

<210> SEQ ID NO 1169
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1169
aacuccacgg aguuuaucua acugaau                                    27

<210> SEQ ID NO 1170
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1170
acggaguuua ucuaacugaa uacgagu                                    27

<210> SEQ ID NO 1171
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1171
ccggcagcgc accggguugc ggagggu                                    27

<210> SEQ ID NO 1172
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1172
ggccauuaua aaaauucgcg gccgggu                                    27

<210> SEQ ID NO 1173
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1173
agugacucuc acgagagccg cgagagu                                    27

<210> SEQ ID NO 1174
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1174
gccgacucgc ccggcagcgc accgggu                                    27
```

```
<210> SEQ ID NO 1175
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1175
ggcgccuacg cccuucucag uuagggu                                          27

<210> SEQ ID NO 1176
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1176
ggaccgacag cgacaacucc acggagu                                          27

<210> SEQ ID NO 1177
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1177
cagaaucuug ucucggcuca gugggau                                          27

<210> SEQ ID NO 1178
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1178
ucucggcuca gugggaugcg uccgagu                                          27

<210> SEQ ID NO 1179
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1179 cccccaacc agcccgcccg agagagu                                           27

<210> SEQ ID NO 1180
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1180
gguuguaaag uuuuuuacgg acagaau                                          27

<210> SEQ ID NO 1181
<211> LENGTH: 27
<212> TYPE: RNA
<213> ORGANISM: Artificial Sequence
<220> FEATURE:
```

-continued

<223> OTHER INFORMATION: Synthetic Sequence

<400> SEQUENCE: 1181
aagggagcgg ccgccgaccg cacggau                                          27

<210> SEQ ID NO 1182
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1182
cgccccuccc ggggaccugc ggcgggu                                          27

<210> SEQ ID NO 1183
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1183
cgcaacccgg ugcgcugccg ggcgagu                                          27

<210> SEQ ID NO 1184
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1184
ugagauaaug ugggaugcua agagaau                                          27

<210> SEQ ID NO 1185
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1185
aagugcaaua gugcuaaaaa caggagu                                          27

<210> SEQ ID NO 1186
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1186
uauucaguua gauaaacucc guggagu                                          27

<210> SEQ ID NO 1187
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1187
ucaccucgac uaccuuaaaa auggaau                                          27

-continued

```
<210> SEQ ID NO 1188
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1188
ccauaaggaa acuauguuau gaugaau                                          27

<210> SEQ ID NO 1189
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1189
auagaguaga ugcuaaaugc uuugagu                                          27

<210> SEQ ID NO 1190
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1190
ucuccagccu cuccuugagc agaggau                                          27

<210> SEQ ID NO 1191
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1191
cuacauuauu aaucuuaagg acugaau                                          27

<210> SEQ ID NO 1192
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1192
cuuaggcccu aaaacuuccc ugugaau                                          27

<210> SEQ ID NO 1193
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1193
aaauuccuau ugcuuauaau cuugagu                                          27

<210> SEQ ID NO 1194
<211> LENGTH: 27
<212> TYPE: RNA
<213> ORGANISM: Artificial Sequence
<220> FEATURE:
<223> OTHER INFORMATION: Synthetic Sequence
```

-continued

<400> SEQUENCE: 1194
gcugacauuu uuuguuugcu cuagaau                                              27

<210> SEQ ID NO 1195
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1195
uaugaugaau gugauaguuu ggagaau                                              27

<210> SEQ ID NO 1196
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1196
cccaggcagc acugacuaca gcagaau                                              27

<210> SEQ ID NO 1197
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1197
gucuugauga gguaaaaaga ggggagu                                             27

<210> SEQ ID NO 1198
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1198
aaaaaaucgu uacaauuuau gguggau                                             27

<210> SEQ ID NO 1199
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1199
guacucaaga uuauaagcaa uaggaau                                             27

<210> SEQ ID NO 1200
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1200
uuaauuucuc uccuuugcau auuggau                                             27

<210> SEQ ID NO 1201
<211> LENGTH: 27

-continued

```
<212> TYPE: RNA
<213> ORGANISM: Artificial Sequence
<220> FEATURE:
<223> OTHER INFORMATION: Synthetic Sequence

<400> SEQUENCE: 1201
ccuacccugc ccccuucucc uuagaau                                              27

<210> SEQ ID NO 1202
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1202
cugcuguagu cagugcugcc ugggaau                                              27

<210> SEQ ID NO 1203
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1203
cacuuagcac aguaccuuac auagagu                                             27

<210> SEQ ID NO 1204
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1204
acuuagauau gaaggggaaa gaagggu                                             27

<210> SEQ ID NO 1205
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1205
ugcaguuuua cauauaaaug acaggau                                             27

<210> SEQ ID NO 1206
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1206
guugcggagg gugggccugg gaggggu                                            27

<210> SEQ ID NO 1207
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1207
```
aaaaauguga ugaucaaaac uaggaau                                27

<210> SEQ ID NO 1208
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1208
ggcauucuaa ggagaagggg gcagggu                                27

<210> SEQ ID NO 1209
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1209
aaagaagggu uugagauaau gugggau                                27

<210> SEQ ID NO 1210
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1210
ugugauaguu uggagaauaa auugaau                                27

<210> SEQ ID NO 1211
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1211
gcagaugcua ugaaagaaaa aggggau                                27

<210> SEQ ID NO 1212
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1212
uaugagccac cgcacccggc cgcgaau                                27

<210> SEQ ID NO 1213
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1213
cgcuucggcc ucccaaagug cuggau                                 27

<210> SEQ ID NO 1214
<211> LENGTH: 27
<212> TYPE: RNA
<213> ORGANISM: Artificial Sequence -continued

```
<220> FEATURE:
<223> OTHER INFORMATION: Synthetic Sequence

<400> SEQUENCE: 1214
ccagcacuuu gggaggccga agcgggu                                              27

<210> SEQ ID NO 1215
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1215
cacuuuggga ggccgaagcg gguggau                                              27

<210> SEQ ID NO 1216
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1216
uuuuguguuu uuaguagaga cgggggu                                              27

<210> SEQ ID NO 1217
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1217
ugucucagcc uccugaguag cugggau                                              27

<210> SEQ ID NO 1218
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1218
cgauucucgu gucucagccu ccugagu                                              27

<210> SEQ ID NO 1219
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1219
cuacucagga ggcugagaca cgagaau                                              27

<210> SEQ ID NO 1220
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1220
gcucacugca accucugccu cccgggu                                              27
```

```
<210> SEQ ID NO 1221
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1221
ugcucuuucg cccaggcugg auggagu                                        27

<210> SEQ ID NO 1222
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1222
agucuugcuc uuucgcccag gcuggau                                        27

<210> SEQ ID NO 1223
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1223
uaacgauuuu uuuuuuugag acggagu                                        27

<210> SEQ ID NO 1224
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1224
gcccaacucu ucgcgguggc agugggu                                        27

<210> SEQ ID NO 1225
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1225
ccccauugcc ggcgaggggu gacggau                                        27

<210> SEQ ID NO 1226
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1226
aacuaccccc agaugauccu aaggaau                                        27

<210> SEQ ID NO 1227
<211> LENGTH: 27
<212> TYPE: RNA
<213> ORGANISM: Artificial Sequence
<220> FEATURE:
<223> OTHER INFORMATION: Synthetic Sequence
```

<400> SEQUENCE: 1227
acugcaugug ugagccgagu ccugggu                                        27

<210> SEQ ID NO 1228
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1228
cacaagcccc cauugccggc gaggggu                                        27

<210> SEQ ID NO 1229
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1229
gaucucgacc aguccccuca acggggu                                        27

<210> SEQ ID NO 1230
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1230
gaggcaccca cugccaccgc gaagagu                                        27

<210> SEQ ID NO 1231
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1231
gcccaccuuu agggugauag ccugaau                                        27

<210> SEQ ID NO 1232
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1232
guugccugga gccguuccug cgugggu                                        27

<210> SEQ ID NO 1233
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1233
aaaaagcgau cuuagaucac cuugagu                                        27

<210> SEQ ID NO 1234

```
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1234
gcaccuccaa agucggccaa aaugaau                                        27

<210> SEQ ID NO 1235
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1235
cuauuaccua aguagguccc cuggaau                                        27

<210> SEQ ID NO 1236
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1236
ggccgcagga agaggaacgg agcgagu                                        27

<210> SEQ ID NO 1237
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1237
ucccagccgg cagucuccca caagaau                                        27

<210> SEQ ID NO 1238
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1238
gguggugcag ggccgugaag caagaau                                        27

<210> SEQ ID NO 1239
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1239
gggugcacgu cccacagcuc agggaau                                        27

<210> SEQ ID NO 1240
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1240
```

-continued caugcacuug ucuguaguuc aaggagu                                              27

<210> SEQ ID NO 1241
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1241
guguauauaa aggcccaccu uuagggu                                             27

<210> SEQ ID NO 1242
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1242
cuggcccagu cagucagguu uggggu                                              27

<210> SEQ ID NO 1243
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1243
uugugggaga cugccggcug ggagggu                                             27

<210> SEQ ID NO 1244
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1244
ugauccuaag gaauugaagg uauggau                                             27

<210> SEQ ID NO 1245
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1245
ugacuucuga cuuucaauca ucaggau                                             27

<210> SEQ ID NO 1246
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1246
agacugccgg cugggagggu uggggu                                              27

<210> SEQ ID NO 1247
<211> LENGTH: 27
<212> TYPE: RNA

<213> ORGANISM: Artificial Sequence
<220> FEATURE:
<223> OTHER INFORMATION: Synthetic Sequence

<400> SEQUENCE: 1247
uucaauuccu uaggaucauc uggggu                                        27

<210> SEQ ID NO 1248
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1248
ugauuuugcc aagaacuugu cuagagu                                       27

<210> SEQ ID NO 1249
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1249
aggagucccc gcccuugcaa aagggau                                       27

<210> SEQ ID NO 1250
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1250
aaagcgaacu gcauguguga gccgagu                                       27

<210> SEQ ID NO 1251
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1251
uaccuugucg ugauaagugg gcagaau                                       27

<210> SEQ ID NO 1252
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1252
aagcaagaau ggccacagac ugggaau                                       27

<210> SEQ ID NO 1253
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1253
uugccaagag agagagcagc caggggu                                       27

```
<210> SEQ ID NO 1254
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1254
gggccgaccg cggccuccag gcggggu                                             27

<210> SEQ ID NO 1255
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1255
aagaguuggg cucugucagc cgcgggu                                             27

<210> SEQ ID NO 1256
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1256
agauacauuu cuuagcacua uuagaau                                            27

<210> SEQ ID NO 1257
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1257
agaagcaaaa guaccacuag auggagu                                            27

<210> SEQ ID NO 1258
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1258
caaaaugaau gggcagugag ccggggu                                            27

<210> SEQ ID NO 1259
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1259
gcaugguuuu guggaaaagu aaggaau                                            27

<210> SEQ ID NO 1260
<211> LENGTH: 27
<212> TYPE: RNA
<213> ORGANISM: Artificial Sequence
<220> FEATURE:
```

<223> OTHER INFORMATION: Synthetic Sequence

<400> SEQUENCE: 1260
auugaaggua uggauuuggg acggaau                              27

<210> SEQ ID NO 1261
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1261
ugagagauca uuuaacauuu aaugaau                              27

<210> SEQ ID NO 1262
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1262
aaauccauac cuucaauucc uuaggau                              27

<210> SEQ ID NO 1263
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1263
uaagaaaugu aaaaaaaccu cuagagu                              27

<210> SEQ ID NO 1264
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1264
cggcugggag gguugggggu gggggu                               27

<210> SEQ ID NO 1265
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1265
ucccacucug ucacccagag cuggagu                              27

<210> SEQ ID NO 1266
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1266
uuauuggaac gcuaagcuug uggggu                               27

```
<210> SEQ ID NO 1267
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1267
gaggguuggg gguggggggu guggaau                                          27

<210> SEQ ID NO 1268
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1268
cugcacucca gcucugggug acagagu                                          27

<210> SEQ ID NO 1269
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1269
cuuggcgaug accuugagca guaggau                                          27

<210> SEQ ID NO 1270
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1270
uuucuucucu uucuuuugag acggagu                                          27

<210> SEQ ID NO 1271
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1271
uggggacacu gcacuccagc ucugggu                                          27

<210> SEQ ID NO 1272
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1272
uucucucagc cucccaagua gcugggu                                          27

<210> SEQ ID NO 1273
<211> LENGTH: 27
<212> TYPE: RNA
<213> ORGANISM: Artificial Sequence
<220> FEATURE:
<223> OTHER INFORMATION: Synthetic Sequence
```

-continued

```
<400> SEQUENCE: 1273
cugaaaauac aaaaaaauca gccgggu                                              27

<210> SEQ ID NO 1274
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1274
gcgggcggau caccugaggu caggagu                                              27

<210> SEQ ID NO 1275
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1275
cacuuuggga ggcagaagcg ggcggau                                              27

<210> SEQ ID NO 1276
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 1276
cgcuucugcc ucccaaagug cugggau                                             27
```